(12) United States Patent
Bird

(10) Patent No.: US 11,833,394 B2
(45) Date of Patent: *Dec. 5, 2023

(54) EXERCISE APPARATUS WITH MOTOR INDUCED RESISTANCE

(71) Applicant: John M. Bird, Sparks, NV (US)

(72) Inventor: John M. Bird, Sparks, NV (US)

( * ) Notice: Subject to any disclaimer, the term of this patent is extended or adjusted under 35 U.S.C. 154(b) by 129 days.

This patent is subject to a terminal disclaimer.

(21) Appl. No.: 17/385,876

(22) Filed: Jul. 26, 2021

(65) Prior Publication Data

US 2021/0354003 A1  Nov. 18, 2021

Related U.S. Application Data

(63) Continuation of application No. 16/231,566, filed on Dec. 23, 2018, now Pat. No. 11,071,890, which is a
(Continued)

(51) Int. Cl.
*A63B 24/00* (2006.01)
*A63B 21/005* (2006.01)
(Continued)

(52) U.S. Cl.
CPC ........ *A63B 24/0087* (2013.01); *A63B 21/005* (2013.01); *A63B 21/0058* (2013.01);
(Continued)

(58) Field of Classification Search
CPC .............. A63B 24/0087; A63B 21/005; A63B 21/0058; A63B 21/151; A63B 21/153;
(Continued)

(56) References Cited

U.S. PATENT DOCUMENTS 3,848,467 A * 11/1974 Flavell ................ A63B 21/153
482/4
3,858,873 A 1/1975 Jones
(Continued)

FOREIGN PATENT DOCUMENTS

| WO | WO 91/07214 | 5/1991 |
| WO | WO 03/041809 A2 | 5/2003 |

OTHER PUBLICATIONS

Tullman Sports International Corporation, Tumman Human Performance System, Ariel Computerized Exercise System (ACES).
(Continued)

*Primary Examiner* — Sundhara M Ganesan

(57) ABSTRACT

A resistance exercise system having, in certain embodiments, a DC power supply system, a DC motor connected to the DC power supply system, a drive section connected to a drive element, a resistance delivery element connected to the drive element, and an extractable exercise resistance delivery section, a predetermined variable resistance section intermediate the DC power supply system and DC motor, an electrical condition sensor, and a variable resistance section control in communication with the electrical condition sensor and the predetermined variable resistance section. In some embodiments, the resistance exercise system includes a computing facility providing the ability to configure the exercise system to provide predetermined static or variable exercise resistance during exercise, and for example, during a positive or negative exercise stroke. Some embodiments allow users to create and, if desired, display varying and complex resistance exercise routines with or without use of resistance weights.

30 Claims, 71 Drawing Sheets

Related U.S. Application Data continuation of application No. 15/660,835, filed on Jul. 26, 2017, now Pat. No. 10,159,870, which is a continuation of application No. 14/613,259, filed on Feb. 3, 2015, now Pat. No. 9,717,952, which is a continuation of application No. 13/956,337, filed on Jul. 31, 2013, now Pat. No. 8,968,155.

(60) Provisional application No. 61/778,101, filed on Mar. 12, 2013, provisional application No. 61/677,640, filed on Jul. 31, 2012.

(51) Int. Cl.
| | |
|---|---|
| A63B 21/00 | (2006.01) |
| A63B 23/035 | (2006.01) |
| G16Z 99/00 | (2019.01) |
| G16H 20/30 | (2018.01) |
| A63B 23/12 | (2006.01) |
| A63B 71/00 | (2006.01) |

(52) U.S. Cl.
CPC .......... *A63B 21/151* (2013.01); *A63B 21/153* (2013.01); *A63B 21/156* (2013.01); *A63B 21/4043* (2015.10); *A63B 23/03525* (2013.01); *G16H 20/30* (2018.01); *G16Z 99/00* (2019.02); *A63B 21/0053* (2013.01); *A63B 23/1263* (2013.01); *A63B 23/1281* (2013.01); *A63B 2024/0093* (2013.01); *A63B 2071/0072* (2013.01); *A63B 2220/13* (2013.01); *A63B 2220/17* (2013.01); *A63B 2220/30* (2013.01); *A63B 2225/20* (2013.01); *A63B 2225/50* (2013.01)

(58) Field of Classification Search
CPC .............. A63B 21/156; A63B 21/4043; A63B 23/03525; A63B 21/0053; A63B 23/1263; A63B 23/1281; A63B 2024/0093; A63B 2071/0072; A63B 2220/13; A63B 2220/17; A63B 2220/30; A63B 2225/20; A63B 2225/50; G16H 20/30; G16Z 99/00

See application file for complete search history.

(56) References Cited

U.S. PATENT DOCUMENTS

| | | | |
|---|---|---|---|
| 3,869,121 A | 3/1975 | Flavell | |
| 4,211,930 A | 7/1980 | Fengler | |
| 4,261,562 A | 4/1981 | Flavell | |
| 4,354,676 A | 11/1982 | Ariel | |
| 4,535,263 A * | 8/1985 | Avery | H02K 26/00 310/49.39 |
| 4,540,171 A | 9/1985 | Clark et al. | |
| 4,563,003 A | 1/1986 | Bugallo et al. | |
| 4,569,518 A | 2/1986 | Fulks | |
| 4,609,189 A | 9/1986 | Brasher | |
| 4,650,185 A | 3/1987 | Cartwright | |
| 4,765,315 A * | 8/1988 | Krukowski | F16D 48/064 482/901 |
| 4,765,613 A | 8/1988 | Voris | |
| 4,811,946 A | 3/1989 | Pelczar | |
| 4,842,274 A | 6/1989 | Oosthuizen et al. | |
| 4,869,497 A | 9/1989 | Stewart et al. | |
| 4,891,764 A * | 1/1990 | McIntosh | G05B 19/237 482/901 |
| 4,930,770 A | 6/1990 | Baker | |
| 5,020,794 A | 6/1991 | Englehardt et al. | |
| 5,037,089 A | 8/1991 | Spagnuolo et al. | |
| 5,117,170 A | 5/1992 | Keane et al. | |
| 5,267,925 A | 12/1993 | Boyd | |
| 5,308,303 A | 5/1994 | Rawls et al. | |
| 5,324,242 A | 6/1994 | Lo | |
| 5,328,429 A | 7/1994 | Potash et al. | |
| 5,346,452 A | 9/1994 | Ku | |
| 5,360,382 A | 11/1994 | Chi | |
| 5,387,170 A | 2/1995 | Rawls et al. | |
| 5,431,609 A | 7/1995 | Panagiotopoulos et al. | |
| 5,433,678 A | 7/1995 | Chi | |
| 5,435,798 A | 7/1995 | Habing et al. | |
| 5,476,428 A | 12/1995 | Potash et al. | |
| 5,583,403 A | 12/1996 | Anjanappa et al. | |
| 5,993,356 A | 11/1999 | Houston | |
| 6,027,429 A | 2/2000 | Daniels | |
| 6,050,920 A | 4/2000 | Ehrenfried | |
| 6,280,361 B1 | 8/2001 | Harvey et al. | |
| 6,386,251 B1 | 5/2002 | Koch | |
| 7,095,214 B2 | 8/2006 | O'Gorman et al. | |
| 7,096,098 B2 | 8/2006 | Auguet et al. | |
| 7,157,869 B2 | 1/2007 | Ishikawa | |
| 7,185,591 B2 | 3/2007 | Kumar et al. | |
| 7,193,395 B2 | 3/2007 | Ogorman et al. | |
| RE40,875 E | 8/2009 | Minogue et al. | |
| 7,682,287 B1 | 3/2010 | Hsieh | |
| 7,867,151 B2 | 1/2011 | Hayes et al. | |
| 8,052,584 B2 | 11/2011 | Keiser | |
| 8,287,434 B2 | 10/2012 | Zavadsky et al. | |
| 8,323,158 B2 | 12/2012 | Keiser | |
| 8,337,364 B2 | 12/2012 | Ishii | |
| 8,475,338 B2 | 7/2013 | Greenhill | |
| 8,968,155 B2 | 3/2015 | Bird | |
| 9,717,952 B2 | 8/2017 | Bird | |
| 10,159,869 B2 | 12/2018 | Bird | |
| 10,159,870 B2 | 12/2018 | Bird | |
| 11,071,890 B2 | 7/2021 | Bird | |
| 2003/0207734 A1 | 11/2003 | La Stayo et al. | |
| 2006/0229164 A1 | 10/2006 | Einav | |
| 2007/0202992 A1 | 8/2007 | Grasshoff | |
| 2008/0248926 A1 | 10/2008 | Cole | |
| 2009/0233767 A1 | 9/2009 | Huang | |
| 2010/0069202 A1 | 3/2010 | Olsen | |
| 2010/0125026 A1 | 5/2010 | Zavadsky et al. | |
| 2011/0086742 A1 | 4/2011 | Burnfield et al. | |
| 2011/0172058 A1 | 7/2011 | Deaconu | |
| 2011/0245049 A1 | 10/2011 | Keiser | |
| 2011/0251021 A1 | 10/2011 | Zavadsky et al. | |
| 2012/0088634 A1 | 4/2012 | Heidecke | |
| 2015/0148194 A1 | 5/2015 | Bird | |
| 2015/0165272 A1 | 6/2015 | Bird | |
| 2017/0333756 A1 | 11/2017 | Bird | |
| 2019/0151716 A1 | 5/2019 | Bird | |

OTHER PUBLICATIONS

International Search Report and Written Opinion of the International Searching Authority for International Application PCT/US2013/053104, dated Nov. 1, 2013.
Restriction Requirement for U.S. Appl. No. 13/956,337, dated Apr. 18, 2014.
Office Action for U.S. Appl. No. 13/956,337, dated Jun. 12, 2014.
Notice of Allowance for U.S. Appl. No. 13/956,337, dated Oct. 8, 2014.
Supplementary Partial European Search Report for International Application PCT/US2013/053104, dated Apr. 4, 2016.
Notice of Allowance for U.S. Appl. No. 14/613,259, dated Oct. 17, 2016.
Supplemental European Search Report for EP Patent Application No. 13825328.1, dated Aug. 2, 2016.
Office Action for Canadian Patent Application No. 2917687, dated Nov. 22, 2016.
Office Action for U.S. Appl. No. 14/613,261, dated May 11, 2017.
Office Action for U.S. Appl. No. 15/660,835, dated Oct. 11, 2017.
Final Office Action for U.S. Appl. No. 14/613,261, dated Mar. 15, 2018.
Notice of Allowance for U.S. Appl. No. 15/660,835, dated Sep. 24, 2018.

* cited by examiner

"Normal" Bias

"Reverse" Bias

EXERCISE APPARATUS WITH MOTOR INDUCED RESISTANCE

CROSS REFERENCE TO OTHER APPLICATIONS

This application is a continuation of U.S. application Ser. No. 16/231,566, filed Dec. 23, 2018, entitled "RESISTANCE APPARATUS, SYSTEM, AND METHOD", which is a continuation of U.S. application Ser. No. 15/660,835, filed Jul. 26, 2017, entitled "RESISTANCE APPARATUS, SYSTEM, AND METHOD" (now U.S. Pat. No. 10,159, 870), which is a continuation of U.S. application Ser. No. 14/613,259, filed Feb. 3, 2015, entitled "RESISTANCE APPARATUS, SYSTEM, AND METHOD" (now U.S. Pat. No. 9,717,952), which is a continuation of U.S. application Ser. No. 13/956,337, filed Jul. 31, 2013, entitled "RESISTANCE APPARATUS, SYSTEM, AND METHOD" (now U.S. Pat. No. 8,968,155), which claims priority to U.S. Provisional Patent Application No. 61/677,640, entitled "PROGRAMMABLE ELECTRONIC RESISTANCE SYSTEM AND METHOD OF USE," filed on Jul. 31, 2012, and to U.S. Provisional Patent Application No. 61/778,101, entitled "PROGRAMMABLE ELECTRONIC RESISTANCE SYSTEM AND METHOD OF USE," filed on Mar. 12, 2013, all of which are expressly incorporated by reference herein. In the event of any inconsistency between the priority applications recited above and this application, this application shall prevail.

FIELD

The present disclosure relates to resistance training systems in general and, in one embodiment, to a system that provides resistance simulating physical weights (mass subject to gravity) through electrical and mechanical components.

BACKGROUND

It has long been known that resistance training can provide functional benefits as well as improve overall health and well-being. For example, resistance training has long been known to improve posture, provide improved support for joints, increase bone density, improve cardiac function, and reduce the risk of injury from everyday activities. As a result, resistance training has often been used in conjunction with other physical activity such as cardiovascular activity.

Aging individuals often have participated in resistance training to assist in prevention of some of the loss of muscle tissue that normally accompanies aging, and to help prevent osteoporosis. For many people in rehabilitation or with an acquired disability, such as those experiencing a stroke or orthopedic surgery, resistance training has often been a central element to a recovery program. The use of resistance machines that operate within an isolated range of motion have aided in the rehabilitation of injuries without aggravating existing injuries or risking new ones.

Common resistance training and rehabilitation programs have included the use of resistance to muscular contraction in order to improve such attributes as strength, anaerobic endurance, muscle size, etc. Resistance-training programs have been customized in order to emphasize improvement of specific physical attributes and conditions.

For example, one common program uses fewer repetitions with relatively higher degrees of resistance. Such a program is often used when strength improvement is desired. Conversely, another common program has utilized increased repetitions with relatively lower degrees of resistance. Such programs have often been used for muscle toning and for rehabilitation of injuries.

In addition, programs have incorporated combinations in which resistance can be increased or decreased between sets or even between or during repetitions. One common form of increasing and decreasing of resistance is known a "pyramiding," which increases resistance to a peak level during a series of sets and then decreases the resistance during another series of sets. Another form of varying resistance, called "ramping" or "static training," increases or decreases resistance near or at the end of a exercise stroke. Yet another variable resistance technique, called "muscle confusion," involves varying the types of resistance experienced by given muscles between exercise sessions or sets of sessions. Other common weight changing terminology is "weight stripping" (removing weight during or in between exercises) and "weight augmenting" (adding weight during or in between exercises).

To optimize training time and training efficiency, trainers often prepare customized resistance training programs in advance of training an individual. These programs are often hand written or stored on a portable electronic device to be referred to and/or followed during training. While these programs can be shared with a trainee, the trainee may lack the expertise to perform the exercises properly on their own. A professional athlete, for example, may be on an extended trip to locations remote from the trainer. The trainer can send customized training programs to the athlete, but they may not be able to perform the exercises properly, and most often there will be no objective record of how or when training was performed.

Conventional resistance training systems therefore have long included structure for varying the degree of resistance during use. One common type of such system is a gravity weight system. This gravity weight system provides differing weights that can be engaged and disengaged in order to obtain the desired level of resistance.

One problem with the gravity weight system is that the weight of the system increases as the maximum gravity-weight-based resistance provided by the system increases. As a result, gravity weight based systems, particularly those that can provide hundreds of pounds of resistance, are cumbersome, costly and difficult to ship, and difficult to otherwise move. They can also present substantial risk of injury from use of weights and the possibly of mechanical failure of system components.

For example, a gravity weight system presents injury risk due to the inertial mass of the weights in the system. The resulting higher level of force required to overcome the inertia of a given weight or group of weights, and thus initiate movement of the weight(s), can create a risk of excessive strain on the user's muscles and tendons. This risk increases with use of heavier weight(s) in the system, which have greater inertial mass and require greater levels of force to overcome associated inertia and at the same move the weight against the force of gravity.

One solution to the size, weight, and inertial mass presented by gravity weight systems has utilized elastic bands, arms, or springs rather than weights to provide resistance. This type of system, often referred to as an elastometric system, can be much lighter and easier to package, ship, and move. It typically presents much less inertial mass to be moved by the user as well.

One problem with elastometric systems is that the elastic bands, arms, and springs provide limited resistance zones because they can only be stretched or bent so far before they will cease stretching or bending (or even possibly break). This results in a limited maximum stroke length for a particular resistance training movement. Further, elastometric systems present relatively inconsistent and unreliable levels of resistance due to, among other things, diminishing levels of resistance provided by the band, arm, or spring structures as they deteriorate through use and age.

In addition, like weight resistance systems, the number of levels of resistance provided by elastometric systems are typically relatively limited to the relatively few levels of elastometric bands, arms, or spring included in an elastometric system or the number of weights in a weight system. Although the number of resistance levels can be increased in these systems by providing further numbers of bands, arms, or springs, or weights, the size, weight, expense, and difficulty of these systems increases along with the increase in numbers of such components.

Another problem presented by elastometric systems is that they often do not provide, as is often desired, the same level resistance throughout a desired exercise stroke or the ability to reverse the nature of the varying resistance presented to the user. Thus, in elastometric systems in which resistance increases during the first, outgoing stroke (i.e., the positive stroke) and decreased during the reverse, ingoing stroke (the negative stroke), they do not provide the ability to reverse that aspect of their operation and decrease resistance during the positive stroke, and increase it during the negative stroke.

In this regard, differential resistance training varies resistance depending on the direction of the stroke, with the positive stroke usually presenting a lower degree of resistance than that provided during the negative stroke. As explained above, other types of resistance training present significant other variations in resistance levels during repetitions (e.g., ramping), from repetition to repetition, set to set (e.g., pyramiding), and exercise session to exercise session or groups of sessions to session or group of sessions (e.g., muscle confusion).

One method of differential resistance training has utilized a weight based system. Differential resistances are achieved by a partnering assistant who helps lift the weight during the positive stroke and refrains from assisting during the negative stroke. Partnering also been used to also accomplish other weight based, variable resistance exercise formats, such as ramping, pyramiding, muscle confusion, spotting, and others.

One problem with the partnering method is that it requires an additional person to achieve the desired varying resistance. In addition, the partnering method is inefficient and imprecise, as it relies on the partner's sense of what degree of assistance to provide and when to provide it. The partnering method also does not ensure a full range of motion for the person performing the positive and negative stroke due to the partner's exercise of discretion about when to provide or cease providing assistance. Similarly, the partnering method further does not provide the type of rapid yet precise change in resistance that may often be desired, such as with a resistant rapid ramp at the end of an exercise stroke.

One attempt to provide greater reliability and consistency in varying resistance exercise has utilized a hydraulic system or motor to assist or oppose movement of a traditional weight stack. These types of systems, however, still require the use of a weight stack and have the same types of weight, size, and movement problems provided by weight based systems noted above.

Another method of providing variable resistance has utilized a hydraulic mechanism to provide an adjustable resistance level without the use of weighted elements. The hydraulic mechanism typically provides passive resistance, providing resistance only when the user pushes or pulls against linkage connected to a hydraulic cylinder. As a result, such hydraulic systems do not provide forced variable resistance training such as that provided by elastometric systems. They also do not provide any resistance, much less variable resistance, when stroke movement stops, such as at the beginning or end of a stroke. Hydraulic systems usually are also relatively slow in changing resistance levels.

Pneumatic resistance systems have also been developed. Some of these types of systems utilize electronic regulators to supply air cylinders and accumulator tanks with compressed air. The electronic regulator controls pressure and maintains a selected pressure setting by adding or relieving air during each movement or stroke made by the user. These pneumatic systems typically have relatively imprecise structures for determining and setting the resistance level. They also typically have not included mechanisms for forcing differential or other varying resistance levels at varying levels specified by the user; and pneumatic systems are typically slower than hydraulic systems in changing resistance levels.

Further, pneumatic systems typically do not provide resistance similar to that of a weight stack or free weights. The differing pneumatic type of resistance can negatively impact the exercise experience and result in reduced motivation in engaging in or completing an exercise regimen.

Other systems and methods for creating variable resistance include a resistance mechanism that progressively varies resistance applied to a lifting mechanism during the positive stroke, and decreases resistance to substantially zero during the negative strokes. Some of these systems utilize motors or hydraulic forces to either create the resistance or modify or oppose the resistance provided by a traditional weight stack. Such systems have been utilized to provide pyramiding exercise schemes for example. However, these systems lack full adjustability and present issues such as those described above, such as inability to implement other resistance profiles, differing exercise programs, etc.

Some prior systems have use a brake or similar system to create increased resistance on the return stroke of a cable or lever. These systems, however, can produce excess heat, inefficiently use power via thermal losses, and lack precise configurability or programmability due to lack of control in applying the brake instantaneously or consistently as the brake system wears through use.

Yet other systems utilize a motor coupled to a clutch, such as a frictionless eddy-current clutch, or torque converter to provide an adjustable resistance to a load member to oppose a predetermined training movement performed by a user. These systems detect the location and direction of the load member and modify the torque applied to the load member to provide a consistent resistance felt by a user during both a positive and negative stroke. Although these systems can eliminate the need for a bulky weight stack, they utilize power inefficiently by controlling the torque and hence the resistance felt by the user via a clutch, i.e., underutilizing power supplied to the motor. Furthermore, these systems, although allowing for some adjustability of resistance versus the position of the load member, do not provide a precise programmable resistance profile to implement varying other resistance techniques, such as elastometrics, ramping, pyramiding, or muscle confusion.

Other systems have utilized a low voltage DC motor to simulate a weight stack, except that the amount of resistances provided the motor is dependent on the amount of displacement during an exercise stroke. These systems thus provide for a "soft start," providing lower starting resistance (unlike that inertial mass that must be overcome in a weight based system) to enhance user safety. However, these systems have not themselves provided other types of variable resistance techniques such as ramping, elastometric resistance, pyramiding, or differential resistance.

Other systems provide for adjustability relative to position and relative to resistance, such as constant velocity variable resistance or more traditional variable resistance applications and further provide for customizable resistance profiles. However, these systems do not provide for accurate simulations of elastometric resistance profiles or customize end ramping or forced negative profiles.

Programmable systems utilizing motors or hydraulic forces to emulate pyramiding often lack the ability to combine other exercise profiles with pyramiding, such as, for example, elastomeric pyramiding.

SUMMARY

The present specification discloses various novel systems, apparatus, and processes. In one aspect, systems, apparatus, and processes are provide programmable variable resistance for use in strength training, rehabilitation, and other resistance-based training that may solve one or more of problems mentioned above with current weight training methods. In some embodiments, the system can provide programmable fixed or variable resistance during the positive and negative exercise stroke.

Some such systems apply a programmable and adjustable resistance via a flexible exercise resistance member, such as cable in some embodiments, to provide a wide variety of differing resistance training exercises, such as elastometric, reverse elastometric, end-ramping, forced negative or differential, weight stripping, weight augmenting, and muscle confusion resistance exercises. Some instances can include a struggle detection system, reducing resistance when user struggle is detected.

In some embodiments, the mass of components to be moved during exercise with the system can, if desired, be very low regardless of the amount of resistance developed by the system. Some embodiments can thus require the user to thus incur relatively little if any inertial resistance due to inertial mass while providing resistance levels from 1 pound to over 300 pounds during the positive and negative stroke.

In some embodiments, a variable resistance system includes a motor, such as a DC motor, that supplies resistance via torque generated by the motor against a cable (or other exercise resistance element) connected to or driven by the DC motor. In certain embodiments, the level of resistance provided by the DC motor is controlled by a control system that varies the amount of current supplied to the DC motor, thus changing the resistance opposing movement of the cable. Some systems can thus completely dispense with use of gravity weights to generate exercise resistance.

In some systems, the variable resistance system includes (i) a sensor for sensing voltage or other aspect (such as current for example) generated by or resulting from the DC motor and (ii) circuitry for varying DC input to the DC motor in response to the voltage or other aspect sensed by the sensor.

In some embodiments, the DC motor has a high current and/or high voltage power source, such as an AC motor coupled to an alternator, or an amplifier, such as a class D amplifier for example. Some systems can receive power from, for example, a standard household socket. The motor or other drive circuitry can be controlled by an automated user interface in some applications.

In some embodiments, the motor and associated controller is programmable to vary the motor current, providing varied resistance through the flexible exercise resistance member in accordance with a desired resistance profile. The controller senses one or more of stroke direction of the flexible member, stroke location, flexible member position, and velocity of the cable in real-time. The controller changes the DC motor current and thus exercise resistance depending on one or more of the sensed aspects. For example, sensing of real-time cable position and, optionally, velocity can allow the controller to vary resistance as a function of sensed position and, optionally, velocity.

Further, in some systems, resistance with respect to time are also programmable, allowing for stepped changes in resistance or smooth transitions from one resistance level to the next. In some cases, this can reduce or eliminate a jerking effect due to sudden change in resistance.

In some embodiments, the controller and an automated user interface allow a user to program a multitude of different resistance profiles, such as stepped resistance, forced negative resistance, muscle confusion, weight stripping, ramping up or down, elastometric resistance, and reverse elastomeric resistance profiles, as well as combinations of one or more such or other profiles.

In certain instances, exercise resistance can be programmed to vary as a function of stroke n other ways as well. For example, ramp times can also be programmable, for example in one micro-second or other increments.

In certain instances, the exercise resistance can be programmed to be directionally equal and constant, directionally unequal and constant, positionally variable and directionally equal (like a spring) or positionally variable and directionally unequal (i.e. heavier variable weight going one direction). The programmable electronic resistance system can accommodate the differing approaches without the assistance of spotters. Further, this functionality can help influence, and validate, or invalidate, the effectiveness of the different approaches of the varying negative weight training programs.

In some embodiments, a stroke indicator is programmable to indicate cable position in real-time to the user. In some cases, the stroke indicator can have approximately a ¼ inch resolution and can indicate position during the full cable stroke. In some embodiments, the user can program the desired stroke length for a given resistance training movement or exercise, and the stroke indicator can be calibrated to indicate cable position relative to the desired stroke length.

In some embodiments, the cable position and optional speed sensing circuitry enables the programmable electronic resistance system to sense when the user is struggling to complete a stroke. In response, the controller can automatically reduce resistance when, for example, the flexible member (such as a cable for example) exceeds a retraction threshold or the set stroke length is achieved. In some applications, user safety can be enhanced as a result of the prompt removal of resistance, thus reducing the likelihood of injury due to the user having to manage and control resistance or weights.

In certain instances, exercise resistance can be applied to the user by motor rotation force (torque) via a flexible member attached to a take-up drum or reel, linear or other retractor, such as a chain drive or timing belt, or other device. In some embodiments, the system inertial mass presented to the user may consist of a cable (for example), cable attachment structure on both ends, and the motor inertia, which may be multiplied or divided by the gearing ratio of gears intermediate the motor drive and the cable. In some cases, the system inertia mass may remain fixed for any variation in weight/resistance experienced by the user, and if desired, the inertial mass can be very low as compared to a weight based system for example.

In some embodiments, a user can configure or adjust one or more of the resistance parameters via a user interface in communication with a programmable resistance motor apparatus. In some cases, the user can adjust one or more resistance parameters via a computer, wirelessly via a smart phone, a tablet, or a user interface controlling a microcontroller in communication with the programmable resistance motor apparatus.

In some systems for example, the user can set or adjust a static resistance level (simulating free weights) or can program or select a pre-programmed resistance profile (such as an elastomeric profile similar to existing elastic bands) that can change resistance relative to time, stroke rate, position in the stroke of the cable for a particular resistance training movement, or any other useful measuring point for resistance training. In some cases, the user can program or select one of many types of resistance profiles, such as differential resistance programs, high repetition training programs that allow for significant variations in resistance, resistance reduction profiles for safety precaution, muscle confusion profiles, pyramiding profiles, end-point ramping training profiles, and/or completely customizable profiles particular to a specific sport, activity, etc.

In some embodiments, the maximum, or a portion of, the resistance level provided by the apparatus is not provided by weights. This can allow the weight and size of the apparatus to be reduced, rendering the apparatus less cumbersome, easier to ship and move, and safer to use. In some systems, the weight and size of the apparatus can thus be relatively less than traditional exercise machines.

In some systems, the inertial mass of components moved during the resistance exercise is fixed regardless of amount of resistance provided by the apparatus. In some systems, the inertial mass of such components is reduced or very low, particularly as compared to weight resistance systems. Certain of these types of systems can help reduce stress on muscles and tendons due to the typical need to overcome inertial mass resistance with weight based systems, particularly at the In some embodiments, the apparatus can retrofit to conventional resistance equipment, including, for example, machines having a weight stack, such as a universal workout station, or machines that employ a cable tie-in to resistive elements, such as a Bowflex™. In some of these embodiments, one or more of the following advantages are realized. The return on investment in existing equipment can be improved by enabling some such equipment to be functionally extended with modification and without necessarily requiring the purchase and installation of additional weight elements.

Some systems detect cable slackening and add a retracting force to maintain or remove the slack in the cable. Some embodiments can sense cable droop (horizontally due to the gravitational force on the cable) or cable separation from one or more pulley guides (vertically due to the gravitational force on the cable); in response, a controller can issue commands to accomplish correction to reduce or eliminate the slack condition. Slack detection and counteraction can, in some instances, provide a resistance training system that feels more like traditional training device using weighted elements. Some embodiments can allow the user to pull the cable at any desired user speed without having the resistance change, so that a set resistance is independent of velocity of the cable.

In some embodiments, during the outward stroke (cable extension), the motor is moving is the non-preferred direction of rotation, thus against the voltage that supplies current to the motor, such as an alternator-generated voltage, and will generate a voltage in the opposite polarity of the supplied voltage. In some cases, if this negative voltage is of sufficient amplitude to forward bias the alternator rectifier diodes, user can feel an increase in resistance, since the motor generates its own current and thus resistance through the diodes. This unwanted increased resistance may be corrected for by placing one or more resistor, in some embodiments a low value resistor, in series with the motor. In some embodiments, the resistor value can be reduced or even minimized to reduce resistor power dissipation (in some embodiments, the current to or from the motor flows through this resistor, generating heat). The reduced or minimum resistor value can be determined iteratively by inserting a resistor in the motor-alternator connection path, generating flexible member velocity, for example maximum outward cable velocity in some embodiments, at a desired user resistance, and then inspecting the results. The addition of the series resistor may also provide, in certain instances, the benefit of aiding in drive circuitry smoothing, particularly at the lower resistance levels.

In some instances, the programmable electronic resistance system can create, store, and toggle between two or more user profiles, allowing participants in a joint training session to quickly and easily change resistance configurations in accordance with each trainees custom training program. This rapid reconfiguration can, in some applications, provide one or more of reduction in overall workout time, reduction in the risk of injury, improvement in exercise timing and rhythm, and enhancement of the overall training experience.

In some implementations of the programmable electronic resistance system, trainers can prepare customized training programs on a computing device disconnected from the resistance apparatus or network. These programs can be shared with a trainee, other trainers, or any other user of the programmable electronic resistance system, who can then, if desired, use the training program with a programmable electronic resistance system. The sharing of custom such configuration programs can transfer the expertise of the program author to a trainee, enabling the trainee to acquire such expertise. In some cases, a trainer can send customized training programs to a trainee in a remote location, enabling the trainer to add improved consistency to a trainee's training regimen. Further, in some implementations, historical information relating to exercises performed is persistently stored providing an objective record of how or when training was performed, allowing the trainer to better assess and tailor subsequent training.

Some systems include other features such as drive drum-unspooling detection and prevention systems. Certain embodiments can include or more height adjusting mechanisms, such as a mechanism to adjust the height of the exercise resistance flexible member.

It is to be understood that the foregoing is only a brief summary of some aspects of this specification. The present specification discloses many other novel features, problem solutions, and advantages. They will become apparent as this specification proceeds. Thus, the scope of a given claim is to be determined by the claim as issued and not by whether it addresses an issue set forth in the above Background or includes a feature set forth in this Brief Summary.

BRIEF DESCRIPTION OF THE DRAWINGS

A further understanding of the nature and advantages of the embodiments may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

Figure 1:
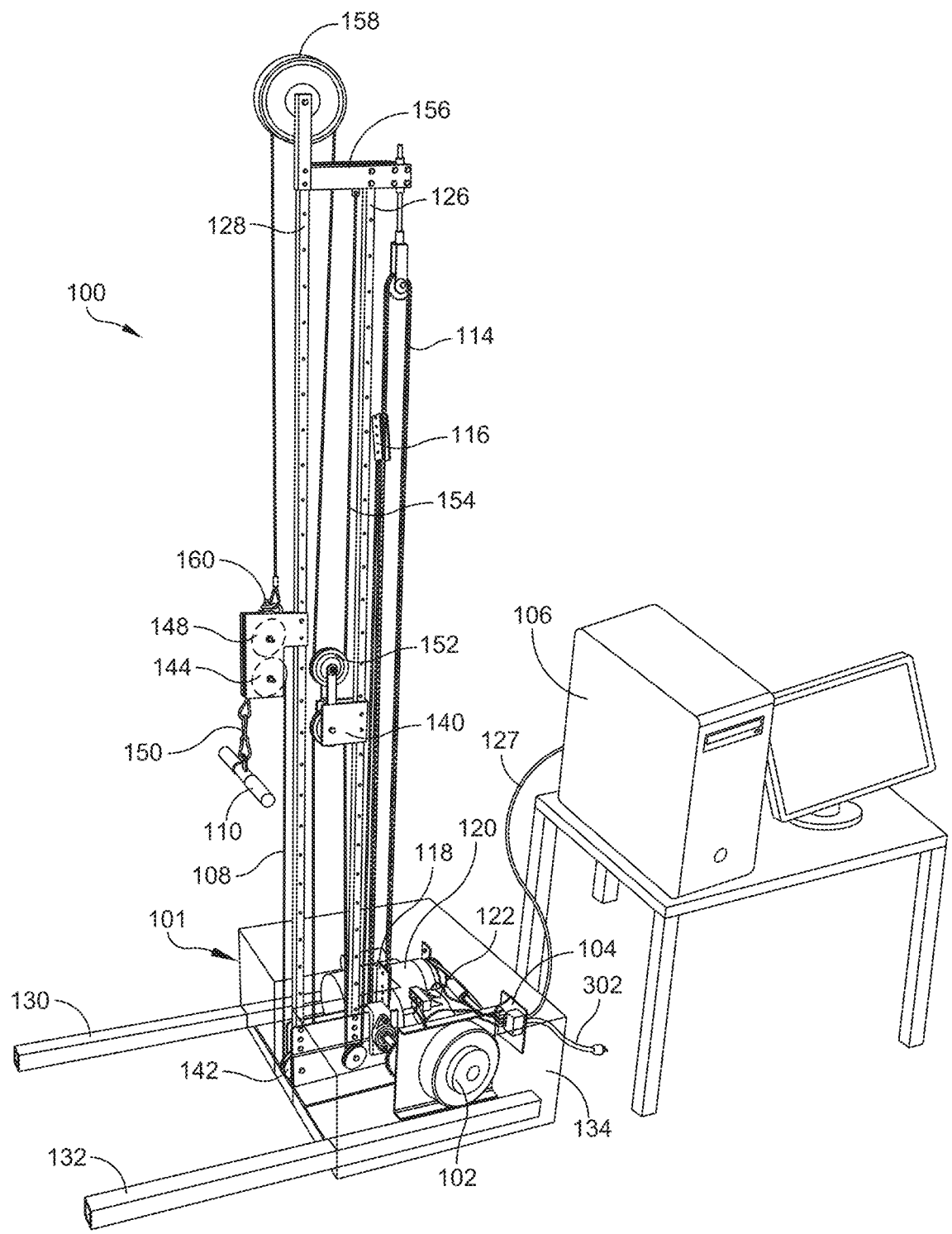
FIG. 1 is a front-side perspective view of an Resistance system including a programmable electronic resistance box.
Figure 2:
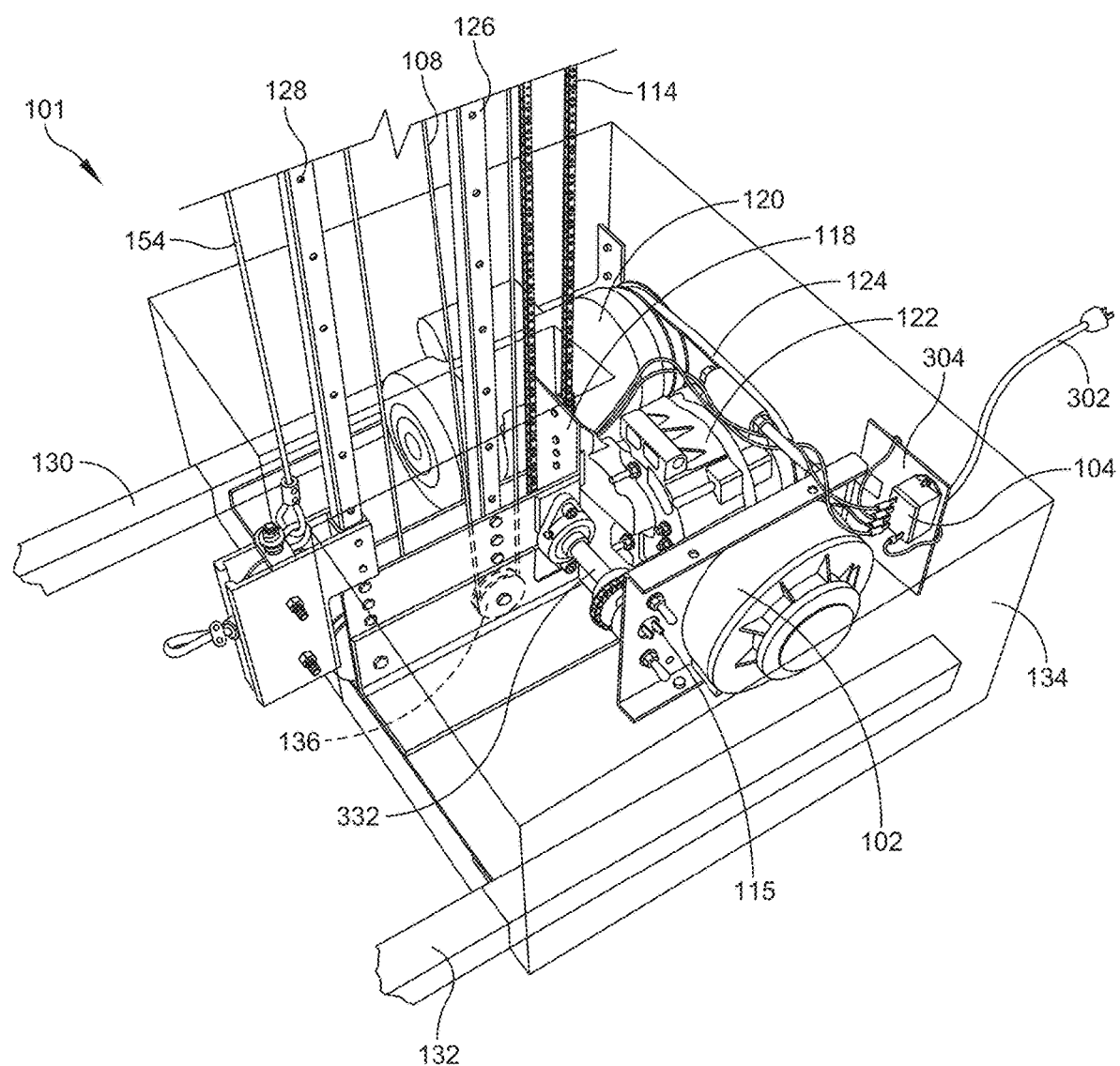
FIG. 2 is another perspective view of the Resistance system including the programmable electronic resistance box of FIG. 1.

Systems, devices, methods, and software are described for providing programmable electronic resistance for use in strength training, rehabilitation and other resistance-based training. This description provides examples, and is not intended to limit the scope, applicability or configuration of the various embodiments of programmable electronic resistance systems, devices, methods, and/or software. Rather, the ensuing description will provide those skilled in the art with an enabling description for implementing various embodiments. Various changes may be made in the function and arrangement of elements.

Thus, various embodiments may omit, substitute, or add various procedures or components as appropriate. For instance, it should be appreciated that the methods may be performed in an order different than that described, and that various steps may be added, omitted or combined. Also, aspects and elements described with respect to certain embodiments may be combined in various other embodiments. It should also be appreciated that the following systems, methods, devices, and software may individually or collectively be components of a larger system, wherein other procedures may take precedence over or otherwise modify their application.

One Embodiment of an Electric Weight System

In reference to FIGS. 1-7, an Electric Weight System 100 includes a programmable electronic resistance box 101 containing at least one motor 102 controlled by a controller 104, and a host computing device 106 (not shown), which may be external to the programmable electronic resistance box 101, in communication with the controller 104. The motor 102, which may be a DC motor, drives a cable 108 that terminates via attachment to a training interface 110, which may be an exercise bar, a rope handle, or any other type of interface that allows a user to apply a force through the cable 108 by moving the cable 108 against the motor 102. The motor 102 drives a chain 114 via one or more gears, such as spur or worm gears, for example. The chain 114 is coupled to the cable 108, allowing for the motor 102 to apply a force against movement of the cable 108 both during the out stroke and the in stroke of the cable 108. A potentiometer 115 is coupled to the output of the motor 102, such as to the shaft of the motor 102, and provides position and/or velocity information of the cable 108 to the controller 104. The chain 114 is also coupled to two stop plates 116, 118 that limit the range of motion of the cable 108 to enhance user safety, limit cable excursion, and protect the potentiometer while performing resistance training movements using the Electric Weight System 100. In some embodiments, any position sensing device can be coupled to the output of the motor 102, such as to the shaft of the motor 102, or to a shaft of the cable driving mechanism, such as a shaft of a take-up reel when no chain is implemented, or a chain drive gear shaft, etc., to provide position and/or velocity information of the cable 108 to the controller 104.

The DC motor 102 is supplied power from an AC motor 120 that drives an alternator 122 via a belt 124. The AC motor 120 and the controller 104 are powered via a power cable 302 supplying 120V AC. In some embodiments, the alternator 122 may also be directly driven by the AC motor 120, where the shafts of the two machines are coupled together (in-line). The host computing device 106 sends configuration data and commands to the controller 104 via communication cable 127. Based on the configuration data and commands, the controller 104 adjusts the amount of power output from the alternator 122, and thus the current supplied to the DC motor 102, to control the amount of resistance applied to movement of the cable 108. In yet other embodiments, the DC motor 102 may be powered via one or more amplifiers (not shown) via a 120 or 240 V AC power supply 125 (not shown), such as from a standard wall socket. The various designs and implementations of the drive circuitry and host computing device will be described in greater detail below.

The programmable electronic resistance box 101 configures and drives the alternator 122 as a constant-current (variable-voltage) power supply to drive the motor 102, which is a brushed DC motor. In turn, the motor 102 provides resistance to a user when the user pulls the cable 108 via the training interface 110. Various embodiments of the present disclosure provide an electrically programmable resistance mechanism through the use of a high torque-constant/low voltage-constant motor 102 in conjunction with an alternator 122. The alternator 122 is used to supply the required current (thus resistance) and voltage (thus cable retraction speed) to the DC motor 102. High torque (or high torque-constant) DC motors are known, and can require significant current at the upper torque operational region, often on the order of 100 Amps or more. Electronically, currents of this scale generally result in silicon destruction and/or short life spans. In an effort to reduce the current requirement to extend the life of the silicon, prior designers have tried applying gear reducers (transmissions) to high voltage-constant/low torque-constant motors. Although this can reduce the stress on the driving silicon, it also has many negative side effects—particularly an increase in the motor inertia felt by the user, and the drag (losses) of the transmission (gear box). This results in a feel to the user that does not closely simulate a traditional weight sack and does not provide a consistent resistance value through both the out-stroke and in-stroke of resistance movements. To minimize transmission losses and motor inertial loading, as well as to closely simulate a transitional weight stack or other traditional resistance training devices while providing a large resistance range, any gearing between the motor and the training interface should be as close to unity or below as possible, which results in current requirements that are (often) destructive on silicon devices.

Embodiments of the present disclosure reduce the need for silicon as the main driving systems through the use of an alternator 122. In some embodiments, the alternator 122 is configured as a current-controlled variable voltage power supply. The controller 104 senses the DC motor 102 current and compares it with the desired current that will result in the desired resistance. The alternator 122 rotor current is adjusted by the controller 104 to maintain the current through the DC motor 102. The controller 104 communicates with a host computing device 106, sense amplifier(s), error amplifier(s), and drive electronics. The alternator 122 provides a variable and/or constant high current output to the DC motor 102 via control of the current through the alternator's rotor. The alternator 122 output is converted to DC by using rectifiers. Side benefits of using an alternator 122 include, for example, complete electrical isolation so that the alternator output can be isolated from the any other electrical systems including the controller 104, AC supply voltage, etc. Furthermore, multiple safety shutdown points can be provided via the alternator 122, such as by cutting the alternator drive, cutting rotor current, and setting maximum DC motor current output to match the maximum alternator output, among other things. Also, the use of an alternator 122 reduces power electronic device sizes such as switching devices, with the ability to drive high current and low and moderate voltage, and motors (rotor control requires significantly smaller driving devices for a given output than would be realized by driving the output directly using solid state devices).

In some embodiments, the DC motor torque constant and torque range gear ratios between the DC motor 102 and a drive shaft turning chain 114 determine the minimum and maximum weight resistance. For example, a ratio between the diameter of the DC motor gear 326 and the diameter of the first and/or second drive gears 330, 352 of 1.05 provides a 127.5 lbs maximum resistance, adjustable by half pound increments, via a 100 amp DC motor 102 with a torque constant of 1.69. A gear ratio of 3.09 via the same DC motor 102 provides a 510 lbs maximum, with the resistance adjustable in increments of 2 lbs. These builds implement an 8 bit PWM driver incorporated into a 5V controller 104, thus yielding 255 different resistance settings, with a voltage per bit step of 0.02 volts. In other cases, the DC motor 102 can have a different torque constant and have different current requirements/maximum current ratings. In some cases, DC motors that can operate safely with a 1-10 amp current supply can be used with higher gear ratios to provide a similar high maximum resistance. Furthermore, DC motors with a maximum current rating anywhere between below 1 and up to 120, 140 amps can be used depending on the specific application, such as home use, physical therapy, etc. To ensure durable operation of the Electric Weight system 100 and/or the programmable electronic resistance box 101, the DC motor 102 can be driven below the maximum current specified for the motor, such as 10-20% below the maximum current.

The AC motor 120 and alternator 122 determine the maximum alternator 122 output, and the alternator 122 will determine the maximum output current to the DC motor 102. Any of these can be changed as necessary for a particular application.

The Electric Weight System 100 allows a user, such as a trainer or a person using the machine for resistance training, to program resistance applied by the motor 102 to the cable 108 via the host computing device 106 for various resistance training movements according to a fully programmable resistance profile relative to position of the cable 106 via the output of the potentiometer 115 (or any other position sensing device), time, or any combination thereof. Real-time cable position and/or optional velocity sensing information provided by the potentiometer 115 allows variations in resistance as a function of position to be programmable by the user via the host computing device 106. Resistances with respect to time are also fully programmable via the host computing device 106, allowing for stepped changes in resistance or smooth transitions from one resistance level to the next. In some cases, this may ensure that the user does not experience the "jerk" effect of a change in resistance provided by the DC motor 102.

In some embodiments, the host computing device 106 can include or be implemented using a custom console, PC program, Smart Phone, Tablet computer, etc. and a physical link (USB, RS-232), or wireless connection. The host computing device 106 can enable the user to set the desired resistance (e.g., in pounds) which in turn via the controller 104 will control the output of the alternator 122 to provide the correct current to the DC motor 102, corresponding to the resistance selected by the user.

Via the host computing device 106, the user can program a multitude of different resistance profiles, such as stepped resistance, forced negative resistance, muscle confusion resistance, elastometric resistance, and reverse elastomeric resistance profiles, as well as combinations of one or more such or other profiles. Resistances can be varied as a function of stroke, either during the stroke itself and/or at the stroke end points, for example, such that resistance can be changed up or down at either the beginning or ending stroke position. All ramp times can also be programmable, for example in 1 ms increments. A user via the host computing device 106 can also program the resistance to vary during the stroke in response to changes in the speed of the inward stroke and/or the outward stroke.

The host computing device 106 includes a full stroke indicator that is programmable to indicate, visually and/or numerically, cable position in real-time to the user. In some cases, the stroke indicator provides approximately a ¼ inch cable 108 position resolution and encompasses the full cable stroke/excursion. In some embodiments, the user can program the desired stroke length for a given resistance training movement or exercise, and the stroke indicator may be calibrated to indicate cable position relative to the desired stroke length. Stroke endpoint indication can also be signaled by sound from the controller 104 and/or host computing device 106, such as via a beep.

The potentiometer 115 (an example of a cable position sensing device) senses cable position and/or optional cable velocity and via controller 104, can signal to the controller 104 to reduce resistance when, for example, the cable velocity exceeds a retraction speed threshold, or the cable 108 goes below a set or pre-programmed stroke start or end point. The reduction in resistance can prevent user injury when, for example, the user experiences fatigue and cannot return the cable 108 to a rest position safely.

The above functionality, including the different resistance profiles and their detailed implementations, will be described in greater detail below.

In some embodiments, the cable 108 is supported via first and second support members 126, 128 that rise vertically from and normal to two parallel base rails 130, 132 supporting the motor 102 and controller 104. The motor 102 and the controller 104 are housed in a rectangular enclosure 134, which can reduce noise of the DC motor 102 experienced by the user, and can protect the drive system from abuse, damage, etc. In some embodiments, the enclosure 134 may be constructed out of a transparent material, such as Plexiglas, or an opaque plastic. In other embodiments, the enclosure 134 may be constructed out of a metal, such as aluminum, wood, composites, etc., or combinations thereof. The base rails 130, 132 extend outwardly from the enclosure 134 parallel to each other in one direction so that the cable 108 can be extended from the Electric Weight System 100 without causing any imbalance of the Electric Weight System 100. However, other support structures are contemplated herein, such as any number of support rails extending in various directions from the programmable electronic resistance box 101, made out of various materials such as metal, composites, etc. The cable 108 is routed from the chain 114 down around a first lower pulley 136 mounted to the first support member 126. The cable 108 is then routed to a mid pulley 138 that slidably engages the first vertical support member 126 via an adjustable cable height bracket 140. The cable 108 is then routed down around a second lower pulley 142 mounted to the second support member 128. The cable 108 then is routed around a first adjustable bracket pulley 144, up and around a second adjustable bracket pulley 146 (not shown), both mounted to an adjustable bracket 148, and terminates in a clasp mechanism 150 that is engagable by the training interface 110. The adjustable bracket 148 is slidably engagable on the second vertical support member 128 and can be adjusted by the user to rest at various heights along the second support member 128.

The adjustable cable height bracket 140 also mounts to a lower cable tension pulley 152 which routes a support cable 154 attached to a mid-point of a top bracket 156 that spans between the first and second support members 126, 128, adding stability and weight bearing capacity to allow a substantial range of resistance to be applied through the cable 108. The support cable 154 routes from a mid-point of the top bracket 156, around the lower cable tension pulley 152, up and around an upper cable tension pulley 158 and terminates on a support cable hold 160 mounted to the adjustable bracket 148. When the adjustable bracket 148 is adjusted vertically by a user along the second vertical support member 128, the position of cable 108 may change, i.e. relative to the potentiometer 115, thus affecting the position calibration of cable 108 with respect to the controller 104. The adjustable cable height bracket 140, the support cable 154, and associated pulleys 152, 156 allow the user to adjust the cable 108 height for different resistance training movements via the adjustable bracket 148 without having the cable 108 itself move relative to the potentiometer 115. This prevents the problems of the retracting mechanism (e.g. the chain drive in this example) having to account for the added cable length needed to position the cable in the first place, which could be up to 8 feet either up or down via adjusting the cable 108 height with the adjustable bracket 148; the potentiometer having to resolve that (wasted) cable 108 positioning (thereby reducing position resolution); and third, requiring turning on the Electric Weight System 100 to make cable 108 height adjustments. The support cable 154 allows the adjustable cable tension bracket 140 to move in an opposite direction of the adjustable bracket 148 to allow the tension in the cable 108 to remain constant. This further supports more adjustability for the user to engage in different weight training movements utilizing the Electric Weight system 100. However, the claimed subject matter is not so limited, such that any type of adjustable bracket, pulley, or cable routing system is contemplated herein.

In other embodiments, the cable 108 may consist of a Kevlar strap, a rounded strap, or possibly a cord, that can be used, for example, with a chain drive system. A Kevlar strap, for example, may be particularly suited for physical therapy applications and hence lower resistance values because of its flexibility.

Figure 3:
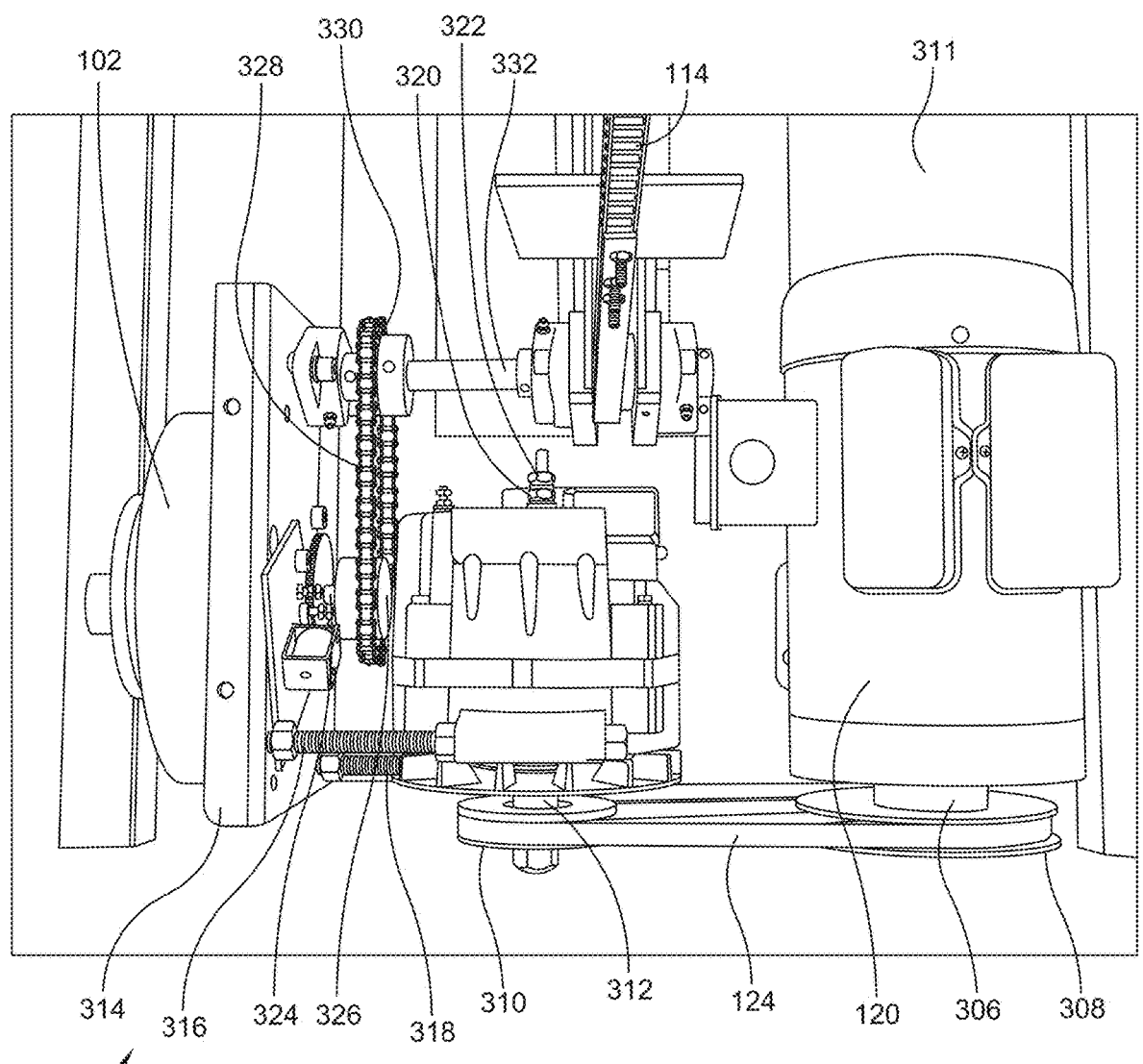
FIG. 3 is a top view of the programmable electronic resistance box of FIG. 1.
Figure 4:
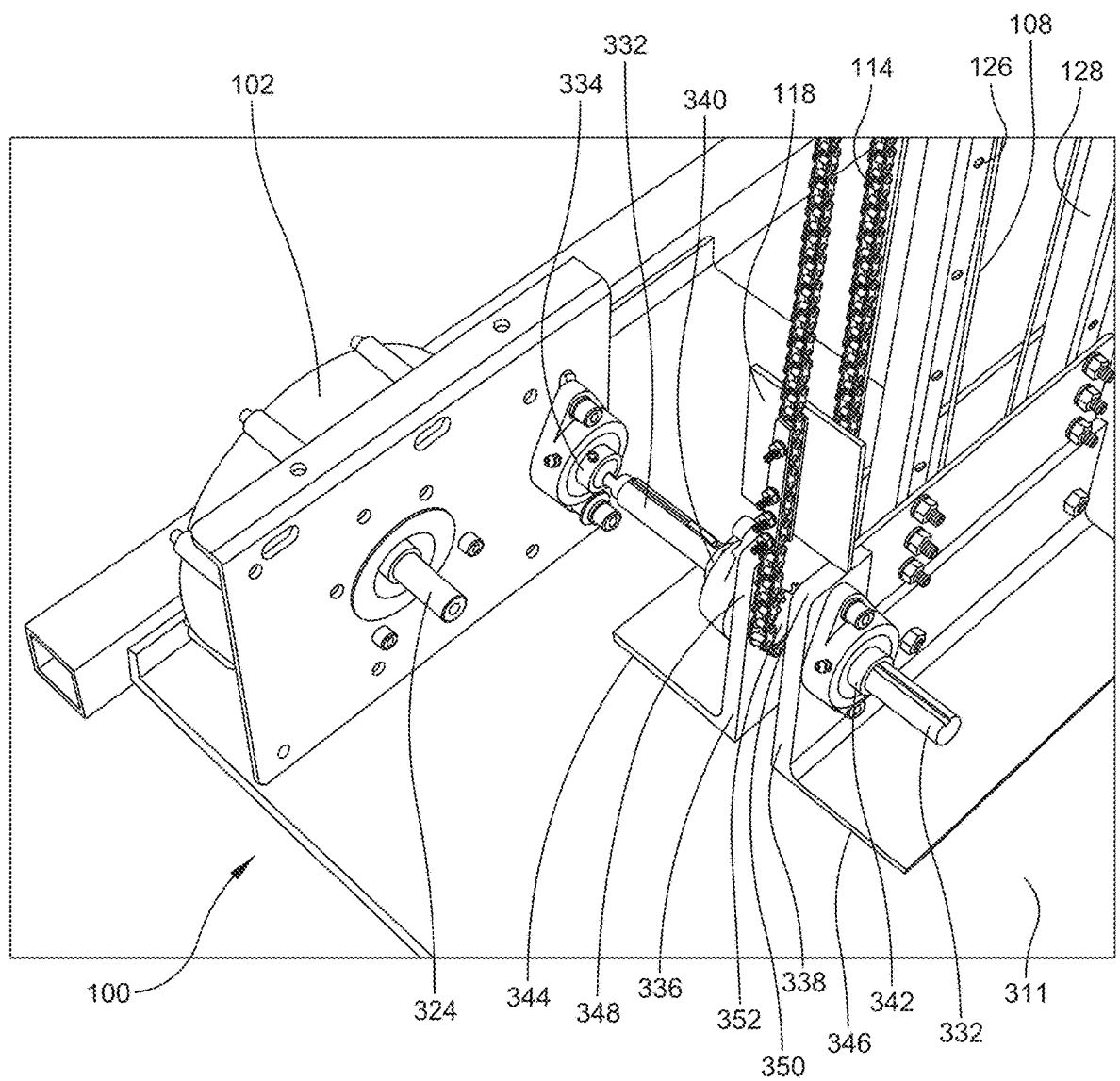
FIG. 4 is a side perspective view of a partially-assembled Resistance system including the programmable electronic resistance box of FIG. 1.

In particular reference to FIGS. 3 and 4, the programmable electronic resistance box 101 provides a user with fully programmable resistance relative to cable 108 position and/or time implemented through a cable 108, is shown. Power is supplied via a power cable 127, 302 to the AC motor 120 and controller 104 mounted on a PCB board 304, for example. In some cases, the controller 104 may further consist of a PCB board 304 including a micro-controller and/or micro-processor and support circuitry, such as one or more DACs, ADCs, a communication I/O, one or more switches, etc. In other embodiments, the PCB board 304 may include programmable logic (FPGA, CPLD, etc.), which may be programmed with a soft processor able to execute programs suitable for system (controller 104) operation, and support circuitry.

In other embodiments, the controller 104 can be implemented with one or more application-specific integrated circuits (ASICs) adapted to perform some or all of the applicable functions in hardware. Alternatively, the controller functions can be performed by one or more other processing units (or cores), on one or more integrated circuits. In other embodiments, other types of integrated circuits can be used (e.g., Structured/Platform ASICs, Field Programmable Gate Arrays (FPGAs), and other Semi-Custom ICs), which can be programmed in any manner known in the art. The functions of each unit can also be implemented, in whole or in part, with instructions embodied in a memory, formatted to be executed by one or more general or application-specific processors.

The AC motor 120 drives an AC motor shaft 306 connected to an AC motor pulley 308. The AC motor pulley 308 drives a belt 124 that in turn drives an alternator pulley 310 connected to an alternator shaft 312 of an alternator 122. To effectuate a simple belt drive arrangement, the AC motor 120 can be aligned alongside and parallel to the alternator 122, so that the AC motor pulley 308 and the alternator pulley 310 are aligned with one another facing toward an interior wall of the enclosure 134. In some embodiments, the AC motor 120 is mounted to the planar base 311 of the enclosure 134 and the alternator 122 is mounted to a support wall 314, which is generally parallel to a side mounting face of the alternator 120 transverse to the base 311, via alternator mounting bolts 316, 318.

The output of the alternator 122 via alternator terminals 320, 322 is supplied to the DC motor 102 via 2 DC motor terminals (not shown). The output of the alternator 122 is controlled by the controller 104 such that the current supplied to the DC motor 102 is proportional to the resistance specified by the user. The DC motor 102 is mounted to a side of the support wall 314 with a DC motor shaft 324 protruding through the support wall 314. The DC motor shaft 324 is coupled to a DC motor gear 326, which drives a linkage chain 328, which in turn rotates a first drive gear 330 mounted on a drive shaft 332. The drive shaft 332 rotatably penetrates a first bearing 334, mounted to the support wall 314, a second bearing 340 mounted to a first support bracket 336, and a third bearing 342 mounted to a second support bracket 338. The first and second support brackets 336, 338 form an "L" shape in cross-section, each with a base 344, 346 facing outwardly, so that a chain drive gap 347 is formed between each leg 348, 350 of the first and second support brackets 336, 338. The second bearing 340 is mounted to an external face of leg 348 of the first support bracket 336 and the third bearing 342 is mounted to an external face of leg 350 of the second support bracket 338 such that drive shaft 332 penetrates both of the first and second support brackets 336, 338 and can freely rotate via the second and third bearings 340, 342. Further, a second drive gear 352 is mounted on the drive shaft 332 between legs 348, 350 of the first and second support brackets 336, 338 within the chain drive gap 347. The second drive gear 352 drives chain 114 attached to cable 108, such that the DC motor 102 can resist and/or drive movement of the chain 114, and hence resist and/or drive movement of the cable 108. The first and second support brackets 336, 338 are mounted to the base 311 of the enclosure 134 and sandwich the first and second support members 126, 128. The first and second support brackets 336, 338 are rigidly attached to the first and second support members 126, 128, such as via 6 bolts, 3 panning vertically for each support member. In this way, support wall 314, the first and second support brackets 336, 38, the first and second support members 126, 128, drive shaft 332, and the first, second and third bearings 334, 340, 342 provide a strong support structure for the DC motor 102 to transfer an amount of force necessary for a broad range of resistance training exercises and movements through linkage chain 328 and chain 114 to cable 108 via spur gears 326, 330, and 352 (other types of gears can be used depending on the type of transmission used).

A potentiometer 115 is mounted on the support wall 314 in close proximity to the DC motor shaft 324 such that the potentiometer 115 may detect rotation of a potentiometer gear 354 coupled to the DC motor shaft. Three wires (power, ground, and wiper) connect the potentiometer 115 to the controller 104 to provide data indicative of the position of the chain 114 and hence the cable 108 and/or of the velocity of the cable 108. The controller 104 then converts this data to be used in conjunction with the host computing device 106 to allow a user to program various resistance levels relative to the position and/or velocity of the cable 108. Further functionality of potentiometer 115 and other implementations thereof will be described further in reference to FIGS. 5-7.

Sizes and shapes of components used in the various embodiments are sometimes determined by the specific sizes and shapes of the mated component or components in the system.

In the embodiments of FIGS. 1-8, the AC motor pulley 308 is ⅝ inch bore and approximately 6 inches in diameter. The diameter is a function of the maximum desired enclosure dimensions and the alternator 122 drive requirements. The alternator pulley 310 is a 3 inch OD pulley. Full load RPM of the AC motor 120 is matched with the alternator 122 RPM range. to place the alternator 122 within an acceptable power band to provide the DC motor 102 with a sufficient amount of current (in this case up to 100 amps) to provide a large range of resistance values. The AC motor 120 is rated as a single phase 120/220 VAC 1.5 HP, continuous duty machine, such as MTR-1P5-1AB18 made by Automation Direct (One HP is 550 ft-lbs/sec (746 Watts), thus the 1.5 HP is 825 ft-lbs/sec (1118.6 Watts)). Alternate embodiments may use a ¾ or 1 HP motor, or any other AC motor 120 that can spin fast enough to drive the alternator to provide enough current to the DC motor 102 to provide the requisite level of resistance to the user.

The alternator 122 is a high current small footprint device, such as ALT-0070P made by UNI-POINT having a minimum current output of 100 amps. In some embodiments, the high current is provided by Delta—as opposed to Wye—winding configuration. The DC motor 102 is a 10 HP brushed device, such as PMG 132, manufactured by Perm Motor GMBH. This motor weighs approximately 25 lbs. and provides a modest footprint. However, other components may be used depending on the gear drive system implemented between the DC motor 102 and the cable 108 drive system, and depending on the maximum resistance desired.

In the embodiment shown, the programmable electronic resistance box 101 is 11.75 inches in height, 16 inches in length, and 17 inches in width and weighs approximately 105 lbs. The weight of the programmable electronic resistance box 101 includes the DC motor 102 at approximately 25 lbs, the AC motor 120 at 45 lbs. (for a 1.5 HP device), the alternator 122 at approximately 10 lbs, the enclosure 134 at about 15-20 lbs, the pulleys at approximately 4 lbs, and the gears at approximately 2-4 lbs. Furthermore, the base rails 130, 132 are approximately 21 inches in length and run parallel to one another and also parallel to the width of the programmable electronic resistance box 101.

In one embodiment, the DC motor shaft 324 is ¾ inch in diameter to match up with the DC motor gear 326, which is also ¾ inch in diameter. Chain 114 and linkage chain 328 may both have a tensile strength of 3,125 lbs. and a working load of 810 lbs (#40), and are light as compared to many alternative chains. In an alternate embodiment, chain (#35) is used for both chain 114 and linkage chain 328, having a load of 480 lbs. In yet another embodiment, chain (#50), with a tensile strength of 4,880 lbs. and 1,430 lbs. working load is used. In other embodiments, the tensile strength of chain 114 and linkage chain 328 may be different to accommodate different implementations.

The programmable electronic resistance box 101 and hence the Electric Weight System 100 can be configured to implement various weight ranges corresponding to resistance applied through the cable 108 according to various resistance/weight increments by which the weight/resistance can be adjusted. For example, for physical therapy, it may be beneficial to implement approximately a 0.25 lbs step, allowing for a range of 0.25 lbs to approximately 63.75 lbs, or possibly for a 0.33 lbs step, allowing for a range of 0.33 lbs to approximately 85.0 lbs, the difference in implementation being, for example, the size/number of teeth of the DC motor gear 326, the first drive gear 330, and/or the second drive gear 352 (all of these builds can be accomplished with the same DC motor 102 and controller 104). In some embodiments, it can be useful to implement other weight step and range values, for example for a standard production unit and/or for retrofitting an existing weight machine, such as a 0.5 lbs step allowing for a range of 0.5 lbs to 127.5 lbs, or a 1.0 lbs step, allowing for a range of 1.0 lbs to 255 lbs. It may further be possible to increase the maximum weight to 375 lbs, for instance, by using only standard off-the-shelf components. In other builds, it may be possible to obtain a maximum weight of 510 lbs with a 2 lbs step, or even a 680 lbs maximum, with a 2.67 lbs step. All of the above builds can be implemented using the same electronics, i.e., DC motor 102, alternator 122, AC motor 120, controller 104, drive circuitry, etc., by modifying the gear ratio between the DC motor gear 326 and the first and/or second drive gears 330, 352 (or the take-up real gear 912/take-up reel 908 diameter in the take-up reel embodiment). In some cases, a changeable gearing system may be implemented to further increase the range of resistance values possible while maintaining a smaller step value. Thus, the programmable electronic resistance box 101, utilized in either the Electric Weight System 100 or a retrofit system, can be modified to suit a huge range of resistance training needs and/or programs.

The above is only meant as an example, whereas the claimed subject matter is not intended to be limited by the properties/sizes of the individual components.

Figure 5:
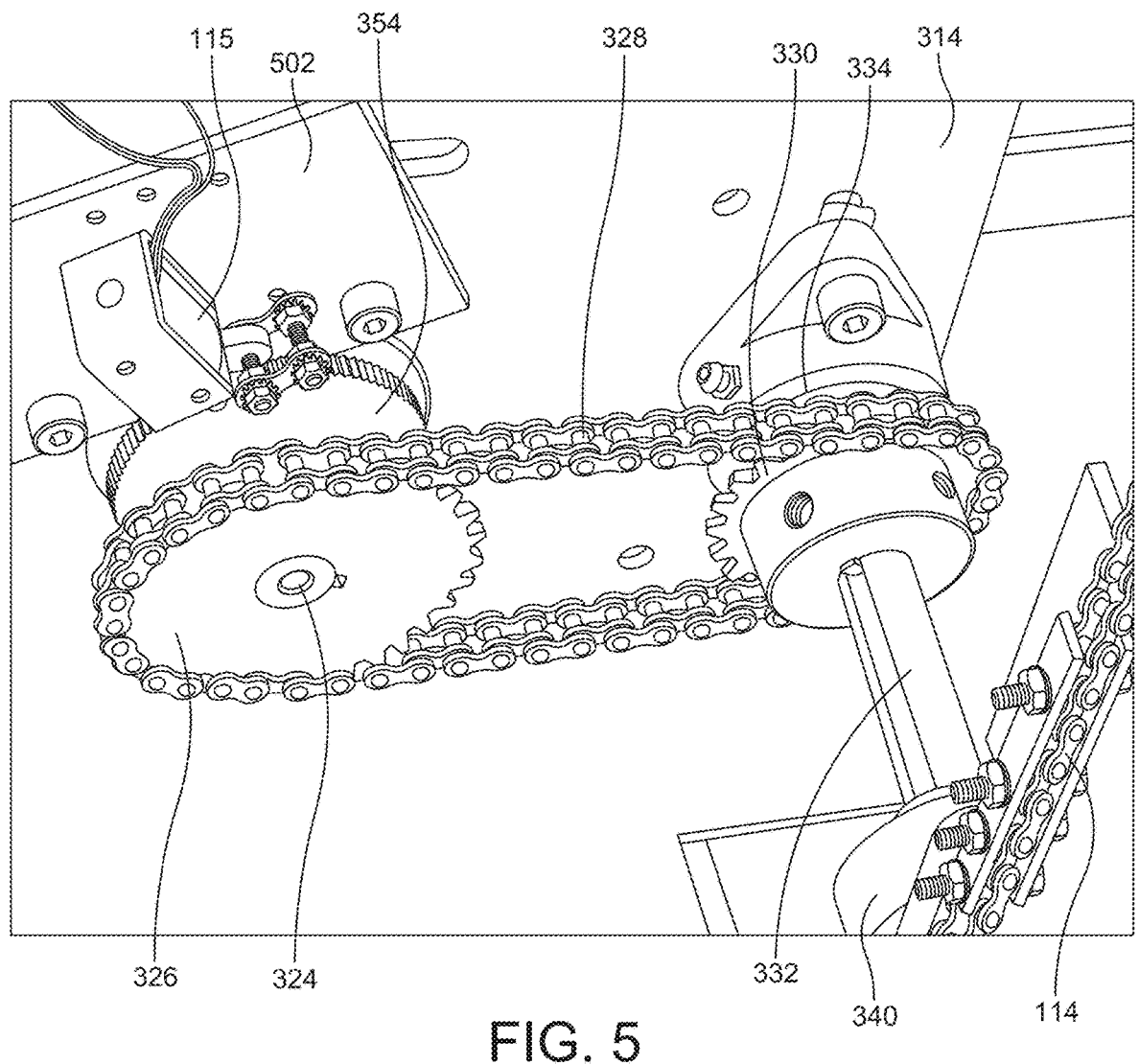
FIG. 5 is a side perspective view of a drive assembly including a potentiometer of the Resistance system of FIG. 1.
Figure 6:
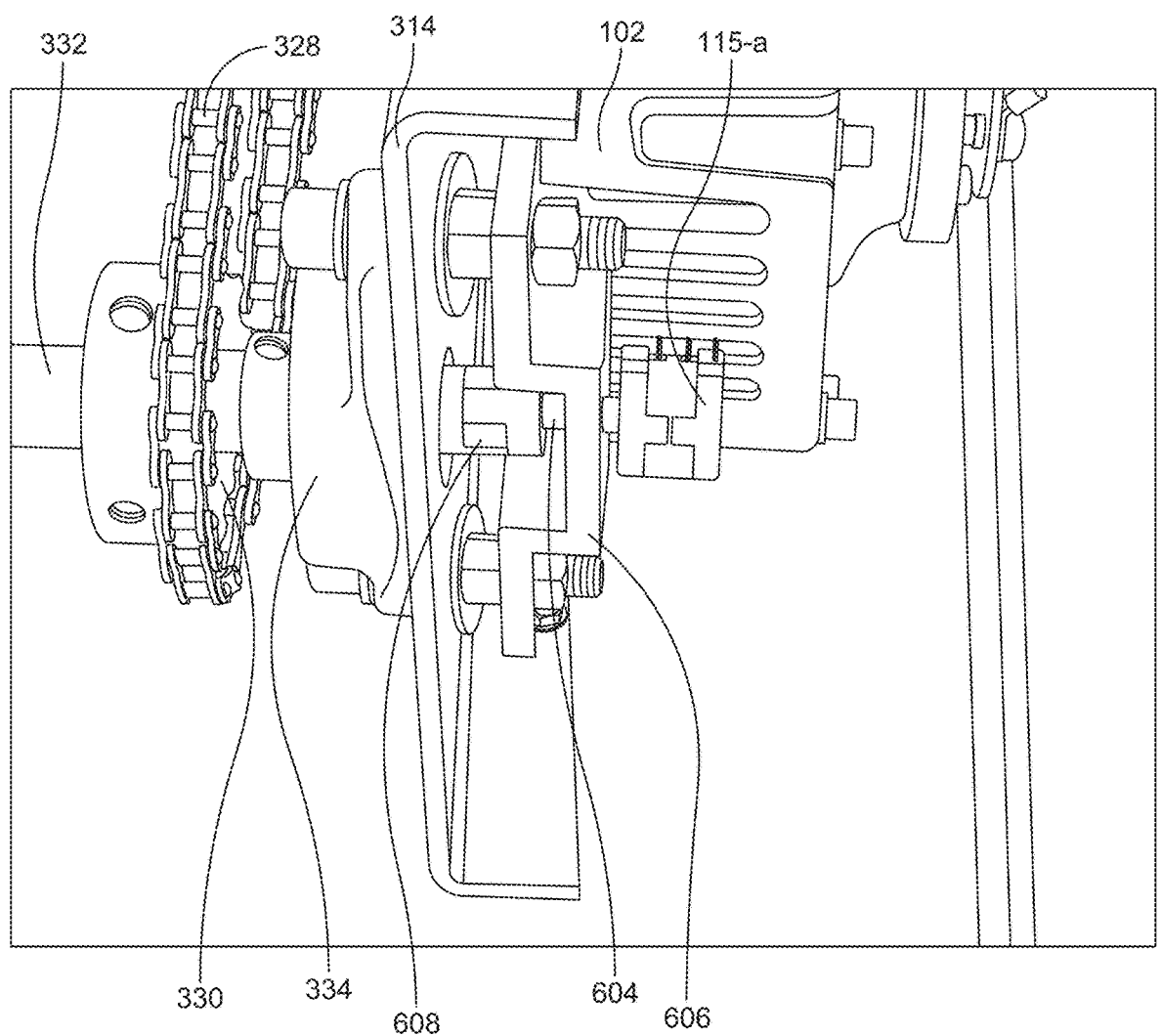
FIG. 6 is a perspective view of an alternative embodiment of the potentiometer of the Resistance system of FIG. 5.
Figure 7:
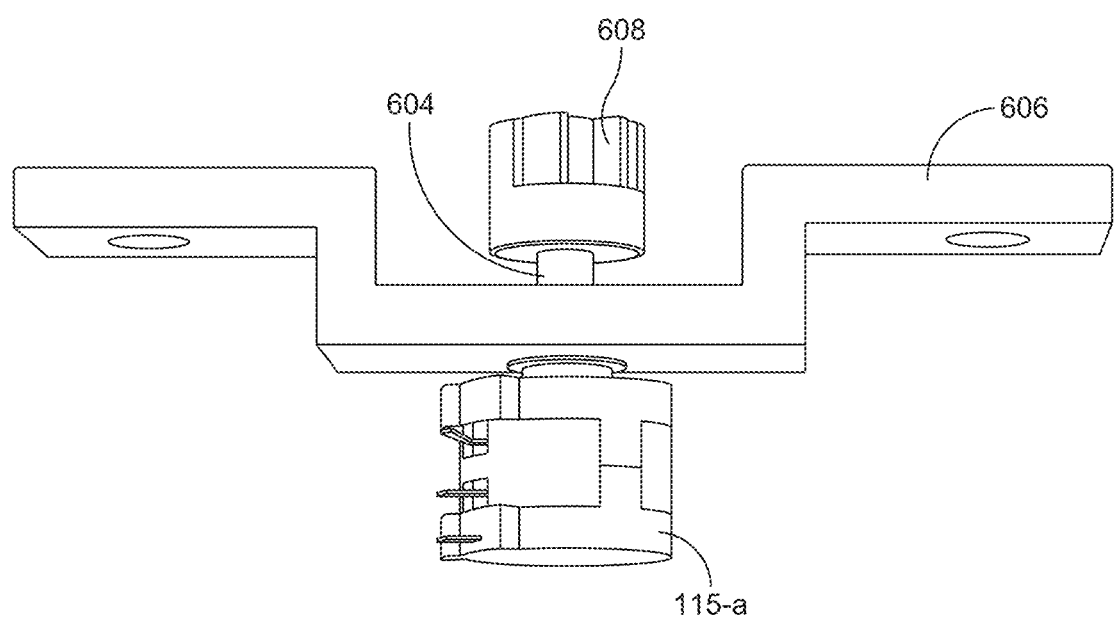
FIG. 7 is a side view of the potentiometer of the Resistance system of FIG. 6.

In particular reference to FIGS. 5-7, two embodiments of the potentiometer 115, 115-a (which may also be referred to herein as a position pot) and its implementation in the programmable electronic resistance box 101 are shown. With reference to FIG. 5, the potentiometer 115 is mounted to the support wall 314 slightly above the DC motor shaft 324 via a mounting plate 502. The potentiometer 115 contacts a potentiometer gear 354 coupled to the DC motor shaft 324 via potentiometer linkage 504, and is electrically connected via three wires (power, ground, and wiper) to the controller 104. In this way, the potentiometer 115 can sense when and how much the potentiometer gear 354 and hence the DC motor shaft 324 moves. The output signal of the potentiometer 115 can then be calibrated by the controller 104 based on the size/number of teeth of the potentiometer gear 354, the DC motor gear 326, and the first and second drive gears 330, 352 to determine a movement position and/or a velocity of the cable 108. This information can then be utilized by the controller 104 in combination with input from the host computing device 106 to program varied resistances relative to cable 108 position and/or velocity.

The size of the potentiometer gear 354 to the DC motor gear 326, and the first and second drive gears 330, 352, and hence the ratio between the potentiometer gear 354 and turns of the drive shaft 332, determines the number of drive shaft revolutions per potentiometer gear 354 revolutions as well as the effective bit-per-step value. In some embodiments, the potentiometer 115 is a 10-turn device. A 1:1 gear ratio would yield a maximum of 10 turns for the shaft. An 8-bit conversion would then yield (360 degrees)*10/255 or 14 degrees/bit. In one embodiment, the DC motor gear 326 is a 20 Deg Pressure Angle Spur Gear 32 Pitch, 72 Teeth, 2.25" Pitch Dia, ¼" Bore, while the potentiometer gear 354 is a 20 Deg Pressure Angle Spur Gear 32 Pitch, 24 Teeth, 0.75" Pitch Dia, ¼" Bore. This yields a 3:1 ratio (3 potentiometer turns/shaft turn) or 4.706 degrees/bit resolution.

Referring now to FIGS. 6 and 7, a second embodiment of a potentiometer 115-a and its implementation in the programmable electronic resistance box 101 is shown. In this embodiment, the potentiometer 115-a is coupled to a potentiometer shaft 604 rotatably mounted to a potentiometer bracket 606 via a hole in the center of the potentiometer bracket 606. A drive shaft coupler end 608 of the potentiometer shaft 604 opposite the potentiometer 115-a couples to the drive shaft 332 on a side of the support wall opposite the first bearing 334. The potentiometer bracket 606, via 2 bolts, attaches to the support wall 314 adjacent to the DC motor 102 and aligns the drive shaft coupler end 608 of the potentiometer shaft 604 so that it rotatably engages the drive shaft 332. The potentiometer bracket 606 in cross section forms a square "C" shape with 2 tabs extending outwards and having fastener passages for attachment to the support wall 314. The potentiometer 115-a has three pins, which via wires connects to the controller 104, enabling the potentiometer 115-a to communicate data indicative of cable 108 position and/or velocity to the controller 104, in a fashion similar to that described above in reference to FIG. 5.

In some embodiments, either the configuration of potentiometer 115 or potentiometer 115-a can be used based on space/size constraints of the enclosure 134, mounting requirements, size of the DC motor 102, etc. In other embodiments, both potentiometers 115 and 115-a may be used to increase accuracy of cable 108 position and or velocity sensing, or any other such purpose. The above description is only an example, and is not limiting of the scope of the claimed subject matter. Various other designs and implementations of a potentiometer for cable 108 position and/or velocity sensing, such as various placements and/or attachments are contemplated herein.

Figure 8:
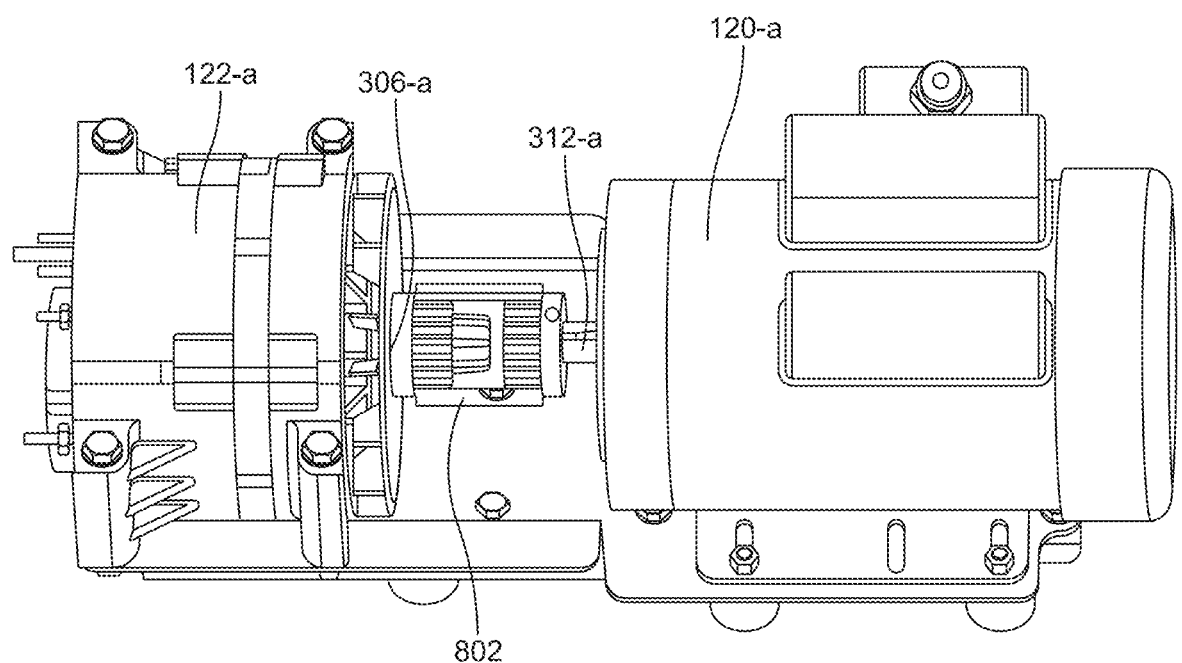
FIG. 8 is a perspective view of the programmable electronic resistance box of FIG. 1.

Referring now to FIG. 8, an alternative embodiment of the programmable electronic resistance box 101-*a* is coupled to controller 104-*a* and host computing device 106-*a* (not shown) and can provide programmable resistance functionality for various resistance training movements, exercises, etc. For continuity, the same reference numbers will be used to describe the various components of the programmable electronic resistance box 101-*a* that are used to describe the same or very similar components in reference to the programmable electronic resistance box 101 above, and differences will be described. However, this convention is not intended to limit the components of the programmable electronic resistance box 101-*a* to those described previously.

In this FIG. 8 embodiment, the alternator 122-*a* and the AC motor 120-*a* are aligned such that the alternator shaft 312-*a* is coaxial with the AC motor shaft 306-*a*. In this way, the AC motor pulley 308, the alternator pulley 310, and the belt 124 may be eliminated (not shown). The alternator shaft 312-*a* is coupled to the AC motor shaft 306-*a* via a shaft coupler 802 so that the AC motor 120-*a* directly drives, i.e., turns, the alternator shaft 312-*a*. This configuration can increase longevity of the programmable electronic resistance box 101-*a* by reducing the amount of moving parts for example. This configuration can also allow for enclosure 134-*a* to be smaller by eliminating the need for space around the moving belt 124.

In some embodiments, the alternator 122-*a* and AC motor 120-*a* can be located directly behind the first and second support members 126, 128 so that the DC motor 102-*a* (not shown) can line up directly with the drive shaft 332. This can allow for the DC motor shaft 324 to couple directly with the drive shaft 332 so that the DC motor 102 can directly drive the second drive gear 352, eliminating the need for the DC motor gear 326 and the first drive gear 330. This configuration can also reduce the size of the support wall 314. In some cases, the potentiometer 115-*a*, can be mounted to the drive shaft 332 adjacent the third bearing 342, with a potentiometer bracket, such as potentiometer bracket 606, mounting to an external face of the leg 350 of the second support bracket 338.

In some embodiments, unless otherwise noted, the description of the programmable electronic resistance 101 may apply to the programmable electronic resistance box 101-*a*.

Another Embodiment of an Electric Weight System

Figure 9:
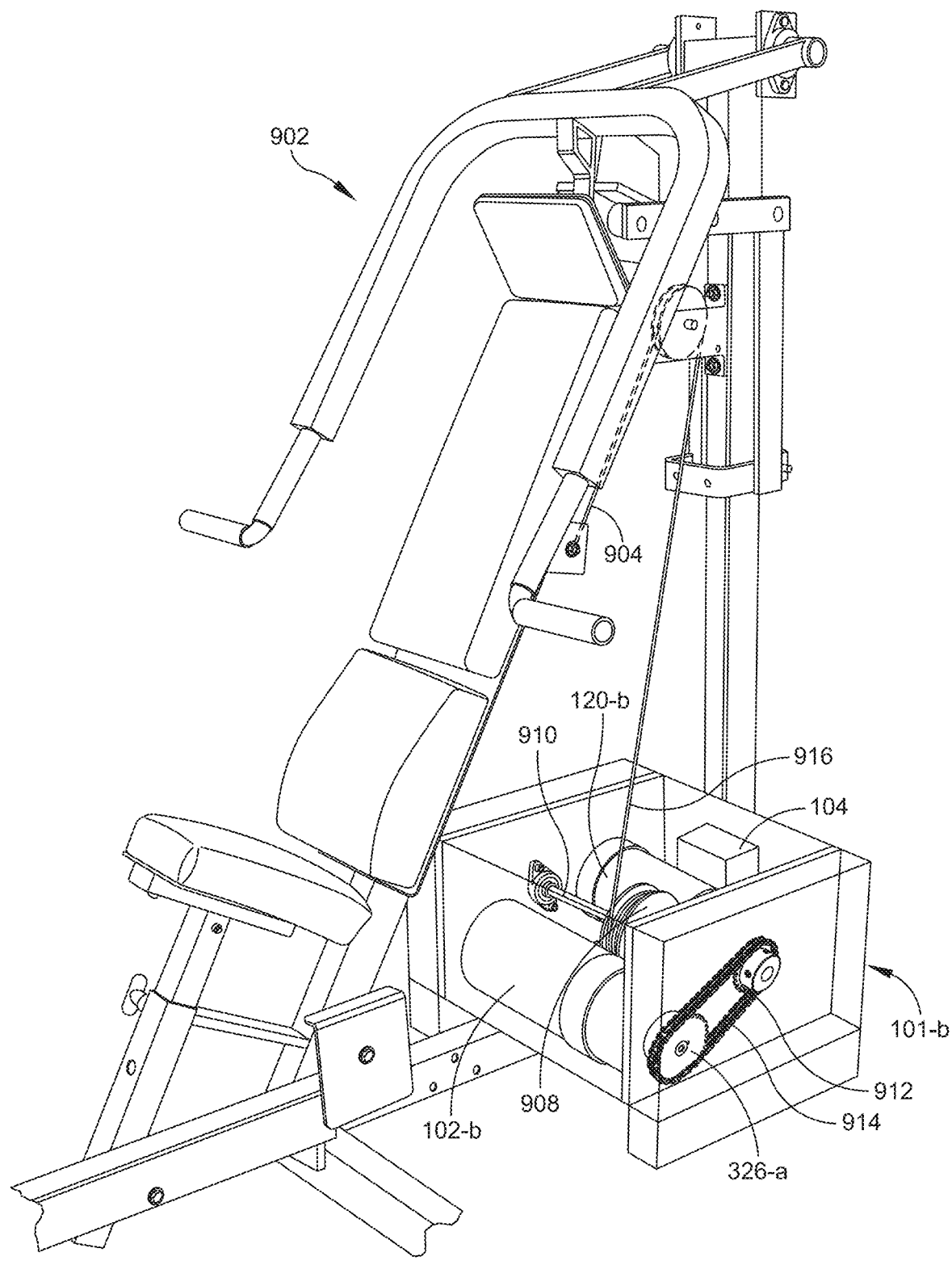
FIG. 9 is a front-side view of a retrofit Resistance system.
Figure 10:
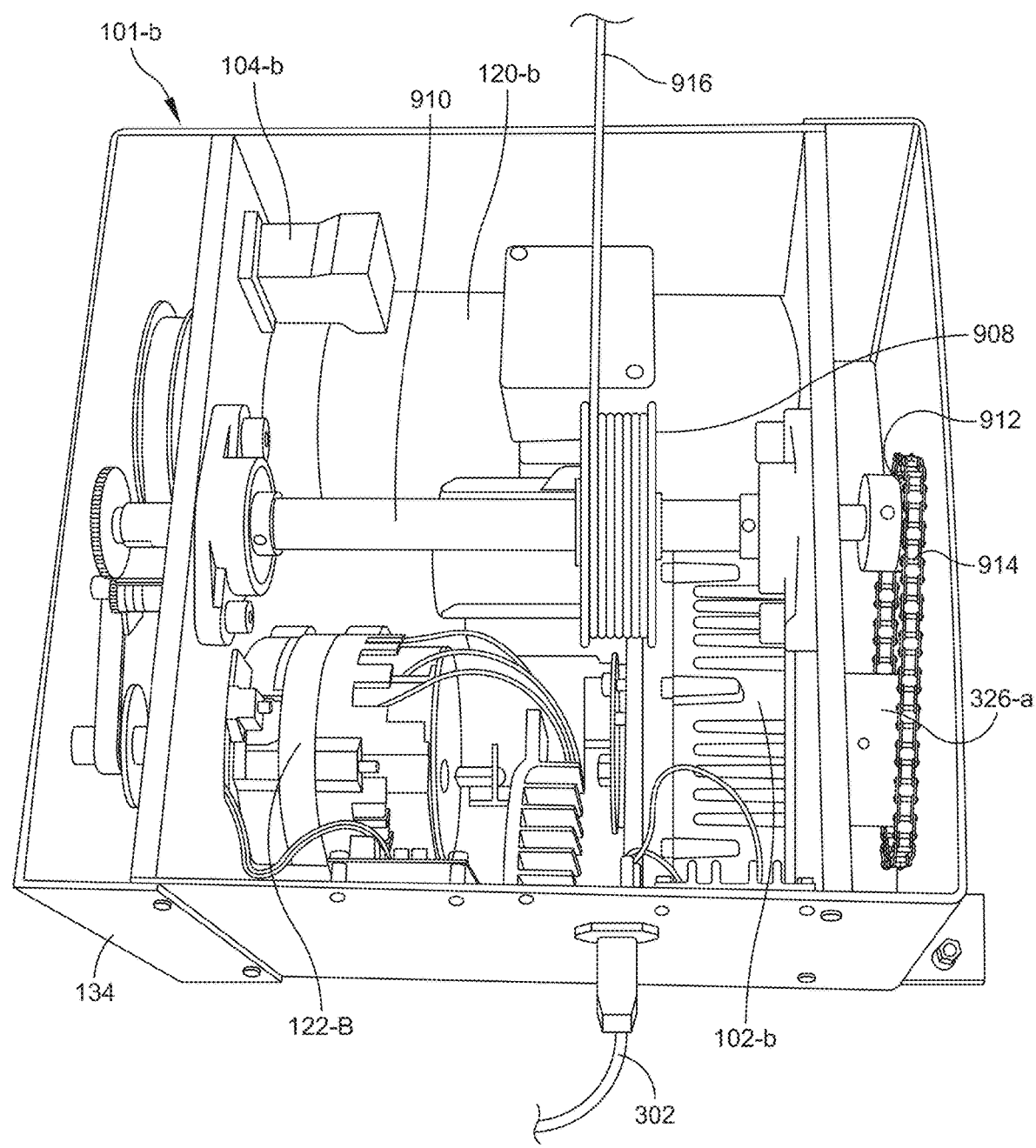
FIG. 10 is a side perspective view of the retrofit Resistance system of FIG. 9.

With reference now to FIGS. 9-10, an existing weight system 902 can be retrofitted with a programmable electronic resistance box 101-*b*, providing fully programmable resistance to a user via a host computing device 106. The programmable electronic resistance box 101-*b* and the host computing device 106, unless otherwise noted, can be similar to or the same as the programmable electronic resistance box 101 and the host computing device 106 as described above in reference to FIGS. 1-8. As described below, some components and functionality of the programmable electronic resistance box 101-*b* can differ from the programmable electronic resistance box 101 previously described.

The programmable electronic resistance box 101-*b* includes a DC motor 102-*b* with current supplied to the DC motor 102-*b* via an alternator 122-*b* driven by an AC motor 120-*b*, with the output of the DC motor 102-*b* controlled by the controller 104-*b*.

In some embodiments, the programmable electronic resistance box 101-*b* can interface with an existing cable 904 of the existing weight system 902 via a chain drive as described above in reference to FIGS. 1-8, with an existing cable 904 of the existing weight system 902 attaching to a chain, such as a chain 114-*b*, driven by the DC motor 102-*b* in the programmable electronic resistance box 101-*b*. In this way, the programmable electronic resistance box 101-*b* provides resistance through the existing weight system 902 in a similar manner as described above in reference to FIGS. 1-8, with the current driving the motor 102-*b* controlled by the controller 104-*b* via the host computing device 106 allowing for full programmability of the resistance profile experienced by the user through the existing cable 904. This may very accurately simulate the conventional feel provided by the un-retrofitted existing weight system 902.

In the embodiment shown, a take-up real 908 (also referred to as a cable drum) connects to the existing cable 904 so that, when the DC motor 102-*b* spins in one direction, the existing cable 904 is spooled around the take-up reel 908, and when the user applies a force to overcome the force of the DC motor 102-*b*, the cable is unspooled from the take-up reel 908. The take-up reel 908 includes peripheral cable guide grooves to coordinate the spooling and unspooling of the existing cable 904. The take-up reel spins 908 on a take-up reel support shaft 910 with a take-up reel gear 912. The take-up reel gear 912 is driven by a take-up reel chain 914 rotating about a DC motor gear 326-*a* coupled to the DC motor shaft 324-*b* of the DC motor 102-*b*. In this way, the programmable electronic resistance box 101-*b* can adapt to retrofit a multitude of existing systems, as less space and moving parts external to the programmable electronic resistance box 101-*b* are needed to drive an existing cable 904 of various existing weight systems, such as existing weight system 902.

In some embodiments, a take-up reel cable 916 is attached to and spools around the take-up reel 908. This can allow easier retrofitting of existing devices by only requiring that the take-up reel cable 916 be attached to an existing cable 904 of an existing weight system 902, such as by a removable clip 918, and not requiring any re-spooling of the take-reel 908.

The controller 104-*b* monitors the current supplied to the DC motor 102-*b*, making adjustments as necessary to maintain the desired resistance. The controller 104-*b* in various embodiments is capable of maintaining the required current (resistance) as well as adjusting the take-up speed (voltage) of the take up reel 908 so that the existing cable 904 does not become slack. In some embodiments, the AC motor 122-*b* drives a delta (as opposed to wye)-configured alternator 122-*b*, the output of which drives a DC motor 102-*b* having a generally higher high torque-constant. In other embodiments, the DC motor 102-*b* has a high speed constant and generally lower torque-constant with a Wye-configured alternator 122-*b*.

In some embodiments, the DC motor torque constant, the current supplied to the DC motor 102, and the turn ratio between the DC motor 102-*b* and take-up reel support shaft 910 and the take-up reel 908 diameter determines the minimum and maximum weight/resistance. The AC motor 120-*b* and alternator 122-*b* determine the maximum alternator 122-*b* output, and the alternator 122-*b* will determine the maximum output current to the DC motor 102-*b*. Any of these can be changed as necessary for a particular application.

For example, in some embodiments, the take-up reel support shaft 910 is 1.00 inch in diameter because the take-up reel 908 (i.e., cable drum) has a standard shaft diameter size of 1.00 inch. The take-up reel gear 912 in this example is 1 inch bore and disk shaped having a circular outer periphery, and the selection of suitable off-the-shelf pitches is dictated by that bore diameter. For example, a ratio between the DC motor gear 326-*a* and the take-up reel 908 diameter, along with the current rating of the DC motor 102, determines the maximum resistance possible. For example, using a take-up reel and DC motor gear 326 with a turn ratio of 1.55 provides 127.5 lbs maximum resistance, adjustable by half pound increments, with a 100 Amp DC motor 102 with a torque constant of 1.69. Various other gear to take-up reel diameter ratios can be used with different dc motors to provide different ranges and adjustments of resistance. This and other similar builds implement an 8 bit 5V controller, thus yielding 255 different resistance settings, with a voltage per bit step of 0.02 volts.

The cable drum 908 can be implemented in the programmable electronic resistance box 101-*b* in various sizes, such as with diameters of 8, 4, and 3 inches, and in various shapes, such as disk shaped having a circular outer periphery, or having other outer periphery shapes. These diameters work in conjunction with the chain/gear ratios to determine the resistance spread, and thus the maximum/minimum resistances. The larger diameter reduces the effective resistance for a given gear ratio while the smaller diameter increases said resistance. The larger diameter drum also yields a greater cable feed length per revolution than the smaller drum.

The selection of a take-up reel cable 916 or the selection to attach and spool an existing cable 904 directly to and around the take-up reel 908 can be determined by the following factors: 1) the size of the cable drum 908, meaning the cable 904, 916 is selected to ensure it fits within the cable drum grooves); 2) the maximum resistance to be applied through the cable 108; and 3) cable softness (flexibility). In some embodiments where low resistance products are desired, softer cables are used since the cable's propensity to straighten will tend to un-spool the un-tensioned cable 904, 916 off of the drum. Softer cables may also have a lower working load. In other embodiments where high resistance products are desired, stiffer cables can be used where DC motor 102-*b* inertia assists in keeping the cable 904, 916 from un-spooling.

In other embodiments, the programmable electronic resistance box 101 can interface with various other existing weight or resistance training systems in various other ways. For example, the programmable electronic resistance box 101 can interface with one or more cables coupled to a weight lifting bar, with a cable attached to a training arm having handles, etc., with each system interfacing with the programmable electronic resistance box 101 via a chain drive or a take-up reel system as described above interference to FIGS. 1-10.

It should be appreciated also that various other apparatus and systems for coupling the drive of motor 102 to the training interface 108 can be utilized. For example, the cable 108 cam be coupled to a weight lifting bar, such as a bench press bar, and may be oriented in such a way as to allow other resistance training movements not supported by the above-described tower support structures. These other implementations can also include coupling the cable or other means connected to motor 102 to a fixed handle arm to be used with a work-out bench, to be used for bench pressing and other related resistance training movements, etc. In some embodiments, the programmable electronic resistance box 101 may have different footprints and sizes to accommodate the variations in existing exercise equipment. These variations can include, but are not limited to, dimensions that approximate a weight stack, dimensions that approximate a cube, for example to fit under a seat of existing exercise equipment, or any other dimensions that may enable the programmable electronic resistance box 101 to engage and interface with other existing exercise/resistance training equipment, such as existing weight system 902. The programmable electronic resistance box 101 can be designed to replace current weight stacks, hydraulic or pneumatic, bow, spring, or rubber band systems, by taking the place of the existing resistance component and simply connecting a cable 108, 916 of the programmable electronic resistance box 101 to the existing cable 904 of the existing weight system 902, for example.

In yet other embodiments, the programmable electronic resistance box 101-*b*, including the take-up reel drive mechanism can be implemented in a new (not retrofit) system, such as the Electric Weight System 100 and/or the programmable electronic resistance box 101, 101-*a* described in reference to FIGS. 1-8. In some cases, this can decrease the overall size of an Electric Weight System, such as System 100, by requiring less moving parts external to the programmable electronic resistance box 101 and can eliminate the need for space for a chain drive, etc.

In reference to FIGS. 11A-11C, 2 different embodiments of a cable pinching or anti-unspooling system 1100, 1100-*a* are shown. The cable anti-unspooling systems 1100, 1100-*a* can be implemented in any Electric Weight System 100/ programmable electronic resistance box 101, utilizing a take-up reel drive, as described above in reference to FIGS. 9-10. A unique problem with the take-up reel drive of the programmable electronic resistance box 101 can be solved by the use of one or more cable anti-unspooling systems 1100, 1100-*a*, as described below.

The Electric Weight System, such as Electric Weight System 100, can provide a constant force (i.e., resistance) independent of gravitation pull unlike standard weight/ resistance systems. This can be beneficial, by providing a constant motor inertia independent of the amount of resistance applied, particularly at heavy resistances. However, in some cases this can also be problematic, particularly for light/lighter resistances. In this particular embodiment, gravity does not present any substantial resistance to pulling of the cable 108, contrary to traditional weight systems in which the weight resists pulling of the cable; rather, in this embodiment the resistance is provided solely the constant force torque of the motor 102 pulling on the cable 108. During cable 108 retraction (in-stroke), if a user releases the cable 108 to allow quick retraction of the cable 108, the cable 108 can become slack during the retraction period. This may be particularly noticeable at low resistance levels during which the constant resistance setting may be insufficient to act as a gravitational pull. A low resistance setting will only retract the cable 108 at a rate necessary to maintain that resistance and no more. If the user moves the cable 108 inward faster than the set resistance will allow retraction, the cable 108 can become slackened. This may take place when the cable 108 is moved inwardly and outwardly using a take-up reel 908, but may not arise in the linear/chain drive cable retraction mechanism described above in reference to FIGS. 1-8. If the cable 108 goes slack, it might jump the cable guides causing cross-over cable winding, leading to noise and/or cable damage, and in extreme conditions, completely un-spool off the take-up reel 908. This condition might also take place when power to the DC motor 102 or alternator 122 is interrupted after the user has extended the cable 108. If the user releases the cable 108, the cable 108 might unspool off of the take-up reel 908. If the user tries to push the cable 108 into the programmable electronic resistance box 101, it may un-spool from the take-up reel 908.

In some embodiments, cable slacking can be detected and a retracting force can be added to maintain or remove the slack. Since cable 108 by its nature will droop (horizontally due to the gravitational force on the cable 108) or separate from its pulley guides, such as in pulleys 136, 138 (vertically due to the gravitational force on the cable 108), sensing one or both of these conditions can allow for controller correction to reduce or eliminate the condition.

One system for reducing or eliminating cable slackening provides a circuit consisting of a cable guide resting on or connected to a plunger that measures the amount of droop (such as a position indicator). The sensing element can consist of a variable resistor, variable capacitor, variable inductor, Hall Effect device, etc., with the variable output being converted into a signal suitable to help control the retracting force via the controller 104. The more the cable 108 droops, the more the sensing device output varies, and the more retracting force is applied to the DC motor 102 by the controller 104.

Another sensing system provides an optical sensor to "detect" the cable 108 droop or the amount of cable separation in a pulley (sheave) or cable guide. As stated above, the optical sensing output is converted into a signal suitable to help control the retracting force communicated to the controller 104.

The slack detector system can also be combined with a cable anti-unspooling system 1100, 1100-*a*, to prevent cable unspooling in a cable drum system, where inward cable motion is prevented. This is controlled, for example, by an electro-mechanical solenoid 1102 or other mechanical device that prevents cable slack from affecting the take-up reel 908. This can be useful for interrupted power conditions as well where, for an extended cable 108, the cable slack correction system 1100, 1100-*a* "pinches" the cable 108 to prevent it from un-spooling off of the take-up reel 908.

Figure 11A:
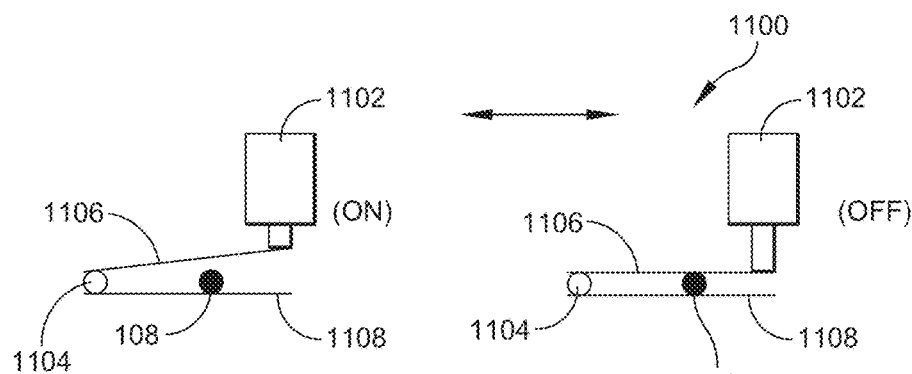
FIG. 11A is a schematic diagram of an embodiment of a cable slack correction system of an Resistance system.

Referring now to FIG. 11A, a cable anti-unspooling system 1100 can include a spring-loaded hinge 1104 with a first arm 1106 and a second arm 1108 forming, for example, a V or U shape. A lever arm 1110 of a solenoid 1102 rests on the first arm 1106 of the hinge 1104. In some embodiments, the solenoid 1104 is activated (i.e., with the lever arm 1110 of the solenoid 1101 in the retracted position) during good power conditions and normal exercise allowing the hinge 1104 to open, and deactivated (i.e., with the lever arm 1110 of the solenoid 1101 in the extended position) during un-powered conditions or when for whatever reason slack detection occurs, forcing the hinge 1104 to close and urge the cable 108 to remain in position on the take-up reel 908-*a*.

Figure 11B:
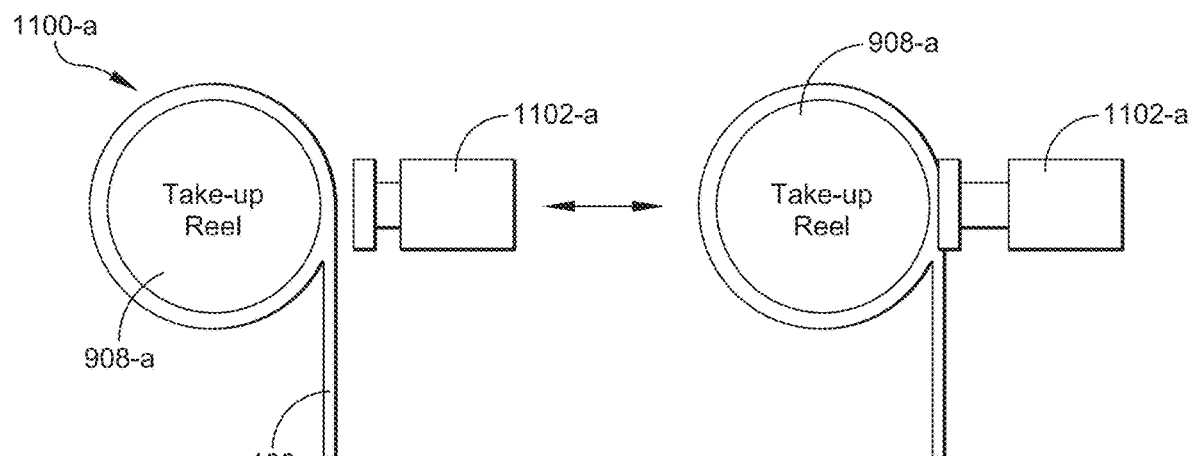
FIG. 11B is a schematic diagram of another embodiment of a cable slack correction system of an Resistance system.
Figure 11C:
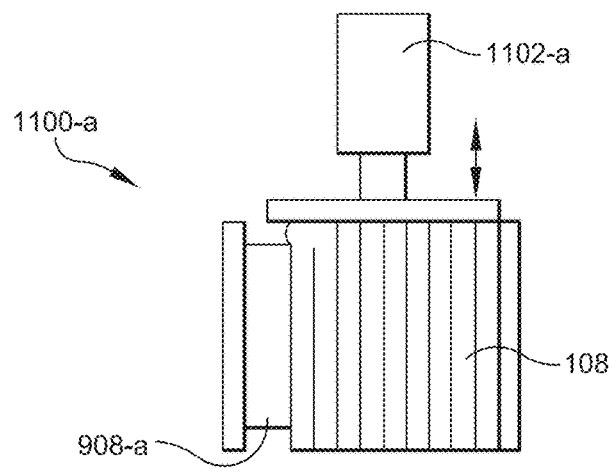
FIG. 11C is a schematic diagram of the embodiment of a cable slack correction system of an Resistance system of FIG. 11B.

With reference to FIGS. 11B-11C, another cable anti-unspooling system 1100-*a* includes a solenoid 1102-*a* aligned to apply a slack correcting force on the cable 108 when spooled on the take-up reel 908-*a*. In this embodiment, a lever arm of 1110-*a* of the solenoid 1102-*a* is retracted away from contact with the cable 108 when the cable 108 is under tension and power is applied to the system. When power is removed from the system (intentionally or otherwise), the solenoid 1102-*a* is de-energized (either by a loss of power or by the controller 104) and the lever arm rests against the take-up reel 908-*a*, thus preventing the cable 108 from unspooling from the take-up reel 908-*a*.

The above embodiments of a cable anti-unspooling system 1100, 1100-*a* are only examples. Various other configurations can be provided, such as other cable braking systems for example.

Alternative Embodiments of a Current Source

With reference to FIGS. 12-23, different configurations of various solid state embodiments) can supply power/current to the DC motor 102. These particular solid state embodiments are implemented in the programmable electronic resistance housing 101 in place of the alternator 122, AC motor 120, and related structures and mechanisms. Because these current sources do not implement an alternator or AC motor, they can be smaller in volume and weigh significantly less than the alternator-AC motor configurations described above in association with FIGS. 1-10. In some cases, the space needed for a solid state current supply may be reduced to approximately a cubic foot and the weight can be reduced to 5-10 lbs. (from approximately 50 lbs of the AC motor 120 and the alternator 122 embodiment and at least a space of 2 cubic feet). Further, at least some these types of current sources can require that the DC motor 102 have different operational parameters, such as torque and speed constants for example. However, in some embodiments, these solid state current sources may provide a smaller resistance range, thus making them better suited, for example, for physical therapy or home use.

Embodiments of the AC motor/alternator configurations described above can provide a very robust system, including being extremely durable, long lasting, and very reliable. In some embodiments, the Electric Weight System 100 implementing an AC motor/alternator configuration has the capability of delivering in excess of 1000 W (1.34 hp) to the DC motor 102 for an unlimited amount of time. However, there are ways to generate this amount of power in a fully solid state configuration (i.e., eliminating the AC motor-alternator current supply) and maintain the same or similar system performance, robustness, longevity, etc.

One such embodiment can include an amplifier and circuitry that drives the DC motor 102 with a DC voltage derived from voltage rails, and in which no flyback diode(s) are required, as described in further detail below in reference to FIGS. 12-17. Some embodiments, alternatively or additionally include circuitry that drives the DC motor 102 directly from voltage rails and utilizes the use of one or more flyback diode(s) as described in further detail below in reference to FIGS. 18-23.

The first solid state embodiment mentioned in the preceding paragraph utilizes a low-voltage high-current variable DC power supply and a line converted—120/240 AC input. This DC power supplies/drives the DC motor 102. To match the performance of the AC motor-alternator embodiments discussed above, this power supply should deliver up to 100 amps or more, with a DC voltage output as high as 20 volts or more. Current and voltage requirements can be adjusted for other motor/transmission combinations, but, as discussed above, avoiding high gearing ratios can be desired in some embodiments. Generally speaking, increasing the gear ratio effectively reduces the drive current requirement for a given resistance, but conversely may provide a less pleasurable user experience. In some instances, this decrease in the user experience can be caused by, for example, an increased resistance at the beginning of the out-stroke of the cable 108 due to thermal expansion and then cooling of grease in a gear drive, such as a transmission.

There are many ways to convert 120V AC to a variable DC supply. A class D amplifier can be implemented to convert 1 KW or more of variable DC, in a single conversion as described in more detail below in reference to FIGS. 12-17. FIGS. 12-16 and the related descriptions provide single stage voltage conversion embodiments, and FIG. 17 provides a multistage DC voltage conversion embodiment.

Figure 12:
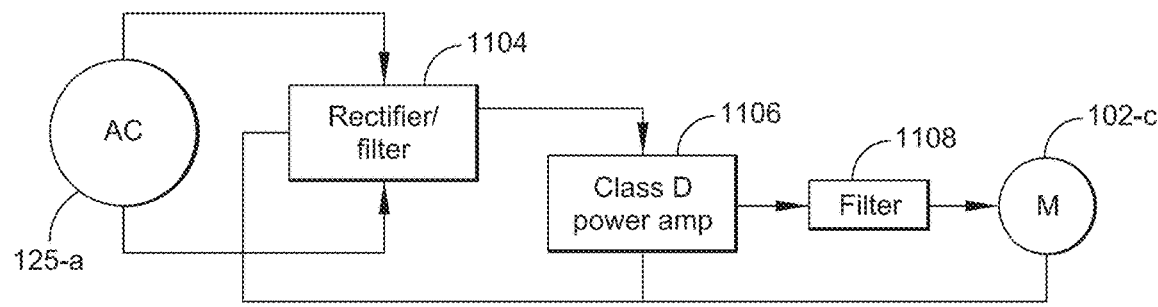
FIG. 12 is a block diagram of an embodiment of a solid state current supply of an Resistance system.

With reference in particular to FIG. 12, a 120V AC power supply 125-*a*, which can be provided via a standard wall socket, is rectified and filtered to approximately 160V DC by a rectifier/filter 1104. The output of the rectifier/filter 1104 is fed into a class D power amplifier 1106, which switches the voltage rail. The output of the class D amplifier 1106 is then smoothed by filter 1108, which during smoothing removes the switched DC signal from the applied signal. The filtered class D amplifier output connects to and drives the DC motor 102-*c*. In some cases, this implementation may be referred to as a 120V AC direct conversion class D amplifier power supply. In some cases, this configuration may require high frequency switching of the various power devices, and it utilizes a high rail voltage. However, possible life-expectancy risk for the power supply due to high rail voltage can be reduced and possibly eliminated by, for example, ensuring that the class D amplifier 1106 operates within its specified safe operating area and by adjusting the switch timing.

Figure 13:
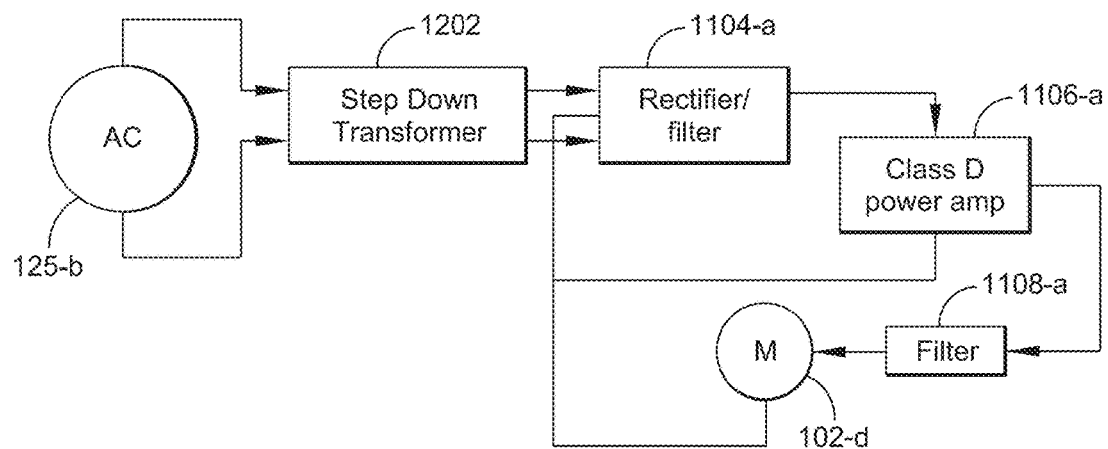
FIG. 13 is a block diagram of another embodiment of a solid state current supply of an Resistance system.

With reference now to FIG. 13, a 120V AC power supply 125-*b*, is stepped down to approximately 60V AC or less (or to any value necessary to drive the highest DC motor 102-*e* voltage level) by an AC step down transformer 1202. The 60V AC output from the step down transformer 1202 is then full wave rectified and filtered by rectifier/filter 1104-*a*. A class D amplifier 1106-*a* then switches the voltage rail of the rectified and filtered 60V AC and drives the DC motor 102-*d* via filter 1108-*a*. In some cases, this implementation may be referred to as a 120V AC step down conversion class D amplifier power supply. In some cases, the AC step down transformer 1202 may be large and costly, especially for a 50/60 HZ, 1 KW specification. However, this potential downside of such a power supply can be offset by off-the-shelf drivers that can handle the switch timing functions of the class D amplifier 1106-*a*.

Figure 14:
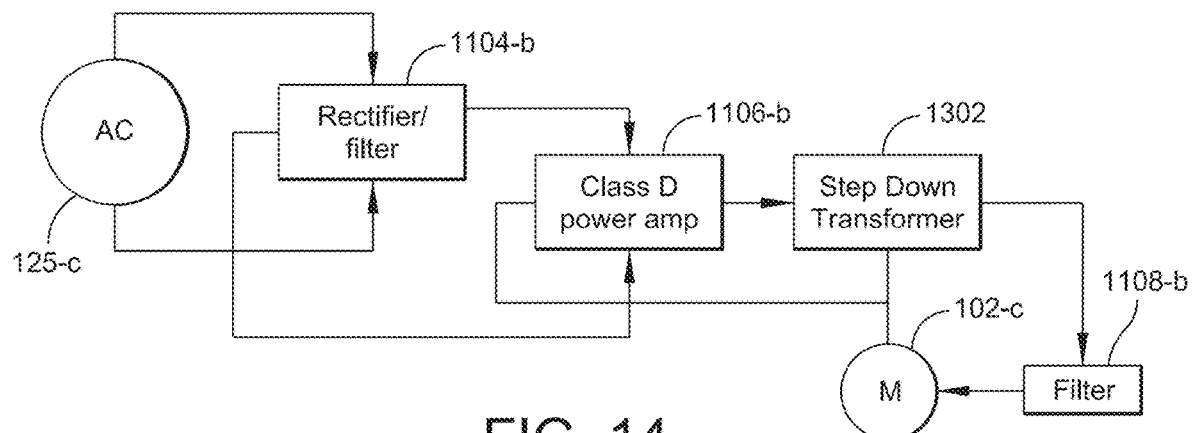
FIG. 14 is a block diagram of another embodiment of a solid state current supply of an Resistance system.

With reference now to FIG. 14, a 120V AC power supply 125-*c* is full wave rectified and filtered by a rectifier/filter 1104-*b* to approximately 160V DC. A class D amplifier 1106-*b* switches the voltage rail of the 160V DC and drives a high frequency step down transformer 1302 (DC) which steps down the voltage to, for example, 60V DC. The high frequency step down transformer 1302 can be driven differentially or single endedly. This 2.67 voltage reduction increases the current capacity by the same multiplier (2.67), reducing the power requirements on the class D drivers. The output of the high frequency step down transformer 1302 is fed to filter 1108-*b*, driving the DC motor 102-*e*. In some cases, this implementation may be referred to as a 120V AC class D amplifier step down power supply. This embodiment reduces the size of the transformer, by replacing the 50/60 Hz step down transformer 1202 of FIG. 13 with the high frequency step down transformer 1302 that passes the high-frequency class D PWM signal. In some cases, increasing the frequency of the signal to be transformed can allow for a reduction in the size of the transformer itself, for example by replacing a transformer designed to transform 50/60 Hz with a transformer designed to transform 100 KHz or more. Issues associated with high voltage rail switching may still be present in some such embodiments (on/off switching of the various power devices), but for such embodiments the driver current requirements can be reduced because, as a function of the turns ratio of the transformer, the voltage goes down and the current goes up.

Figure 15:
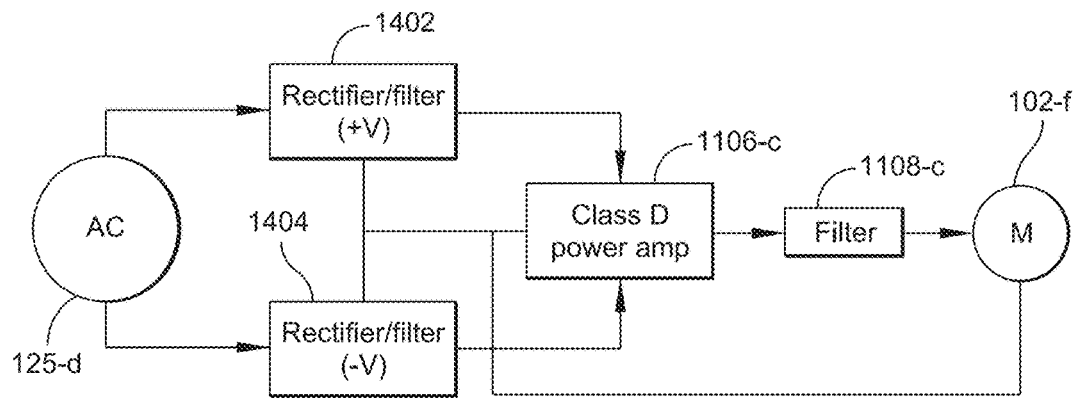
FIG. 15 is a block diagram of another embodiment of a solid state current supply of an Resistance system.

With reference now to FIG. 15, a 120V AC power supply 125-*d* is half wave rectified and filtered by positive voltage rectifier/filter 1402 and negative voltage rectifier/filter 1404 to approximately +−160V DC. A class D amplifier 1106-*c* switches these voltage rails, driving the DC motor 102-*f* via filter 1108-*c*. This configuration can drive the DC motor 102-*f* in both directions, providing the DC motor 102-*f* has one of the supply terminals connected to the 0V of the +−160 VDC supply rails. The ability to drive the DC motor 102-*f* in both directions further aids in maintaining the requisite motor current, and in some cases further in combination with the dynamic range extender functionality of the controller 104, as described in greater detail in reference to FIGS. 27-30. In some cases, this implementation may be referred to as a 120V AC split voltage direct conversion class D amplifier power supply. Some such embodiments can present the issue of high voltage rails (doubled) and switching requirements. However, in some such embodiments, by precisely matching the drive/chain system (also referred to as a transmission) to the specific DC motor 102-F and class D amplifier 1106-*c* requirements, an equivalent system is provided, and, in some cases, the resulting system can be particularly tailored for home use and less expensive packaging, shipping, and ease of system movement due to reductions in system size and weight.

Figure 16:
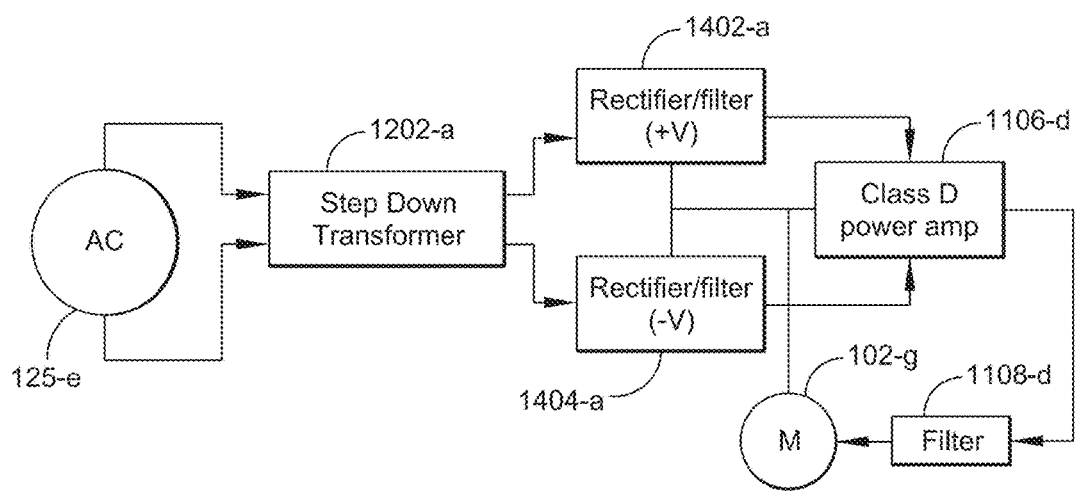
FIG. 16 is a block diagram of another embodiment of a solid state current supply of an Resistance system.
Figure 17:
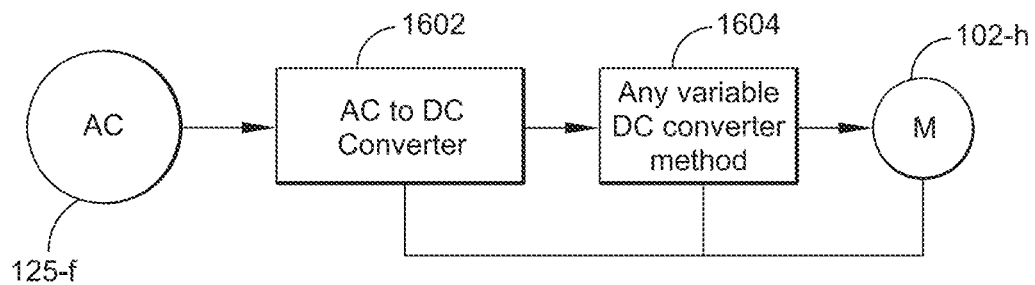
FIG. 17 is a block diagram of another embodiment of a solid state current supply of an Resistance system.

With reference now to FIG. 16, a 120V AC power supply 125-*e* is stepped down to approximately 60V AC or less (or to any value necessary to drive the highest DC motor 102-*g* voltage level) by an AC step down transformer 1202-*a*. The 60V AC output from the step down transformer 1202-*a* is then half wave rectified and filtered by positive voltage rectifier/filter 1402-*a* and negative voltage rectifier/filter 1404-*a* to approximately +−60V DC. A class D amplifier 1106-*d* then switches the voltage rails of the rectified and filtered 60V DC and drives the DC motor 102-*g* via filter 1108-*d*. This configuration can drive the DC motor 102-*g* in both directions, providing the DC motor 102 has one of the supply terminals connected to the 0V of the +−60V DC supply rails. The ability to drive the DC motor 102-*g* in both directions can further aid in maintaining the requisite motor current. In some cases, the ability to drive the DC motor 102-*g* in both directions can be further beneficial in combination with the dynamic range extender functionality of the controller 104, as described in greater detail below in reference to FIGS. 27-30. In some cases, this implementation may be referred to as a 120V AC step-down split voltage conversion class D amplifier power supply. Some such embodiments can utilize a relatively large and costly AC step-down transformer 1202-*a*, which may be 50/60 Hz and provide 1 KW. However, this potential downside of such a power supply can be offset by use of off-the-shelf drivers that can handle the switch timing functions of the class D amplifier 1106-*d*.

In reference to FIG. 17, in some embodiments, a 120/240V AC power provided by power supply 125-*f* can be converted to a lower fixed, or somewhat variable, intermediate voltage via an AC to DC converter 1602. The DC output of the DC converter 1602 can then be converted via a variable DC converter 1604 to provide power having the desired performance requirements to drive the DC motor 102-*h*. For example, the AC to DC converter 1602 can include (i) a universal input, such as 85-264V AC or 120/240V AC, and (ii) a fixed output, such as 48V DC (a standard telephonic level), 24V DC, or even 12 VDC. AC to DC converters with these can be used as the intermediary (first stage) supply, as long as they provide an output sufficient to drive the DC motor 102-h. The first stage output, i.e., the output of AC to DC converter 1602, can be the input for the second stage power supply, i.e., the variable DC converter 1604. This second stage power supply can be provided by standard switching configuration types (buck, boost, buck-boost, etc., as well as a Class D (or Class B) amplifier. The output of this second stage power supply, i.e., to the DC motor 102-h, can be configured to withstand the DC motor 102-h reversing the drive voltage, such as during the out stroke. In this way, another solid state power supply for driving the DC motor 102-h can be implemented to drive the programmable electronic resistance housing 101 or the Electric Weight System 100.

Figure 18:
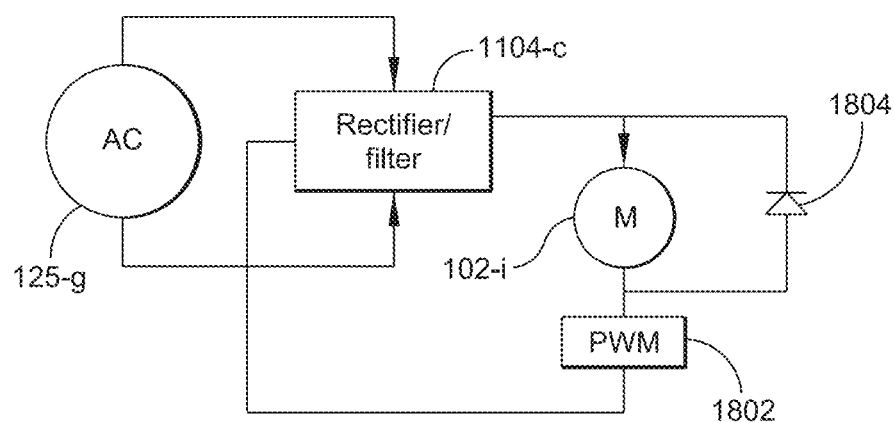
FIG. 18 is a block diagram of another embodiment of a solid state current supply of an Resistance system.

Referring now to FIG. 18, one common way of driving a DC motor 102-i is with Pulse Width Modulation (PWM), such as via a PMW driver 1802, with one terminal of the DC motor 102-i connected to a DC power source and the other terminal alternately switched (through which an electric circuit is made, then broken). The DC power source may originate from an AC power supply 125-g, such as a 120V AC power supply, and then be rectified and filtered by a rectifier 1104-c. The DC output of the rectifier 1104-c can be fed into the PWM driver 1802 to provide a switching source for the other terminal of the DC motor 102-i. A flyback diode 1804 connected across the DC motor 102-i terminals shunts the flyback energy during the switch off time. This flyback energy comes from the collapsing magnetic field of the inductor that compromises the DC motor 102-i. When a flyback diode 1804 is connected to the DC motor 102-i, turning the DC motor shaft in the preferred direction (i.e., the direction of rotation when voltage is applied to the DC motor 102-i so that the flyback diode 1804 is reverse biased) causes the DC motor 102-i to generate a voltage proportional to its rotational speed while the flyback diode 1804 looks like an open circuit. This presents no impediment to rotating the motor shaft. Turning the DC motor 102-i in the non-preferred direction causes the DC motor 102-i to still generate a voltage proportional to the rotational speed of the shaft, but that voltage is shorted by the flyback diode 1804 (acting like a short circuit to the DC motor 102-i). Further, attempting to increase motor shaft speed (still in the non-preferred direction) is met with an increased force requirement as the DC motor 102-i seeks to output still more voltage across the flyback diode 1804. Removing the flyback diode 1804 allows the DC motor 102-i to be turned easily in either direction.

In another embodiment, the DC motor 102-i can be connected to a PWM driver 1802, without a flyback diode 1804. If the DC motor 102-i is PWM driven with no flyback diode 1804 connected, the DC motor 102-i will not turn. Further, while still being driven by a PWM signal, the DC motor 102-i can be easy to turn in either direction regardless of the pulse width.

Accordingly, in some embodiments, a DC motor, such as DC motor 102-i, can deliver a constant torque by keeping the motor current constant. A PWM driver 1802 can be provided to monitor motor current and make drive adjustments to maintain a set (constant) current (torque) to the DC motor 102-i driven in the preferred direction (i.e., via a flyback diode 1804 connected to the DC motor terminals). Further, a PWM driven DC motor 102-i can be turned easily in both directions if the flyback diode 1804 is not connected.

Thus, if a flyback diode 1804 is connected to the DC motor 102-i by circuitry that can determine contact time (i.e., the time when the flyback diode 1804 is connected to or disconnected from the DC motor 102-i terminals), the torque (resistance) can be controlled in the non-preferred direction. Further, if the amount of fly-back connection is properly modulated, the DC motor 102-i can exhibit a constant torque while turning in either direction, i.e., while driving a load (providing resistance to a user) or being pulled in the opposite direction by the load. This can occur during the in-stroke and out-stroke of a cable 108 driven by the programmable electronic resistance housing 101 or the Electric Weight System 100 for example. In some cases, maintaining a constant torque can include maintaining a torque level within +−10%, +−20%, etc. of the desired torque value.

Figure 19:
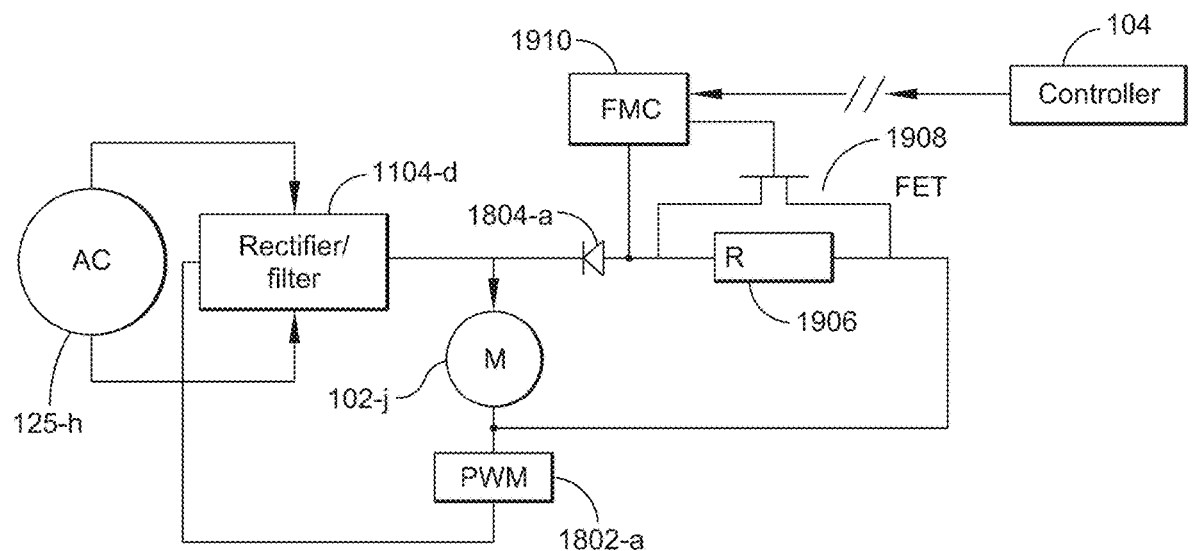
FIG. 19 is a block diagram of another embodiment of a solid state current supply of an Resistance system.

Turning now to FIG. 19, a DC motor 102-j is powered by an AC power supply 125-h (120/240V AC) rectified by a rectifier/filter 1104-d. The output of the DC motor 102-j, specifically the current output corresponding to a resistance value, is controlled via a PWM driver 1802-a. One specific way of implementing a PWM driver with a flyback diode is to put a resistor 1906 in series with a flyback diode 1804-a and modulate a short across the resistor 1906 using a silicon switch, such as a FET 1908, all connected in parallel with the DC motor 102-j. In some cases, flyback modulation circuitry 1910, which receives control information from a controller 104 via isolated signaling, is connected to a gate of the FET 1908 and the flyback diode 1804-a. As a result, the flyback modulation circuitry 1910 can be completely connected or partially connected depending on the state of the switched FET 1908. Thus, when the user is performing an inward stroke, the FET 1908 can be switched fully on, continuously presenting the flyback to the DC motor 102-j. The PWM signal, from the PMW driver 1802-a connected to the DC motor 102-j, drives the DC motor 102-j in such a way as to maintain the desired current, and thus torque. When the user is performing an outward stroke, the PWM signal still drives the DC motor 102-j to maintain the desired current with the addition that the FET 1908 will be modulated to also maintain the desired current flow through the DC motor 102-j. In some cases, unrestrained flyback energy is taken into consideration when implementing this configuration.

Figure 20:
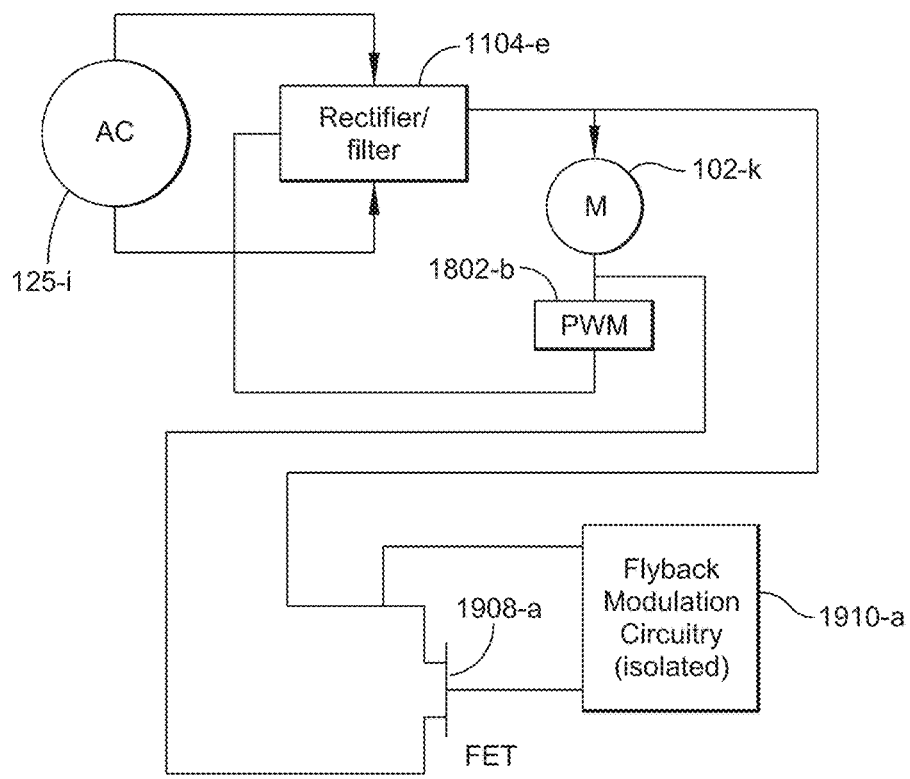
FIG. 20 is a block diagram of another embodiment of a solid state current supply of an Resistance system.

Referring now to FIG. 20, a DC motor 102-k is powered by an AC power supply 125-i (120/240V AC) rectified by a rectifier/filter 1104-e. The output of the DC motor 102-k, specifically the current output corresponding to a resistance value, is controlled via a PWM driver 1802-b. Another way of implementing a PWM driver with a flyback diode is to use an FET 1908-a as the flyback, i.e., by connecting both terminals of the flyback modulation circuitry 1910-a to the FET 1908-a, with the FET 1908-a connected in parallel with the DC motor 102-k. This can be accomplished by turning on the FET 1908-a during periods when flyback suppression is desired and turning off the FET 1908-a when not desired. For instance, during the in-stroke, the FET 1908-a is turned on whenever the PWM driver 1802-b is off. During the out-stroke, the FET 1908-a is modulated in such a way as to assist the PWM driver 1802-b in maintain the desired current through the DC motor 102-k. In some cases, unrestrained flyback energy can be taken into consideration when implementing this configuration. Also in some cases, the FET 1908-a can be configured without an intrinsic drain-source diode, as it can act as a full-time flyback diode regardless of the on/off state of the FET 1908-a.

Figure 21:
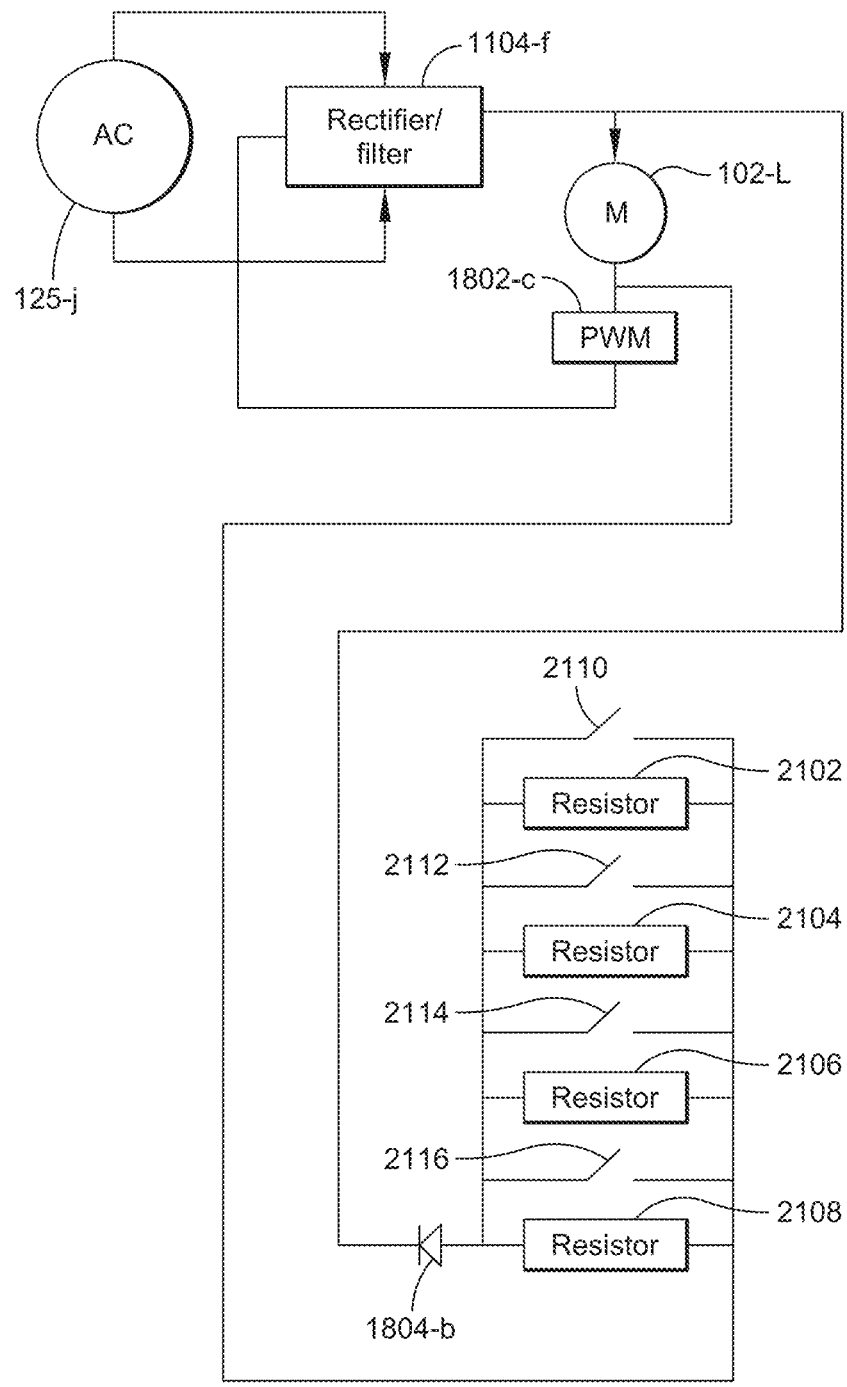
FIG. 21 is a block diagram of another embodiment of a solid state current supply of an Resistance system.

Referring now to FIG. 21, a DC motor 102-1 is powered by an AC power supply 125-j (120/240V AC) rectified by a rectifier/filter 1104-f. The output of the DC motor 102-1, specifically the current output corresponding to a resistance value, is controlled via a PWM driver 1802-c. Another way of implementing a PWM driver with a flyback diode is to use a combination of resistors, e.g., resistors 2102, 2104, 2106, and/2108 each shortable by FETs 2110, 2112, 2114, and 2116 connected in series with a flyback diode 1804-b, all in parallel with the DC motor 102-1. The resistors 2102, 2104, 2106, and/2108 can help limit the (possibly high) unrestricted flyback voltage from the DC motor 102-1 while aiding the FETs 2110, 2112, 2114, and 2116 in managing power dissipation. In other implementations, different numbers of resistors and FETs (and different values) can be used depending on the drive requirements of the DC motor 102-1.

Figure 22:
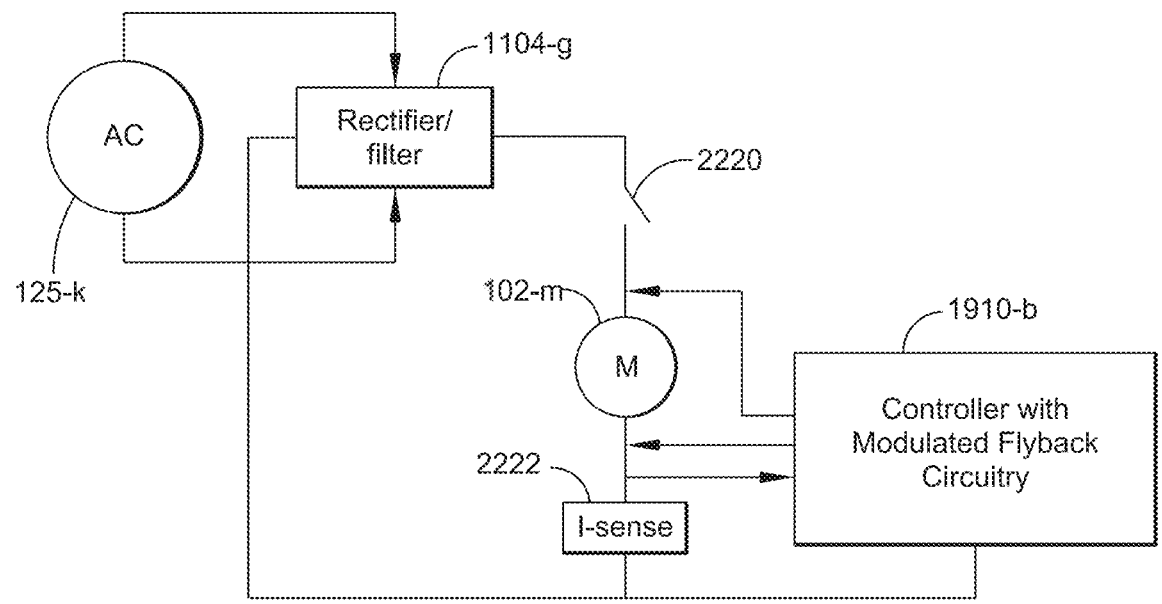
FIG. 22 is a block diagram of another embodiment of a solid state current supply of an Resistance system.

With reference to FIG. 22, a particular modified embodiment of FIG. 20 has a DC motor 102-m powered by an AC power supply 125-k, which is (120/240V AC) rectified by a rectifier/filter 1104-g. Modulated flyback circuitry 1910-b is electrically isolated from, and controlled by, the controller 104. The controller 104 as shown is configured with the on-board modulated flyback circuitry 1910-b, which can include a power supply, with the controller 104 directly in parallel with the DC motor 102-m. This configuration allows PWM control to be sent to isolated switching so that the DC motor 102-m is PWM driven by a PWM electrically isolated high side switch 2220. The PWM electrically isolated high side switch 2220 is connected in series between the rectifier/filter 1104-g and the DC motor 102-m. In some cases, the control electronic signals are referenced to ground. In addition, an I-sense module 2222 (current sensor such a shunt resistor), can be connected in parallel with the controller 104 and connected to the DC motor 102-m to sense and provide a current output of the DC motor 102-m to the modulated flyback circuitry 1910-b. Current information allows the modulated flyback circuitry 1910-b to accurately adjust the current supplied to the DC motor 102-m via the high side switch 2220 to maintain and/or adjust a desired resistance provided by the DC motor 102-m.

Figure 23:
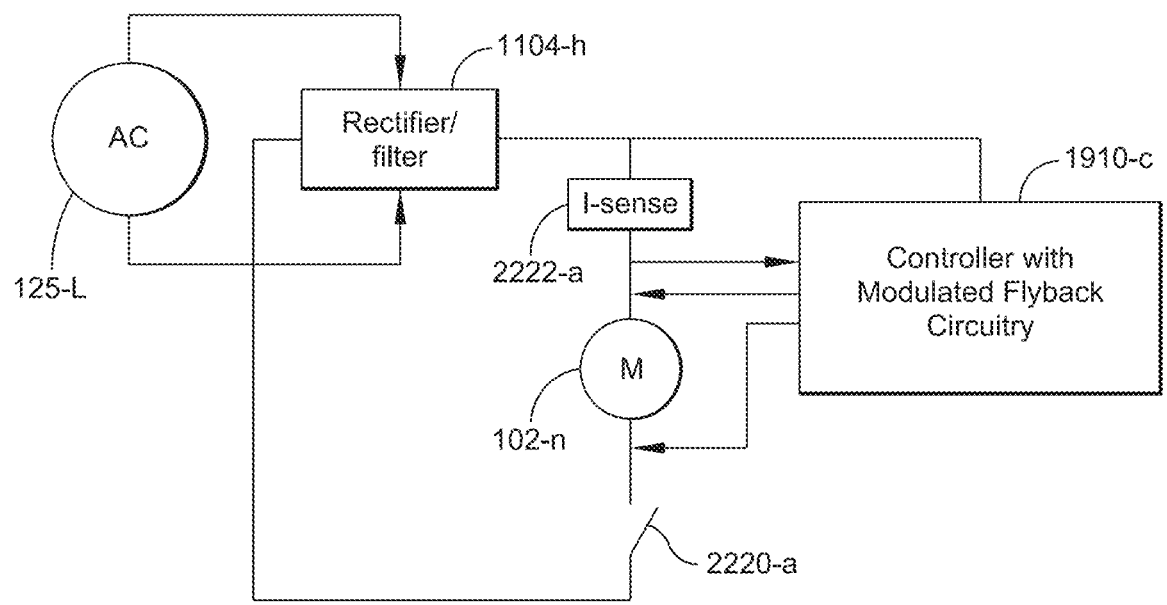
FIG. 23 is a block diagram of another embodiment of a solid state current supply of an Resistance system.

Referring to FIG. 23, another particular modified embodiment of FIG. 20 has a DC motor 102-n powered by an AC power supply 125-1, which is (120/240V AC) rectified by a rectifier/filter 1104-h. Modulated flyback circuitry 1910-c is electrically isolated from, and controlled by, the controller 104. The controller 104 as shown is configured with the on-board modulated flyback circuitry 1910-c, which can include a power supply, with the controller 104 directly in parallel with the DC motor 102-n. This configuration allows PWM control to be sent to isolated switching so that the DC motor 102-n is PWM driven by a PWM electrically isolated low side switch 2220-a. The PWM electrically isolated low side switch 2220-a is connected in series between the rectifier/filter 1104-g and the DC motor 102-m. In some cases, the control electronic signals are referenced to ground. In addition, an I-sense module 2222-a (current sensor such a shunt resistor), can be connected in parallel with the controller 104 and connected to the DC motor 102-m on the high side to sense and provide a current output of the DC motor 102-n to the modulated flyback circuitry 1910-c. Current information allows the modulated flyback circuitry 1910-c to accurately adjust the current supplied to the DC motor 102-n via the low side switch 2220-a to maintain and/or adjust a desired resistance provided by the DC motor 102-n. In some cases, high side and low side PWM switching implementations can be interchangeable with similar results. Variations in design may determine isolation requirements; for example, the flyback FET can be driven by current sensing such that current may be continuously sensed as opposed to sampled during the PWM drive time.

Some issues with solid state embodiments may include silicon durability of the PWM driver 1802 and heat dissipation in the fly-back elements, such as FETs 2110, 2112, 2114, and/or 2116, resistors 2102, 2104, 2106, and/or 2108, etc. However, the technique of modulated flyback control can be particularly useful in reducing or eliminating these issues for motors having fairly low current (and high voltage) requirement. These motors will generally include a speed reducer box, such as a torque converter, etc. for adequate performance.

In some embodiments, a high current low voltage motor can be driven by first generating the low(er) voltage, and then applying the PWM and modulated flyback techniques to the DC motor. Doing so can provide less stress on the driving silicon as well as the flyback resistor (if used).

Control System of an Electric Weight System

Figure 24:
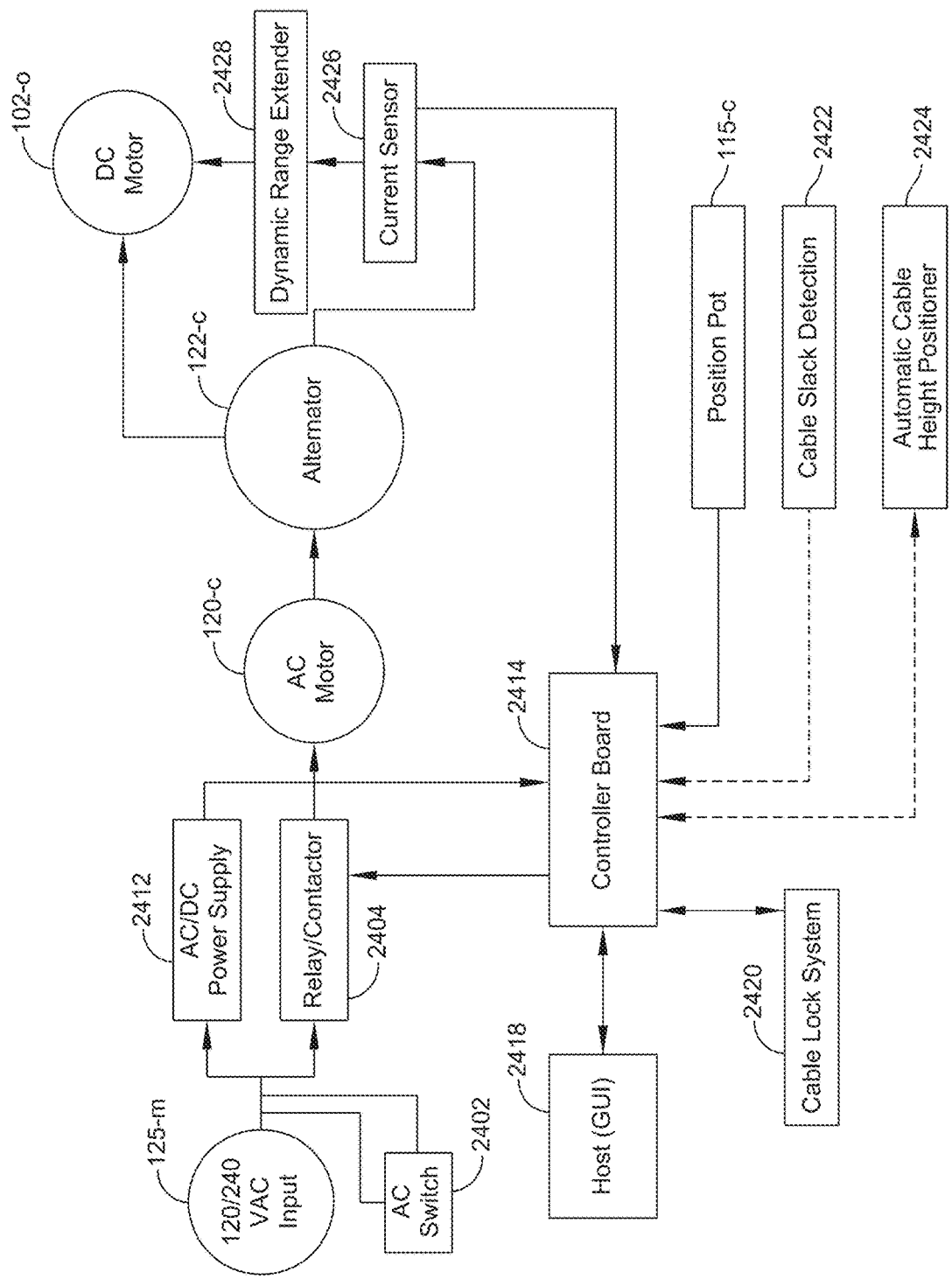
FIG. 24 is a functional block diagram of the Resistance system of FIG. 1.

With reference to FIG. 24, a functional block diagram 2400 of the Electric Weight System 100 is shown. An AC power source 125-m, such as a 120/240V AC input from a standard household socket, supplies AC power to a relay/contactor 2404 via AC receptacle on/off switch 2402. The relay/controller 2404 powers the AC motor 120-c, which in turn mechanically drives the alternator 122-c, such as by belt 124 or shaft coupler 802. The electrical output of the alternator 122-c drives the DC motor 102-o.

The AC power source 125-m also is converted to DC power via an AC/DC power supply 2412, which powers a controller board 2414, which can include some or all of the functionality of controller 104 and/or PCB board 304. The controller board 2414 implements a micro-processor and other circuitry to implement control over the Electric Weight System 100 as will be described below. A more detailed description of the controller board 2414 is described in greater detail in reference to FIG. 26.

The controller board 2414 receives input from the position pot (potentiometer) 115-c, which is connected to a cable drive shaft, such as DC motor shaft 324 and/or drive shaft 332. The input from the position pot 115-c allows the controller board 2414 to determine the position and/or velocity of the cable 108, 904, 916 supplying the exercise resistance to the user, and control the DC motor 102-o based on that information and input from the host computing device 106, which is in 2-way communication with the controller board 2414. The user can program/interact with the host computing device 106 to set a desired resistance profile, such as an elastometric profile, a forced negative profile, a pyramid profile, etc. The controller board 2414 can implement the desired resistance profile via controlling the current supplied from the alternator 122-c to the DC motor 102-o via a PWM driver (not shown) implemented via the controller board 2414. The PWM driver receives real-time current information from the output of alternator 122-c via a current sensor 2426, and by adjusting the duty cycle of the control signal sent to the alternator 122-c, can adjust the current supplied to the DC motor 102-o, and hence can adjust the resistance felt by the user via cable 108.

A Dynamic Range Extender (DRE) 2428 is connected in series with the current sensor 2428 and the DC motor 102-o, and monitors the DC motor 102-o voltage, including voltage applied to the DC motor 102-o via the alternator 122-c. As the DC motor 102-o voltage tends towards negative, thus indicating that the motor is moving in the non-preferred direction of rotation, the DRE 2428 enables resistive elements, either resistors or FETs having suitable internal resistance, in the current path between the alternator 122-*c* and the DC motor 102-*o*. The more the voltage wants to go negative, the more resistance the DRE 2428 will inject into the current path via opening one or more FETs to place one or more resistors in the current path, or closing one or more FETS if the FTES have a suitable internal resistance. In either case, this total resistance allows the desired current to flow through the DC motor 102-*o* so that the desired resistance is experienced. In other words, the DRE 2428 adjusts the operation of the DC motor 102-*o* so that the user can experience the desired resistance through cable 108 without any unwanted electrical feedback from the in-stroke of the cable 108 due to reverse biasing of the DC motor 102-*o*. The maximum resistance the DRE 2428 will enable can be found experimentally, and depends on motor characteristics and maximum desired cable speed in the outward direction. In some cases, the resistance applied by the DRE 2428 can be dynamically adjusted so as to minimize power and heat dissipation thought the resistive elements, while marinating unwanted resistance increases in the in-stroke of cable 108. The operation and functionality of the dynamic range extender 2428 will be described in greater detail below in reference to FIGS. 27-30.

The controller board 2414 also is in two-way communication with a cable lock system 2420, which controls operation of the DC motor 102-*o* by locking and unlocking the DC motor shaft 324 during power-up. The operation of the cable lock system 2420 will be described in greater detail in reference to FIG. 25 below.

In implementations of the Electric Weight System 100 that utilize a take-up reel 908, a cable slack detection system 2422 may communicate with the controller board 2414. The cable slack detection system 2422 may provide the controller board 2414 with information identifying when the cable 108 is slack, or becoming slack, usually on the in-stroke of the take-up reel 908. In response to receiving this information, the controller board 2414 can adjust the speed of the DC motor 102-*o* to compensate for the slackening. The functionality and operation of the cable slack detection system 2422 can be implemented in combination with or separately from the cable anti-unspooling system 1100 as described above in reference to FIGS. 11A-11C.

In some embodiments, the controller board 2414 may also be in two-way communication with an automatic cable height positioner 2424. The controller board 2414 may, upon receiving a cable height input from the user via the host computing device 106, signal the automatic cable height adjustor 2424 to move the adjustable bracket 148 either up or down depending on the current position of the adjustable bracket 148. Automatic cable height positioner 2424 may utilize a threaded rod and running nut configuration to automatically adjust the height of cable 108, for example, by moving the adjustable bracket 148 up and down along a threaded rod parallel to the second support member 128 via the running nut. In some cases, another position potentiometer can be used to determine the position of the adjustable bracket 148. In other implementations, the automatic cable height adjustor can use a chain drive mechanism to adjust the height of the adjustable bracket 148. In yet other implementations, the chain drive mechanism can be coupled with a switch used to find the zero position of the adjustable bracket 148 and an optical sensor can detect the precise height/position of the adjustable bracket 148. The optical sensor can operate by shining light through the chain and determining position by counting the light pulses up or down as the chain moves. The controller board 2414, upon receiving a cable height input from the user via the host computing device 106, signals the automatic cable height adjustor 2424 to move the adjustable bracket 148 either up or down depending on the current position of the adjustable bracket 148. Other similar configurations are also contemplated to allow automatic cable height adjustments.

Figure 25:
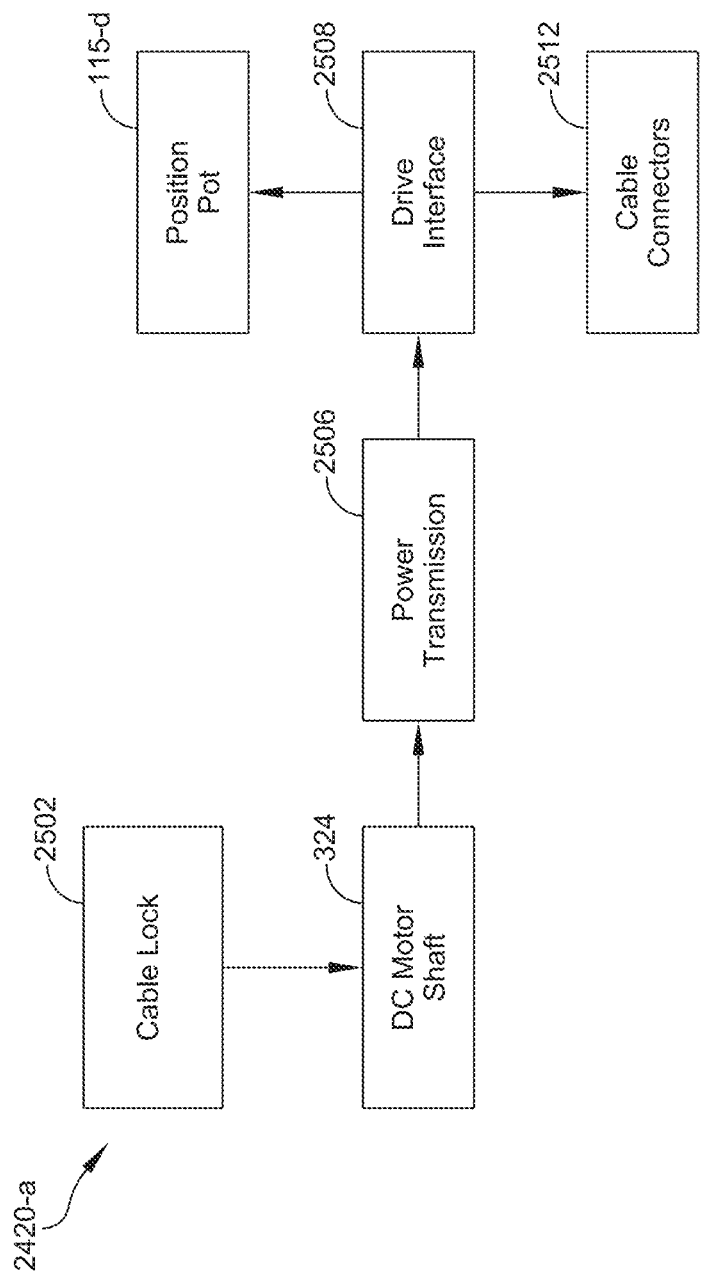
FIG. 25 is another functional block diagram of the Resistance system of FIG. 1.

In reference to FIG. 25, a block functional diagram of a cable lock system 2420-*a*, is shown. A cable lock 2502 includes a ratchet and pawl system, as is well known in the art. The ratchet and pawl system engages and disengages so that the cable 108 may only be extended when the Electric Weight System 100 is ON. The ratchet and pawl system allows the DC motor 102 to retract the cable 108 regardless of the position of the pawl. As a result, the ratchet/pawl prevents the motor shaft 324 from turning in the non-preferred direction when activated. The ratchet and pawl system is controlled by the controller board 2414/controller 104 and a lock/unlock detect switch indicates back to the controller board 2414 the state of the DC motor shaft 324.

The DC motor shaft 324 drives a power transmission 2506 and drive interface 2508, which may include some or all of the components/functionality as described in reference to FIGS. 1-8 for the linear chain drive, or as described in reference to FIGS. 9-10 for the take-up reel drive system. The drive interface 2508 is connected to the position pot (potentiometer) 115, which sends information indicative of cable position and/or velocity to the controller board 2414. In some embodiments, the drive interface 2508 can be connected to an existing cable 904 of an existing weight machine 902 via a cable connector 2512. In other embodiments, other cable lock systems may be utilized to accomplish a similar safety shut-off functionality. Other implementations can utilize off-the-shelf power-off cable locking mechanisms or mechanisms that lock the cable 108 by "pinning" the DC motor shaft 324, such as by placing discrete holes in the DC motor shaft 324 that accept a solenoid plunger or the sort.

Figure 26:
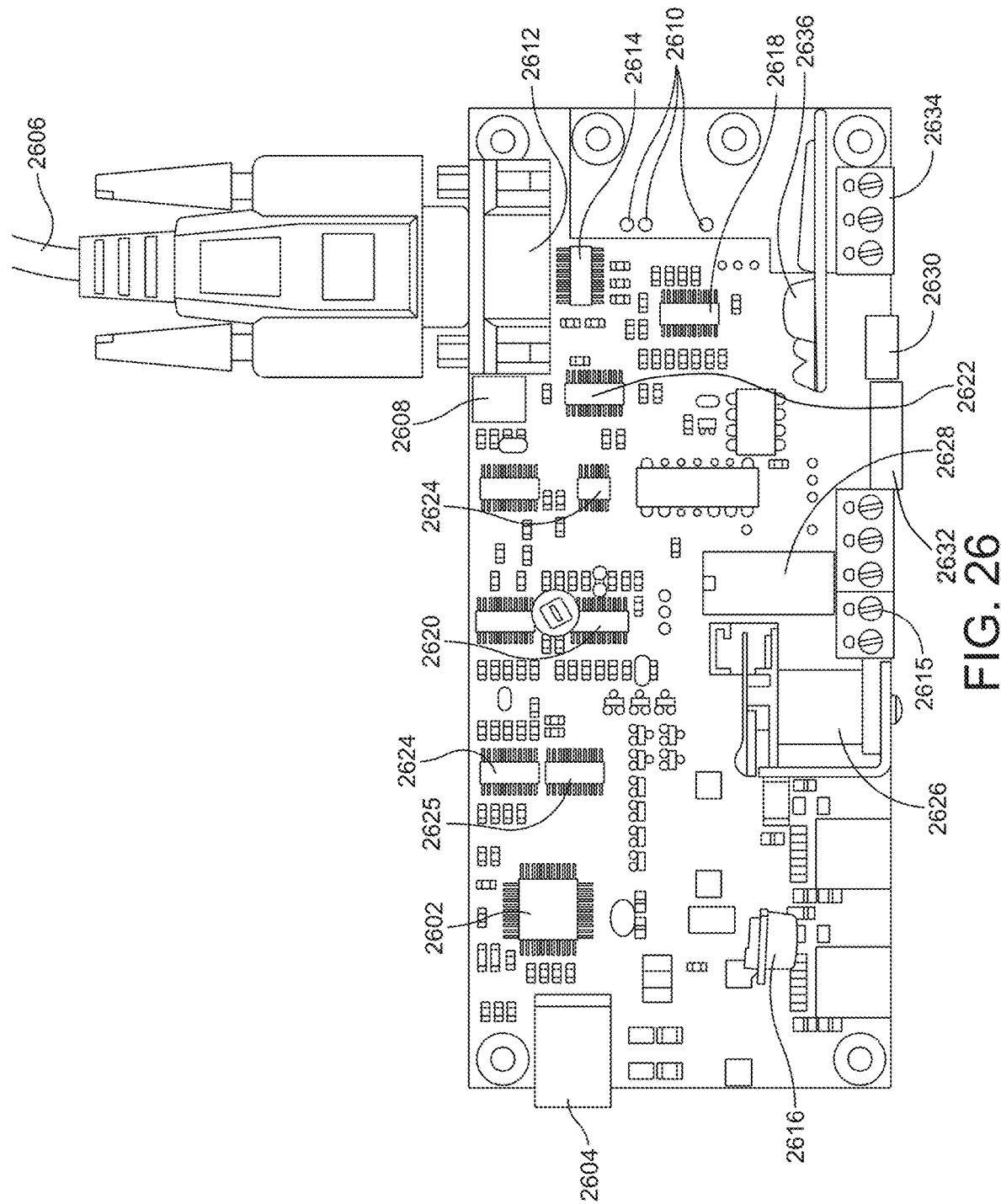
FIG. 26 is a block diagram of a controller of the Resistance system of FIG. 1.

In reference to FIG. 26, a block diagram of a controller board/controller 2600, such as controller 104 or controller board 2414 described above, is shown. The following description of controller 2600 is intended to be an example of a control mechanism for the systems described previously, such as the Electric Weight System 100, the programmable electronic resistance box 101, and as an example implementation of the functional block diagram 2400 of an Electric Weight System. However, other control mechanisms will accomplish the same purpose of the controller 2600, and the scope of the claimed subject matter includes those alternative embodiments.

The controller 2600, and the various components associated with the controller 2600, are powered via an AC/DC Power supply 2412 by 12V DC (nominally, but can be as high as 24V DC) that is received by a DC/DC converter 2616 via power connectors 2615, where the DC/DC converter 2616 converts the 12V DC to 5V DC. Other embodiments have higher AC/DC voltages converted to +12 VDC and +5 VDC.

In the current embodiment, controller 2600 includes a micro controller 2602 that can send and receive information from USB connector 2604, RS 232 cable 2606, and can receive information from a position pot connector 2608 connected to potentiometer 115 and current sensor inputs 2610 connected to current sensor 2426 (which can also include I sense module 2222). The micro controller 2602 communicates with the host computing device 106 via an RS 232 cable 2606, which may be an example of communication cable 127. The RS 232 cable 2606 connects to the controller board 2600 via an RS 232 connector 2612 which is connected in series with an RS 232 converter 2614. The RS 232 converter 2614 conditions signals sent from the host computing device 106 via RS 232 cable 2606 and communicates with micro controller 2602. The RS 232 cable 2606 in conjunction with the RS 232 connector 2612 and the RS 232 converter 2614 transfer commands and data (for example turn on and turn off commands), resistance values, resistance profile settings, ramp times, etc. to the micro controller 2602. In some cases, the USB connector can be used to update the firmware of the micro controller 2602.

The micro controller 2602 uses that information to adjust the current supplied to the alternator 122 via the rotor flyback diode 2622. The current input into the DC motor 102 is adjusted via a PWM generator 2622. The current sensor inputs 2610 receive a current value from the current sensor 2426, indicative of the DC motor 102 current. This current value is amplified by a current sensor amplifier 2618 and sent to an error amplifier 2620, which compares the received current value from the current sensor 2426 with a current level set by the user via host computing device 106. The current level set via the host computing device 106 corresponds to a resistance value, and is communicated to the error amplifier 2620 by the micro controller 2602. The error amplifier 2620 adjusts the current value to correspond to the desired resistance and communicates this to the PWM generator 2622. The error amplifier 2620 uses the results of the comparison of the received current from the current sensor 2416 and the current level set by the host computing device 106 to adjust the duty cycle of the PWM generator 2622, and hence adjust the current supplied to the alternator 122 via the rotor driver (FET) 2630. Because the PWM generator 2622 will cause the rotor driver (FET) 2630 to turn off during off times of the set duty cycle, a rotor flyback diode 2632 is connected to the rotor driver (FET) 2630 to deal with the off cycle power, such as by shunting the rotor flyback energy to ground or to the rotor voltage supply depending on whether high side or low side switching is being used.

The micro controller 2602 further adjusts the current supplied to the alternator 122 and thus the DC motor 102 according to position information of the cable 108 sensed by the potentiometer 115, or other position sensing devices, and communicated to the micro controller 2602 via the position pot connector 2608. The micro controller 2602 adjusts the current supplied to the DC motor 102 via the PWM generator 2622, by adjusting the duty cycle of the PWM generator 2622 output. When an elastomeric or reverse elastomeric resistance profile is selected via host computing device 106, the micro controller 2602 in conjunction with position pot 115 and the elastometric digital pot 2624 adjust the input to the PWM generator 2622. In this way, the various resistance profiles described herein can generally be implemented.

The micro controller 2602 further communicates with an analogue switch 2625 that switches between the outward and inward resistances (i.e. Resistance Out and Resistance In). Further, the outputs of the analog switch 2625 are fed to a programmable RC network that allows for discrete turn-around time adjustment (i.e. how fast or slow the resistance values change between In and Out). The micro-controller 2602 determines the direction of the cable 108 and throws the analogue switch(es) 2625 corresponding to the proper resistance value (Resistance In during cable retraction and Resistance Out during cable extension). In this way the micro-controller 2602 simply has to set-and-forget two PWM registers (Resistance In and Resistance Out) until the user stops exercising, for example, for the stepped and resistance elastometric profiles.

An AC motor contactor/relay connector 2634 controls the operation, i.e. the ON and OFF operation, of the AC motor 120 via instructions from a contactor driver 2636. The contactor driver 2636 receives power ON and power OFF commands from the micro controller 2602, which receives such instructions from the host computing device 106. Further, the micro controller 2602 can turn off the DC motor 102 when, for example, the system hasn't been used for a while (there is currently a 30 second timer—if the machine runs without event for 30 seconds, the micro controller will turn off the AC motor 120). In such case, the micro controller 2602 will inform the host computing device 106 that the AC motor 120 has been turned off. In other embodiments, the micro controller 2602 turns on the AC motor 120 and goes through a calibration routine before communicating with the host computing device 106.

A rotor power relay 2626 is also in communication with the micro controller 2602. The rotor power relay 2626 enables power to be supplied to the rotor via the rotor driver FET 2630. The rotor power relay 2626 can also cut power to the alternator 122 when one or more electrical components exceed pre-set operating boundaries, such as when the DC motor 102 exceeds 100 amps, or if motor current exceeds user specification (for example, if the rotor driver FET 2630 short circuits). This condition can be detected by the micro controller 2602 via input received via the current sensing inputs 2610 from the current sensor 2426. Upon detecting this condition, the micro controller 2606 signals to switch the rotor power relay 2626 to OFF, thus preventing damage or further damage from happening to the Electric Weight System 100 and/or the programmable electronic box 101, or as a safety feature, preventing possible injury to the user.

The micro controller 2602, upon instructions from the host computing device 106 to power down, instructs the cable lock solenoid 2628 to engage the ratchet and pawl system to lock the motor shaft 324 so that the position of the cable 108 cannot change when the Electric Weight System 100 is powered OFF. This prevents cable extraction during times when the cable 108 isn't under tension (note that power off tension is present by having the cable fully retracted before power is removed). For the linear chain drive system, having the cable played out isn't a problem, more of a nuisance (and this can be prevented by locking the cable). For the cable drum 908 system it can be a hazard—pulling the un-tensioned cable 108 out can un-spool the cable 108 from the cable drum and further possibly short electrical components or exposed electrical contacts within the programmable electronic resistance box 101. In extreme cases, the cable 108 can un-spool completely off the cable drum 908, thereby requiring a complete cable/drum reassembly (and re-calibration of the position pot 115).

Providing Broad Dynamic Range for DC Motor

Resistance provided by the Electric Weight System 100 is programmable and can be directionally constant and/or positionally variable, regardless of the direction of motion (i.e. cable 108 being pulled outward or retracting inward). During the outward stroke (cable 108 extension), the DC motor 102 moves in the non-preferred direction of rotation, and thus against the alternator-generated voltage that supplies current to the DC motor 102, and will generate a voltage in the opposite polarity of the supplied alternator-generated voltage. This negative motor-generated voltage is directly proportional in amplitude to the cable 108 velocity, with the voltage amplitude being determined by the motor voltage constant, Kv. Motor spinning force is applied such that pulling the cable 108, in the take-up reel embodiment as descried above in reference to FIGS. 9-11C, spins the take-up reel 908, thereby spinning the take-up reel support shaft 910, thereby spinning the DC motor shaft 324 and hence the DC motor 102 in the non-preferred direction of rotation. This motor spinning generates the reverse polarity voltage. In the linear chain drive embodiments described above in reference to FIGS. 1-8, a similar phenomenon can occur.

If the negative voltage is of sufficient amplitude to forward bias the alternator rectifier diodes, it is possible the user will feel an increase in resistance, since the DC motor 102 will generate its own current (thus resistance) through the diodes. The amplitude of the motor-generated current is a function of the alternator-generated supply voltage minus the motor-generated negative voltage, which is cable velocity dependent. As the cable 108 is drawn outward, the controller will reduce supply voltage to the DC motor 102 depending on the speed of the cable 108, and in order to maintain the desired current. Once the supply voltage reaches zero, motor voltage takes over and the (motor) voltage goes negative. In a given configuration, such as a particular motor/shaft gear ratio, if the cable is drawn out slowly enough, the (motor-generated) negative voltage can be insufficient to overcome the supplied voltage resulting in little or no increase in resistance. If the cable is drawn out fast enough to generate enough reverse voltage to (in turn) generate motor current, and this current exceeds the set current, there can be an increase, in resistance.

This increase in resistance can happen when the negative voltage generated by the DC motor 102 is greater than the alternator-generated supply voltage to the motor (which tends towards zero) and that negative voltage difference is of sufficient amplitude to forward bias the alternator rectifier diodes, resulting in a current through the DC motor 102 that is larger than the user set current supplied by the alternator-generated voltage. This motor induced increase in current increases the resistance to the user, in a potentially undesirable way as the resistance experienced thorough cable 108 may be greater than the resistance set by the user.

When a motor shaft, such as DC motor shaft 324, is rotated by an external force a voltage is generated at the DC motor 102 terminals, such that the DC motor 102 generates voltage. The voltage polarity depends on the direction of rotation. If the motor terminals are open, i.e. not connected to anything, the DC motor 102 is relatively easy to spin and the DC motor 102 generates voltage, the amplitude being directly proportional to the speed of the DC motor shaft 324. This RPM/volt relationship is called the motor voltage constant or Kv. If a diode is placed across the DC motor 102 terminals and the DC motor 102 is spun in the direction that would generate a positive voltage to the cathode (thus negative to the anode, so the diode is reverse biased), the DC motor 102 would still be relatively easy to spin. The applicant believes this is because the diode acts as an electrical open circuit providing no current path.

If the diode connection is reversed to be across the DC motor 102 electrical terminals so that the motor spin generates a positive voltage to the anode and negative to the cathode, such as a forward biased diode connection, the DC motor 102 is (much) harder to spin. The applicant believes this is because the diode is limiting the motor voltage output to its forward biased level and providing a current path. A motor-generated current flows through the diode back into the DC motor 102; this motor-generated-and-absorbed power resists (or loads) the spinning force. To make the DC motor 102 spin faster, an increase in the spinning force is required. Since the motor-generated voltage amplitude is limited by the diode, the motor-generated current will increase proportional to the (motor spinning) shaft RPM. In other words, the faster the DC motor 102 is trying to be spun, the harder it is to spin the DC motor 102.

The increase to the resistance adds an alternator-generated voltage component into the example above, but the unwanted effect of motor-generated current should be clear. The manifestation of increased resistance can depend on motor voltage constant Kv, the speed of the cable 108 extension, and/or the shaft/motor gear coupling. The Kv can be determined or is specified, the maximum cable 108 speed can be defined as a constant, such as an acceptable maximum cable speed (generally determined through experimentation), and the shaft/motor gear ratios can be considered separately:

1) First Case—for a given Kv and a maximum cable velocity and where the user has the mechanical advantage, i.e. when the first/second drive gear 330, 352 size is smaller than the DC motor gear 326 size, the increase in resistance generally does not occur. In this case, motor speed is slower than drive shaft 332 speed, and the DC motor 102 is generally not turned fast enough to generate sufficient negative voltage to forward bias the rectifier diodes. The drive circuitry boundaries are usually not exceeded so that the controller 104 always has control of the motor current.

2) Second Case—for a given Kv and a maximum cable velocity and where the DC motor 102 has the mechanical advantage, i.e. when the first/second drive gear 330, 352 size is larger than the DC motor gear 326 size, the increase in resistance can be manifest at lower resistance values and is felt as an increase in user programmed resistance. This increased resistance is proportional to cable speed. In this case, DC motor 102 speed is faster than drive shaft 332 speed, thus turning the DC motor 102 fast enough to generate sufficient negative voltage to forward bias the rectifier diodes. Drive circuitry operational boundaries can be exceeded, and the controller 104 is not able to adjust the motor current, which is, for the duration of outward motion, generated by the DC motor 102, not the alternator 122.

For a given maximum cable extension velocity and as resistance is increased, such as when voltage supplied to the motor is increased, the undesired dynamic increase in resistance can be decreased. The point, referred to herein as the null point, at which the undesired dynamic increase in resistance is no longer present, and thus not felt, is the setting where the motor-generated negative voltage is less than the alternator-generated supply voltage, and the motor generated voltage therefore does not forward bias the rectifier diodes. The null point is located at the resistance value where the maximum cable extension velocity no longer changes the desired motor current. The null point is the lowest set resistance value, or corresponding weight, where the undesired dynamic increase in resistance is not present, thus the user will not notice a cable-velocity-induced increase in resistance (since it does not exist). The undesired dynamic increase in resistance is usually not present for resistance levels exceeding the null point because the user is generally unable to move the cable with sufficient velocity to cause the DC motor 102 to spin fast enough to generate enough negative voltage to exceed the supplied voltage, and thus does not forward bias the alternator diodes. When manifest, the undesired dynamic increase in resistance is increasingly noticeable at the lower ranges of resistance due to the lower motor supply voltage coupled with the tendency and ability of the user to extend/retract the cable quickly at lower resistances.

Particularly in the second case described above and depending on the Kv, maximum cable velocity and configuration, 31% or more of the lower resistance settings may lie below the null point. In some circumstances, it can be desirable to implement an adjustment to recover these resistance settings, thus increasing the dynamic resistance range of the Electric Weight System 100.

Figure 27:
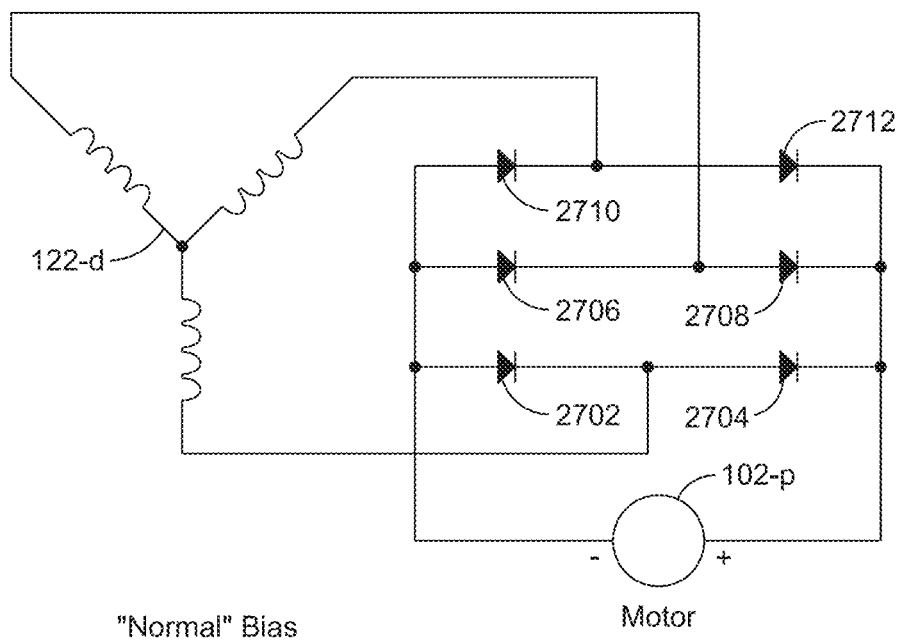
FIG. 27 is an electrical schematic diagram of a motor an Resistance system.

With reference now to FIG. 27, a normal biased DC motor 102 is shown pulling against the user and/or retracting the cable 108. Rectifier diodes 2702 and 2704 are connected in series with the DC motor 102, and connected in parallel with rectifier diodes 2706, 2708, connected in parallel with rectifier diodes 2710, 2712. The alternator supplies 3-phase current to the DC motor 102 via connections in between rectifier diodes 2702 and 2704, in between rectifier diodes 2706 and 2708, and in between 2710 and 2712. In this case, the rectifier diodes 2702-2712 rectify the 3-phase waveform of current supplied from the alternator 122 and appear reverse biased to the DC motor 102. In this way, the controller 104 is still able to control the current supplied to the DC motor.

For the first case described above and depending on the motor used (and particularly with motors having a low Kv), the undesired dynamic increase in resistance may not be present or felt because cable velocity may not make the DC motor 102 spin fast enough to generate sufficient negative voltage to ultimately forward bias the rectifier diodes 2702-2712, so the current, i.e., resistance, always remains within the controllable range.

Figure 28:
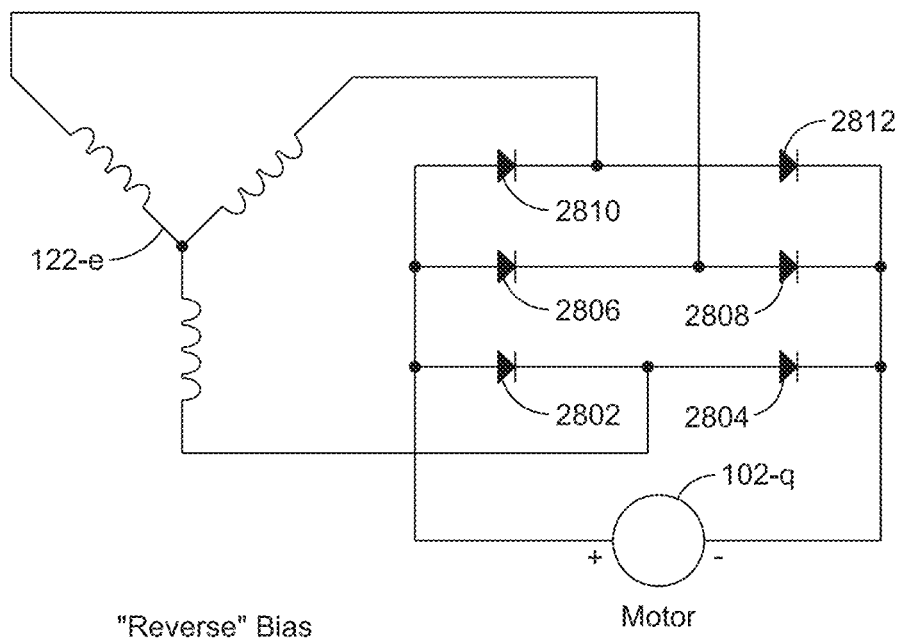
FIG. 28 is an electrical schematic diagram of a motor an Resistance system.

Referring to FIG. 28, a reverse biased DC motor 102 is shown being pulled by the user and moving against the preferred rotational direction, or extending the cable 108. Rectifier diodes 2802 and 2804 are connected in series with the DC motor 102, and connected in parallel with rectifier diodes 2806, 2808, connected in parallel with rectifier diodes 2810, 2812. The alternator supplies 3-phase current to the DC motor 102 via connections in between rectifier diodes 2802 and 2804, in between rectifier diodes 2806 and 2808, and in between 2810 and 2812. The DC motor 102, in this configuration, generates a reverse voltage that subtracts from the supplied voltage, this voltage tending towards zero as the cable is being extended (pulled) (where voltages moves to zero proportional to the speed at which the cable is extended). In this case, the rectifier diodes 2802-2812 rectify the 3-phase waveform of current supplied from the alternator 122 and appear forward biased to the DC motor 102 when the reverse voltage generated by the DC motor 102 is of sufficient magnitude in relation to the supplied voltage from the alternator 122. When the rectifier diodes are forward biased, this in effect shorts out the DC motor 102 leads. As this happens, the supply voltage from the alternator 122 will reduce to zero in an effort to control the increase in resistance.

For the second case described above the undesired dynamic increase in resistance is generally felt because cable velocity can make the DC motor 102 spin fast enough to generate sufficient negative voltage to ultimately forward bias the rectifier diodes, effectively shorting the motor leads together, thus increasing motor load. This rise in current cannot be compensated for by the drive circuitry/controller 104, and the user feels the additional resistance of the outward stroke.

This condition may be adjusted for by placing a resistor, typically a low value resistor, in series with the DC motor 102. The preferred resistance value is as low as possible since the resistor will dissipate power due to the current to/from the motor flowing through this resistor, thus generating heat. The minimum resistor value can be determined iteratively by inserting a resistor in the DC motor 102/alternator 122 connection path, generating maximum cable velocity (outward) at a desired user resistance, and inspecting the results. If the current rises beyond the (user) set value, increase the resistor value. When the current stays constant for all cable velocities, the minimum resistance value for that user setting has been found. An alternative testing method is to monitor the alternator 122 output, or even the DC motor 122 voltage, while running the same stimulation. If, during maximum cable outward excursion, the voltage at the alternator 122, or DC motor 102, swings negative, the resistance value can be increased; if the alternator 122, or DC motor 102, voltage swings to 0V or remains positive (it can go negative but below the rectifier diode forward drops) the resistance value can prevent the loading of the DC motor 102.

This adjusted resistor value can be reduced as the (user) machine resistance is increased, and may be set to zero when the user resistance is set to or beyond the null point. This may be particularly useful in reducing adjusted resistor heat generation/dissipation. By using discrete resistors and FET switches, preferably low Rds-on the devices, controlled by a separate micro controller, for example, a switched resistive network can be configured to optimize performance and reduce heat. An analogue to digital converter is connected to the output of the DC motor 102 and can trigger the micro controller to close or open one or more FET switches, thus increasing or decreasing resistance in the alternator 122/DC motor 102 current path, based on a voltage of the DC motor 102. In some cases, the ADC can be incorporated into the controller 104. In some cases, the DC motor voltage is monitored 20 times per second when power is supplied to the DC motor 102 (i.e., when there is current in the alternator 122/DC motor 102 current path).

In other embodiments, a variable resistance between the DC motor 102/alternator 122 current path can be controlled by a PWM driver. For example, by driving a FET (or other switching device) in parallel with a resistor via a PWM driver, a variable resistance can be achieved by changing the duty cycle of the PWM driver. In a similar manner as described above, an ADC connected to the DC motor 102 can provide a signal to a controller, such as a micro controller or controller 104, that indicates when resistance is needed in the current path (to prevent loading of the DC motor 102). This occurs when the DC motor voltage starts to go negative or approaches a negative value. The micro controller can then configure a duty cycle of the PWM driver to add an appropriate resistance to prevent the DC motor voltage from going negative. In yet other embodiments, either of the above described systems, or others, can detect other DC motor characteristics, outputs, etc. that can indicate that the DC motor voltage is tending towards a negative value. These systems can then account for the negative voltage trend in a similar fashion as described above.

For example, let the null point be 30.67 amps (40 lbs.) with a build configuration of 0.5 lbs. per step, ranging from 0.5 lbs to 127.5 lbs. The maximum cable velocity and Kv are known. Using the procedure to adjust the resistor value (above), adjusted resistor minimum values are determined experimentally to be:

1) 1 Ohm—eliminate the undesired dynamic increase in resistance at 0.5 lbs. (motor current=0.3833 amps)
2) 0.5 Ohms—eliminate the undesired dynamic increase in resistance at 8 lbs. (6.13 amps)
3) 0.25 Ohms—eliminate the undesired dynamic increase in resistance at 16 lbs. (12.27 amps)
4) 0.125 Ohms—eliminate the undesired dynamic increase in resistance at 24 lbs. (18.78 amps)
5) 0.0625 Ohms—eliminate the undesired dynamic increase in resistance at 32 lbs. (24.53 amps)

At 1 Ohm and 0.3833 amps, the adjusted resistor power dissipation would be 0.147 Watts, ranging up to 37.6 Watts at 6.13 amps. If the adjusted value remains at 1 Ohm, power dissipation at 10 amps (roughly 13 lbs.) would be 100 Watts. The null point adjusted power dissipation would be 940.6 Watts, and at 127.5 lbs. would be 9565 Watts.

Using the derived adjusted resistor values for the different user resistance ranges up to the null point yields the following adjusted power dissipations:
1) 1 Ohm—from 0.383 amps to 6.13 amps, 0.147 Watts to 37.6 Watts
2) 0.5 Ohm—from 6.13 amps to 12.27 amps, 18.79 Watts to 75.3 Watts
3) 0.25 Ohm—from 12.27 amps to 18.78 amps, 37.6 Watts to 88.1 Watts
4) 0.125 Ohm—from 18.78 amps to 24.53 amps, 44.1 Watts to 75.2 Watts
5) 0.0625 Ohm—from 24.53 amps to 30.67 amps, 37.6 Watts to 58.8 Watts The power dissipation can be further reduced by only allowing current flow through the adjusted resistors during the outward stroke. Since the DC motor 102 does not generate voltage during the inward stroke (preferred rotational direction), adjusted resistance is not necessary. By shorting the adjustment during the inward stroke, current does not flow through the adjustment, and there is no, or only minimal, power dissipation at that time. If the inward stroke time equals the outward stroke time, the power dissipations would be half. Furthermore, increased motor current generally happens during the inward stroke (the negative), so the adjusted resistors are spared having to dissipate that (higher) current.

Maintaining a short circuit across the adjusted network from the null point up to the maximum user resistance setting reduces the power dissipation (and thus the required power to run the system). For example, if a shorting FET has an Rds-on of 0.0045 Ohm maximum, the network power dissipation at the null point would be 4.23 Watts; at 98 amps it would be 43.2 Watts. If two of these FET devices were paralleled, the power dissipation would be 2.12 and 21.6 Watts respectively. This can provide the advantage of maximizing energy efficiency and reducing power dissipation. In addition, the adjusted resistor presence can aid in drive circuitry smoothing, particularly at the lower resistance levels.

Figure 29:
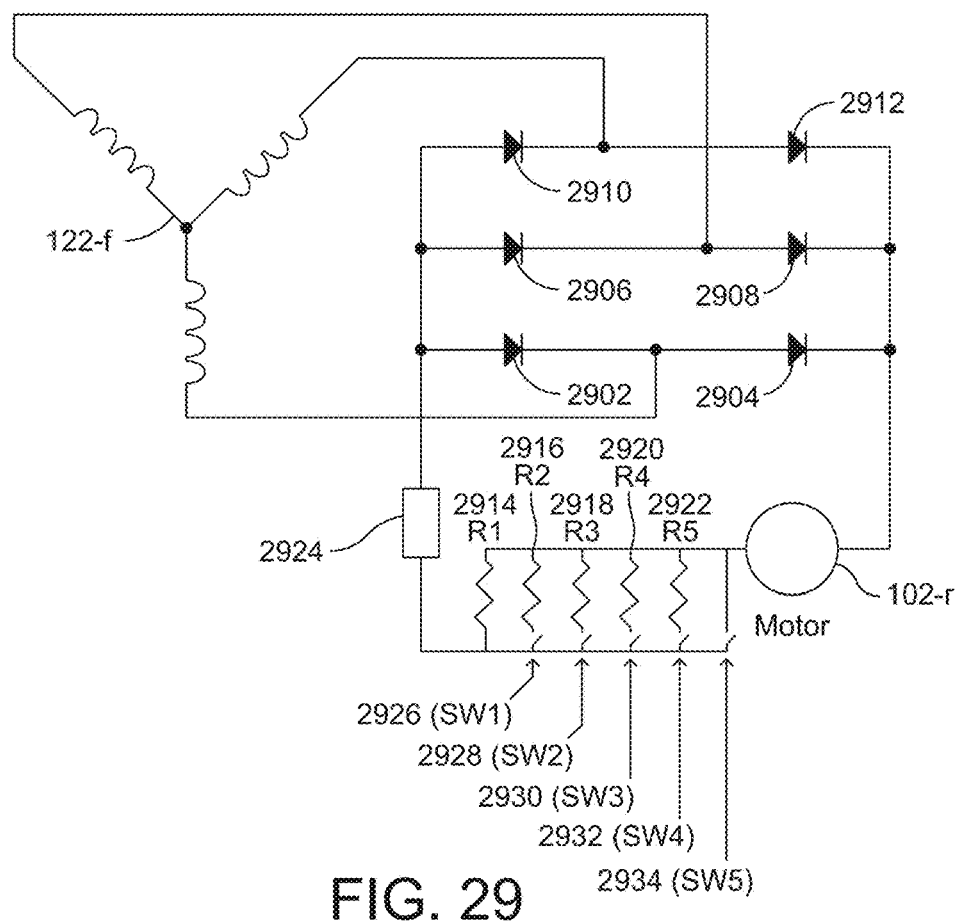
FIG. 29 is an electrical schematic diagram of a motor an Resistance system.

With reference now to FIG. 29, a DC motor 102 is shown with a rectifier circuit rectifying a supply current from an alternator 122. Rectifier diodes 2902 and 2904 are connected in series with the DC motor 102, and connected in parallel with rectifier diodes 2906, 2908, connected in parallel with rectifier diodes 2910, 2912. The alternator supplies 3-phase current to the DC motor 102 via connections in between rectifier diodes 2902 and 2904, in between rectifier diodes 2906 and 2908, and in between rectifier diodes 2910 and 2912. A bank of 5 resistors, R1 2914, R2 2916, R3 2918, R4 2920, and R5 2922 are all connected in parallel with each other, the bank of resistors connected in series with the DC motor 102 and a low side current sensor 2924, which is connected in series with R1 2914. 5 switches, SW1 2926, SW2 2928, SW3 2930, SW4 2932, and SW5 2934 are connected to the resistor bank in such a way as to adjust which resistor(s) is actually connected in the path from the low side current sensor 2924 to the DC motor 102. Opening all the switches, e.g., SW1 2926-SW5 2934, connects only R1 2914 between the low side current sensor 2924 and the DC motor 102. Closing SW1 2926, e.g., connects R1 2914 and R2 2916 between the low side current sensor 2924 and the DC motor 102. Opening SW3 2930, SW4 3932, and SW5 2934 with SW1 2926 and SW2 2928 closed, for example, connects R1 2914, R2 2916, and R3 2918 between the low side current sensor 2924 and the DC motor 102, and so on.

In some embodiments, R1 2914=1 Ohm, R2 2916=1 Ohm; R3 2918=0.5 Ohm; R4 2920=0.25 Ohm; and R5 2922=0.125 Ohm. However, other resistor values may be used for various reasons, such as the current requirements of the DC motor 102, for example. In this embodiment, with SW1 2926-SW5 2934 open, the adjusted resistance is 1.0 Ohm, and with SW1 2926-SW5 2934 closed, the adjusted value is 0.5 Ohm. With this implementation, the minimum resistance can be implemented for a given weight/resistance level set by the user to maximize power efficiency while providing an accurate and un-affected consistent weight/resistance level to the user.

Figure 30:
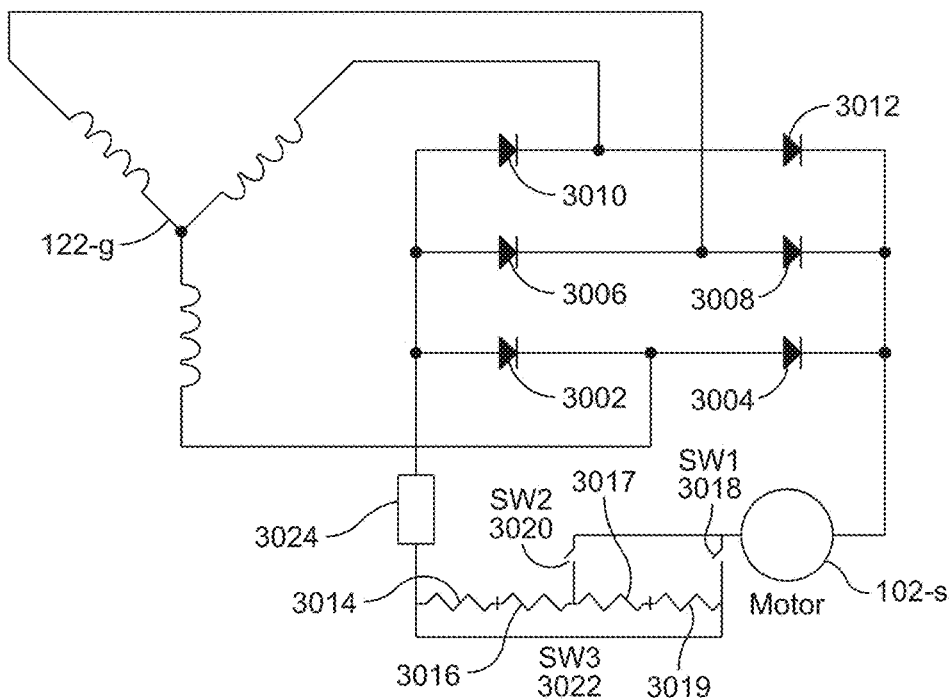
FIG. 30 is an electrical schematic diagram of a motor an Resistance system.

With reference now to FIG. 30, a DC motor 102 is shown with a rectifier circuit rectifying a supply current from an alternator 122. Rectifier diodes 3002 and 3004 are connected in series with the DC motor 102, and connected in parallel with rectifier diodes 2906, 2908, connected in parallel with rectifier diodes 3010, 3012. The alternator supplies 3-phase current to the DC motor 102 via connections in between rectifier diodes 3002 and 3004, in between rectifier diodes 3006 and 3008, and in between rectifier diodes 3010 and 3012. A bank of 4 resistors, R1 3014, R2 3016, R3 3017, and R4 3019 are connected in series with each other, the bank of resistors connected in series with the DC motor 102 and a low side current sensor 3024, which is connected in series with R1 3014. 3 switches, SW1 3018, SW2 3020, and SW3 3022 are connected to the resistor bank in such a way as to allow R1 3014, R2 3016, or R1 3014 and R2 3016 to be connected in the path from the low side current sensor 3024 to the DC motor 102.

In some embodiments, R1 3014=R2 3016=R3 3017=R4 3019=0.25 Ohm. However, other resistor values can also be used. In this embodiment, closing SW1 3018 places 1.0 Ohm in series with the DC motor 102. Closing SW2 3020 and SW3 3022 while leaving SW1 3018 open, places 0.5 Ohm in series with the DC motor 102. Closing SW1 3018 and SW3 3022 shorts the resistor network, such as to eliminate all excess power dissipated in the resistor bank when the velocity of the motor is equal to or above the null point.

It should be appreciated that the above resistor configurations are only examples. Other such means are also contemplated herein.

In some embodiments, the resistor/switch combinations can be replaced with a FET having the same on resistance as the resistor being switched into the circuit. For example, replacing the 1 Ohm resistor with a FET having an Rds-on of 1 Ohm, the second 1 Ohm resistor/switch with a FET having an Rds-on of 1 Ohm and/or replacing the 0.5 Ohm resistor/switch with a FET having an Rds-on of 0.5 Ohms, etc. In this way, the resistor is eliminated and only one or more switches (FETs) are used.

Certain embodiments of the resistance apparatus, system and methods are described with reference to methods, apparatus (systems), and computer program products that can be implemented by computer program instructions. These computer program instructions can be provided to a processor of a general purpose computer, special purpose computer, mobile computing device, or other programmable data processing apparatus to produce a machine, such that the instructions, which execute via the processor of the computer or other programmable data processing apparatus, create means for implementing the acts specified herein to transform data from a first state to a second state.

These computer program instructions can be stored in a computer-readable memory that can direct a computer or other programmable data processing apparatus to operate in a particular manner, such that the instructions stored in the computer-readable memory produce an article of manufacture including instruction means which implement the acts specified herein. The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the acts specified herein.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but in the alternative, the processor can be any conventional processor, controller, microcontroller, or state machine. A processor can also be implemented as a combination of computing devices such as, for example, a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, a hard disk, a removable disk, a CD-ROM, or any other form of computer-readable storage medium known in the art. An exemplary storage medium is coupled to a processor such that the processor can read information from, and write information to, the storage medium. In the alternative, the storage medium can be integral to the processor. The processor and the storage medium can reside in an ASIC. The ASIC can reside in a computer terminal. In the alternative, the processor and the storage medium can reside as discrete components in a computer terminal.

Depending on the embodiment, certain acts, events, or functions of any of the methods described herein can be performed in a different sequence, can be added, merged, or left out all together (e.g., not all described acts or events are necessary for the practice of the method). Moreover, in certain embodiments, acts or events can be performed concurrently such as, for example, through multi-threaded processing, interrupt processing, or multiple processors or processor cores, rather than sequentially. Moreover, in certain embodiments, acts or events can be performed on alternate tiers within the architecture.

Figure 73:
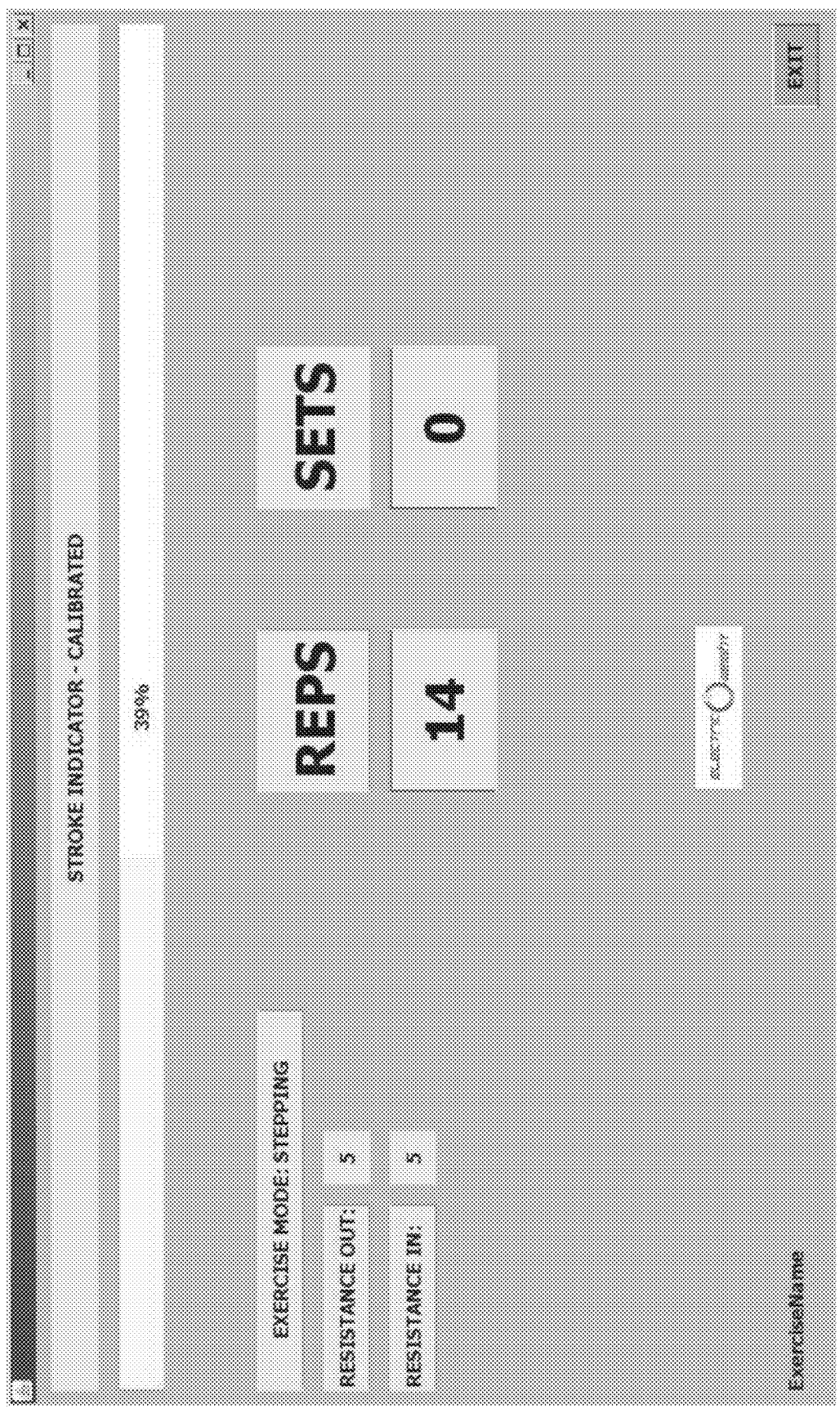
FIG. 73 is a screen capture of the exercise screen displayed on the host device of FIG. 31.
Figure 74:
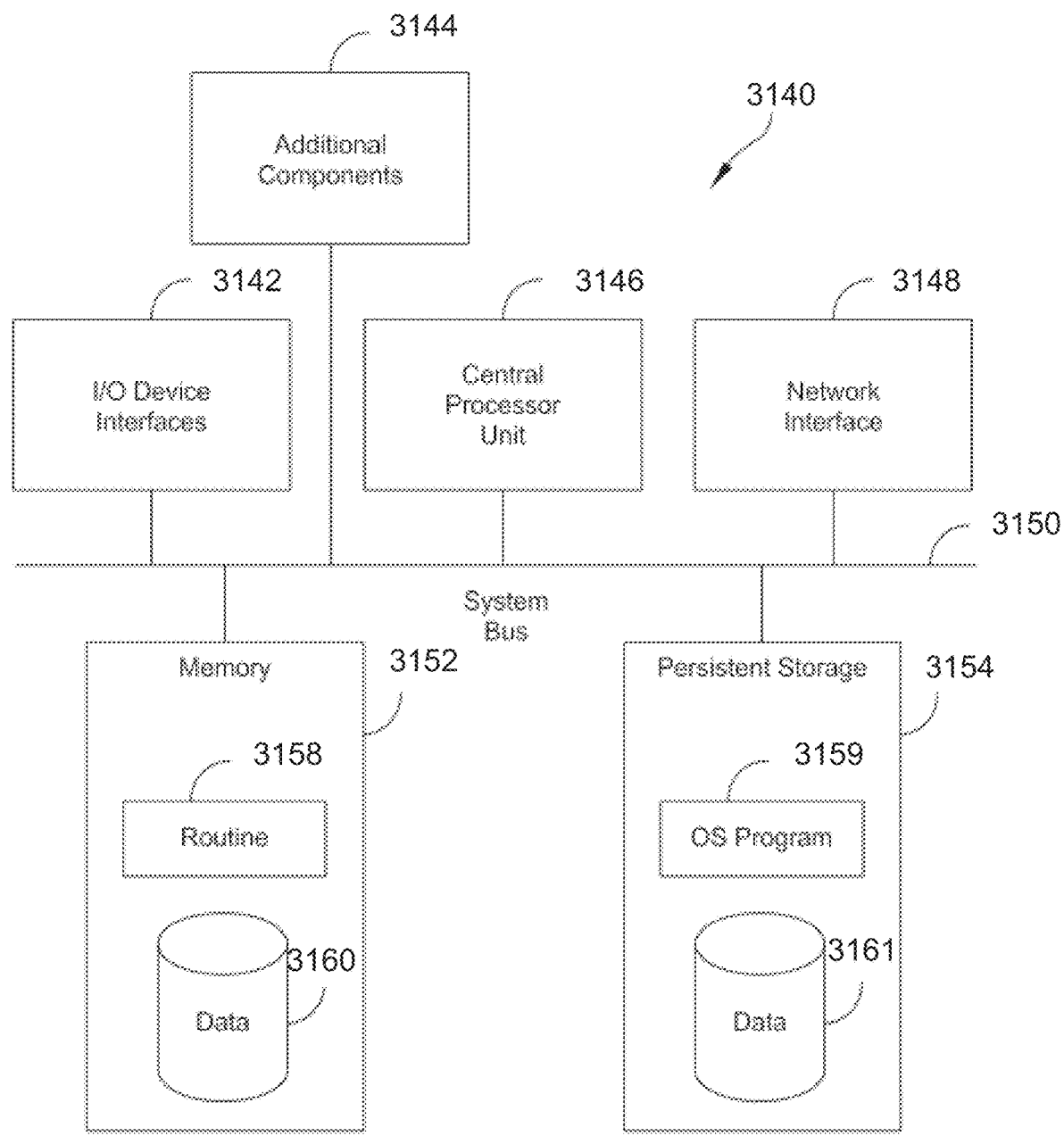
FIG. 74 is a block diagram of the internal structure of a computer used in the computer network of FIG. 31.

With reference to FIG. 73, each component of the host 3140 is connected to a system bus 3150, providing a set of hardware lines used for data transfer among the components of a computer or processing system. Also connected to the bus 3150 are additional components 3144 of the resistance system, such as additional memory storage, digital processors, network adapters, and I/O devices. The bus 3150 is essentially a shared conduit connecting different elements of a computer system (e.g., processor, disk storage, memory, input/output ports, network ports, etc.) and enabling transfer of information between the elements. An I/O device interface 3142 is attached to system bus 3150 in order to connect various input and output devices (e.g., keyboard, mouse, touch-screens, displays, printers, speakers, etc.) to the resistance system. A network interface 3148 allows the computer to connect to various other devices attached to a network. A memory 3152 provides volatile storage for computer software instructions 3158 and data 3160 used to implement methods employed by the system disclosed herein. Disk storage 3154 provides non-volatile storage for computer software instructions 3159 and data 3161 used to implement an embodiment of the present disclosure. A central processor unit 31346 is also attached to system bus 3150 and provides for the execution of computer instructions.

In some embodiment, the processor routines 3158 and data 3160 are a computer program product, including a computer readable medium (e.g., a removable storage medium such as one or more DVDROM's, CD-ROM's, diskettes, tapes, etc.) that provides at least a portion of the software instructions for the system. A computer program product that combines routines 58 and data 60 may be installed by any suitable software installation procedure, as is well known in the art. In certain embodiments, at least a portion of the software instructions may also be downloaded over a cable, communication, and/or wireless connection.

Figure 31:
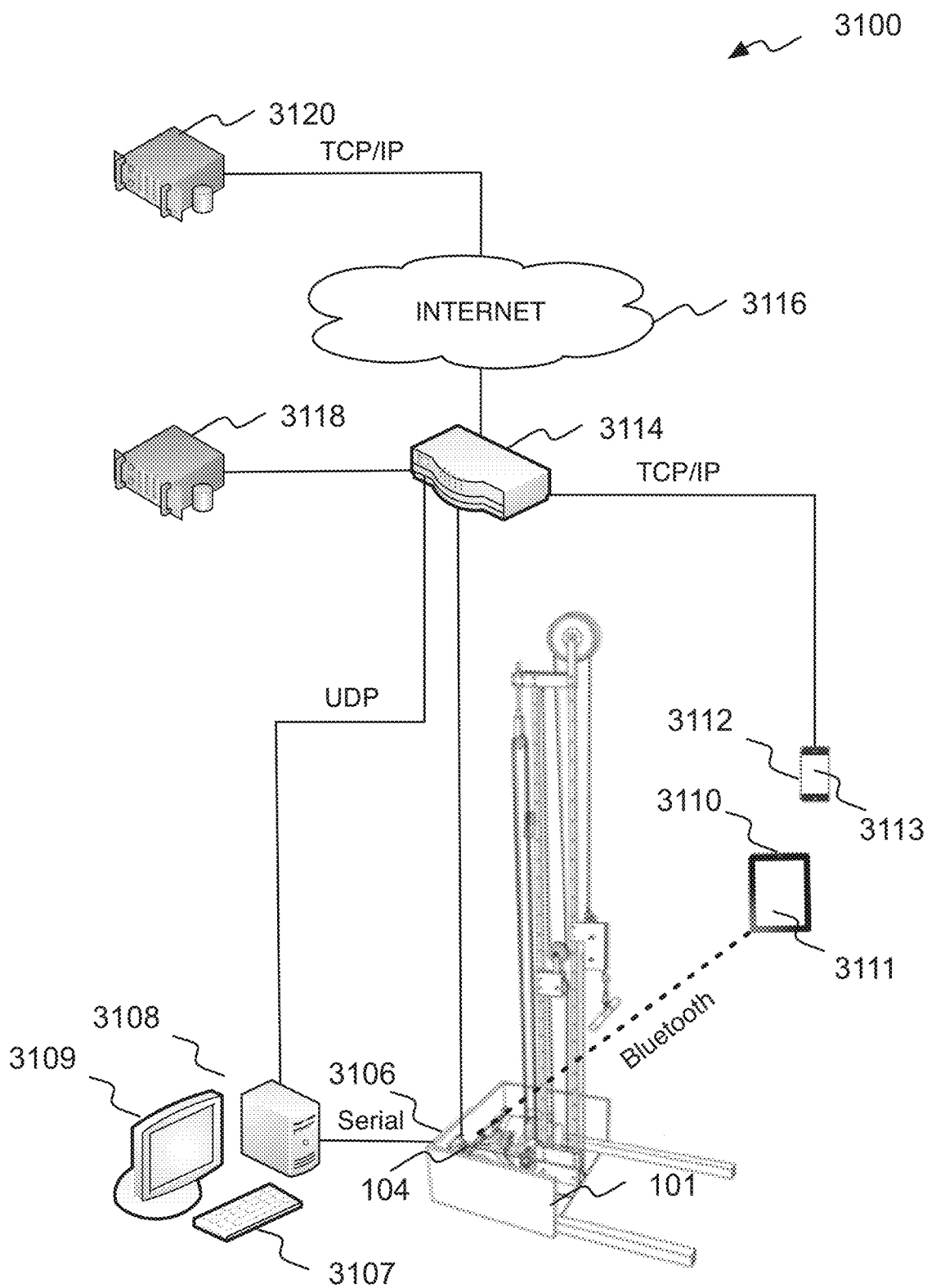
FIG. 31 is a is a block diagram of a programmable resistance system in accordance with various embodiments.

Referring now to FIG. 31, a programmable electronic resistance box 101 includes at least one force-generating apparatus controlled by a controller 104. Controller 104 is communicatively coupled to one or more host computer devices 3108, 3110, 3112, which may be external to the programmable electronic resistance box 101. The controller 104 includes a microprocessor configured to, for example, receive position signals, receive messages from host computing devices, process messages from host computing devices, and send message to host computing devices. Host computing devices 3108, 3110, 3112 may communicate over various protocols such as, for example, RS-232, UDP, TCP/IP and/or HTTP.

The host computing device 3108, 3110, 3112 generally includes an input interface, for example, a keyboard or keypad 3107 such that exercise profiles can be generated, a non-transitory memory configured to persistently store and recall exercise profiles, a communication interface configured to send and receive exercise data, and a display 3109, 3111, 3113 configured to present exercise related information. The controller 104 may have one or more communication interfaces such as, for example, a network interface, a serial connection interface, a short-wavelength radio transmissions interface, such as a bluetooth wireless interface, configured to facilitate communication with host computing devices and/or with a communication network such as the Internet.

A computing network or similar digital processing environment in which the system and method disclosed can be implemented. The present systems and methods can also run on different computing architectures that may include a LAN, WAN, stand-alone PC, stand-alone mobile device, and/or on board processing components. The computing environment 3100 of FIG. 31 is representative of many specific computing arrangements that can support the system and method disclosed. In some embodiments, the host computing device 3108 communicates with the controller over a serial connection. The software on the host computing device 3108 is implemented to run in a java runtime environment on various operating systems such as, for example Windows®, or UNIX®, and in any hardware having enough power to support timely operation of software. In some instances, host computer devices are deployed as virtual instances rather than physical computing devices.

A router 3114, such as for example, the Peplink® Multi Wan Router can distribute traffic inside a local area network, and/or to and from devices external to the local area network, such as data stores hosted remotely 3120 and connected to the Internet 3116. In some deployments, persistent data stores 3118, 3120 are relational databases, xml databases, or the like.

On reading this disclosure, those of skill in the art will recognize that many of the components discussed as separate units may be combined into one unit and an individual unit may be split into several different units. Further, the various functions could be contained in one computer or spread over several networked computers and/or devices. The identified components may be upgraded and replaced as associated technology improves and advances are made in computing technology.

At initial power-on, the controller 104 (See FIG. 1) checks for stored configuration data. If configuration data is present, the controller 104 sends the configuration data to the host 106 (See FIG. 1), then enter the main firmware program. If configuration data is not present, a controller routine loops in the enter configuration mode until a configuration command is received. In certain implementations, while in the enter configuration mode, a visual indicator can be provided, such as, for example, an on-board LED. The controller will not respond to commands from the host 106 and waits for the byte stream ($20$40) to continue with the configuration process.

In some instances, configuration information is stored in the controller's onboard, non-volatile EEPROM and/or an alternative persistent memory store. Configuration data can include, for example, shaft to position potentiometer gear ratio, motor sprocket 326 tooth count, shaft sprocket 912 tooth count, position potentiometer zero position, and take up reel 908 diameter. In some embodiments, the shaft 912 directly drives the position potentiometer 115 resulting in a one to one ratio. The motor drive shaft sprocket 912 tooth count and take-up reel 908 diameter information can be used to determine the absolute minimum and maximum resistances. In some embodiments, a position potentiometer zero position identifies to the controller 104 the appropriate cable 108 position at power up. A controller routine can be implemented that retracts a cable 108 to obtain the position potentiometer zero position. The user type can determine a mode of operation and a host computing device 106 user interface tailored to a particular user configuration, such as, for example, a single user configuration or a multiple user configuration. The firmware version of the controller 104 firmware can be used, in part, to determine when software or firmware upgrades are appropriate.

Figure 32:
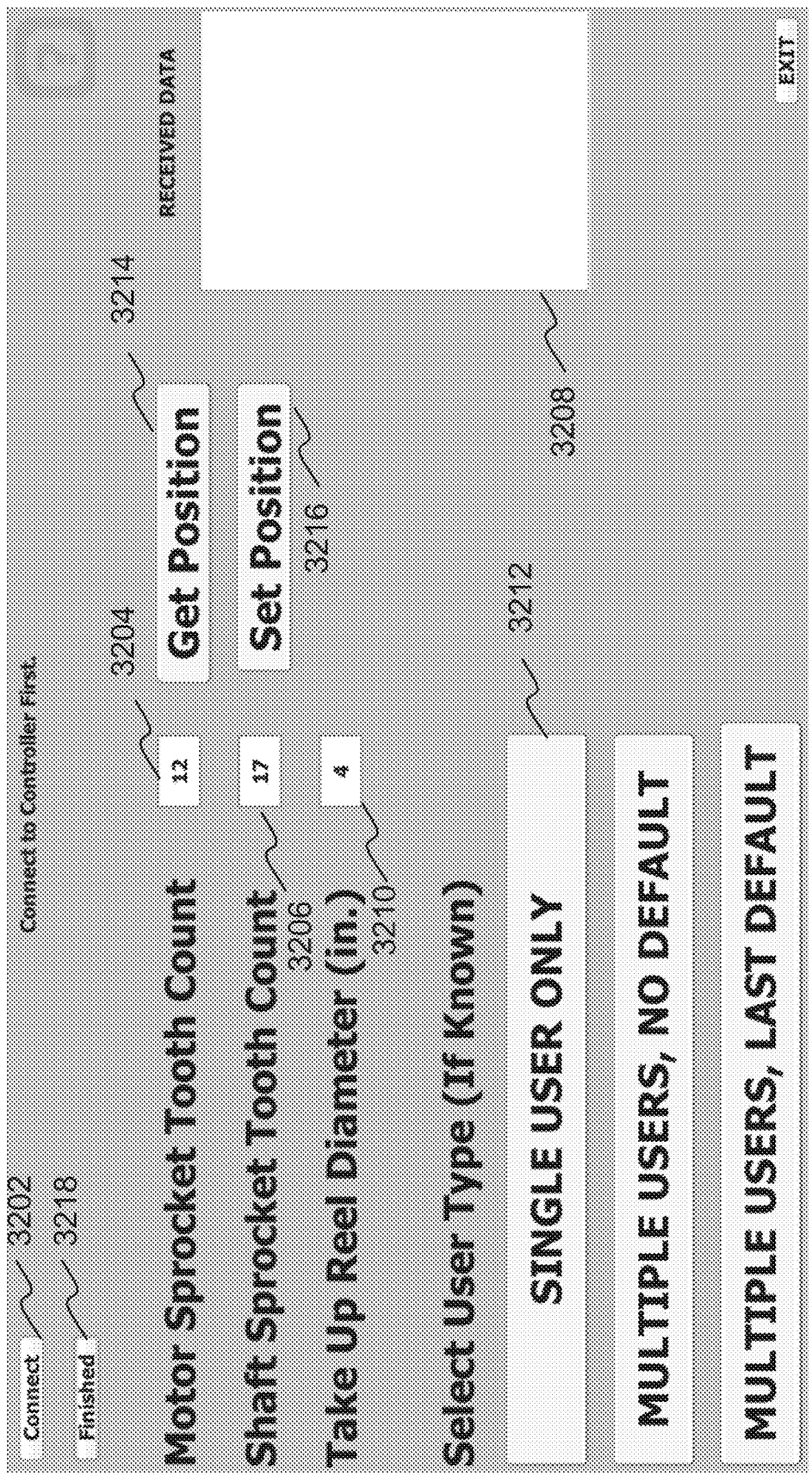
FIG. 32 is a screen capture of a configuration interface displayed on the host device of FIG. 31.

Referring now to FIG. 32, an example of configuration interface on the host 106 is displayed. The host 106 opens a serial communication port and establishes communication with the controller 104. In some embodiments, communication is established via an ethernet connection, an RS-232 connection, or wireless connection. In certain implementations, a connect button 3202 directs the host to send the byte stream ($20$40) to the controller 104. The controller 104 then enters a configuration loop and the byte stream ($40) is sent to the host 106. Edit boxes can be displayed to collect configuration data such as, for example, motor sprocket tooth 326 count 3204, shaft sprocket 912 tooth count 3206, and take up reel 908 diameter 3210. User-specific configurations can be set through selection of user interfaces controls such as selection buttons 3212. In some embodiments, the position potentiometer zero position is set by adjusting the position potentiometer to a candidate position, executing a get position operation upon detection of a Get Position button 3214 press event, obtaining the current position from the position potentiometer 115 displaying the position 3208, and saving the displayed position as the position potentiometer zero position in the controller EEPROM upon detection of a Set Position button 3216 press event. In some embodiments, a visual indicator can change its display pattern or state, for example, an LED strobe pattern is altered, until the remainder of the configuration process is completed. When the host detects a Finished button 3218 press event, the values are marshaled and sent to the controller. During the configuration loop, in some instances, the controller polls the serial port or other engaged communication port awaiting the following commands, echoing with acknowledgments;

| | | |
|---|---|---|
| a) $42/xy- | Motor Sprocket Tooth Count | (Echo $42); |
| b) $43/xy- | Shaft Sprocket Tooth Count | (Echo $43); |
| c) $44/xy- | Take Up Reel Diameter | (Echo $44); |
| d) $45/xy- | User Type | (Echo $45/xx); |
| e) $4F- | Exit configuration loop | (Echo $4F); |
| f) User Type ($45/xy)-$00-Single, $01-Multi, $02-Multi w/default. | | |

In other embodiments, configuration information might include sprocket diameter or tooth count for the chain drive (as opposed to cable drum 908) system.

The controller 104 parses the byte stream and stores the information in onboard, non-volatile EEPROM and/or an alternative persistent memory store. The controller 104 then proceeds to an operational mode, entering the main controller 104 firmware program. In some embodiments, the visual indicator display pattern and/or state is changed to indicate the change in operational mode.

Figure 33:
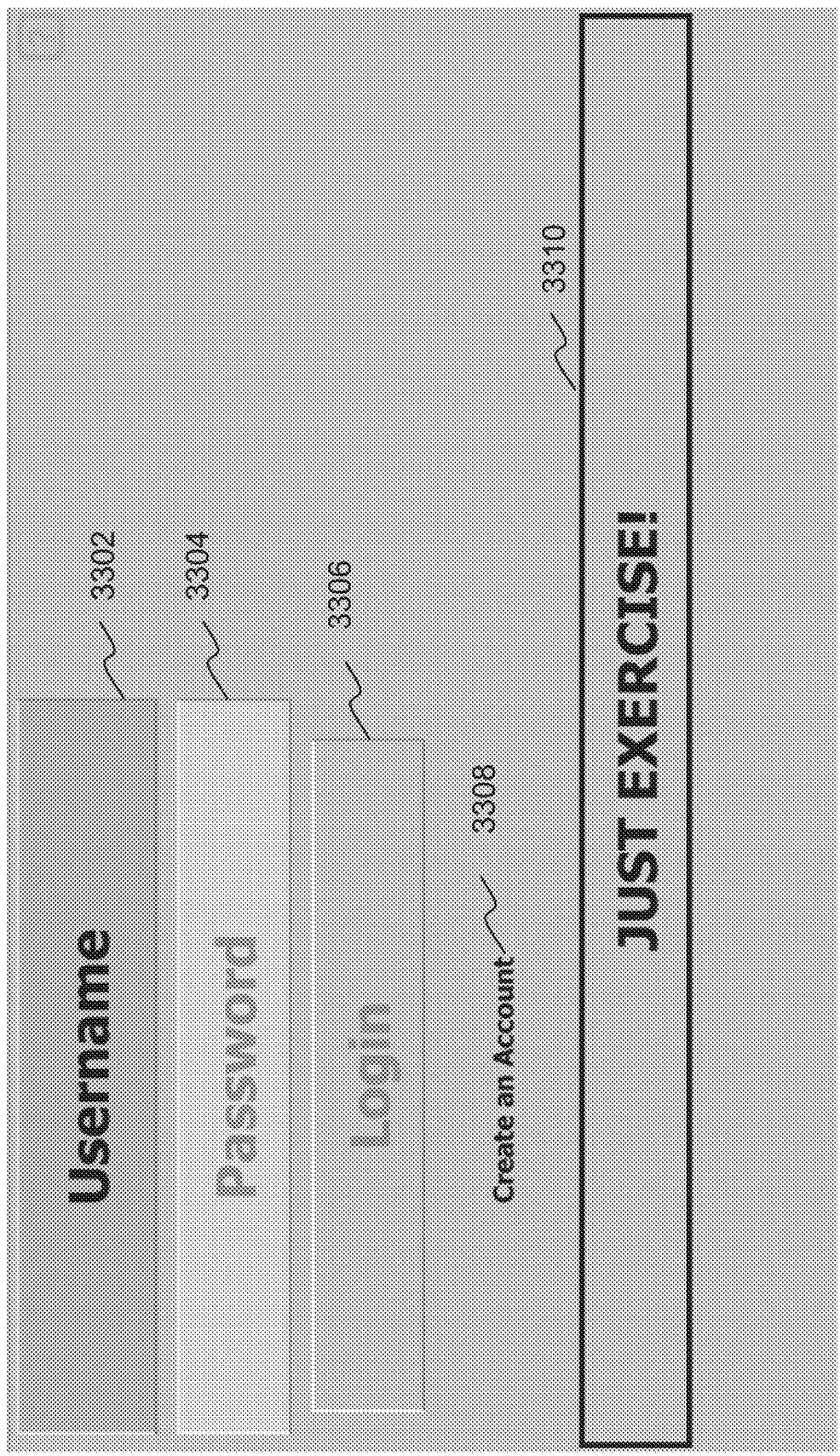
FIG. 33 is a screen capture of a login interface displayed on the host device of FIG. 31.
Figure 34:
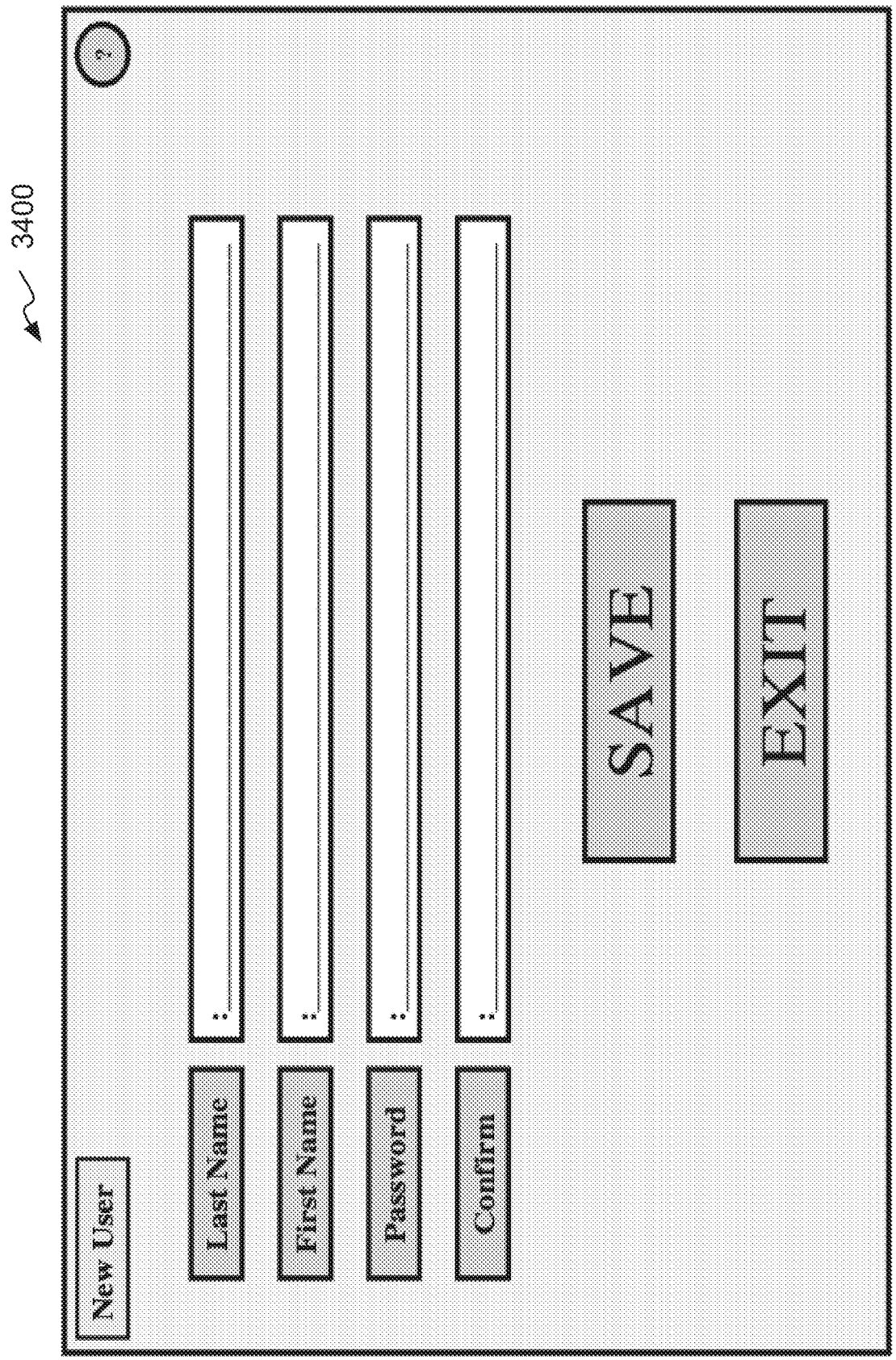
FIG. 34 is a screen capture of an account creation interface displayed on the host device of FIG. 31.
Figure 35:
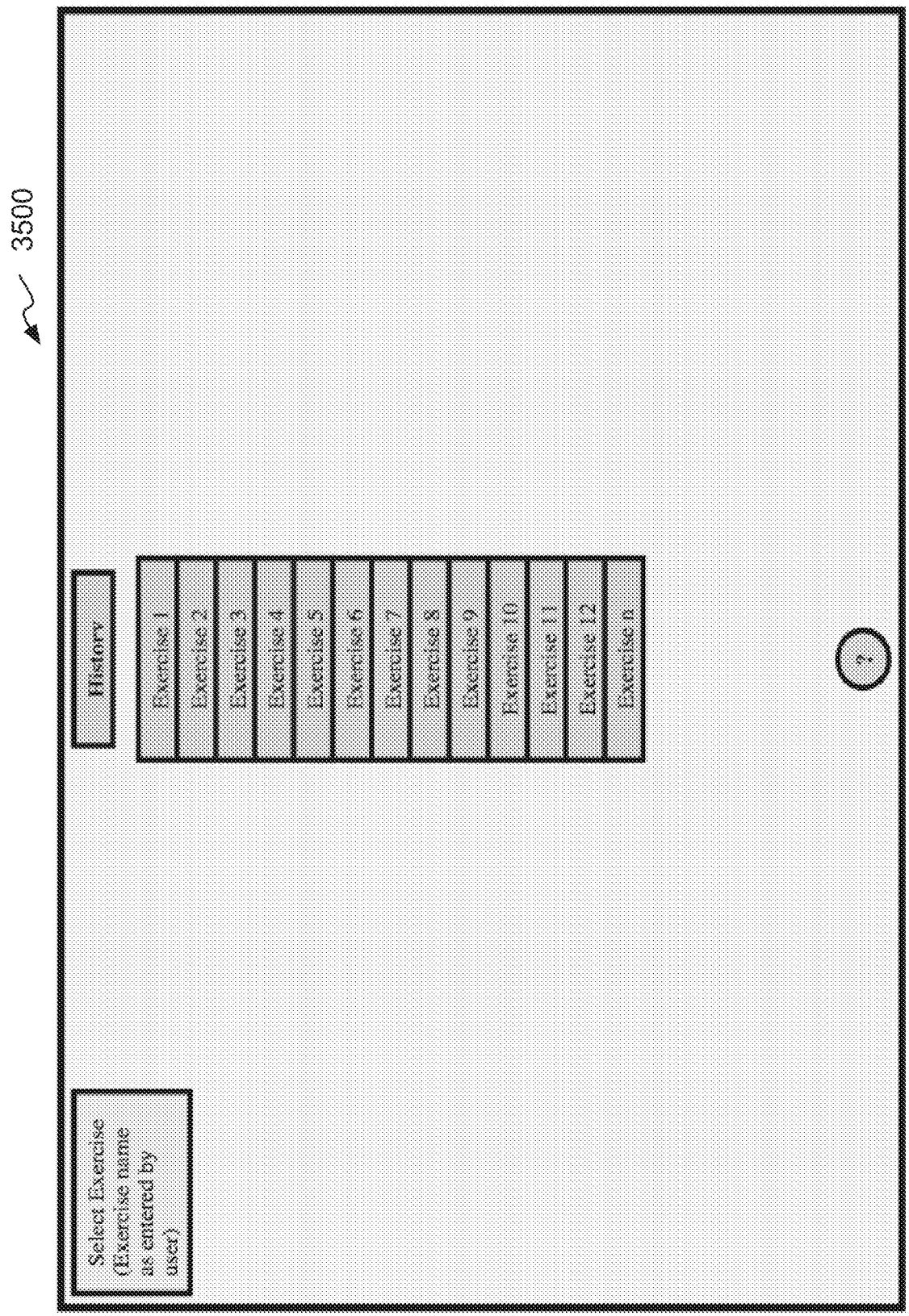
FIG. 35 is a screen capture of exercise history displayed on the host device of FIG. 31.
Figure 36:
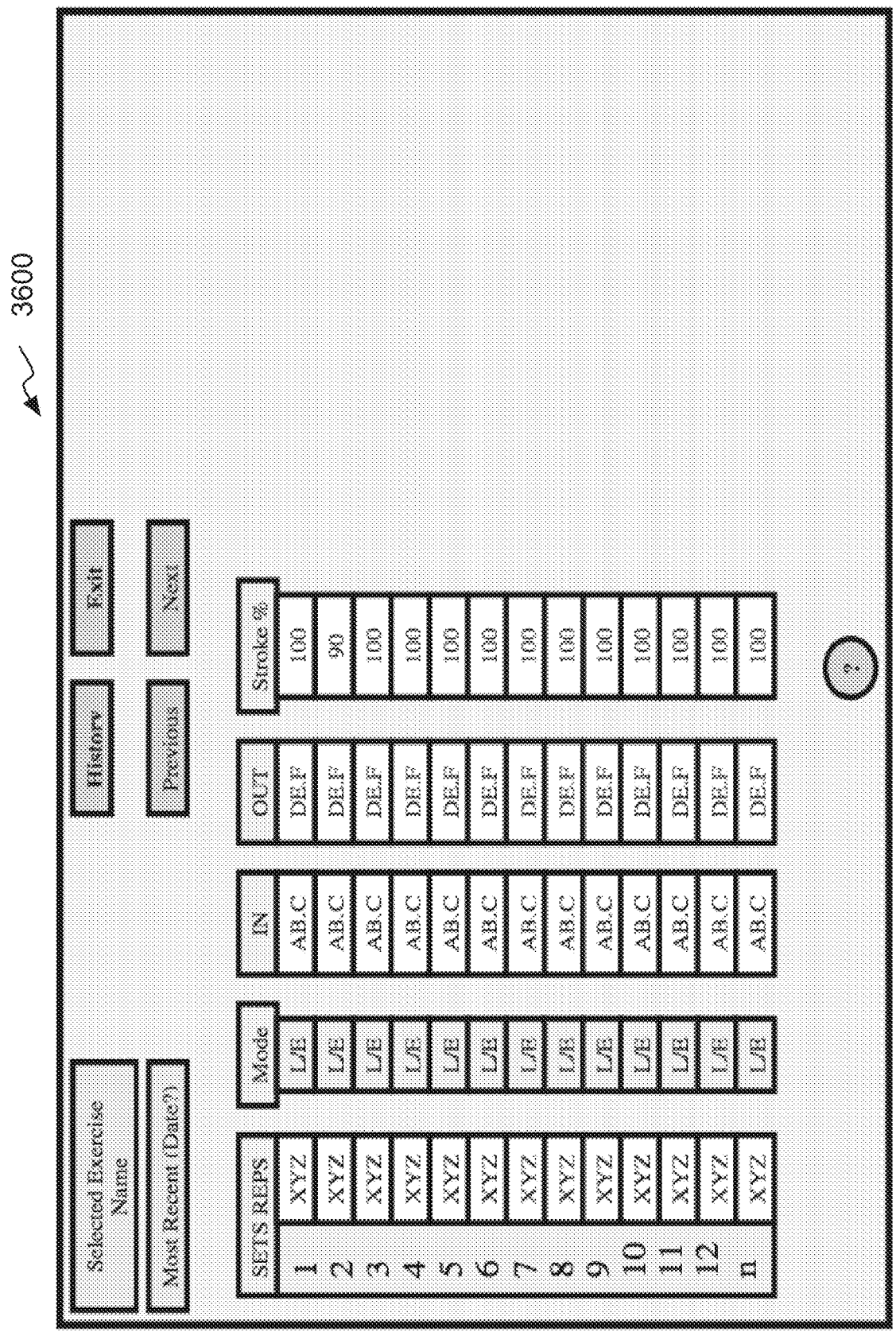
FIG. 36 is a screen capture of exercise history displayed on the host device of FIG. 31.

In some instances, access to the resistance system is conditioned on the entering of user credentials. Referring now to FIG. 33 and FIG. 34, username and password prompts are displayed 3302, 3304 configured to receive user credentials. When the host detects the press event for the Login button 3306, the credentials are marshaled and sent to the controller 104 for validation with credentials stored in the controller's onboard, non-volatile EEPROM and/or an alternative persistent memory store. In some embodiments, credentials are stored external to the programmable electronic resistance box 101, either on the host 106 and/or on a networked data store 3118, 3120 (see FIG. 31) communicatively coupled to the host 106. In some embodiments, a create account control 3308 is displayed allowing a user to create an account. When the host 106 detects the click event for a create account control 3308, a new display window 3400 is displayed. In other embodiments, user accounts are created through an interface accessible to only specific users, for example, a trainer. Referring now to FIG. 35 and FIG. 36, exercise history associated with a one or more users can be stored on the host 106, on the controller 104, and/or in a remote data store 3118, 3120 communicatively coupled to the host. In some systems, exercise history can be organized by exercise 3500, and include exercise specific data such as, for example, repetition and stroke specific information 3600. Referring again to FIG. 33, a Just Exercise button 3310 can be enabled that allows a user to access the user screen and operate the resistance system without logging into a user account.

Figure 37:
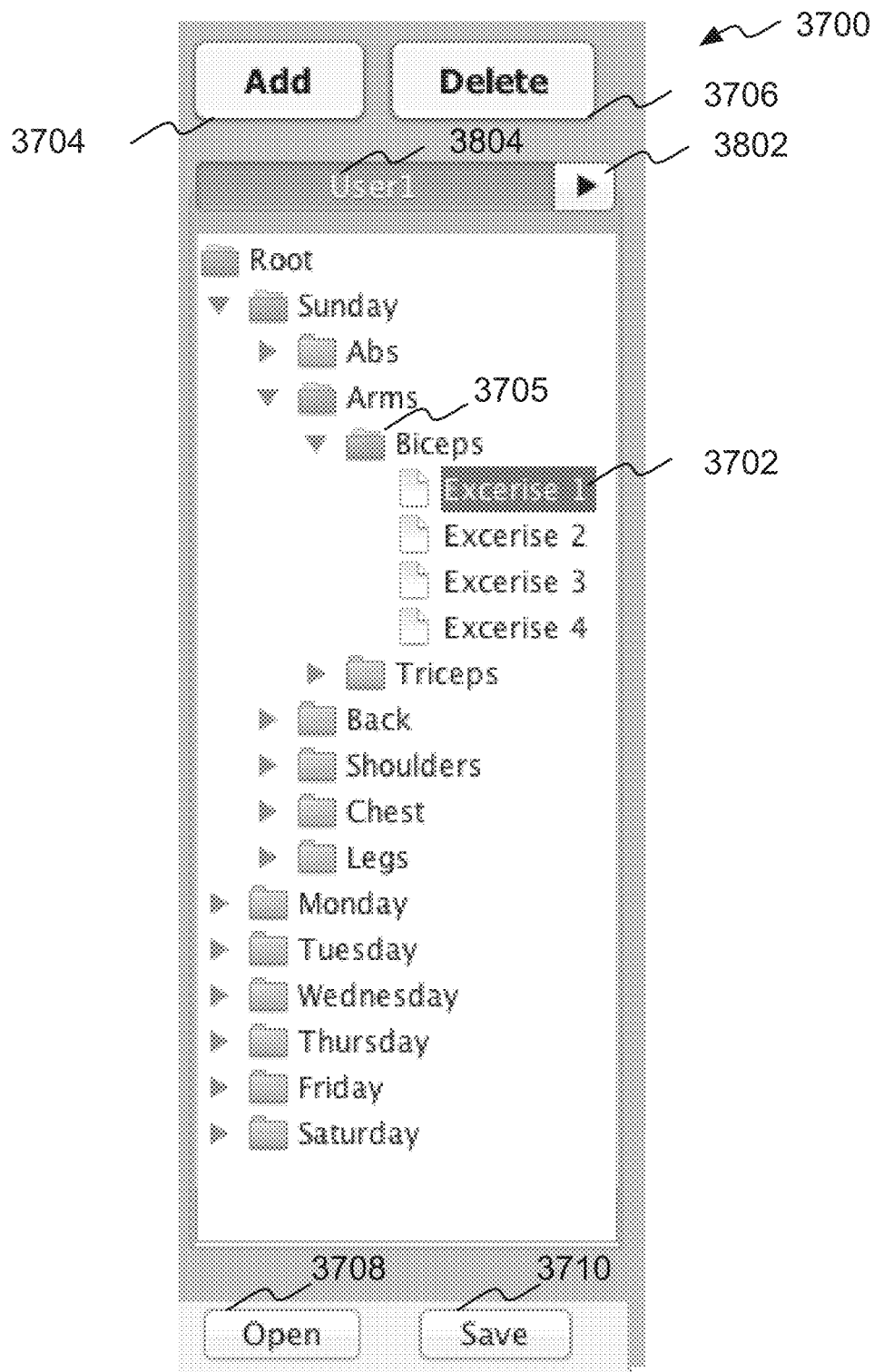
FIG. 37 is a screen capture of the stored exercise profile pane displayed on the host device of FIG. 31.
Figure 38:
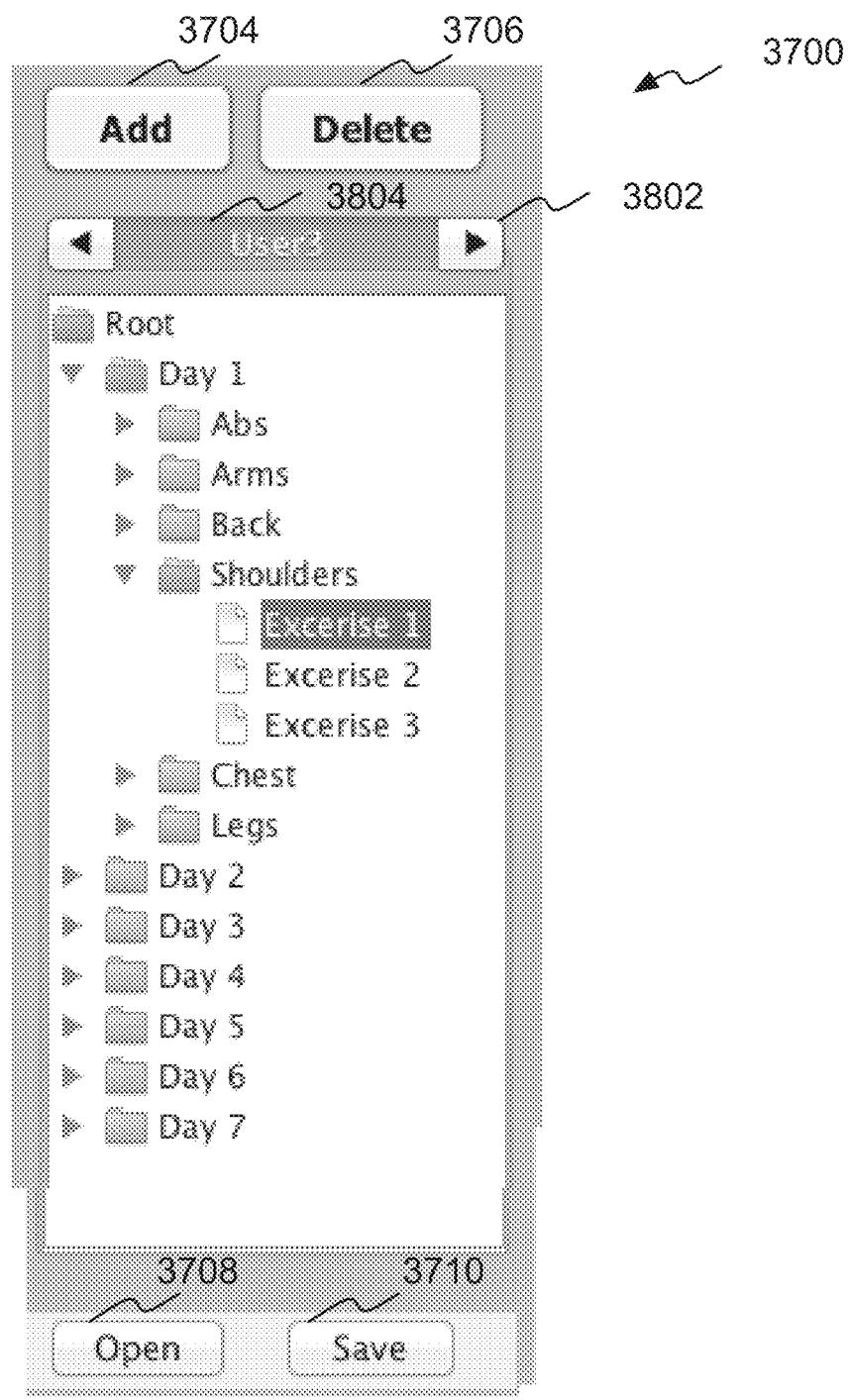
FIG. 38 is a screen capture of the stored exercise profile pane displayed on the host device of FIG. 31.

In certain embodiments, the host supports the storage of and toggling between multiple users during an exercise session. Referring now to FIG. 37, users can design and save exercise profiles 3702. These profiles 3702 can be organized, for example, in a hierarchical folder structure by adding folders and displayed in a stored profile pane 3700. In some embodiments, when the host computing device 106 detects the Add button 3704 press event, a folder 3705 is created. In some instances, the folder can be dragged from one level to another level, and/or to different locations within a level. When the host computing device 106 detects the press event for the Delete button 3706, the selected exercise profile or folder will be deleted. If the folder contains exercise profiles and folders, all contents will also be deleted. The host will open a selected exercise profile and populate the values in the exercise profile pane 3900 (see FIG. 39) when an Open button 3708 press event is detected by the host 106. When a Save button 3710 press event is detected, the current exercise profile displayed in the stored profiles pane 3700 will be saved and an exercise profile will be added to the folder structure in the stored profiles pane 3700. In some embodiments, the host computing device 106 can store exercise profiles for multiple users in an onboard persistent data store and/or on a networked data store communicatively coupled to the host. Referring now to FIG. 38, when a toggle button 3802 press event is detected, the user display 3804 moves from one user to another. The stored exercise profile pane 3700 and the exercise profile pane 3900 (not shown) are updated with the hierarchical structure and exercise profiles for the user.

Figure 39:
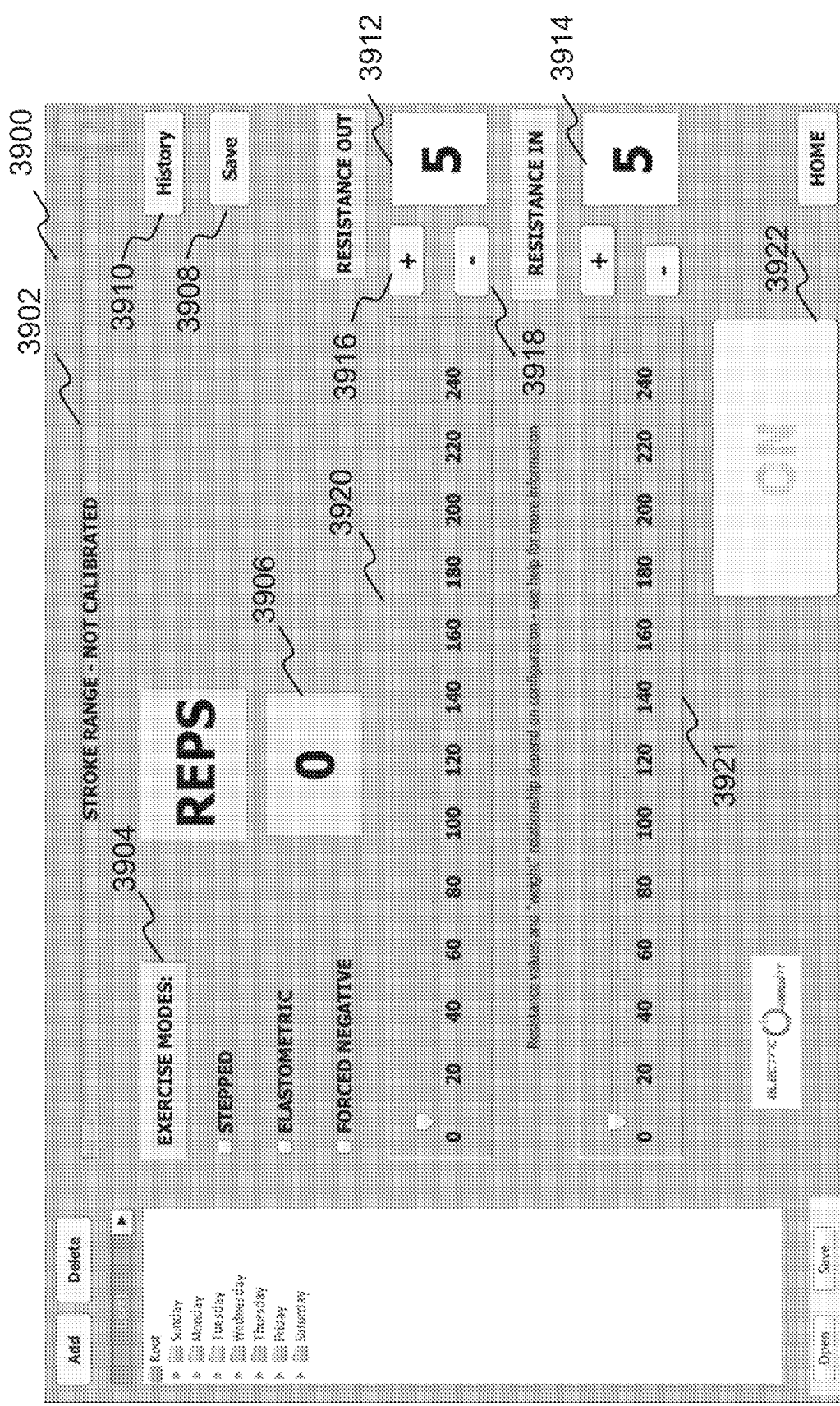
FIG. 39 is a screen capture of the initial stored exercise profile pane and exercise profile pane displayed on the host device of FIG. 31.

Referring now to FIG. 39, a main operational window is displayed. In some embodiments, the window includes a stored profiles pane 3700 and an exercise profile pane 3900. The stored profile pane 3700 has been described previously. The exercise profile pane may include various profile parameters and/or status indicators. A full stroke indicator 3902 can dynamically display the stroke as an exercise is performed. The indicator can also act as a status bar providing information to a user such as, for example, that stroke calibration has not yet occurred. One or more exercise modes can be selected individually or in combination 3904. Repetitions 3906 can be displayed as they occur during exercise performance. When a Save button 3908 press event is detected, the host computing device 106 marshals and sends the current exercise profile values to the controller 104, which can store them in RAM, in on-board, non-volatile EEPROM, and/or in an alternative persistent memory store. When a History button 3910 press event is detected, the exercise history for the user is displayed as described previously. Depending on the exercise mode selected, numeric parameter prompts 3912, 3914 may be displayed to obtain parameters used to implement one or more of the selected exercise modes 3904. In some embodiments, these parameters can be set by, for example, directly entering a value, by using an increment/decrement control 3916, 3918, by using a slider control 3920, 3921, and/or by other data entry means.

In some instances, the presence of the On button 3922 in the exercise profile pane 3900 indicates that the power on sequence was successful, but that the exercise initialization routines have not occurred. In some embodiments, the power on sequence can include one or more of the following activities:
  a) initialize controller (registers and peripherals);
  b) blink On-board LED n times;
  c) activate contactor (AC motor 120 on);
  d) enable rotor voltage;
  e) perform system calibration, disengage locking solenoid;
  f) ramp up DC motor 102 current to minimum resistance level;
  g) get and store retracted cable 108 position;
  h) engage locking solenoid;
  i) ramp DC current to zero; and
  j) deactivate contactor (AC motor 120 off).

Figure 40:
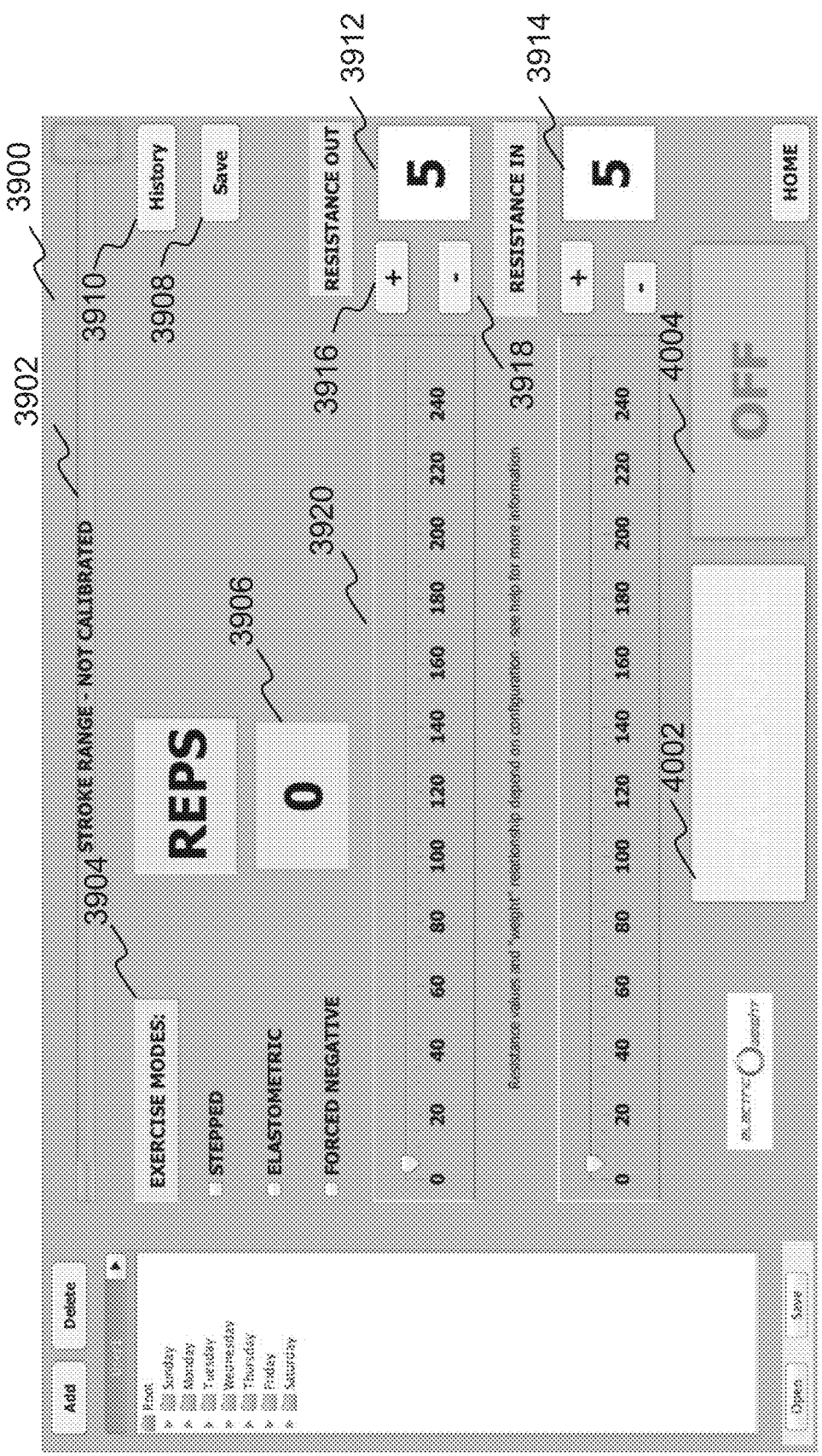
FIG. 40 is a screen capture of the post power up stored exercise profile pane and exercise profile pane displayed on the host device of FIG. 31.

Upon detecting the button press event for the On button 3922, the host computing device 106 sends a command ($20$27) to the controller 104 to perform exercise initialization activities. These can include, for example, activating the contactor, enabling rotor voltage, ramping to a minimum resistance level, disengaging the locking solenoid, and initializing an end-of-exercise timer in firmware. Referring now to FIG. 40, once initialized, the On button 3922 (see FIG. 39) is no longer visible, and the Calibrate button 4002 and Off button 4004 are made visible. The controller 104 sends SFA to the host computing device 106 when the controller 104 detects cable movement, then waits to receive the 'Begin Exercise' command ($20$25) from the host 106. When the host computing device 106 receives SFA from the controller 104, the host computing device 106 marshals and sends the relevant exercise profile values to the controller 104. The controller 104 stores one or more values in RAM and sends and acknowledgement to the host computing device 106. Referring now to FIG. 73, the host then displays the exercise screen. Detection of the button press event for the Off button 4004 directs the host 106 to send a command to the controller 104 to perform de-initialization procedures.

Figure 41:
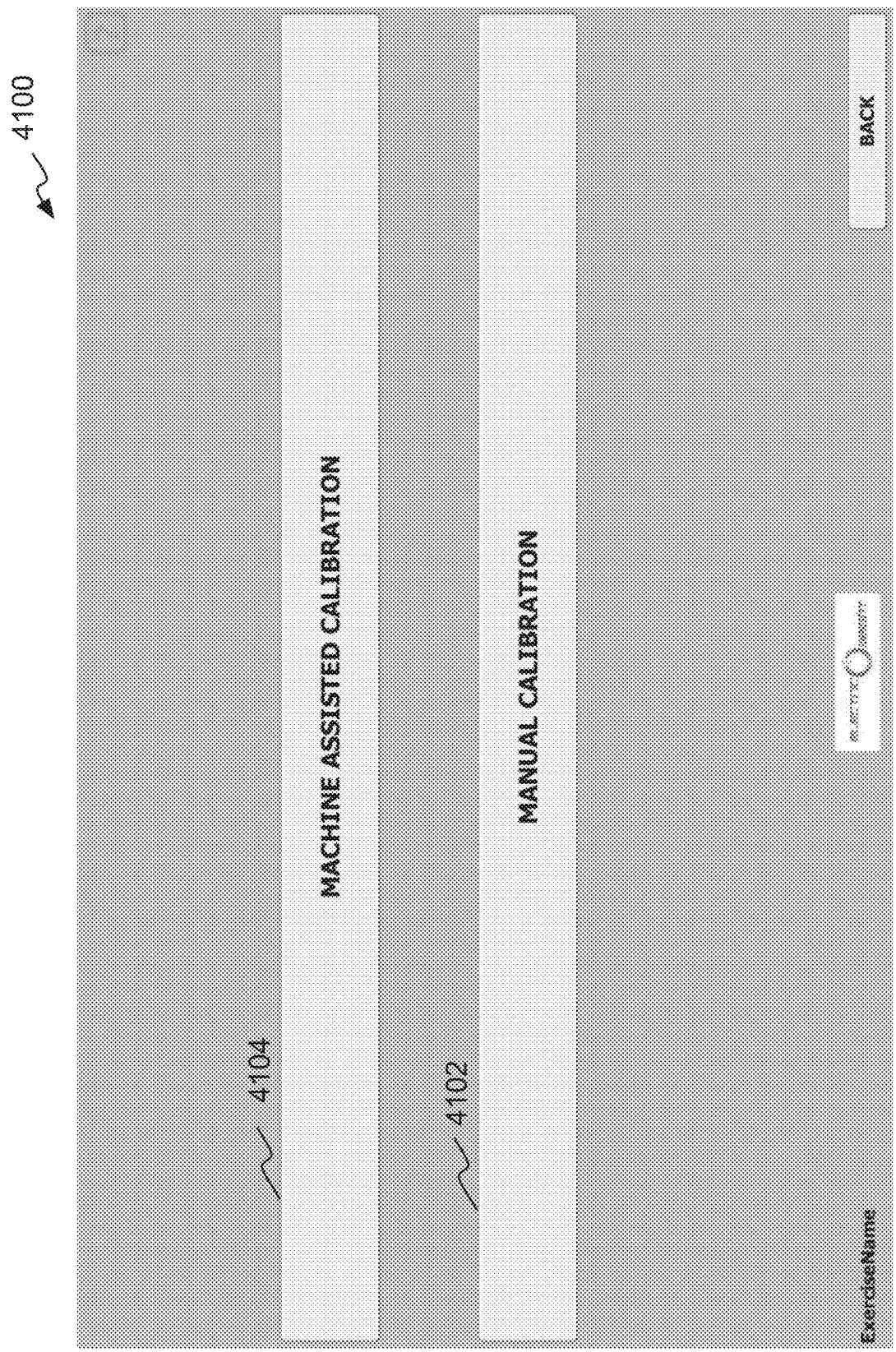
FIG. 41 is a screen capture of a calibration options interface displayed on the host device of FIG. 31.
Figure 42:
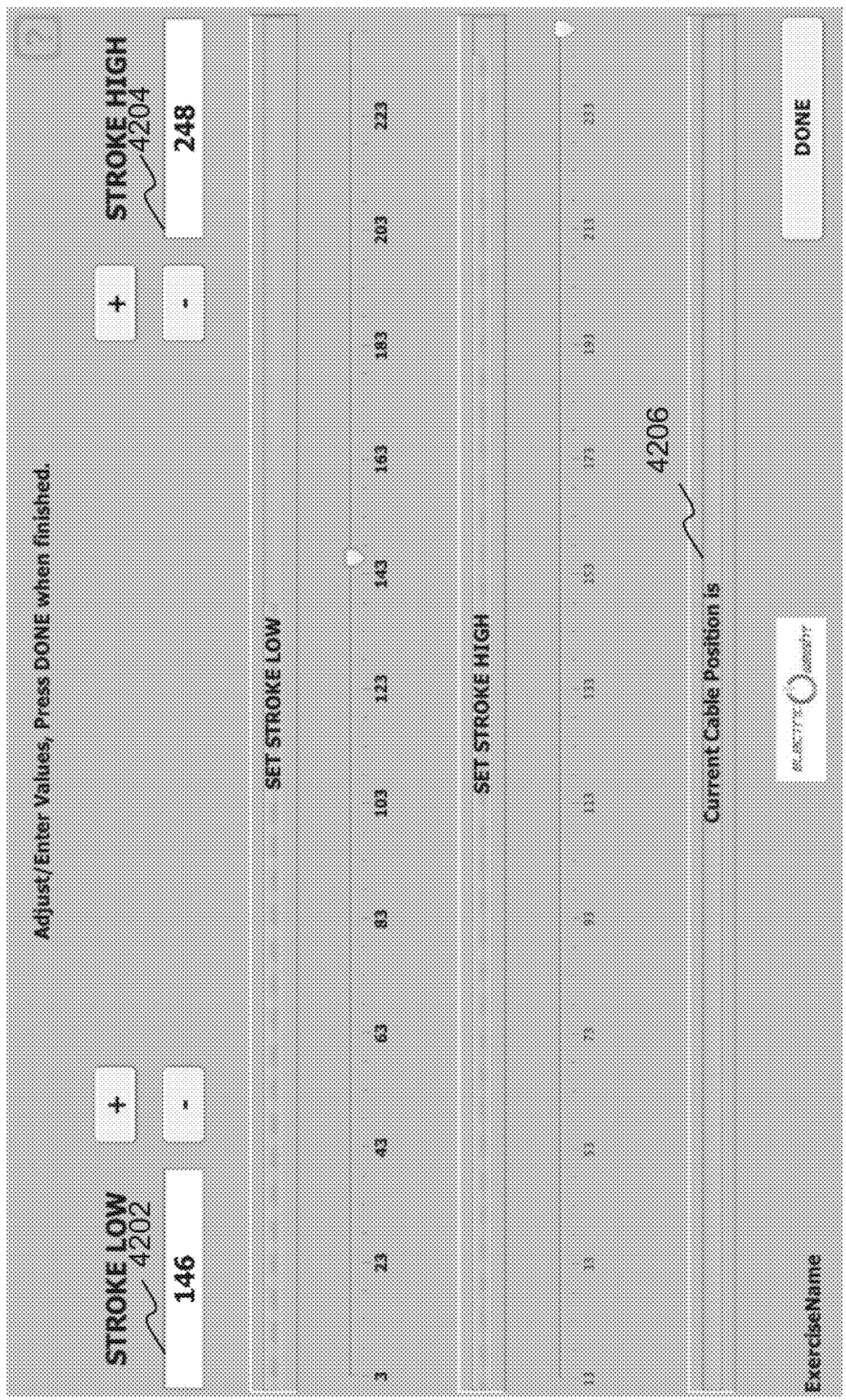
FIG. 42 is a screen capture of a manual calibration options interface displayed on the host device of FIG. 31.

In some systems, the stroke range for an exercise is defined through the execution of a calibration routine. Stroke is the distance between the calibrated stroke start value and stroke stop value, which correlates with the range of motion for a given exercise. Stroke length can vary by exercise, and a stroke will likely fall within the full range of motion for the resistance mechanism. Referring now to FIG. 41 and FIG. 42, the host computing device 106 displays the calibration options 4100 upon detection of a Calibrate button 4002 (see FIG. 40) press event. In some implementations, calibration can be manual 4102 and/or machine-assisted 4104. In the case of a manual calibration, the stroke start value 4202 and stroke stop value 4204 can be entered manually. In some instances, the current position value is displayed and can provide guidance for setting the values manually 4206. In the case of machine-assisted calibration, the user may be prompted to engage in a series of stroke-related actions that generate values used by the controller 104 to determine the stroke start value and the stroke stop value.

Figure 43:
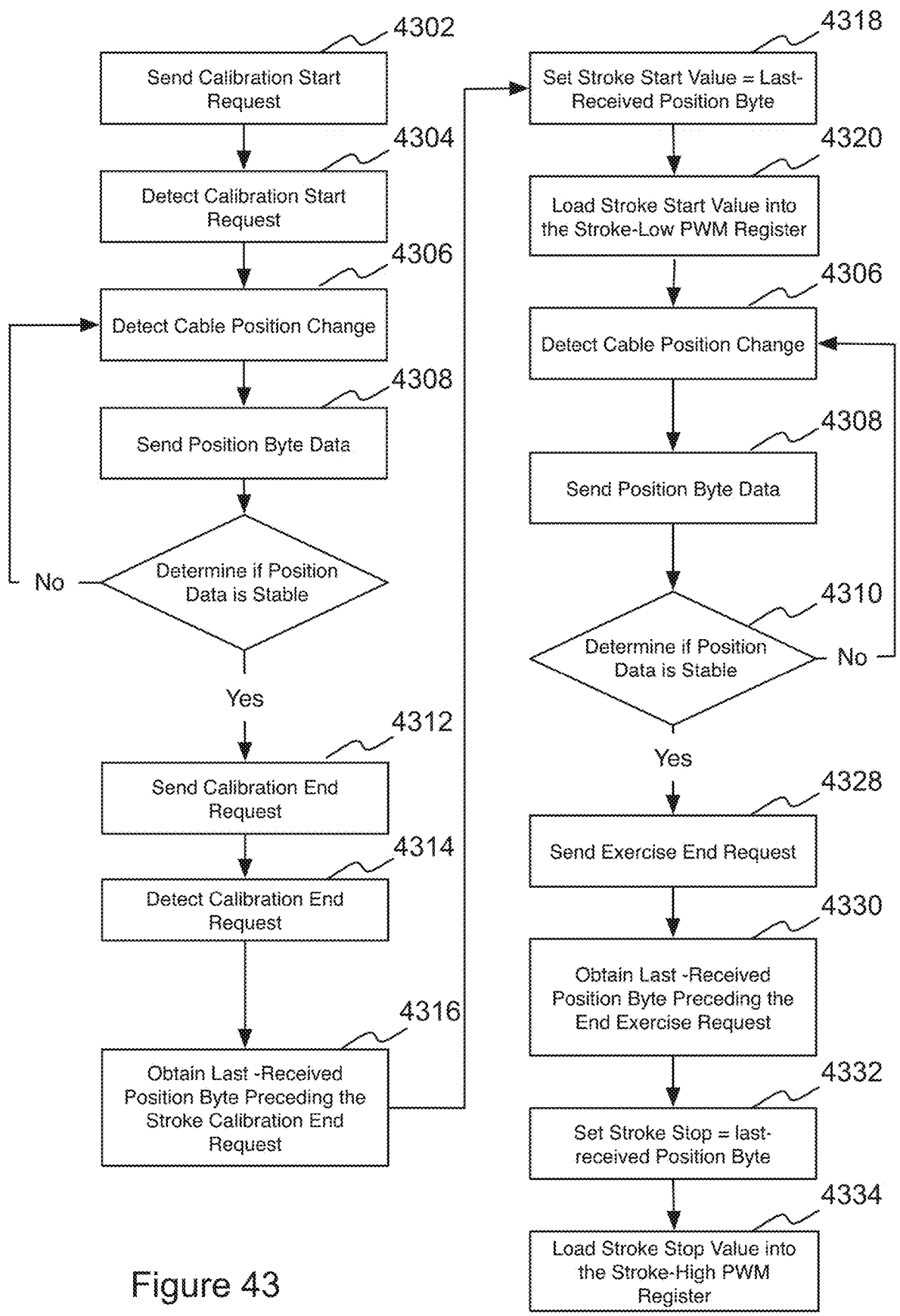
FIG. 43 is a flow diagram of a method for calibrating the programmable Resistance system of FIG. 31.

Referring now to FIG. 43, a machine-assisted calibration method is provided. The host computing device 106 sends a Stroke Calibration Start command ($20$21) to the controller 4302. Upon detection of the request 4304, the controller 104 responds with an acknowledgement ACK ($00). In some instances, an indication to begin stroke related actions is provided. When the controller 104 detects that the cable 108 has changed position 4306, position byte data is streamed to the host computing device 4308. When the host computing device 106 determines the position data values are stable 4310, the host computing device 106 sends a Stroke Calibration End command ($20$22) 4312 to the controller 104, and the controller 104 responds with an acknowledgement ACK ($00) upon detection of the command 4314. The last received Position Byte prior to issuing the Stroke Calibration End command is determined 4316 and the stroke start value is set to the last received Position Byte value 4318. This value is written to the low register 4320. The host computing device 106 may wait for a defined period of time and then listen for incoming position data. In some embodiments, the wait time is displayed by the host computing device 106 and/or an indication is provided to begin stroke related actions upon detection of position data. When the host computing device 106 determines the position data values are stable 4310, the host computing device 106 sends an Exercise End Command ($20$26) to the controller 104, and the controller 104 responds with an acknowledgement ACK ($00) upon receipt of the command. The last received position byte prior to issuing the Exercise End Command is determined 4330 and the stroke stop value is set to the last received position byte value 4332. This value is written to the high register 4334.

Figure 44:
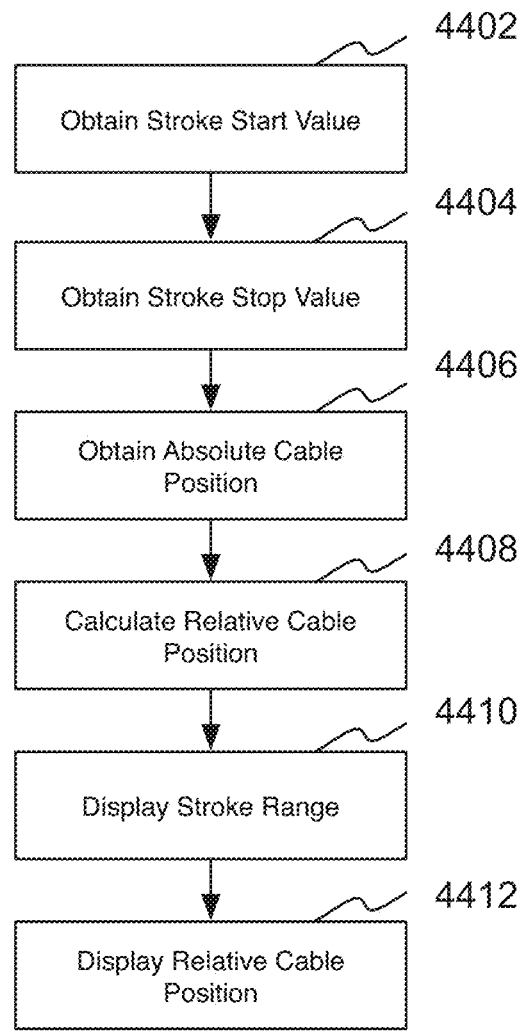
FIG. 44 is a flow diagram of a method for generating and displaying a full stroke indicator on the host device of FIG. 31.

Once stroke calibration is complete, a full stroke indicator can be provided. Referring now to FIG. 44, the host computing device 106 obtains the stroke start value and stroke stop value from the host 106 resident memory 4402, 4404. In some instances, the absolute position of the resistance mechanism, in this example the absolute cable position, is obtained 4406 by the controller 104 from the potentiometer 115. The host computing device 106 then calculates the relative cable position 4408 using an algorithm such as, for example, ((Absolute Position)−(Stroke Start))/((Stroke Start)−(Stroke Stop)), which can then be used to plot the relative cable position along a calibrated stroke range continuum 4410, 4412.

With full programmability of resistance values relative to cable 108 position and/or time during the outstroke and in-stroke of the cable 108, multiple resistance profiles can be applied simultaneously and in combination during a single exercise. One such resistance profile includes negative training, such that the negative weight exceeds the ability of the user to move the weight in the positive direction. The resistance system 100 allows configuration of the positive out-stroke resistance level such that the user can move into the position to begin the negative cycle. Once this position is attained, the user holds that position and the resistance system increases the negative resistance until cable retraction is detected, which can, in some instances, be indicated by inward cable movement. In some embodiments, once cable retraction is detected, a negative resistance value is set for the full length of the in-stroke, regardless of cable retraction speed. In other embodiments, resistance may be ramped up, including, in some cases, multiple times during the in-stroke, when cable retraction speed equals 0 or otherwise falls below a set minimum level. Ramp time to cable motion can be configured, which can control how fast resistance is increased prior to the detection of cable retraction. Cable retraction speed can also be programmed.

Figure 45:
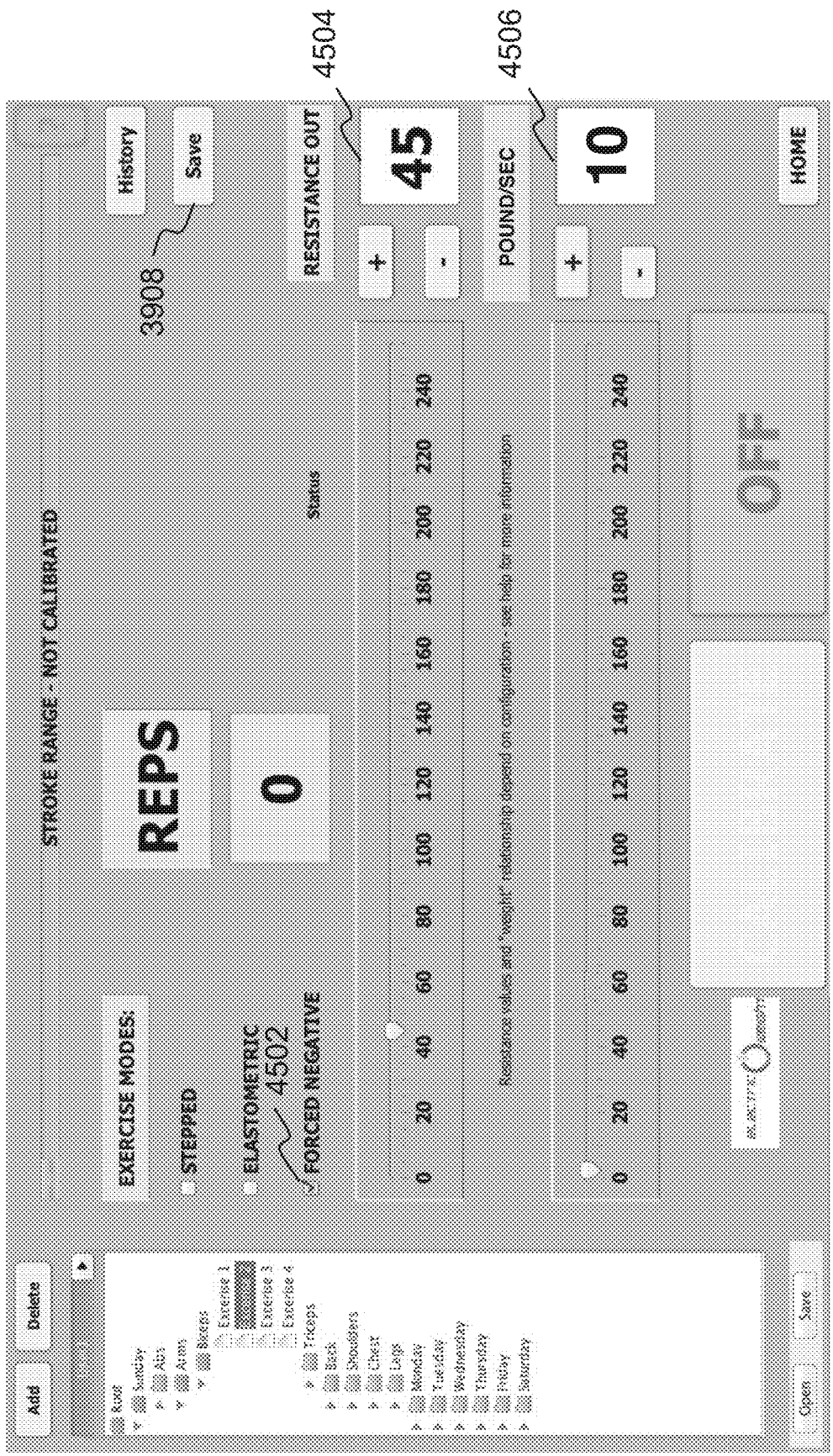
FIG. 45 is a screen capture of a forced negatives exercise profile displayed on the host device of FIG. 31.

Referring now to FIG. 45, the host computing device 106 detects the selection of a static forced negative exercise profile 4502. In response, the host computing device 106 displays a prompt for the resistance out 4504, which is the force to be applied during the out stroke, and displays a prompt for the pounds per second 4506, which can define the rate of increase to the resistance level upon reaching the stroke stop position. Upon detecting the button press event for the Save button 3908, the host computing device 106 marshals and sends the values to the controller 104, which can store them in RAM, in on-board, non-volatile EEPROM, and/or an alternative persistent memory store.

Figure 46:
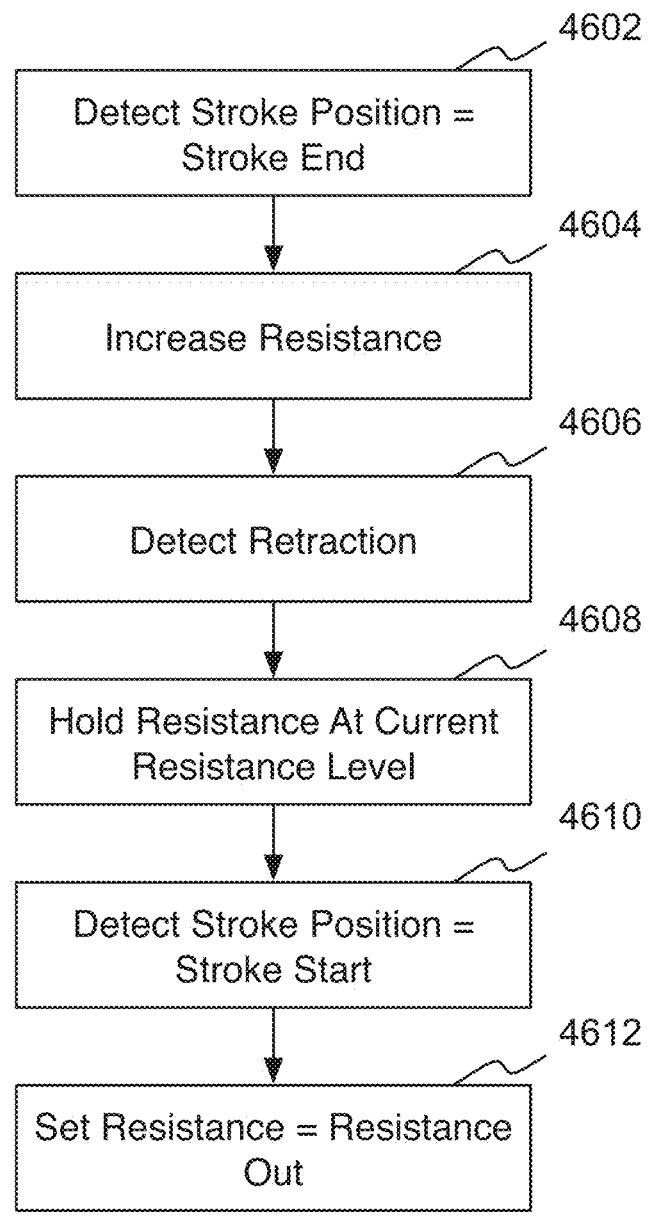
FIG. 46 is a flow diagram of a method for implementing a forced negative exercise for the programmable Resistance system of FIG. 31.
Figure 47:
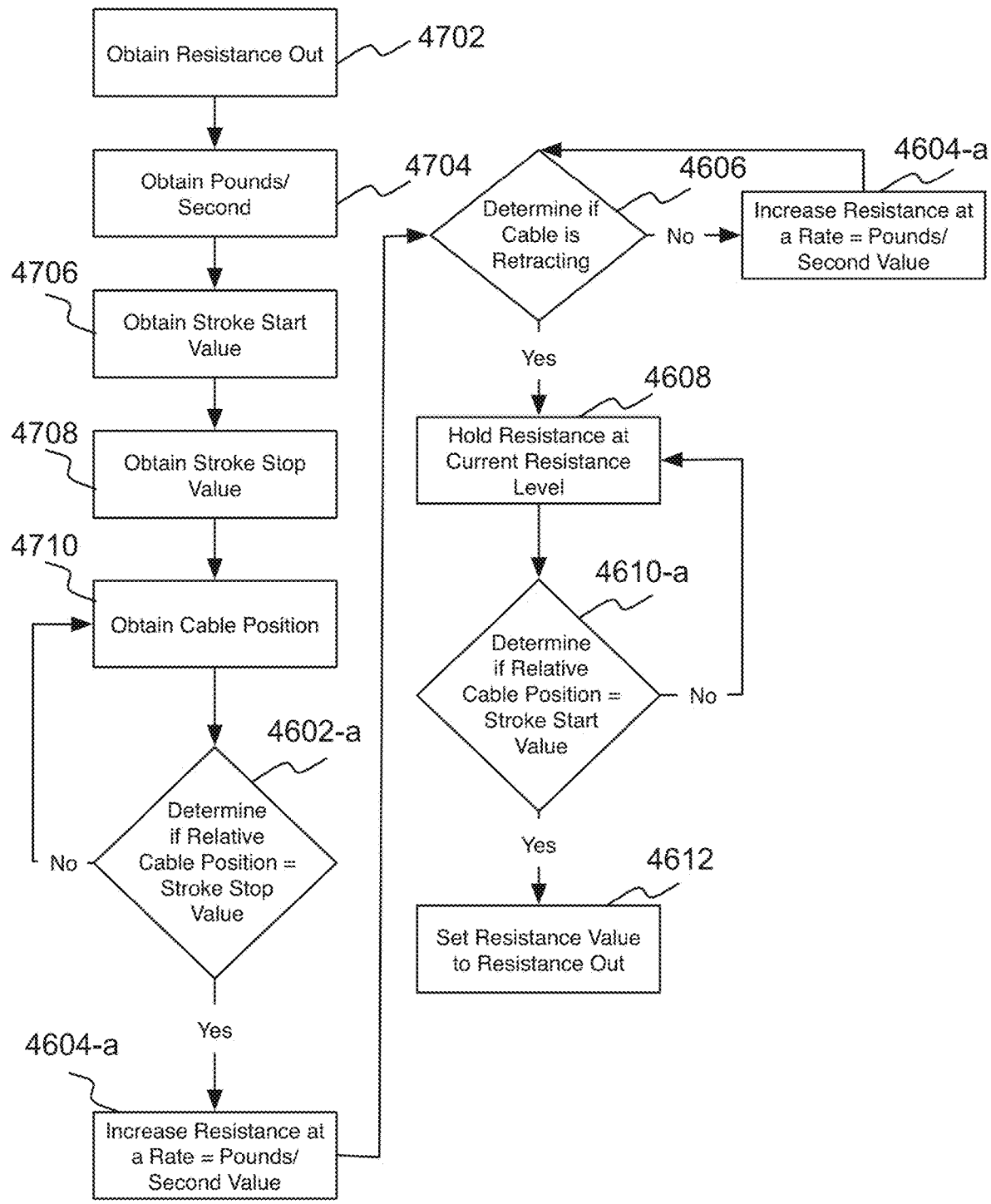
FIG. 47 is a flow diagram of a method for implementing a forced negative exercise for the programmable Resistance system of FIG. 31.

In some embodiments, the resistance system 100 maintains a constant resistance level without accounting for retraction speed. Referring now to FIG. 46 and FIG. 47, the controller 104 obtains the resistance out 4702, pounds per second 4704, stroke start value 4706, and the stroke stop value 4708 from EEPROM or an alternative persistent memory store. In this example, the controller 104 receives the absolute cable position 4710 from the potentiometer 115 and calculates the relative cable position. In some embodiments, the controller 104 detects if the stroke stop position is reached 4602 by determining if the relative cable position is equal to the stroke stop value 4602-a. If the controller 104 detects this condition, the resistance level is increased 4604 at the rate defined by the pounds per second value 4604-a. The user may attempt to hold the position as the machine increases the resistance. In this example, until cable retraction is detected 4606, resistance continues to increase 4604 at the rate defined by the pounds per second value 4604-a. In some implementations, upon detection of cable retraction 4606, the resistance level can be held constant 4608 until the controller 104 detects the stroke start position is obtained 4610-a. The resistance level is then set to the resistance out value 4612.

Figure 48:
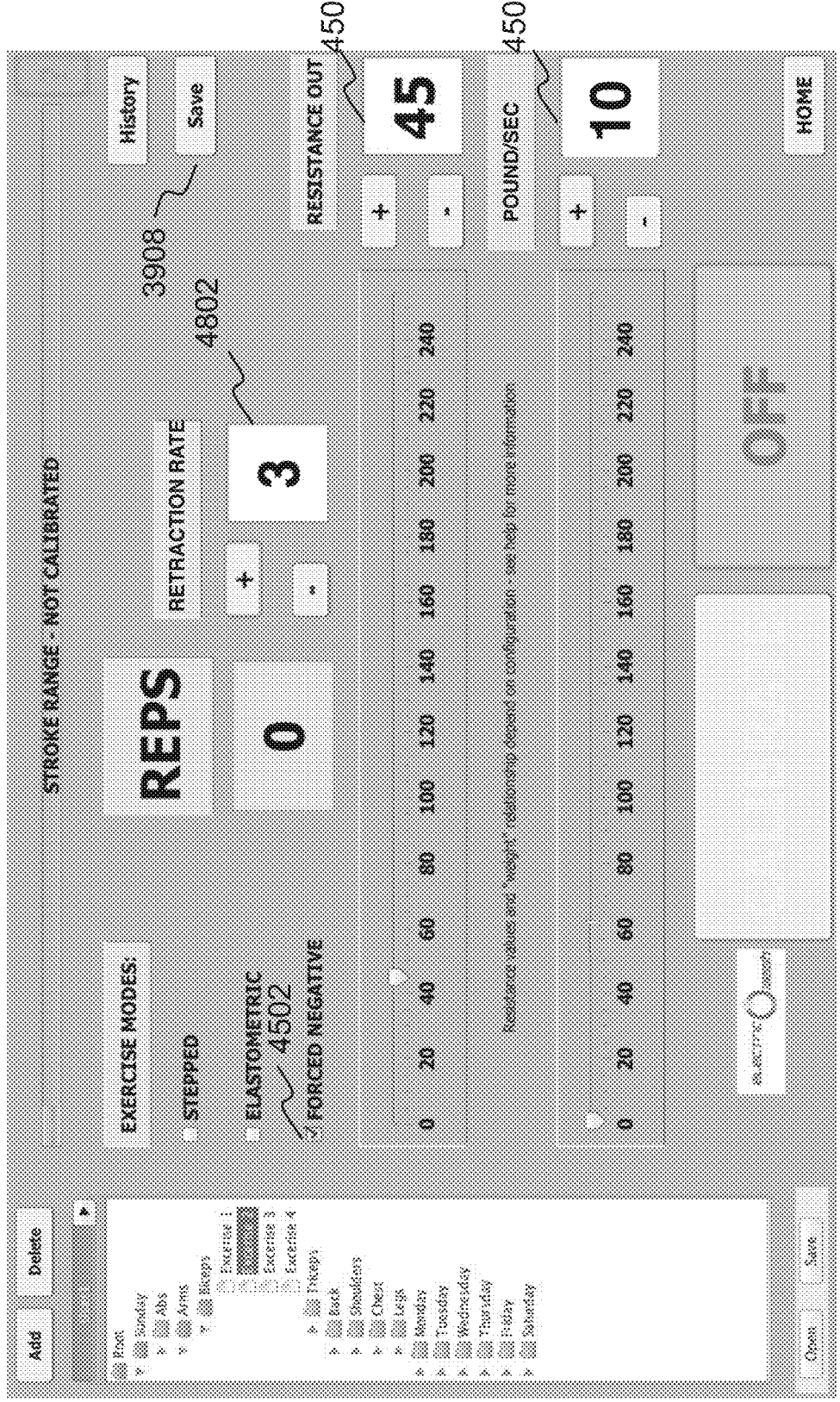
FIG. 48 is a screen capture of a forced negatives exercise profile displayed on the host device of FIG. 31.

In some embodiments, the resistance system 100 varies resistance levels in response to variations in retraction speed. Referring now to FIG. 48, the host computing device 106 detects the selection of a static forced negative exercise profile 4502 (see FIG. 45). In response, the host computing device 106 displays a prompt for the resistance out 4504, which is the force to be applied during the out stroke, and displays a prompt for the pounds per second 4506, which defines the rate of increase to the resistance level upon reaching the stroke stop position. A prompt for retraction rate 4802 is also included. This value can be used to define the retraction speed threshold, under which, the controller 104 will increase resistance. Upon detecting the button press event for the Save button 3908, the host computing device 106 marshals and sends the values to the controller 104, which can store them in RAM, in on-board, non-volatile EEPROM, and/or in an alternative persistent memory store.

Figure 49:
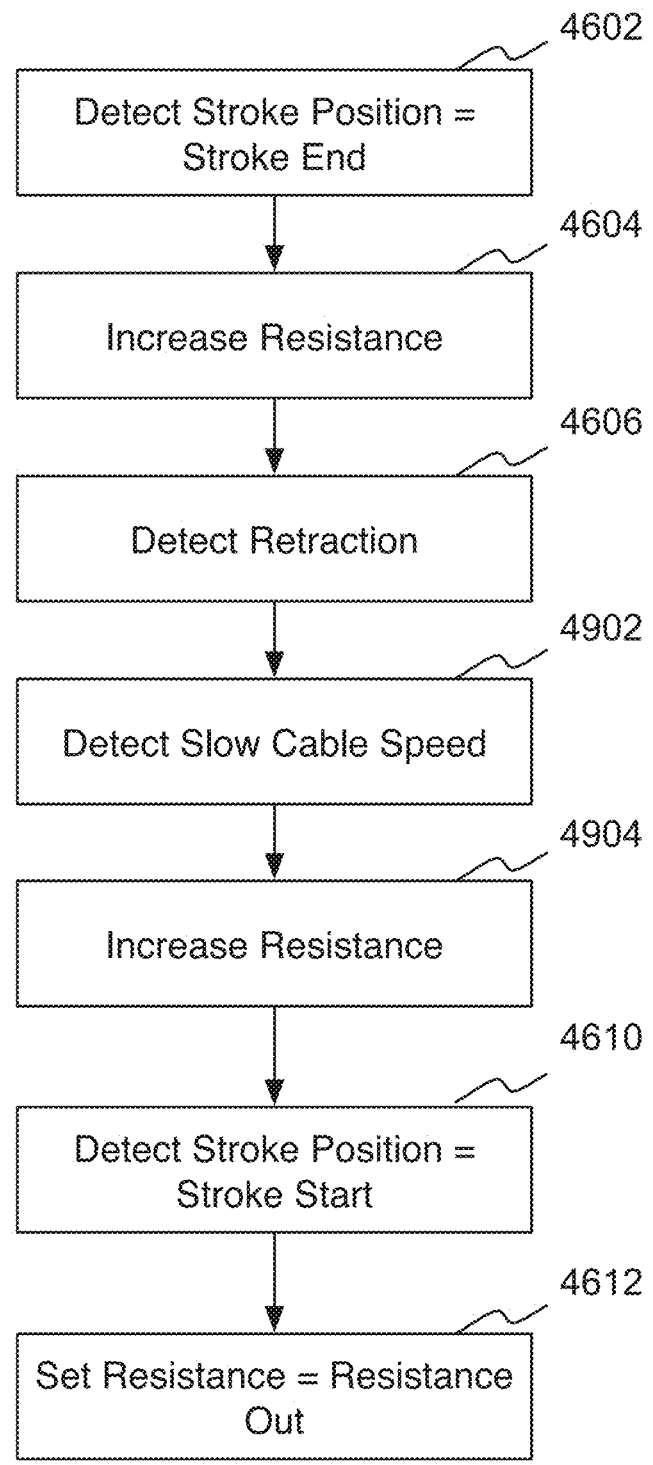
FIG. 49 is a flow diagram of a method for implementing a forced negative exercise for the programmable Resistance system of FIG. 31.
Figure 50:
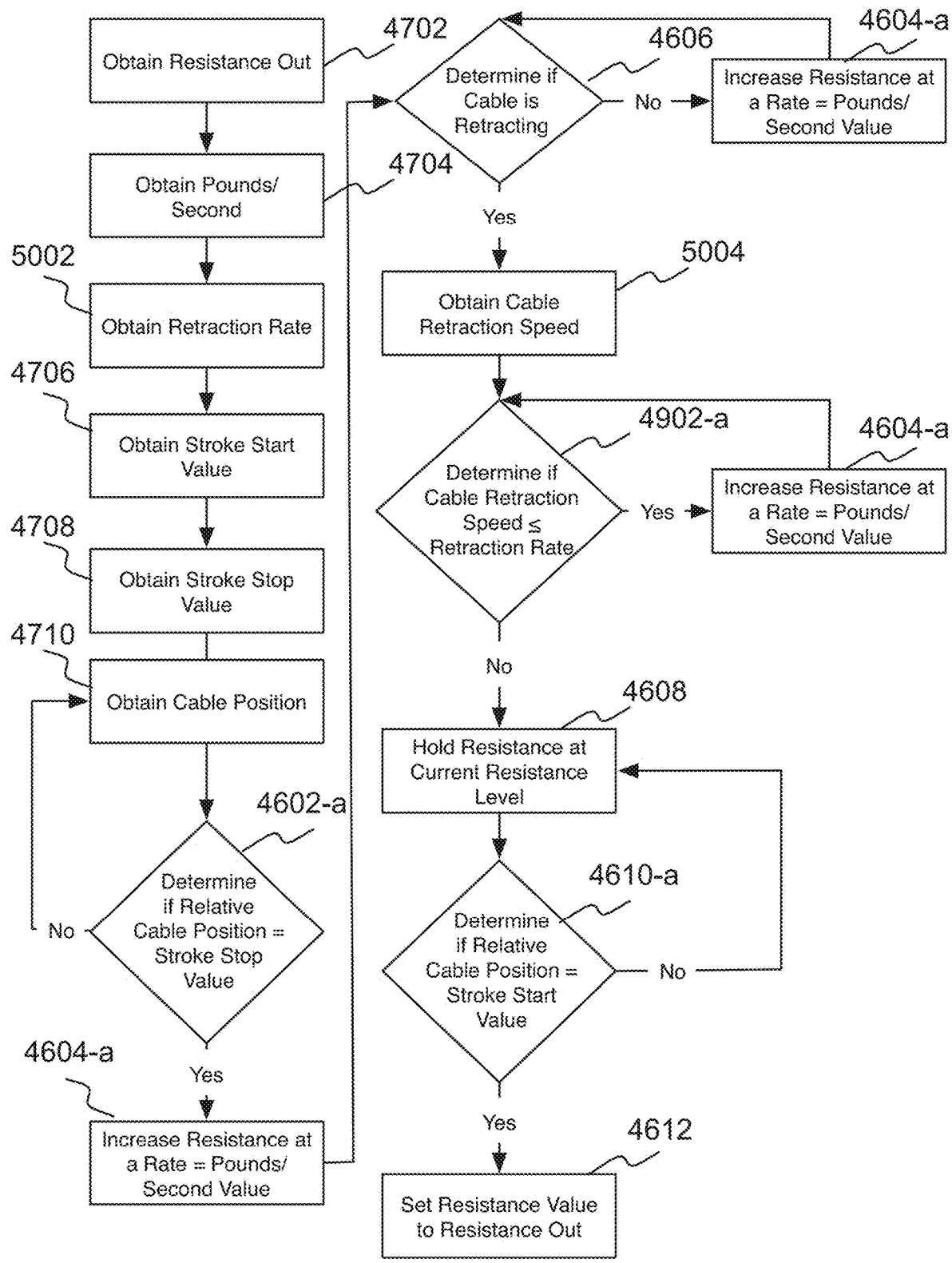
FIG. 50 is a flow diagram of a method for implementing a forced negative exercise for the programmable Resistance system of FIG. 31.

Referring now to FIG. 49 and FIG. 50, the controller 104 obtains the resistance out 4702, pounds per second 4704, retraction rate 5002, stroke start value 4708, and the stroke stop value from EEPROM or an alternative persistent memory store. In this example, the controller 104 receives the absolute cable position 4710 from the potentiometer 115 and calculates the relative cable position. In some embodiments, the controller 104 detects if the stroke stop position is reached 4602 by determining if the relative cable position is equal to the stroke stop value 4602-a. If the controller 104 detects this condition, resistance is increased 4604 at the rate defined by the pounds per second value 4604-a. The user may attempt to hold the position as the machine increases the resistance. In this example, until cable retraction is detected 4606, resistance continues to increase 4604 at the rate defined by the pounds per second value 4604-a. In addition, the retraction speed, in this example, the cable retraction speed, is obtained 5004. In some instances, the controller 104 determines cable speed by summing a series of position samples obtained over time x from the position potentiometer and dividing that sum by x. In some implementations, upon detection of a slow absolute cable retraction rate 4902, such as a rate less than that the defined cable retraction rate 4902-a, the controller 104 will increase the resistance level 4604. In some implementations, the resistance can increase until the controller 104 detects the stroke start position is obtained 4610. The resistance level is then set to the resistance out 4612.

Figure 51A:
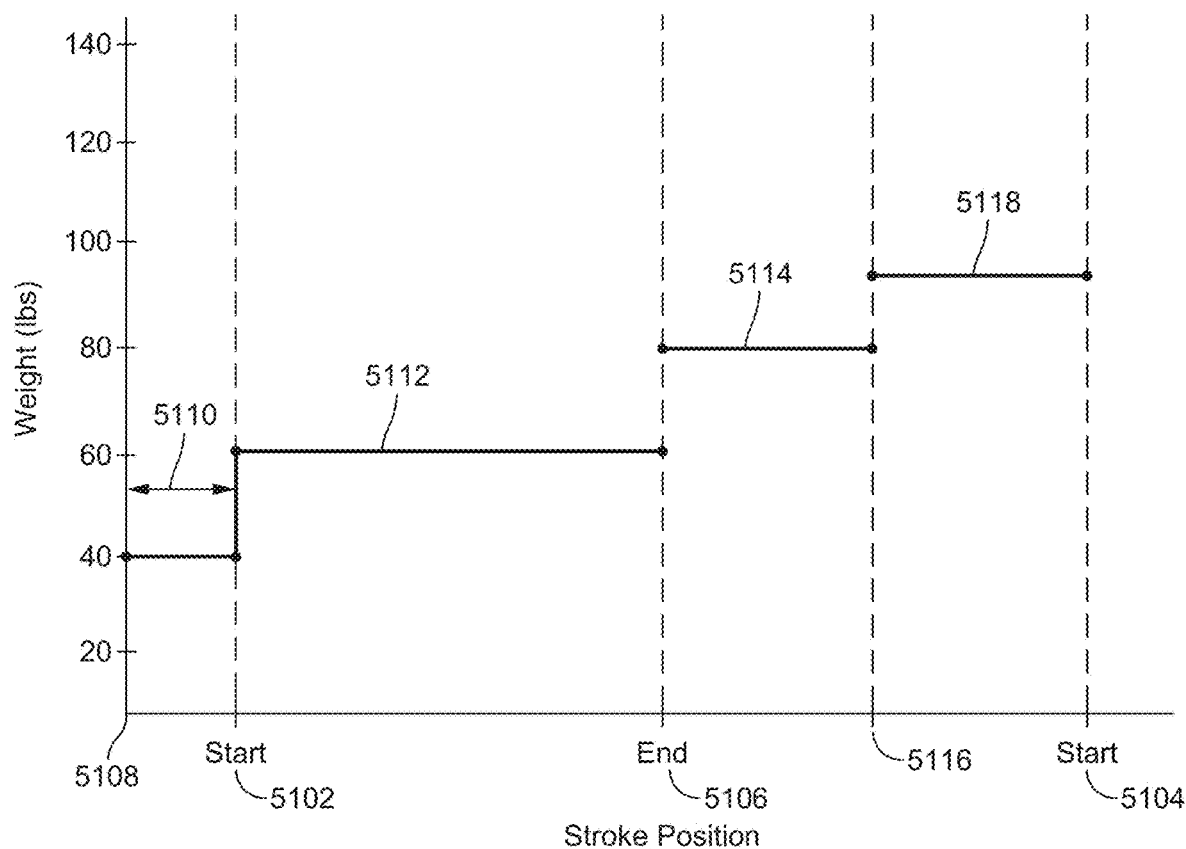
FIG. 51A is a forced negative resistance profile diagram implemented in a programmable Resistance system of FIG. 31.

Referring now to FIG. 51A, a forced negative resistance profile 5100 defined by applied resistance or weight in pounds on the vertical axis and stroke position on the horizontal axis is shown. In some embodiments, a first and second start stroke position 5102, 5104 can be pre-defined by the host computing device 106 such as where the cable 108 is extended 12 inches from a rest position, or calibrated either manually or automatically as described above in reference to FIGS. 39-43. Further, an end stroke position 5106 may be similarly predetermined by the host computing device 106, for example, to correspond to a cable extension of 118 inches, or calibrated. For a stroke position of the cable 108 between 0 extension 5108, and a start stroke position 5102, which may be referred to as an initialization stroke 5110, the resistance in weight applied to the cable 108 may be less than the full or maximum profile resistance value, such as 40 lbs as shown. In other cases, the resistance applied during the initialization stroke 5110 may be 0, or any percentage of the full or maximum profile resistance value, according to a predetermined value profile value.

Out-stroke resistance is set 5112 to 60 lbs. for example. This resistance is applied through cable 108 from the start stroke position 5102 to the end stroke position 5106. At the end stroke position 5106, the resistance will then ramp up at a rate chosen by a user, or a predetermined rate if so selected, to an in-stroke resistance level 5114, which in the embodiment shown, is 80 lbs. In some cases, the in-stroke resistance level 5114 may be defined by the user, or may be determined/set when cable retraction is detected, thus possibly indicating that the user can no longer maintain a force equal to the applied resistance. In this case, where the user selects the variable in-stroke mode of the forced negative resistance training program, the user may stop the cable from retracting further mid in-stroke of cable 108, at stroke position 1516. In this case, the resistance level may be further ramped up until cable retraction is further detected, at the same rate applied in the first ramping, or possibly a different rate, for example a slower rate to account for user fatigue. Once the cable 108 begins to re-tract, a second in-stroke resistance level 1518 may be maintained until the start stroke position 5104 is reached, whereupon the resistance level will be dropped back to the out-stroke resistance level 5112.

Figure 51B:
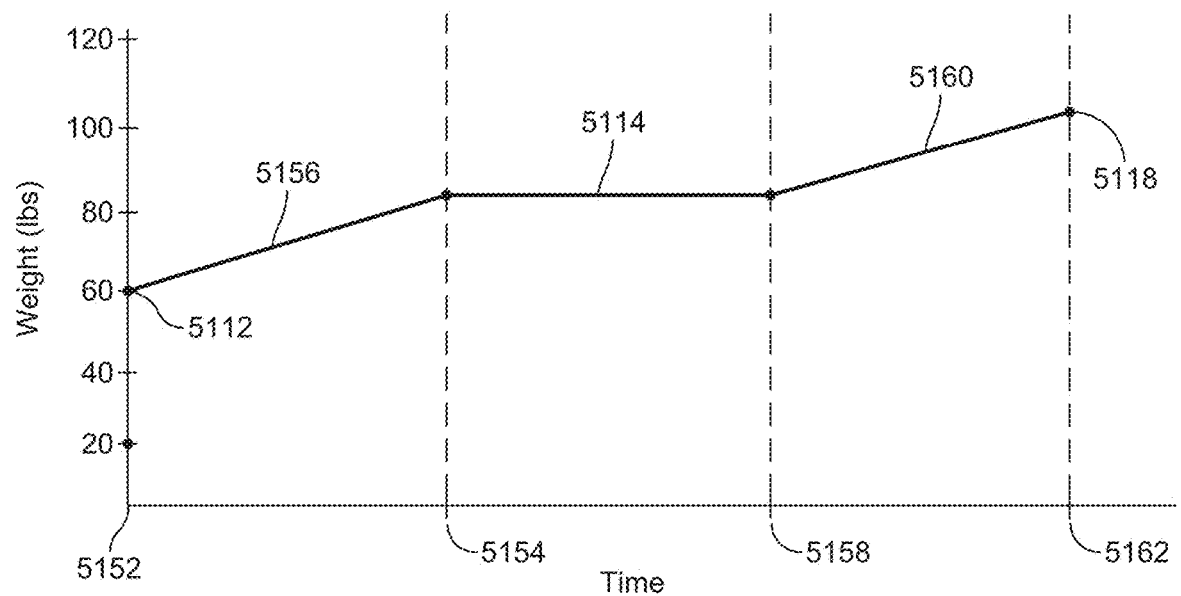
FIG. 51B is a forced negative resistance profile diagram implemented in a programmable Resistance system of FIG. 31.

With reference now to FIG. 51B, a forced negative resistance profile 5150 defined by applied resistance or weight in pounds on the vertical axis and time on the horizontal axis corresponding to the forced negative resistance profile 5100 is shown. At time 5152, which corresponds to the end stroke position 5106, the resistance is at the out-stroke resistance level 5112. The resistance then ramps up until a time 5154 according to a user defined/selected ramp rate, represented by ramp 5156, to the in-stroke resistance level 5114. From time 5152 to time 5154, the cable 108 maintains at the end stroke position 5106. From time 5154 to 5158, which corresponds to stroke position 5116, the in-stroke resistance level 5114 is maintained. At time 5158, no retraction, or a retraction rate below a set minimum rate, is detected, and the resistance is ramped up, represented by ramp 5160 until time 5162 when cable 108 retraction, or retraction above a minimum set rate, is detected. At time 5162, the resistance is maintained at the second in-stroke resistance level 5118 until the cable 108 reaches the start stroke position 5104, where resistance is reset to the out-stroke resistance level 5112. In this way, a forced negative resistance profile may be implemented by the resistance system. The above profile is only an example of profiles programmable and implementable by the resistance system.

Figure 52:
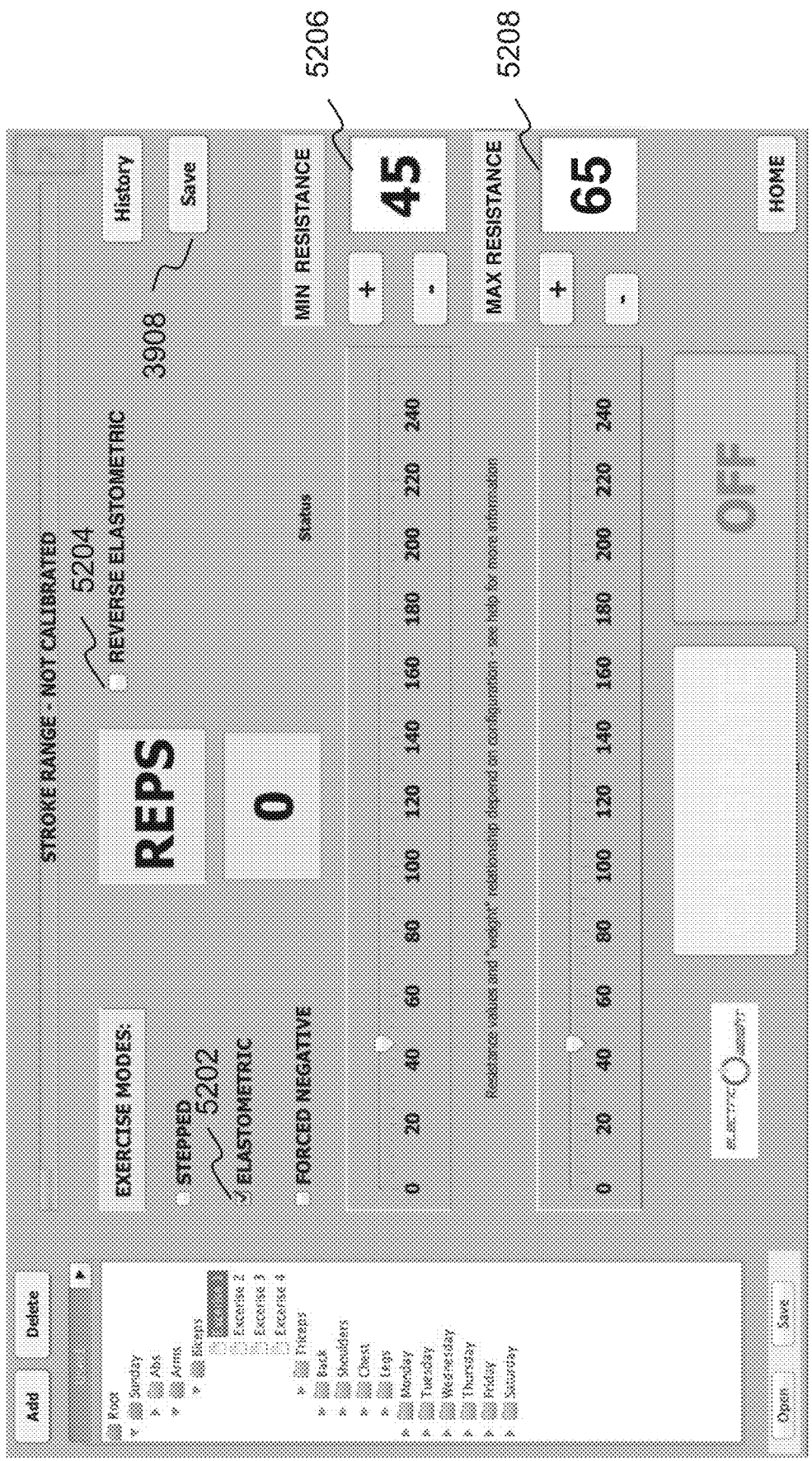
FIG. 52 is a screen capture of an elastometric exercise profile displayed on the host device of FIG. 31.

In some embodiments, resistance can be programmable for continuously variable functions such as, for example, elastometrics. In some instances, this can be done by a controller 104 control board 2414. In an elastometric exercise profile, resistance changes continuously and linearly from the stroke start value to the stroke end value, then reverses from the stroke end value to the stroke start value. Referring now to FIG. 52, the programmable electronic weight machine host computing device 106 detects the selection of an elastometric exercise profile 5202. The host displays an edit box for the minimum resistance 5206 and the maximum resistance 5208. For this elastometric profile, the minimum resistance corresponds to the resistance at the stroke start position, and the maximum resistance corresponds to the resistance at the stroke stop position. In some instances, the host computing device 106 can detect the selection of the reverse elastometrics checkbox 5204, which inverts the resistance-to-position relationship just described. Upon detecting the button press event for the Save button 3908, the host computing device 106 marshals and sends the entered values, including the max cable speed, to the controller 104, which can store them in RAM, in on-board, non-volatile EEPROM, and/or in an alternative persistent memory store.

Figure 53:
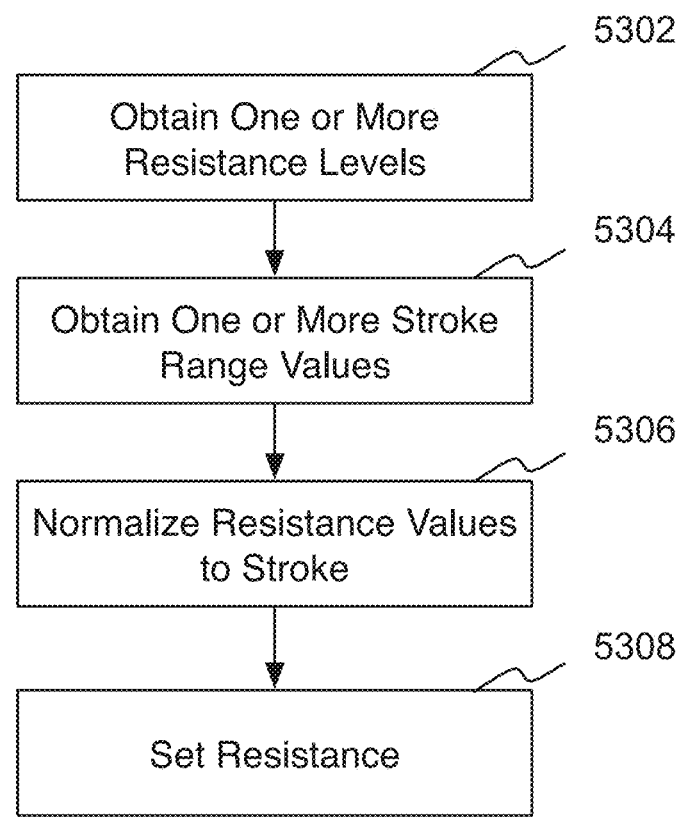
FIG. 53 is a flow diagram of a method for implementing an elastometric exercise for the programmable Resistance system of FIG. 31 in accordance with various embodiments.

In some instances, an elastometric engine implemented in firmware utilizes the user resistance stroke range values and resistance values such that any beginning/ending resistance within the range of the machine is accommodated from the minimum stroke length to the maximum excursion. Referring now to FIG. 53, the elastometric engine obtains one or more resistance level values 5302 such as, for example, the minimum resistance 5302-a and maximum resistance 5302-b, and one or more stroke range values 5304 such as, for example, the stroke start value 5304-a and the stroke stop value 5304-b. In certain embodiments, the stroke range values can be obtained from the calibration routine. In another embodiment, the stroke range values can be obtained by averaging start stroke and end stroke values of two or more turn-around events, with a turnaround event defined as either an in-out-in series of strokes and/or an out-in-out series of strokes. Resistance values can be normalized across the stroke range 5306 and the resistance values set in accordance with the normalization calculation 5308.

In some embodiments, an amplitude adjustable triangle waveform generator circuit normalizes resistance through the stroke range of motion. The peak-to-peak amplitude of a triangle wave can be controlled by two DC inputs, the values of which are derived from on-board DACs. In some instances, the values are filtered pulse width modulation signals (PWM). The Stroke-Low PWM determines the lower amplitude of the triangle wave while the Stroke-High PWM determines the upper amplitude. The controller 104 applies the stroke start value to the Stroke-Low PWM output and the stroke stop value to the Stroke-High PWM output fitting the peak-to-peak amplitude of the triangle wave to the stroke.

Figure 54:
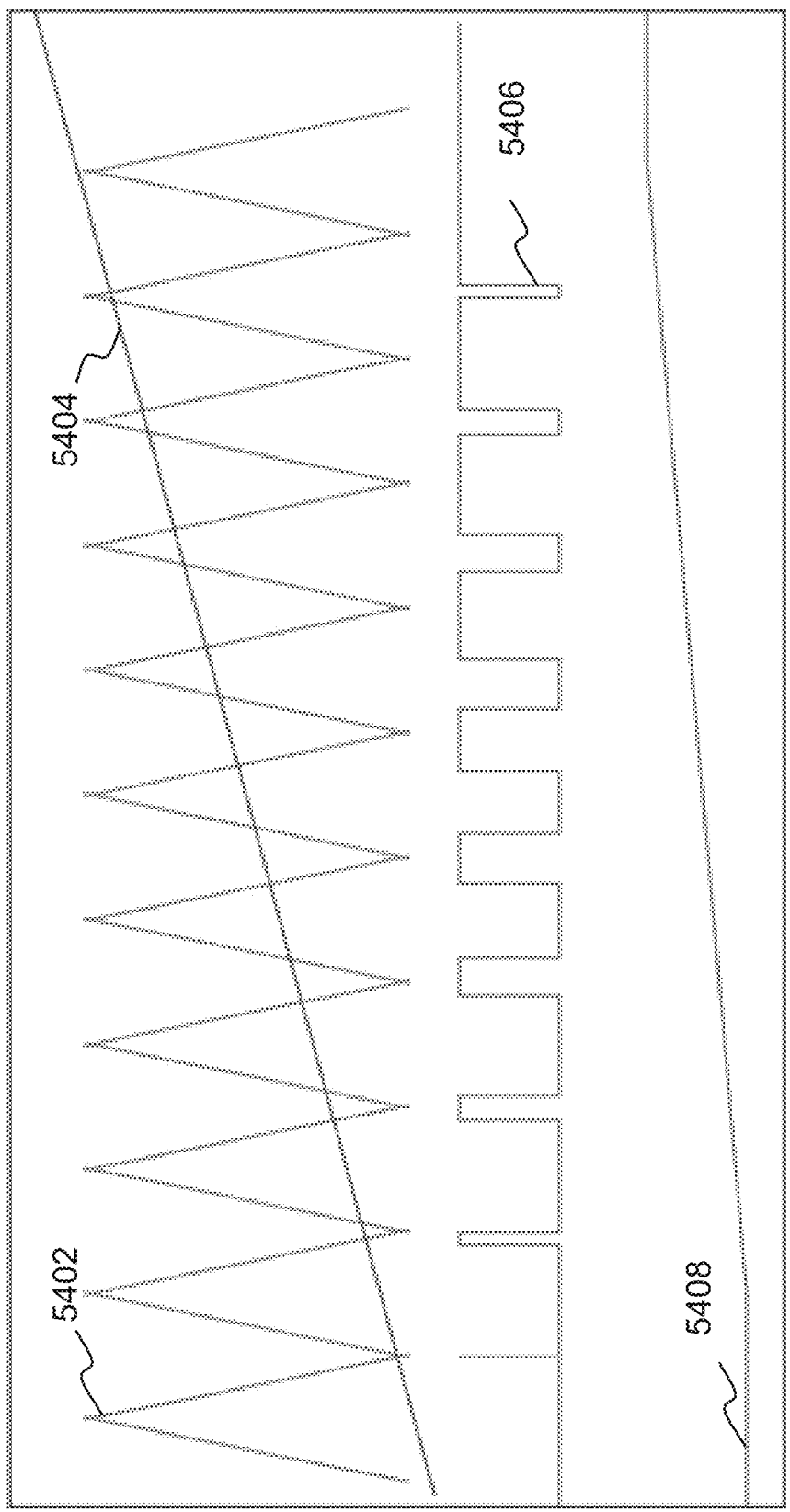
FIG. 54 is a line diagram of a triangle wave function implemented in the programmable Resistance system of FIG. 31.
Figure 55:
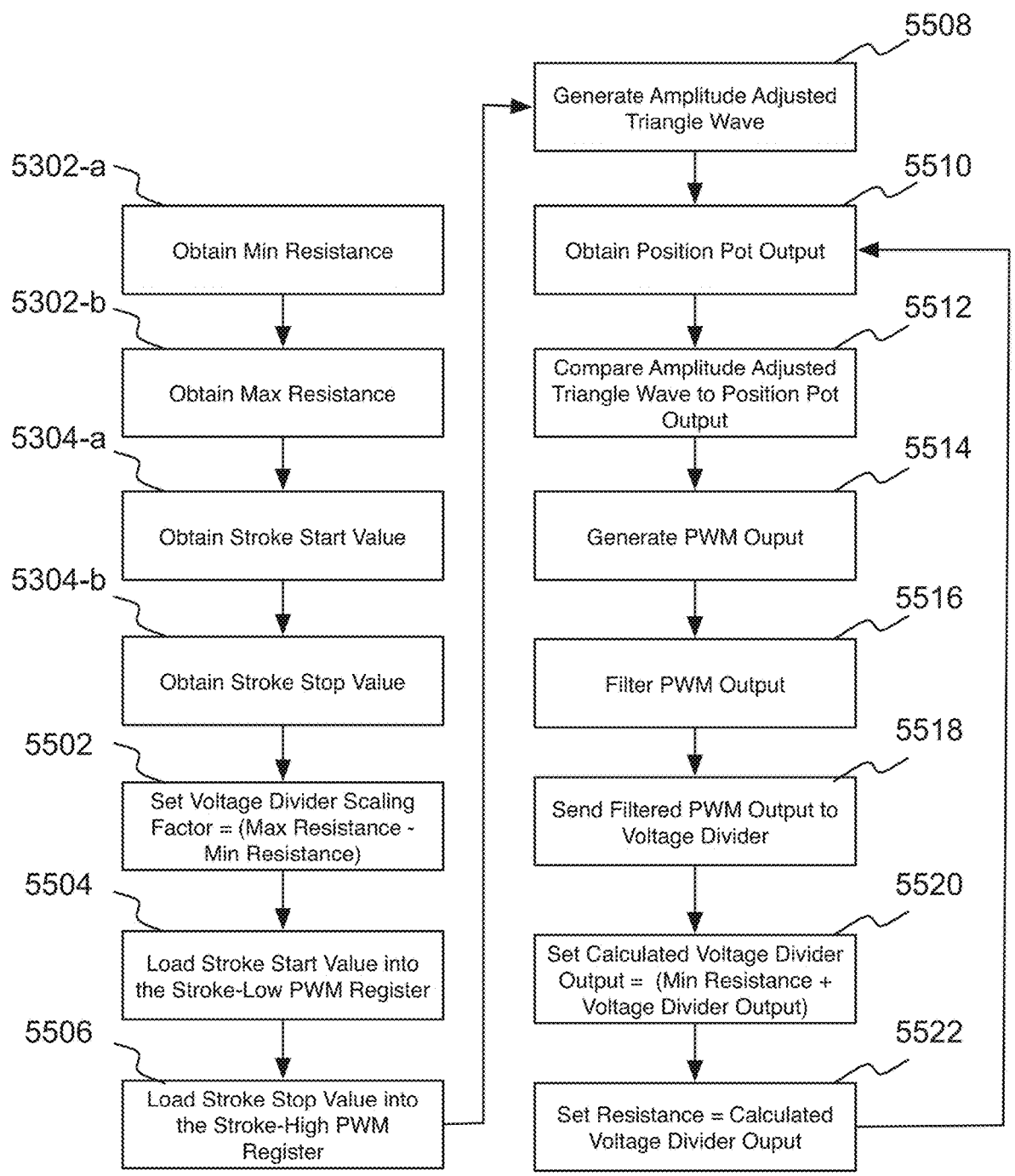
FIG. 55 is a flow diagram of a method for implementing an elastometric exercise for the programmable Resistance system of FIG. 31 in accordance with various embodiments.
Figure 56:
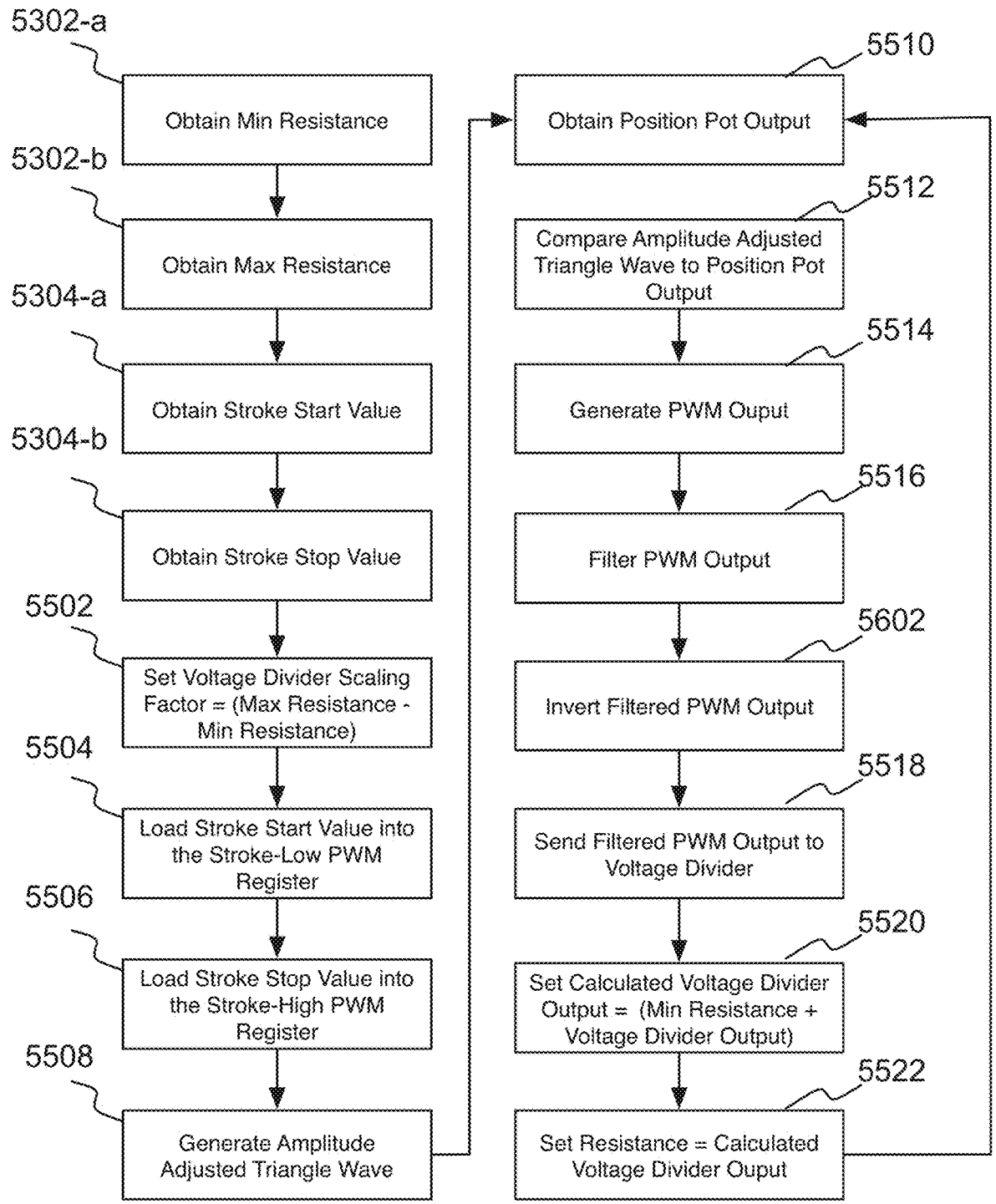
FIG. 56 is a flow diagram of a method for implementing an inverted elastometric exercise for the programmable Resistance system of FIG. 31 in accordance with various embodiments.

Referring now to FIG. 54, the triangle wave 5402 is compared to the position potentiometer output 5404 generating the resultant PWM output 5406 (see FIG. 55). The pulses are then filtered 5408 to produce a 0-5 VDC output. This 0-5 VDC output follows the stroke, thus allowing full resistance excursion as a function of stroke. With reference to FIG. 55, since the elastometric engine output encompasses the full resistance range, it is scaled to accommodate the configuration profile. A voltage divider, such as, for example, a digital 8-bit potentiometer 2624 with input on one end and output at the wiper, can be used to scale the output. The value written to the digital potentiometer 2624 is the maximum resistance value minus the minimum resistance value 5502. The controller applies the amplitude adjusted triangle wave and position potentiometer output to a comparator 5512 to generate a PWM output 5514 ranging from 0% to 100%, where 0% is less-than-or-equal-to the start value and 100% is greater-than-or-equal-to the end value 5512. This PWM output encompasses the calibrated stroke range from start point to end point, where start point is the triangle peak minimum and the end point is the triangle peak maximum. If the stroke is uncalibrated, the PWM output encompasses the entire resistance range of the resistance system, in this instance, represented as 0-255 or ($S00-$FF). The PWM output is filtered 5516 and sent to the digital potentiometer for scaling 5518. The digital potentiometer wiper is configured to scale this value by applying the voltage divider scaling factor. The calculated voltage divider output, in this instance, the wiper output, is the elastometric value. This value is summed with the minimum resistance and sent to the error amplifier. When the stroke position is at or below start point, the PWM output is zero and the minimum weight is equal to the minimum resistance. When the stroke position is at or above the end point, the PWM output is the maximum resistance representing the maximum force possible for a particular build of the resistance system, and the weight is the sum of minimum resistance plus the scaled PWM output. Therefore, the scaled output is the desired maximum resistance minus minimum resistance. For example, let minimum resistance=20 and maximum resistance=80. The scaled output would be 60, such that at start point the resistance is 20+0.6*0=20 and the resistance at end point is 20+0.6*100=80. Error amp control is driven by the sum of the minimum resistance and with the wiper voltage divider output 5520. The controller then sets the resistance to this calculated voltage divider output 5522. Referring now to FIG. 56, in the case of reverse elastometric exercise profiles, the process can be similar to that just described, with the addition of a step inverting the filtered PWM output 5602.

As an example, let the minimum resistance equal 20 ($14), the maximum resistance equal 150 ($96), the stroke start value equal 16 ($10), and the stroke stop value equal 120 ($78). The resistance varies from (14-96), and the stroke range is 25.62" (2.14'). ($10) is loaded into the stroke-low PWM register. ($78) is loaded into the stroke-high PWM register. These filtered values are the low/high, in this case 2.039V peak-to-peak, values of the triangle waveform against which the position pot output is compared. The resulting PWM output is filtered and sent to the voltage divider, for example, a digital pot, for scaling. The output is scaled by subtracting the minimum resistance value from the ending resistance value, in this case 150−20=130 ($82). This value is written to the voltage divider, in this case, a digital potentiometer 2624. The output from the wiper of the digital potentiometer 2624 will vary from 0 to 130 as a function of stroke (0-255). This variation is summed with the minimum resistance value of 20, yielding the desired resistance range of 20 to 150. This will remain the case even if the stroke range is exceeded in either direction. The resistance variation is linear throughout the stroke.

Turning now to FIG. 57, an elastomeric resistance profile is 5700 defined by applied resistance or weight in pounds on the vertical axis and stroke position on the horizontal axis is shown. In some embodiments, a first and second start stroke position 5702, 5704 can be pre-defined by the host computing device 106, such as where the cable 108 is extended 12 inches from a rest position, or calibrated either manually or automatically as described above in reference to FIGS. 39-43. Further, an end stroke position 5706 may be similar predetermined by the host computing device 106, for example, to correspond to a cable extension of 118 inches, or calibrated. For a stroke position of the cable 108 between 0 extension 5708, and a start stroke position 5702, which may be referred to as an initialization stroke 5710, the resistance in weight applied to the cable 108 may be less than the full resistance value set by the user, such as 40 lbs as shown. In other cases, the resistance applied during the initialization stroke 5710 may be 0, or any percentage of the full resistance value set by the user, according to a predetermined value, or enterable by the user.

A user may set a starting resistance 5712, such as 40 lbs as shown, and an ending resistance 5714, such as 100 lbs as shown. The elastomeric engine, as described previously, can configure a resistance profile based on the starting and ending resistances 5712, 5714, and on the starting and ending stroke positions 5702, 5704 and via controller 104, can drive the DC motor 102 to implement such a resistance profile in cooperation with at least one potentiometer 115. The elastomeric resistance profile may include a ramped out-stroke resistance 5716 from the start stroke position 5702 to the end stroke position 5706 and a ramped in-stroke resistance 5718 from the end stroke position 5706 back to start stroke position 5704. In this way, resistance training via an elastic band may be simulated with the resistance system.

Figure 57A:
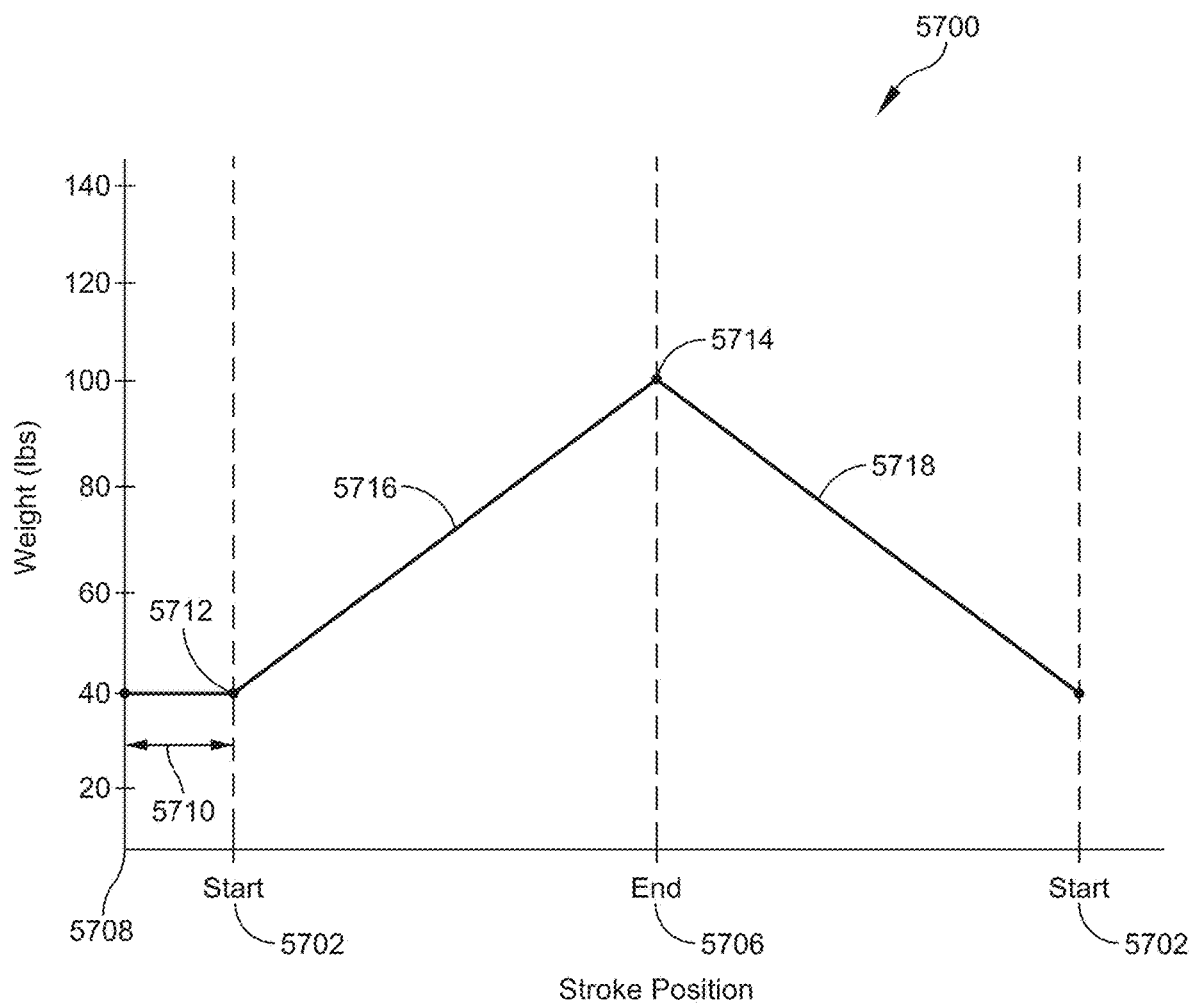
FIG. 57A is an elastometric resistance profile diagram implemented in a programmable Resistance system of FIG. 31.
Figure 57B:
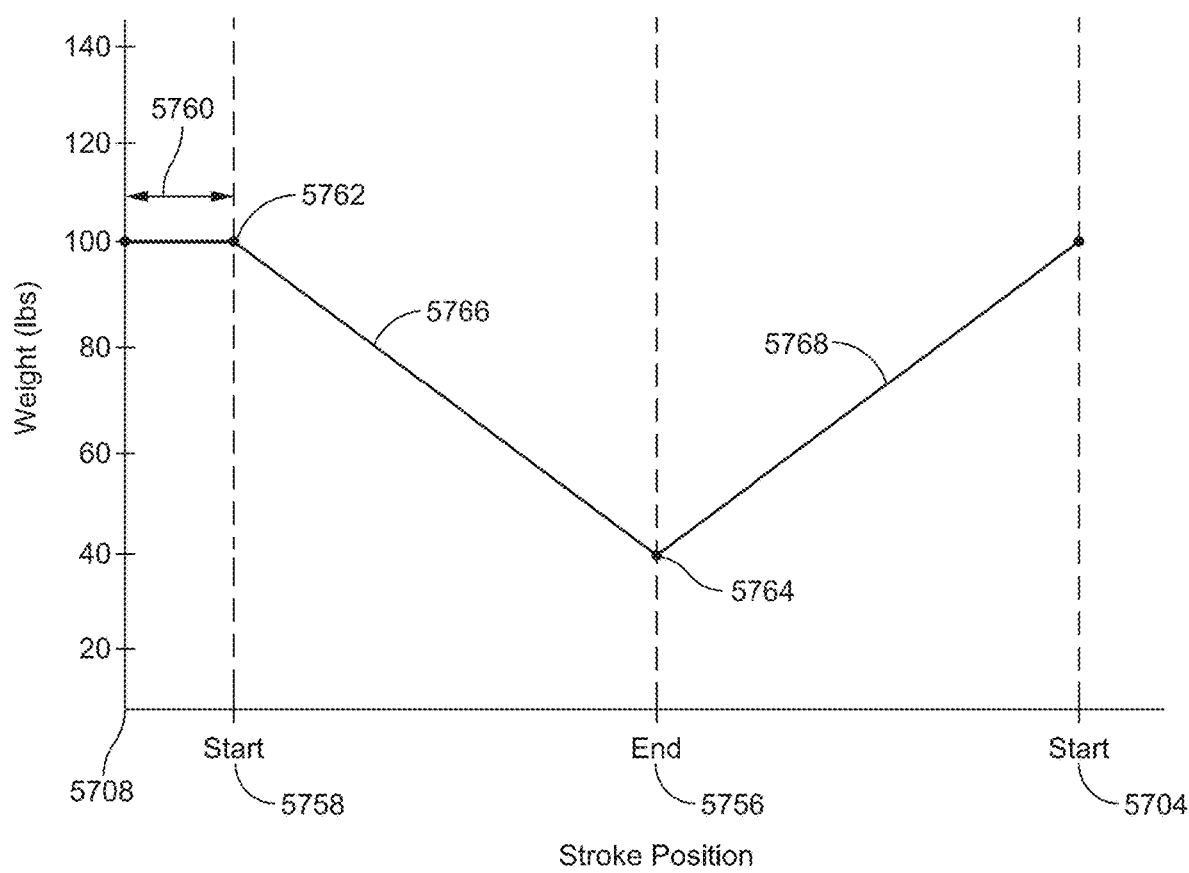
FIG. 57B is an inverted elastometric resistance profile diagram implemented in a programmable Resistance system of FIG. 31.

With reference to FIG. 57B in some embodiments, the elastomeric resistance profile 5700 of FIG. 57A may be reversed, via an analog inverter for example, to create and apply a reverse elastometric resistance profile 5750 to a cable 108. A reverse elastomeric resistance profile 5750 can be defined by applied resistance or weight in pounds on the vertical axis and stroke position on the horizontal axis. In some embodiments, a first and second start stroke position 5752, 5754 can be pre-defined by the host 106, such as where the cable 108 is extended 12 inches from a rest position, or calibrated either manually or automatically as described above in reference to FIG. 39 through FIG. 43. Further, an end stroke position 5756 may be similar predetermined by the host computing device 106, for example, to correspond to a cable extension of 118 inches, or calibrated. For a stroke position of the cable 108 between 0 extension 5758, and a start stroke position 5752, which may be referred to as an initialization stroke 5760, the resistance in weight applied to the cable 108 may be less than the full resistance value set by the user, or the full weight, such as 100 lbs as shown. In other cases, the resistance applied during the initialization stroke 5760 may be 0, or any percentage of the full resistance value set by the user, according to a predetermined value, or enterable by the user.

The user may set a starting resistance 5762, such as 100 lbs as shown, and an ending resistance 5764, such as 40 lbs as shown. The elastomeric engine, as described previously, can configure a resistance profile based on the starting and ending resistances 5762, 5764, and on the starting and ending stroke positions 5752, 5754 and via controller 104, can drive the DC motor 102 to implement such a resistance profile in cooperation with at least one potentiometer 115. The reverse elastomeric resistance profile may include a ramped out-stroke resistance 5766 from the start stroke position 5752 to the end stroke position 5756 and a ramped in-stroke resistance 5768 from the end stroke position 5756 back to start stroke position 5104.

In some embodiments, the programmable electronic resistance machine varies the resistance level at one or more discreet locations. In certain implementations, this step-based approach involves identifying one or more positions, either from a fixed set of positions or along a continuum, and setting independent resistance values for one or more positions. The controller 104 can continuously detect cable position via the potentiometer 115 and set the resistance levels accordingly, stepping to each resistance value in a discrete manner or in a smoothed manner.

For a stepping values approach, the user determines the positions of interest and configures the desired resistance value for each of the cable positions. The controller 104 changes the resistance level as defined by the user for each sensed cable placement, such as input from the potentiometer 115. Cable velocity and/or acceleration may not be considered when providing this type of operation given it is only a resistance/placement operational type.

For a smoothed values approach, the user determines the positions of interest and configures the desired resistance value for each of those cable positions. The rate of change from point to point is taken into account, as well as the resistance level. The controller 104 determines the rate of change of cable positioning from point to point and inter-leaves resistance changes between the points of interest making the resistance changes feel continuous (i.e. smooth).

Alternately, the elastometric engine can integrate the smoothing functions as described previously. In another alternate embodiment, a communicatively coupled computing device external to the controller 104 modifies and communicates those modified values to the controller 104, possibly reducing the programming and operational overhead of the controller 104.

Figure 58A:
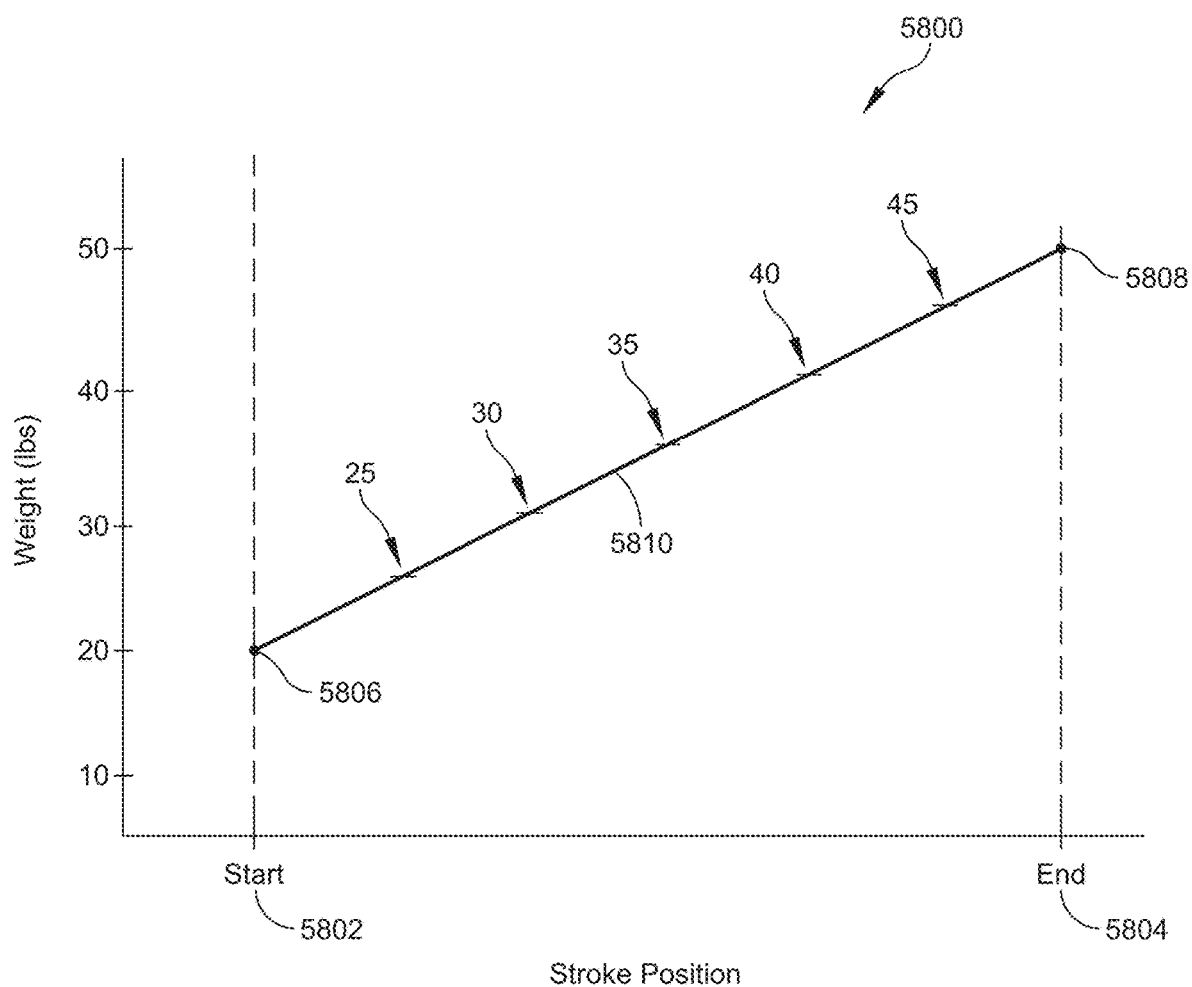
FIG. 58A is a stepped resistance profile diagram implemented in a programmable Resistance system.

In reference to FIG. 58A, resistance profile 5800 with discrete steps, such as an elastomeric positive stroke with discrete steps, is shown relative to resistance or weight level on the vertical axis and stroke position on the horizontal axis. In some embodiments, a start stroke position 5802 can be pre-defined by the host computing device 106, such as where the cable 108 is extended 12 inches from a rest position, or calibrated either manually or automatically as described above in reference to FIG. 39 through FIG. 43. Further, an end stroke position 5804 may be similar predetermined by the host computing device 106, for example, to correspond to a cable extension of 118 inches, or calibrated. The user may further program a start resistance 5806 and an end resistance 5808, which may, for example, be 20 lbs and 50 lbs respectively. Accordingly, a ramp resistance 5810 may be applied through cable 108 such that at equal stroke position intervals, the resistance may be increased a set amount, for example, in 5 lbs increments as shown. This may result in a smooth resistance ramp 5810 from 20 lbs of resistance at the start stroke position 5802 to 50 lbs of resistance at the end stroke position 5804. In this embodiment, the resistance profile 5800 may be generated by the elastomeric engine and may not require further input from the user to implement the ramp resistance 5810 lasting the entire set stroke length.

Figure 58B:
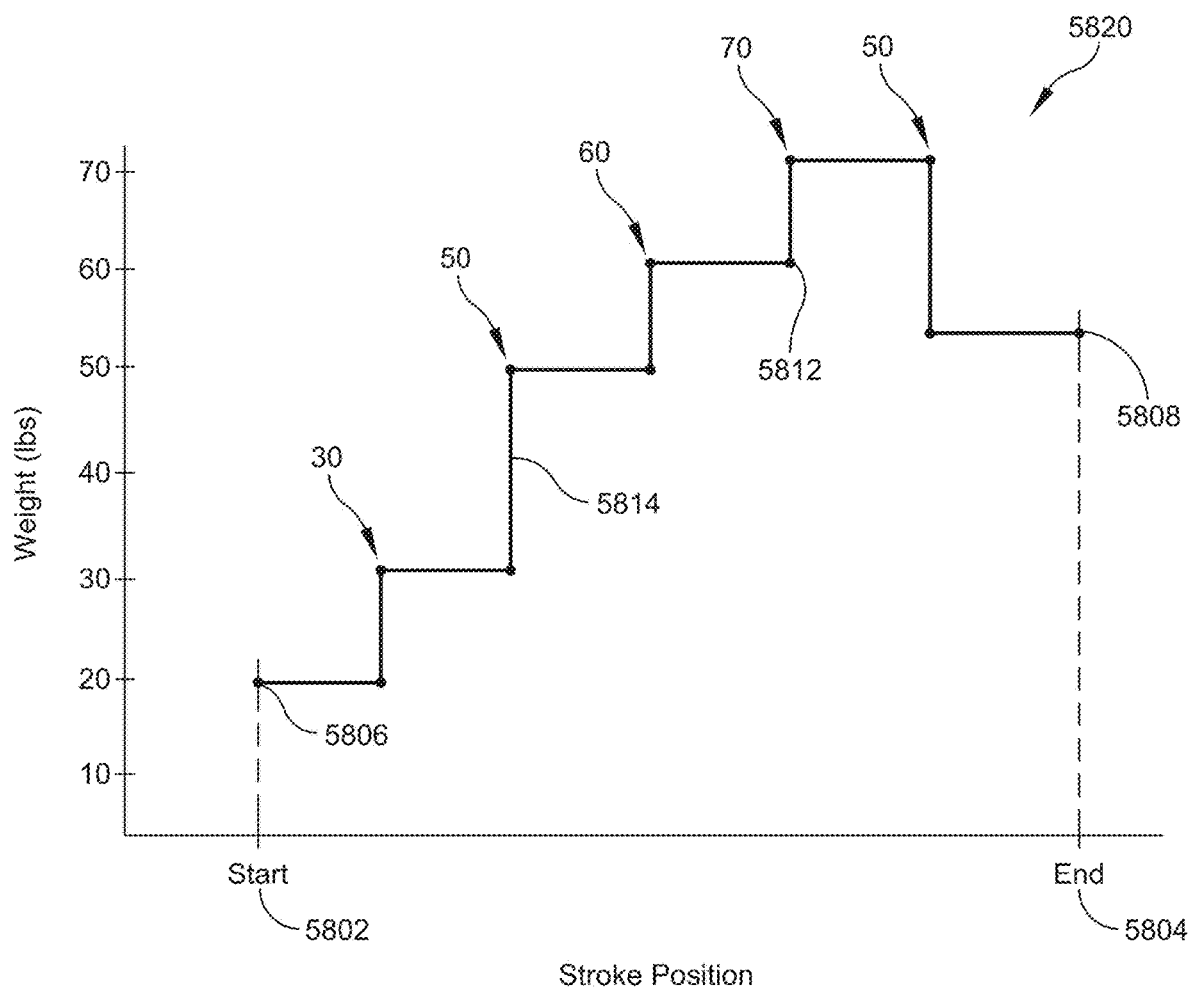
FIG. 58B is a stepped resistance profile diagram implemented in a programmable Resistance system.

With reference to FIG. 58B, resistance profile 5820 with discrete steps is shown modified for step functions at the displayed cable locations relative to resistance or weight level on the vertical axis and stroke position on the horizontal axis. In some embodiments, a start stroke position 5802 can be pre-defined by the host 106, such as where the cable 108 is extended 12 inches from a rest position, or calibrated either manually or automatically as described above in reference to FIG. 39 through FIG. 43. Further, an end stroke position 5804 may be similar predetermined by the host computing device 106, for example, to correspond to a cable extension of 118 inches, or calibrated. The user may further program a start resistance 5806 and an end resistance 5808, which may for example be 20 lbs and 50 lbs respectively. In this embodiment, the user may also set a maximum resistance 5812, for example 70 lbs, and set multiple discrete resistances according to stroke position. Accordingly, a ramp resistance 5814 may be applied through cable 108 such that at the user set stroke position intervals, the resistance may be increased to the corresponding user set resistance in a stepped manner In some implementations, such as that shown, each step in resistance may be 10 lbs up or down, and may occur at equal or different cable stroke positions.

Figure 58C:
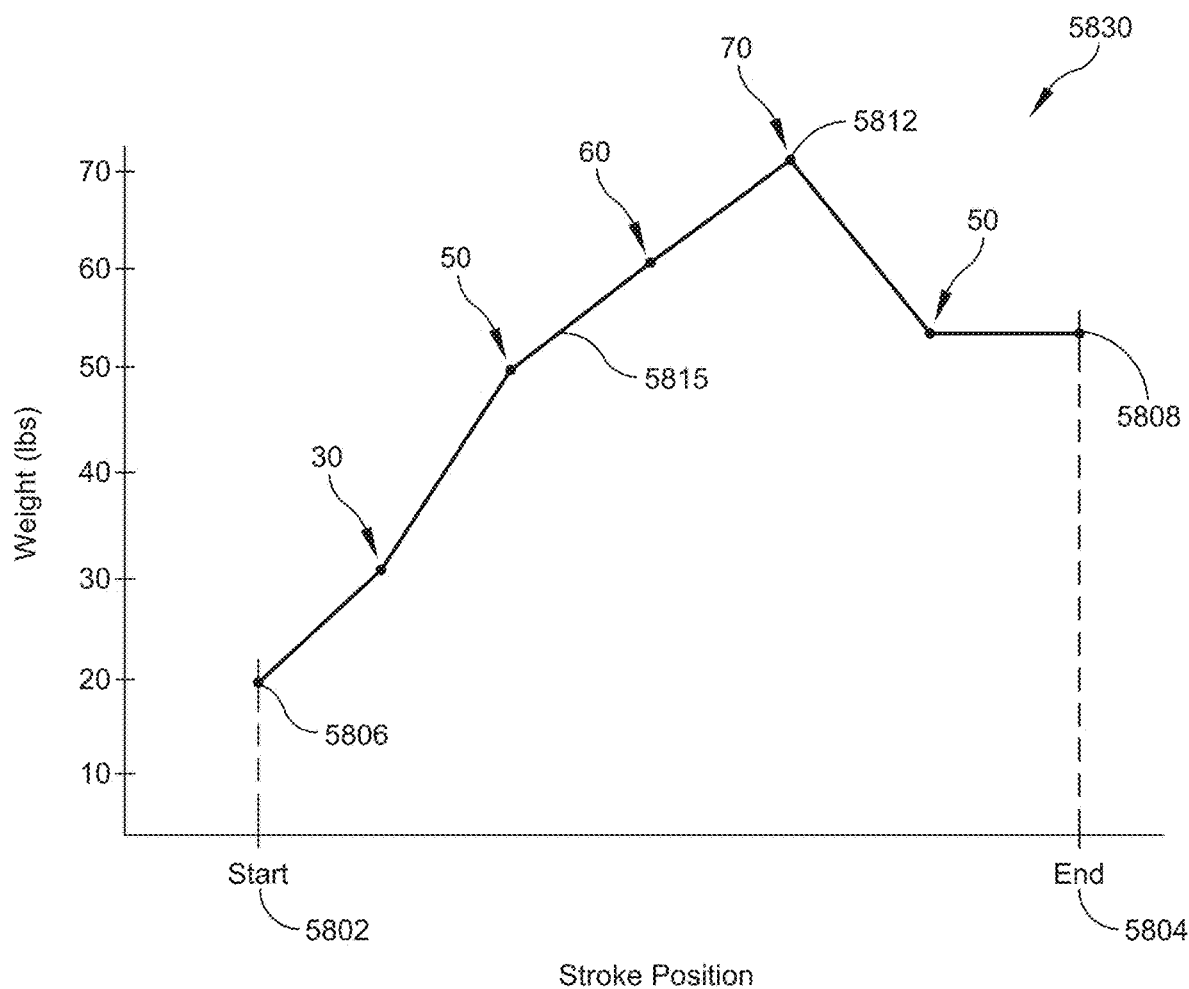
FIG. 58C is a stepped resistance profile diagram implemented in a programmable Resistance system.

In reference to FIG. 58C, resistance profile 5830 with discrete steps modified for step functions at the displayed cable locations and smoothed is shown relative to resistance or weight level on the vertical axis and stroke position on the horizontal axis. In some embodiments, a start stroke position 5802 can be pre-defined by the host 106, such as where the cable 108 is extended 12 inches from a rest position, or calibrated either manually or automatically as described above in reference to FIG. 39 through FIG. 43. Further, an end stroke position 5804 may be similar predetermined by the host computing device 106, for example, to correspond to a cable extension of 118 inches, or calibrated. The user may further program a start resistance 5806 and an end resistance 5808, which may, for example, be 20 lbs and 50 lbs respectively. In this embodiment, the user may also set a maximum resistance 5812, for example 70 lbs, and set multiple discrete resistances according to stroke position. The resistance values may then be smoothed according to cable position and/or velocity. Accordingly, a ramp resistance 5815 may be applied through cable 108 such that at the user set stroke position intervals, the resistance may be increased to the corresponding user set resistance, with smooth transitions to each different resistance level. In some implementations, such as that shown, each increase in resistance may be 10 lbs up or down, may occur at equal or different cable stroke positions, and are smoothed. In this embodiment, the maximum resistance value 5812 is not held for any change in stroke position.

Figure 58D:
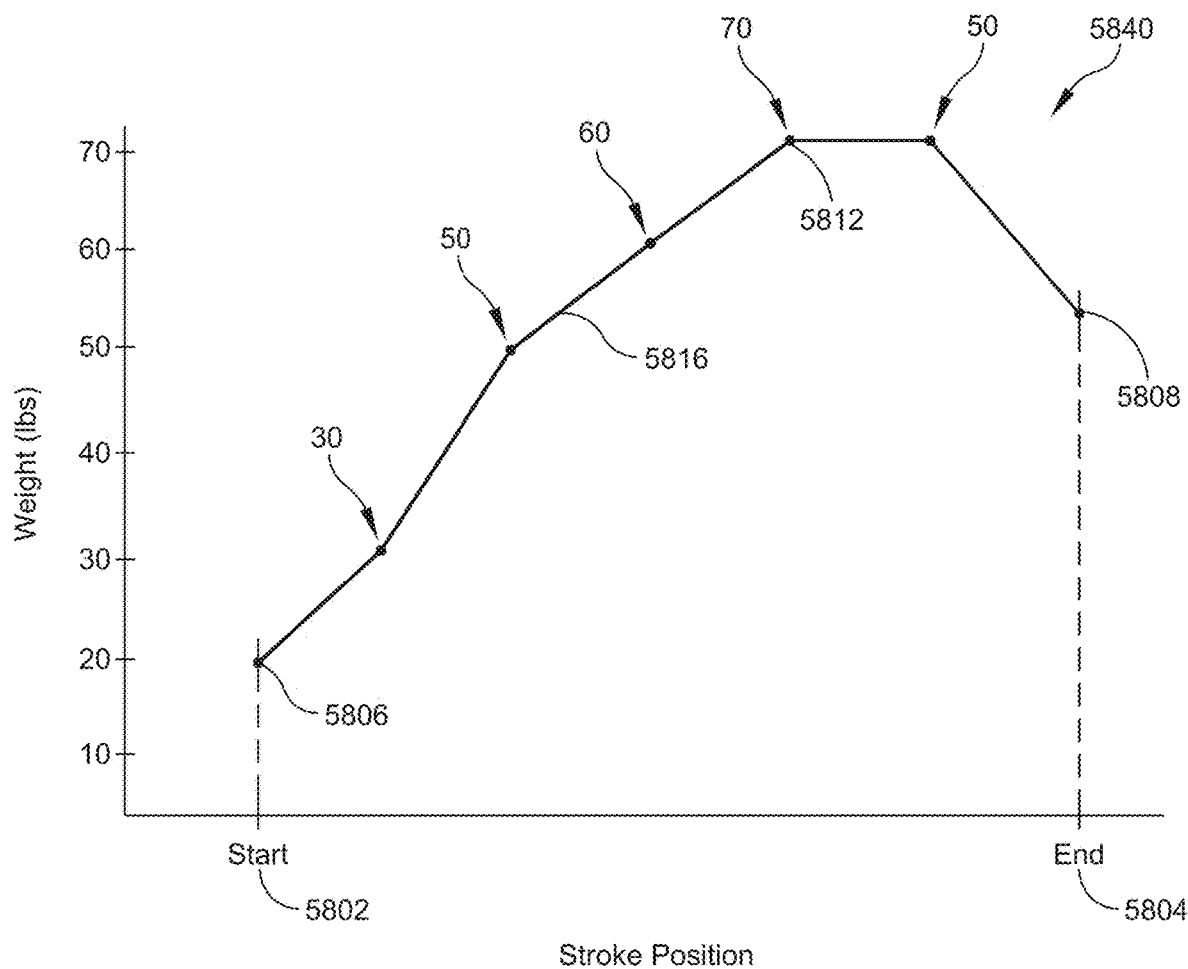
FIG. 58D is a stepped resistance profile diagram implemented in a programmable Resistance system.

Referring now to FIG. 58D, resistance profile 5840 with discrete steps modified for step functions at the displayed cable locations and smoothed, having a greater peak resistance value duration, is shown relative to resistance or weight level on the vertical axis and stroke position on the horizontal axis. In some embodiments, a start stroke position 5802 can be pre-defined by the host computing device 106, such as where the cable 108 is extended 12 inches from a rest position, or calibrated either manually or automatically as described above in reference to FIG. 39 through FIG. 43. Further, an end stroke position 5804 may be similar predetermined by the host computing device 106, for example to correspond to a cable extension of 118 inches, or calibrated. The user may further program a start resistance 5806 and an end resistance 5808, which may for example be 20 lbs and 50 lbs respectively. In this embodiment, the user may also set a maximum resistance 5812, for example 70 lbs, and set multiple discrete resistances according to stroke position. The resistance values may then be smoothed according to cable position and/or velocity. Accordingly, a ramp resistance 5816 may be applied through cable 108 such that at the user set stroke position intervals, the resistance may be increased to the corresponding user set resistance, with smooth transitions to each different resistance level. In some implementations, each increase in resistance may be 10 lbs up or down, may occur at equal or different cable stroke positions, and may be smoothed. In this example, the maximum resistance value 5812 is held for a longer duration in change of stroke position.

Figure 59:
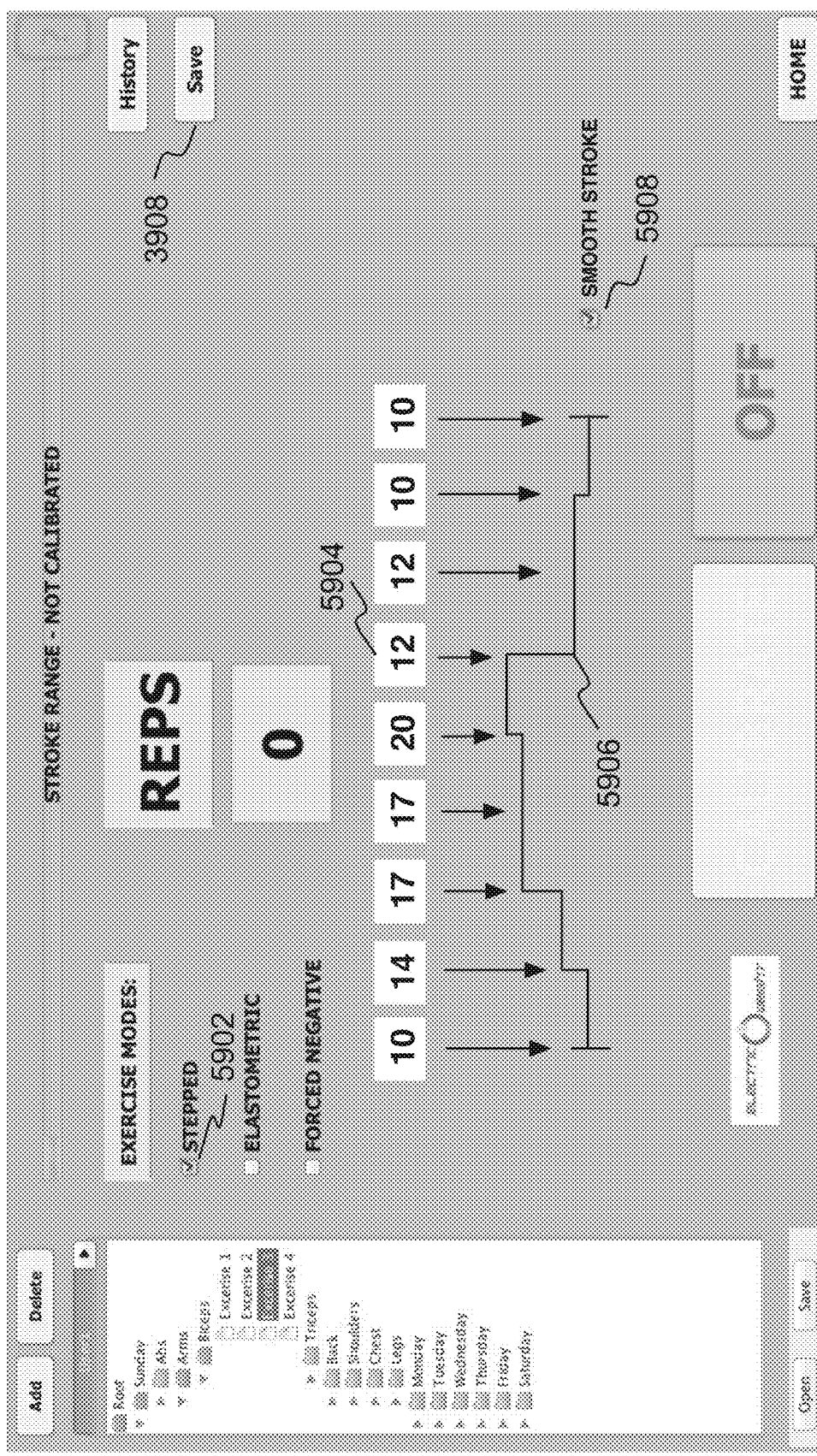
FIG. 59 is a screen capture of a stepped exercise profile displayed on the host device of FIG. 31.

Referring now to FIG. 59, in some embodiments, the host computing device 106 detects the selection of a stepped exercise mode checkbox 5902. In some instances, there is no minimum resistance value or maximum resistance value. The host computing device 106 displays an interface to set independent resistance values 5904 corresponding to discreet positions within the stroke range. In some implementations, the user interface may include a visual representation of the positions and resistance levels 5906. A smoothing option checkbox 5908 may be presented. When the controller 104 detects the selection of the smoothing option check box 5908, resistance changes can be interleaved between the discreet positions along the stroke range. Upon detecting the button press event for the Save button 3908, the host computing device 106 marshals and sends the entered values, including the max cable speed, to the controller 104, which can store them in RAM, in on-board, non-volatile EEPROM, and/or in an alternative persistent memory store.

Figure 60:
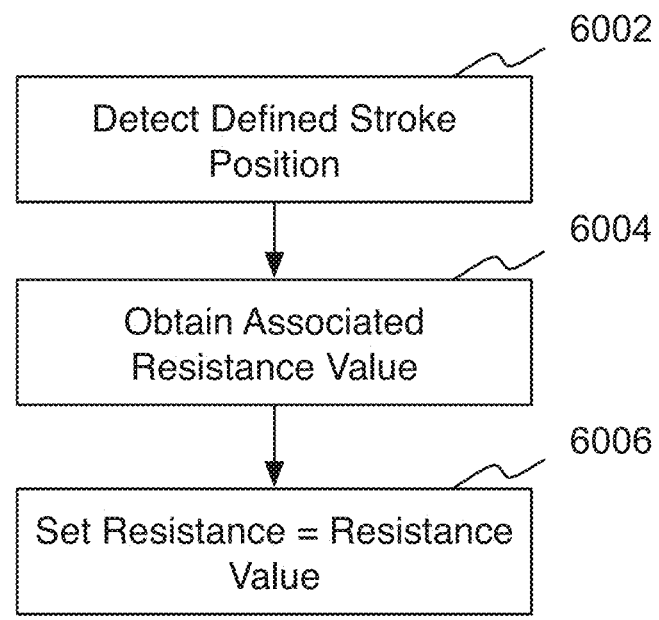
FIG. 60 is a flow diagram of a method for implementing a stepped exercise for the programmable Resistance system of FIG. 31 in accordance with various embodiments.
Figure 61:
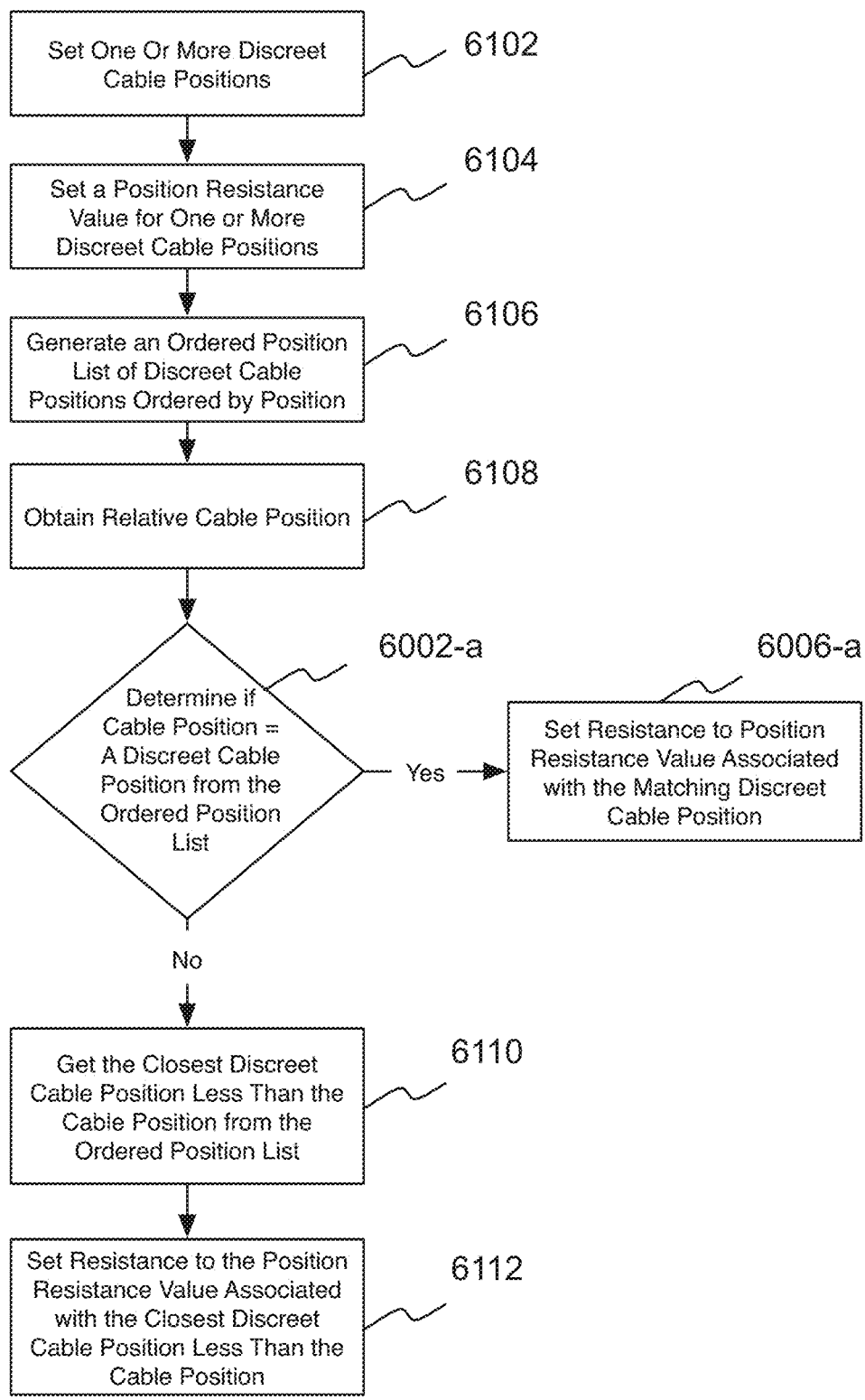
FIG. 61 is a flow diagram of a method for implementing a stepped exercise for the programmable Resistance system of FIG. 31 in accordance with various embodiments.

Referring now to FIG. 60 and FIG. 61, one or more discreet positions in the stroke range are set 6102 and associated with a resistance value 6104. The controller generates a list of positions ordered by position 6106. The controller obtains the absolute resistance mechanism position, in this example from a position potentiometer 115, and calculates the relative position in the stroke range 6108. The controller 104 detects if the defined stroke position is obtained 6002, in this case, by traversing the list for each relative position as it is calculated to determine if the relative position matches a discreet position in the list 6002-*a*. If a match is found, the associated resistance value is obtained 6004, and resistance is set to the position resistance value associated with the matching position 6006, in this example, a cable position 6006-*a*. If no match is found, the closest discreet position less than the relative cable position is retrieved 6110, and the resistance is set to the position resistance value associated with that closest discreet retrieved position 6112.

Figure 62:
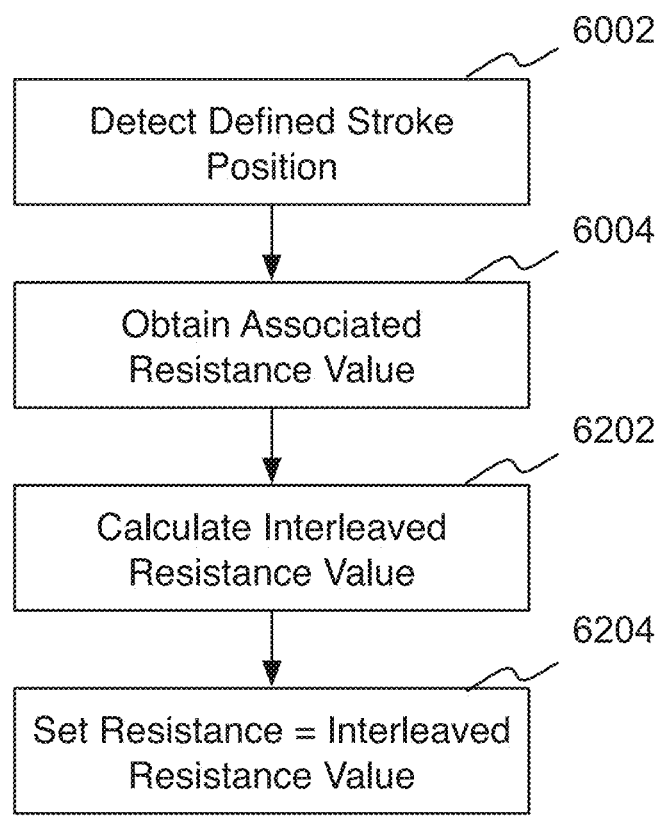
FIG. 62 is a flow diagram of a method for implementing a stepped exercise with smoothing for the programmable Resistance system of FIG. 31 in accordance with various embodiments.
Figure 63:
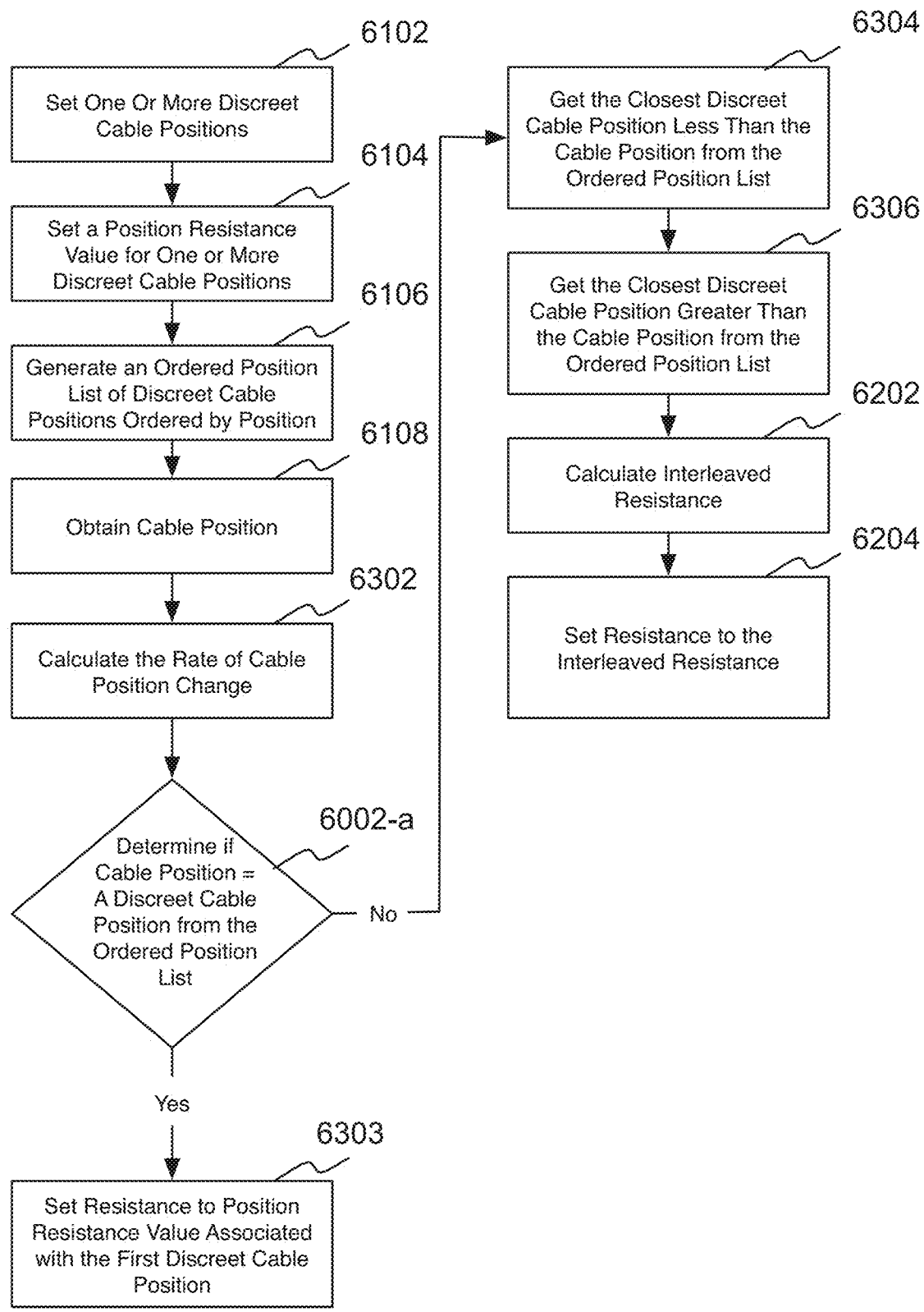
FIG. 63 is a flow diagram of a method for implementing a stepped exercise with smoothing for the programmable Resistance system of FIG. 31 in accordance with various embodiments.

Referring now to FIG. 62 and FIG. 63, a smoothing algorithm can be applied to the stepped exercise mode, calculating and setting interleaved resistance values 6202, 6204 that can be set during the stroke range segments between the defined discreet positions. The controller 104 calculates the rate of change of cable positioning 6302 as it obtains relative position values. If the controller determines that a relative position value (RP) does not match a discreet position in the ordered list, an interleave calculation is performed to determine the resistance value 6202. Such a calculation can include, for example, obtaining the closest discreet position less than the relative cable position (LV) 6304, the closest discreet position greater than the relative cable position (GV) 6306, and the associated resistance values (LR, GR). An interleaved resistance value can be calculated 6202 using an algorithm such as, for example, LR+((RP−LV)/(GV−LV)*(GR−LR)). Resistance can be set to the interleaved values in the order calculated 6204. In an alternate embodiment, the elastometric engine integrates a smoothing function. In another embodiment, the host can implement the processing logic for the interleaving calculations.

Another type of resistance training includes the use of end point ramping. This method provides for ramping up the resistance at an end point in the stroke, such as a starting stroke position or an ending stroke position, at a given rate, holding the higher resistance for a given time, and ramping back down to the original weight/resistance, or any other resistance value. This method can be implemented with other resistance profiles, such with elastometrics, reverse elastometrics, etc.

Figure 64A:
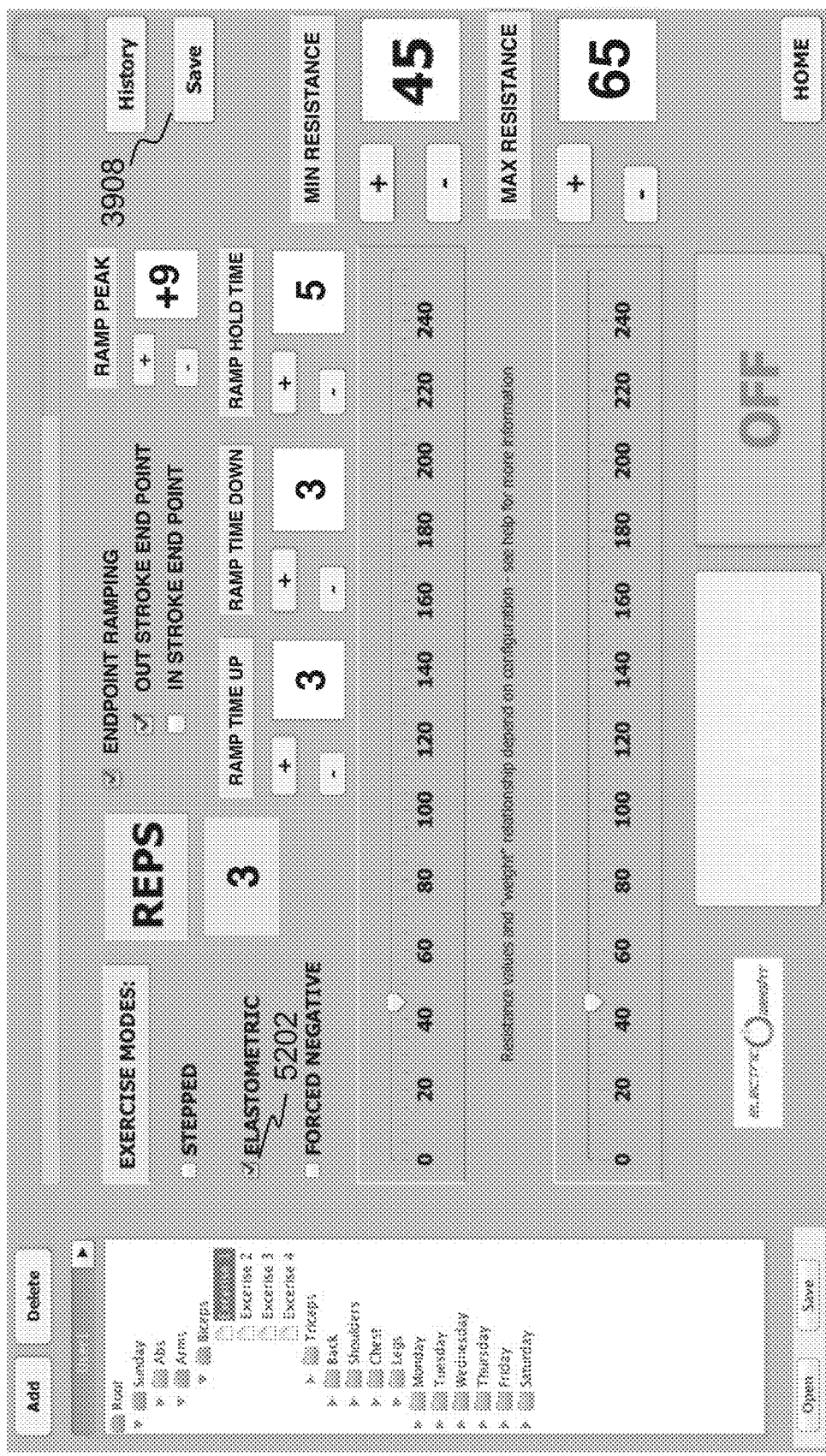
FIG. 64A is a screen capture of an elastometric exercise profile with endpoint ramping displayed on the host device of FIG. 31.
Figure 64B:
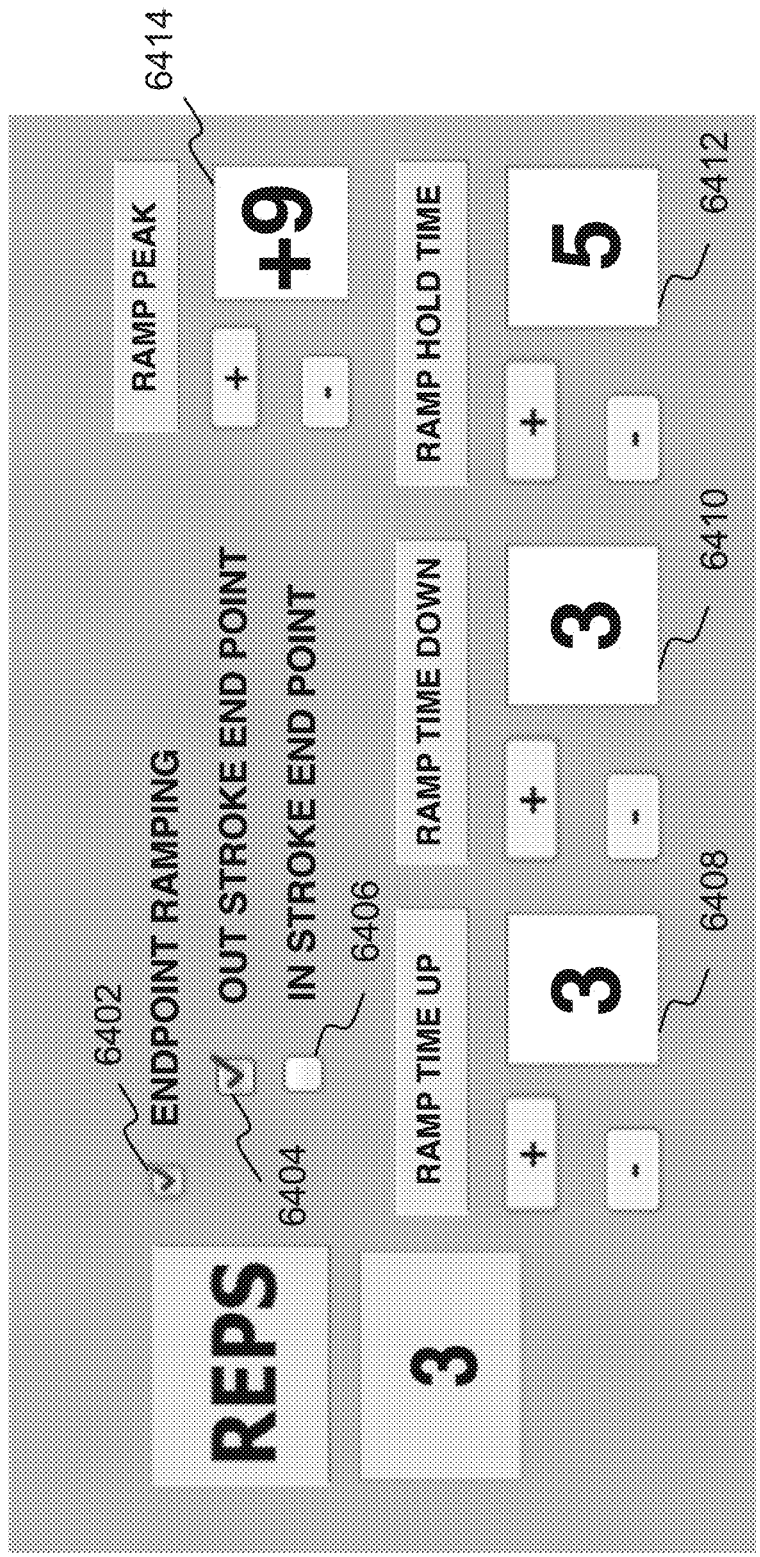
FIG. 64B is a screen capture of an exercise profile with endpoint ramping displayed on the host device of FIG. 31.

Referring now to FIG. 64A and FIG. 64B, in some embodiments, the programmable electronic weight machine host detects the selection of an endpoint ramping checkbox 6402. In some instances, this can be combined with one or more exercise modes such as, for example, elastometric mode 5202. The host computing device 106 can display options for adding endpoint ramping at the end of the out stroke 6404 the in stroke 6406, or both strokes. Time value prompts for ramp time up value 6408, ramp time down value 6410, and/or hold time value 6412 can be displayed. These values can be used to define the timing of the various phases of the endpoint ramp. A ramp peak prompt 6414 is displayed, which, in some embodiments, can accept either a positive or negative number, enabling both positive and negative ramp behavior. Upon detecting the button press event for the Save button 3908, the host computing device 106 marshals and sends the entered values, including the endpoint ramping values, to the controller 104, which can store them in RAM, in on-board, non-volatile EEPROM, and/or in an alternative persistent memory store.

Figure 65:
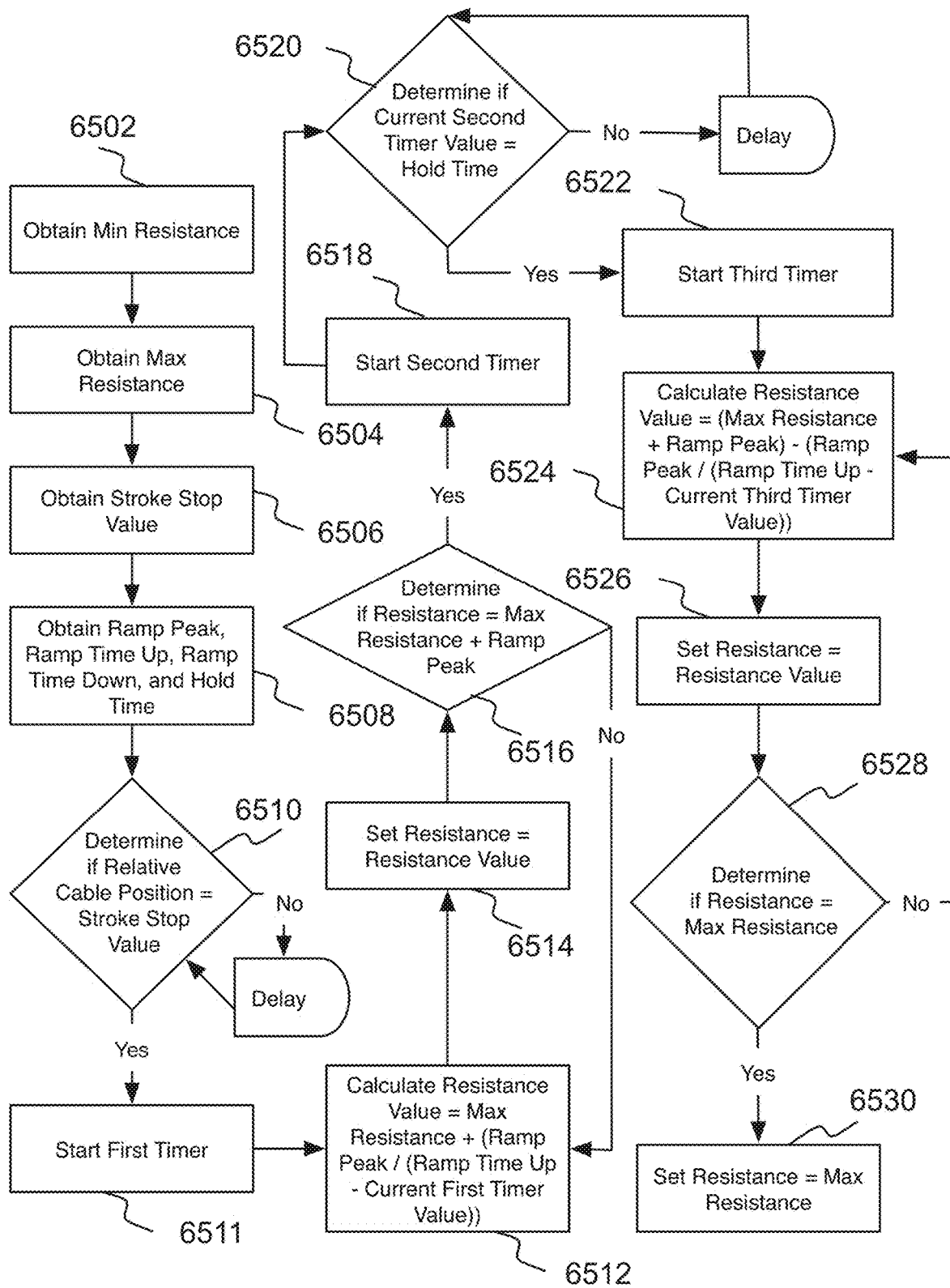
FIG. 65 is a flow diagram of a method for implementing endpoint ramping for the programmable Resistance system of FIG. 31 in accordance with various embodiments.

Referring now to FIG. 65, the controller 104 obtain the minimum resistance value 6502, the maximum resistance value 6504, and the stroke stop value 6506. In addition, the controller 104 may obtain the endpoint ramping parameters, including, for example, ramp peak, ramp time up, hold time, and ramp time down 6508. The controller 104 determines relative cable position and compares the position value to the stroke stop value 6510. If they match, the controller 104 starts a first time corresponding to the ramp time up 6511. Resistance values are repeatedly updated 6514 until the controller 104 determines the resistance is equal to (maximum resistance+ramp peak) 6516. In some embodiments, the repeatedly-updated resistance value is calculated according to an algorithm such as, for example, maximum resistance+(ramp peak/(ramp time up−current first timer value)) 6512. Once resistance is equal to (maximum resistance+ramp peak), the controller starts a second timer corresponding to the hold time 6518, The resistance level is unchanged for the duration of this timer. When the controller determines the current timer value is equal to the hold time 6520, the controller starts a third timer corresponding to the ramp down time 6522. Resistance values are repeatedly updated 6526 until the controller determines the resistance is equal to maximum resistance 6528. In some embodiments, the repeatedly-updated resistance value is calculated according to an algorithm such as, for example, (maximum resistance+ramp peak)−(ramp peak/(ramp time up−current third timer value)) 6524.

Figure 66:
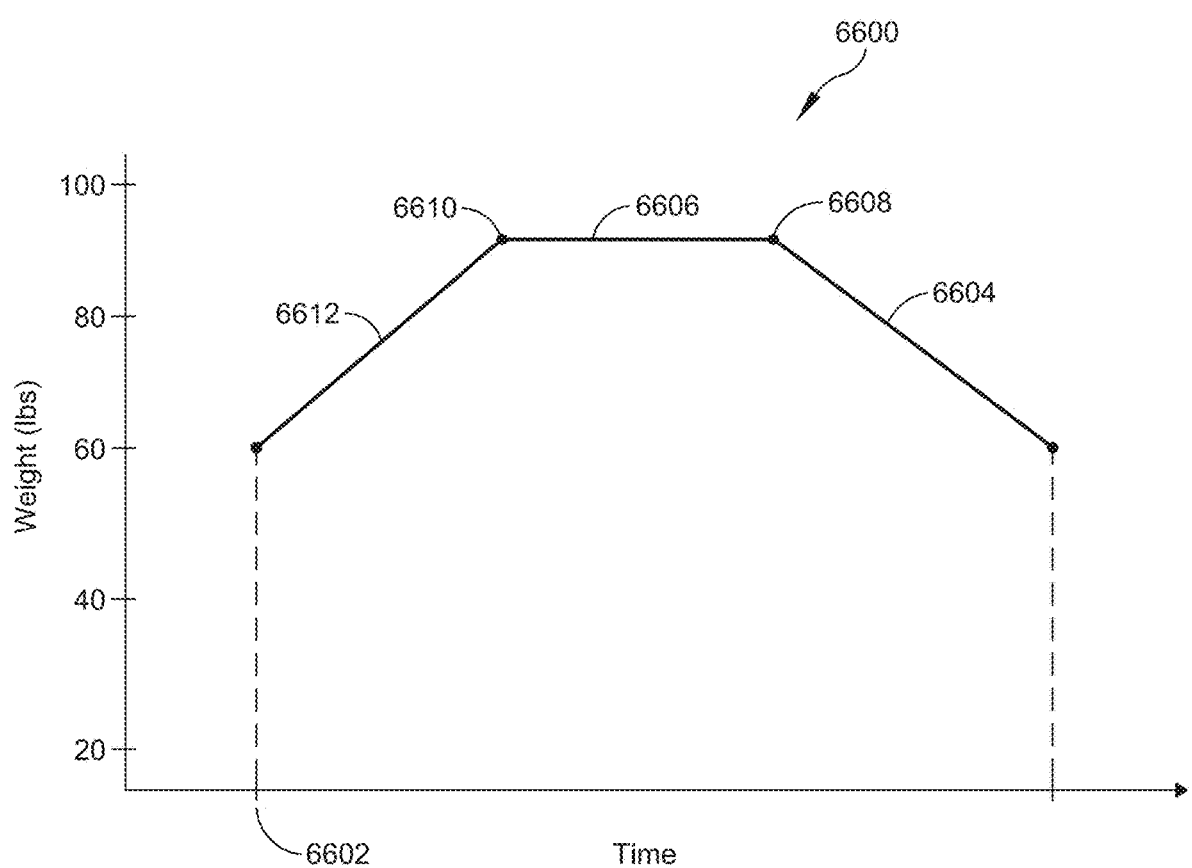
FIG. 66 is an endpoint resistance profile diagram implemented in the programmable Resistance system of FIG. 31.

Referring now to FIG. 66, an end point ramping resistance profile is 6600 defined by applied resistance or weight in pounds on the vertical axis and time on the horizontal axis is shown. The end point ramping resistance profile 6600 may be implemented at a starting or ending position of the cable 108, or any other position where it is desired to hold a particular stoke length. At a start time 6602, a resistance level is at a preset level, such as 60 lbs as shown. The resistance level will ramp up during resistance up-ramp 6604 to a user programmed or selected max resistance level 6606 based on a user programmed or selected ramp time, such as 90 lbs as shown. The max resistance level 6606 will be held for a user selected or programmed time, such as from time 6608 to 6610. The resistance level decreases at a user selected or programmed rate, which may be the same as the up-ramp rate, during resistance down ramp 6612 until an end resistance 6614 is reached, such as 60 lbs as shown.

In some embodiments, a first and second start stroke position 6602, 6604 can be pre-defined by the host computing device 106, such as where the cable 108 is extended 12 inches from a rest position, or calibrated either manually or automatically as described above in reference to FIG. 39 through FIG. 43. Further, an end stroke position 5106 may be similar predetermined by the host computing device 106, for example, to correspond to a cable extension of 118 inches, or calibrated. Referring now to FIG. 57A, for a stroke position of the cable 108 between 0 extension 5108, and a start stroke position 5102, which may be referred to as an initialization stroke 5110, the resistance in weight applied to the cable 108 may be less than the full resistance value set by the user, such as 40 lbs as shown. In other cases, the resistance applied during the initialization stroke 5110 may be 0, or any percentage of the full resistance value set by the user, according to a predetermined value, or enterable by the user.

Figure 67:
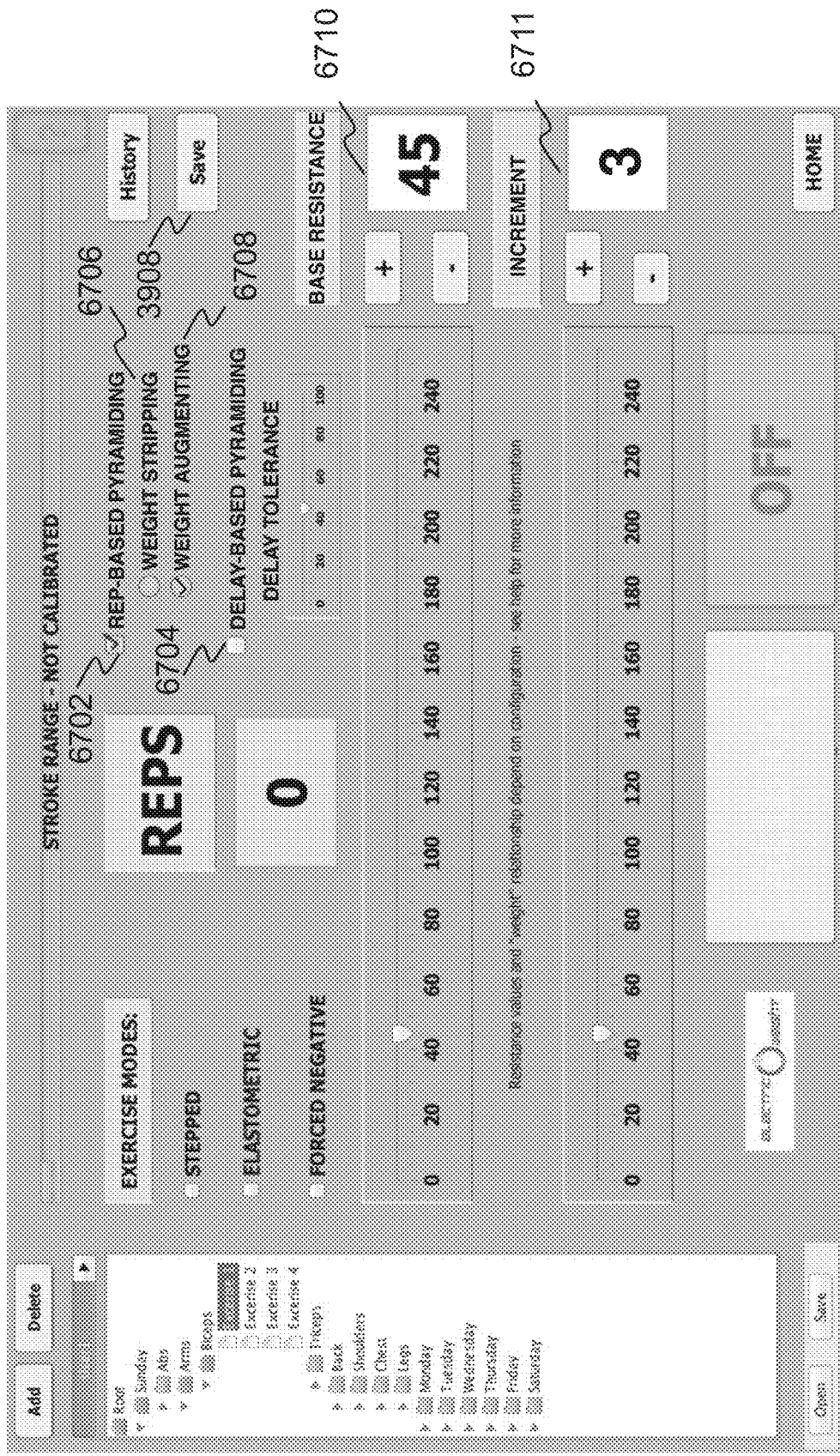
FIG. 67 is a screen capture of an exercise profile with repetition-based pyramiding displayed on the host device of FIG. 31.
Figure 68:
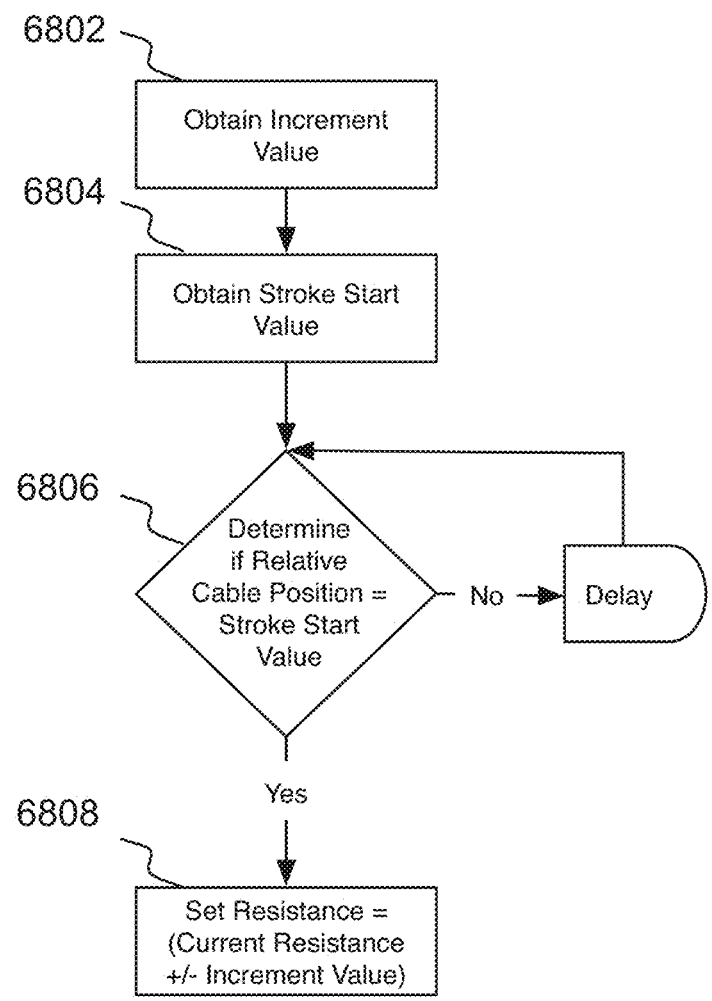
FIG. 68 is a flow diagram of a method for implementing repetition-based pyramiding for the programmable Resistance system of FIG. 31 in accordance with various embodiments.

Referring now to FIG. 67, the host computing device 106 detects the selection of one or more pyramiding checkboxes 6702, 6704. In certain embodiments, the host displays an option for repetition based pyramiding 6702, with additional options to weight strip 6706 or weight augment 6708, where weight stripping involves decreasing resistance and weight augmentation involves increasing resistance. The host computing device 106 displays prompts for base resistance 6710 and a pyramiding increment 6711. The controller 104 can use the pyramiding increment to determine the amount to increase or decrease the resistance level after each repetition. Referring now to FIG. 68, in certain implementations, the controller 104 obtains the increment value 6802 and stroke start value 6804. The controller then compares the relative cable position received to the stroke start value 6806. The matching of these values indicates a repetition has been completed, and the current resistance is increased or decreased by the increment amount in accordance with the weight stripping or weight augmentation selection 6808.

Figure 69:
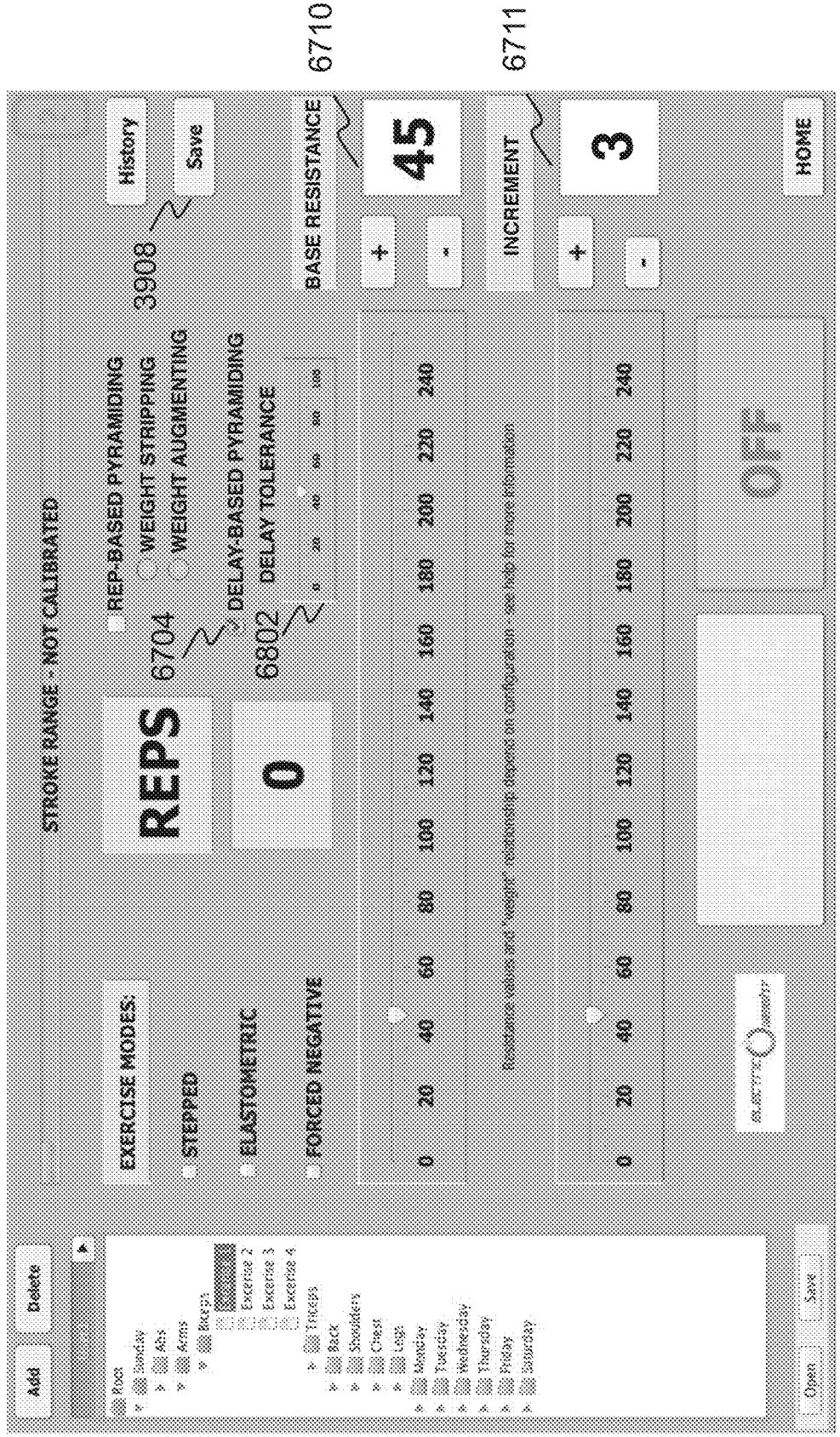
FIG. 69 is a screen capture of an exercise profile with delay-based pyramiding displayed on the host device of FIG. 31.
Figure 70:
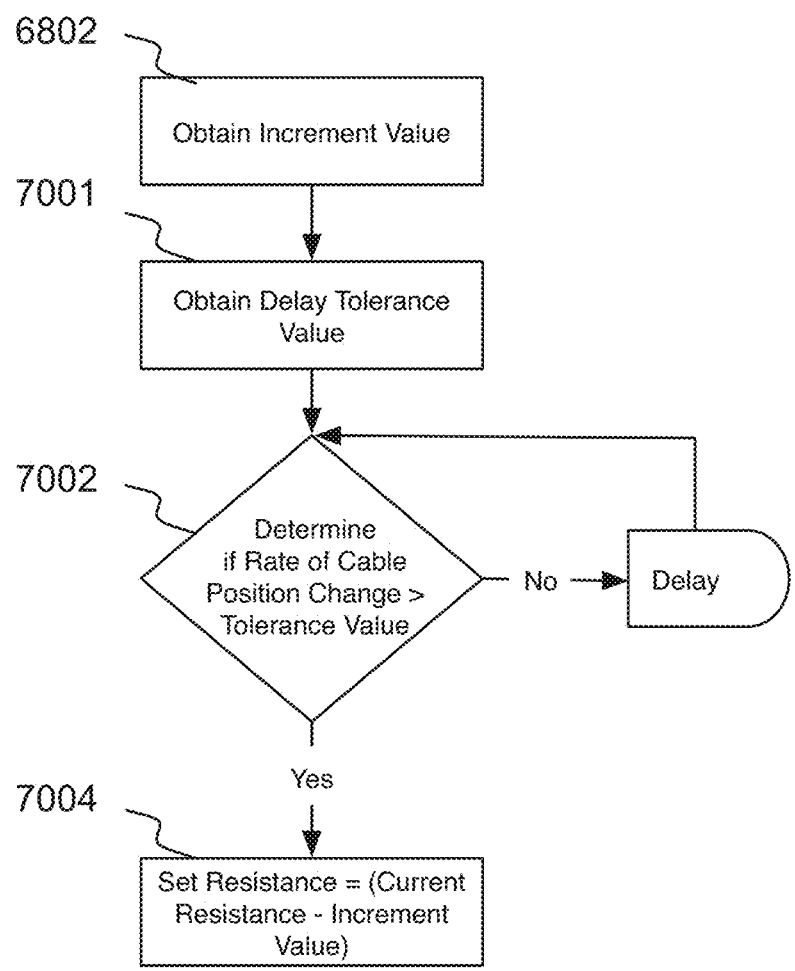
FIG. 70 is a flow diagram of a method for implementing delay-based pyramiding for the programmable Resistance system of FIG. 31 in accordance with various embodiments.

Referring now to FIG. 69, in certain instances, the host computing device 106 displays an option for delay-based pyramiding 6704. Delay-based pyramiding generally involves weight stripping based on a user displaying behavior indicating the user is having difficulty completing the exercise motion as determined by, for example, the detection of a slower rate of movement through the stroke range. Delay can be calculated, for example, as a function of the time it takes to move from one point in the stroke range to another, or alternatively, by detecting a lack of movement. The host computing device 106 displays prompts for base resistance 6710 and the pyramiding increment 6711. The controller can use the pyramiding increment to determine the amount to decrease the resistance level after each repetition. A delay tolerance slider or other edit control may be displayed enabling the selection of a tolerance level 6802. The tolerance level applies a hysteresis factor to the delay function, increasing the degree of change required to trigger a weight stripping event. In an alternate embodiment, the hysteresis factor can be replaced with discreet values that are added to delay periods defined by a tolerance level. Referring now to FIG. 70, in certain implementations, the controller 104 obtains the increment value 6802 and the delay tolerance value 7001. The controller 104 then determines if the rate of cable position change is greater than the threshold tolerance value 7002. If it is greater, this may indicate the user is having difficulty and the current resistance is decreased by the increment amount 7004.

Figure 71:
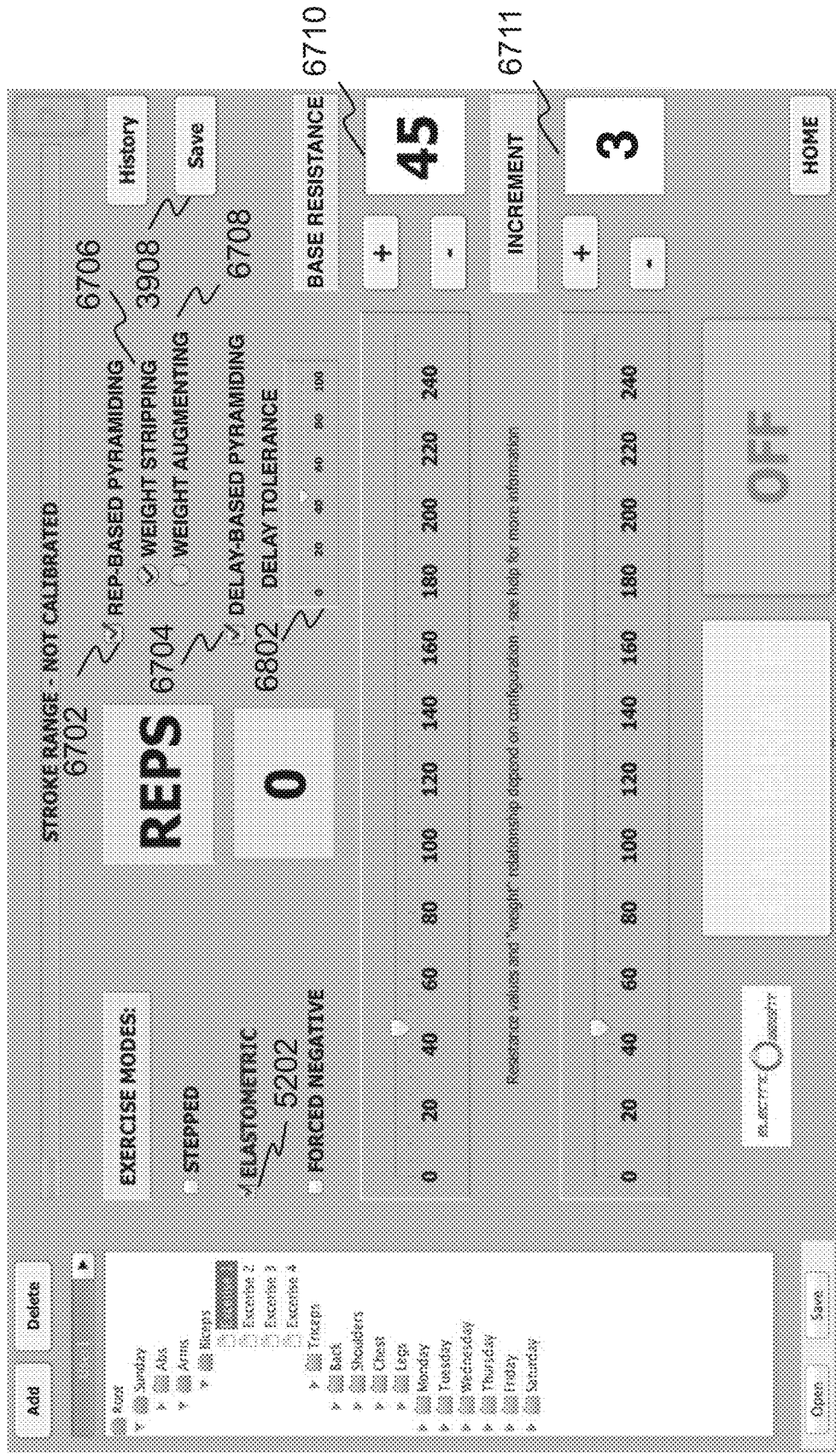
FIG. 71 is a screen capture of an exercise profile with repetition-based pyramiding and delay-based pyramiding displayed on the host device of FIG. 31.
Figure 72:
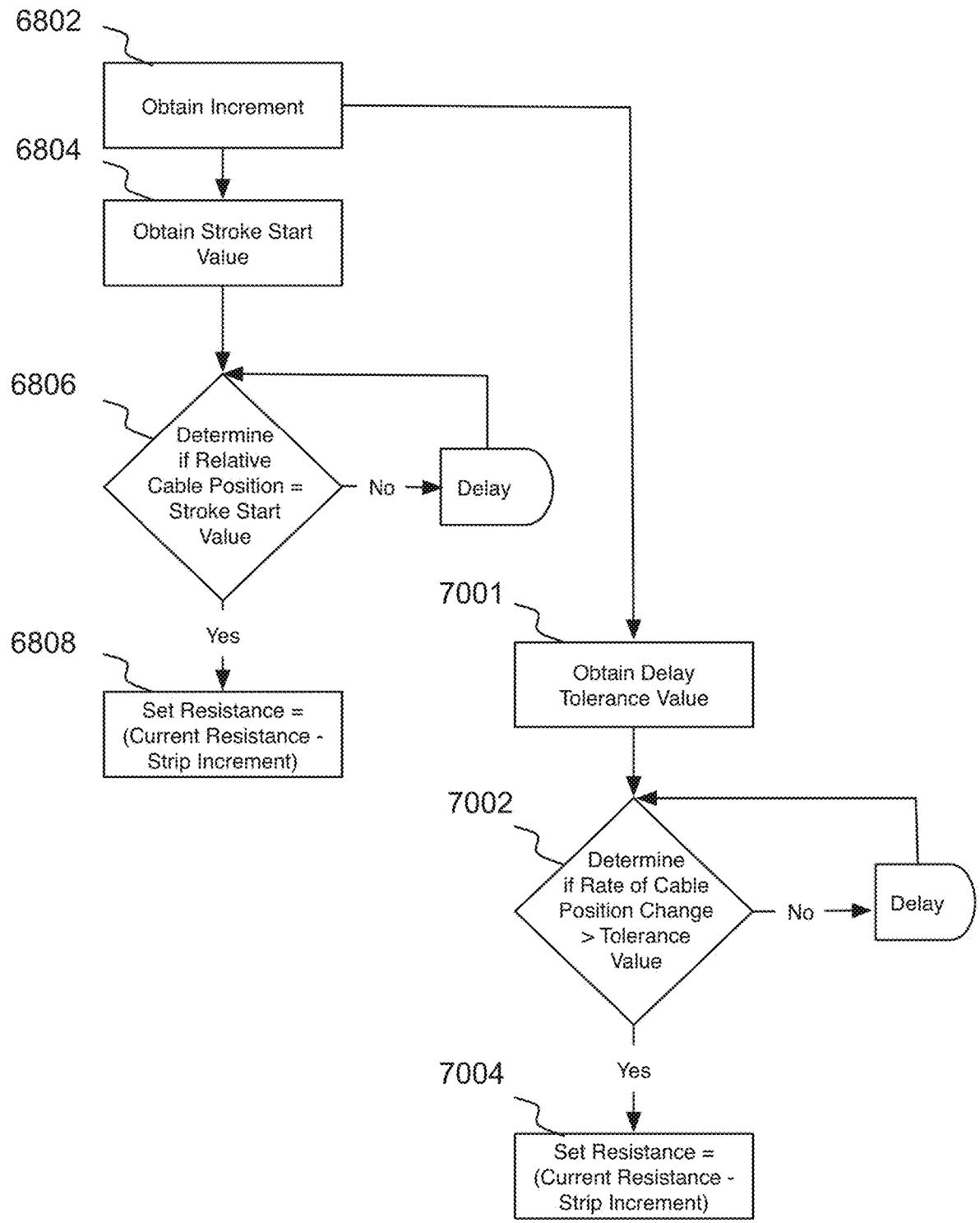
FIG. 72 is a flow diagram of a method for implementing repetition-based pyramiding and delay-based pyramiding for the programmable Resistance system of FIG. 31 in accordance with various embodiments.

The resistance system can support combining various aspects of one or more exercise modes and/or exercise profiles. For example, repetition based pyramiding can be combined with delay based pyramiding. Referring now to FIG. 70 and FIG. 71, both delay-based pyramiding and repetition-based pyramiding are selected. The controller 104 obtains the increment value 6802 the stroke start value 6804, and the tolerance value 7001. Both the repetition-based pyramiding and tolerance-based pyramiding operate as described previously, but they do so concurrently. Depending on the weight stripping and weight augmentation selections 6706, 6708, resistance levels are adjusted accordingly at the end of each repetition 6808, and delays detected by the controller 104 during the stroke range exceeding the tolerance value threshold triggers a resistance reduction 7004. This can, for example, result in a situation where resistance is added at the end of each repetition that exceeds the users ability to complete the stroke. The delay-based pyramiding function can rescue the set by automatically reducing the weight to a level the user can manage. At the end of each repetition, the controller 104 will continue to add resistance, pushing the user, but the delay-based pyramiding function can reduce the likelihood of the set being abandoned due to the users inability to overcome the resistance level.

It should be noted that the methods, systems and devices discussed above are intended merely to be examples. It must be stressed that various embodiments may omit, substitute, or add various procedures or components as appropriate. For instance, it should be appreciated that, in alternative embodiments, the methods may be performed in an order different from that described, and that various steps may be added, omitted or combined. Also, features described with respect to certain embodiments may be combined in various other embodiments. Different aspects and elements of the embodiments may be combined in a similar manner. Also, it should be emphasized that technology evolves and, thus, many of the elements are exemplary in nature and should not be interpreted to limit the scope of the invention.

Specific details are given in the description to provide a thorough understanding of the embodiments. However, it will be understood by one of ordinary skill in the art that the embodiments may be practiced without these specific details. For example, well-known circuits, processes, algorithms, structures, and techniques have been shown without unnecessary detail in order to avoid obscuring the embodiments.

Also, it is noted that the embodiments may be described as a process that is depicted as a flow diagram or block diagram. Although each may describe the operations as a sequential process, many of the operations can be performed in parallel or concurrently. In addition, the order of the operations may be rearranged. A process may have additional steps not included in the figure.

Moreover, as disclosed herein, the term "memory" or "memory unit" may represent one or more devices for storing data, including read-only memory (ROM), random access memory (RAM), magnetic RAM, core memory, magnetic disk storage mediums, optical storage mediums, flash memory devices or other computer-readable mediums for storing information. The term "computer-readable medium" includes, but is not limited to, portable or fixed storage devices, optical storage devices, wireless channels, a sim card, other smart cards, and various other mediums capable of storing, containing or carrying instructions or data.

Furthermore, embodiments can be implemented by hardware, software, firmware, middleware, microcode, hardware description languages, or any combination thereof. When implemented in software, firmware, middleware or microcode, the program code or code segments to perform the necessary tasks may be stored in a computer-readable medium such as a storage medium. Processors may perform the necessary tasks.

Having described several embodiments, it will be recognized by those of skill in the art that various modifications, alternative constructions, and equivalents can be used without departing from the spirit of the invention. For example, the above elements may merely be a component of a larger system, wherein other rules may take precedence over or otherwise modify the application of the invention. Also, a number of steps may be undertaken before, during, or after the above elements are considered. Accordingly, the above description should not be taken as limiting the scope of the invention.

What is claimed is:

1. A method of operating an exercise resistance machine having a resistance provided by a DC motor operatively connected to a resistance delivery section of the exercise resistance machine, the method comprising:
    configuring the exercise resistance machine to controllably provide one or more different levels of resistance via the DC motor during one or both of a positive exercise stroke and a negative exercise stroke with respect to the resistance delivery section, wherein the DC motor is used to at least impose a resistance to movement of the resistance delivery section;
    sensing an electrical condition developed by the DC motor; and
    controlling an amount of electrical resistance electrically coupled to the DC motor in response to the sensed electrical condition developed by the DC motor.

2. The method of claim 1, wherein the electrical condition sensor is a DC motor voltage sensor, wherein the electrical condition sensed is voltage, and wherein the controlling of the amount of electrical resistance electrically coupled to the DC motor uses pulse width modulation to modulate electrical resistance electrically coupled to the DC motor.

3. The method of claim 1, wherein the controlling of the amount of electrical resistance electrically coupled to the DC motor controllably inserts electrical resistance in series with the DC motor.

4. The method of claim 3, wherein the controlling of the amount of electrical resistance electrically coupled to the DC motor controllably electrically connects at least one resistor in series with the DC motor.

5. The method of claim 4, wherein the controlling of the amount of electrical resistance electrically coupled to the DC motor comprises controlling at least one transistor to controllably switch the at least one resistor in series electrical connection with the DC motor.

6. The method of claim 3, wherein the controlling of the amount of electrical resistance electrically coupled to the DC motor controllably electrically connects at least one resistor in series with the DC motor using pulse width modulation to modulate the amount of electrical resistance being electrically coupled to the DC motor.

7. The method of claim 3, wherein the configuring the exercise resistance machine to controllably provide one or more different levels of resistance comprises:
    configuring the exercise resistance machine to provide a first level of resistance while extending the resistance delivery section during at least a portion of the positive exercise stroke; and
    configuring the exercise resistance machine to provide a second level of resistance while withdrawing the resistance delivery section during at least a portion of the negative exercise stroke.

8. The method of claim 7, wherein the method comprises:
    detecting a switch-over point based on the position of the resistance delivery section; and
    automatically switching, on the detecting of the switch-over point, the configuration of the exercise resistance machine from providing the first level of resistance while extending the resistance delivery section during at least a portion of the positive exercise stroke to providing the second level of resistance while withdrawing the resistance delivery section during at least a portion of the negative exercise stroke.

9. The method of claim 1, wherein the controlling of the amount of electrical resistance electrically coupled to the DC motor controllably electrically connects at least one resistor in series with the DC motor.

10. The method of claim 9, wherein the controlling of the amount of electrical resistance electrically coupled to the DC motor comprises controlling at least one transistor to controllably switch the at least one resistor in series electrical connection with the DC motor.

11. The method of claim 1, wherein the controlling of the amount of electrical resistance electrically coupled to the DC motor controllably electrically connects at least one resistor in series with the DC motor using pulse width modulation to modulate the amount of electrical resistance being electrically coupled to the DC motor.

12. The method of claim 1, wherein the configuring the exercise resistance machine to controllably provide one or more different levels of resistance comprises:
    configuring the exercise resistance machine to provide a first level of resistance while extending the resistance delivery section during at least a portion of the positive exercise stroke; and
    configuring the exercise resistance machine to provide a second level of resistance while withdrawing the resistance delivery section during at least a portion of the negative exercise stroke.

13. The method of claim 12, wherein the method comprises:
  detecting a switch-over point based on the position of the resistance delivery section; and
  automatically switching, on the detecting of the switch-over point, the configuration of the exercise resistance machine from providing the first level of resistance while extending the resistance delivery section during at least a portion of the positive exercise stroke to providing the second level of resistance while withdrawing the resistance delivery section during at least a portion of the negative exercise stroke.

14. The method of claim 13, wherein the switching from the first level of resistance to the second level of resistance is done over a plurality of stepped changes in resistance.

15. The method of claim 13, wherein the switching from the first level of resistance to the second level of resistance is done over a plurality of stepped changes in resistance so as to transition from the first level of resistance to the second level in a more gradually manner.

16. The method of claim 1, wherein the method comprises:
  sensing that a user of the exercise resistance machine is struggling to complete a stroke; and
  automatically reducing the resistance level provided to the user by the exercise resistance machine when the sensing indicates that the user of the exercise resistance machine is struggling to complete a stroke.

17. The method of claim 1, wherein the resistance delivery section includes at least a cable, and
  wherein the method comprises:
    sensing a real-time cable position of the cable;
    sensing a real-time velocity of the cable; and
    automatically varying the resistance level provided via the resistance delivery section to the user by the exercise resistance machine on based one or both of the real-time cable position and the real-time velocity of the cable.

18. An exercise resistance apparatus, comprising:
  a rotatable drive element;
  a motor control circuit;
  a DC motor operatively connected to the motor control circuit, the DC motor having a rotatable drive section operatively connected to drive the rotatable drive element, the DC motor being controlled at least in part by the motor control circuit; and
  a physical resistance delivery section operatively connectable to the rotatable drive element,
  wherein the motor control circuit includes at least an electrical condition sensor configured to sense an electrical condition developed at least in part by the DC motor, and an electrical resistance control circuit, the electrical resistance control circuit being configured to control an amount of electrical resistance electrically coupled to the DC motor in response to the sensed electrical condition.

19. The exercise resistance apparatus of claim 18, wherein the electrical resistance control circuit includes at least one resistor, the at least one resistor being switchably electrically coupled to the DC motor.

20. The exercise resistance apparatus of claim 19, wherein the electrical resistance control circuit includes at least one transistor, the at least one transistor configured to controllably switch the at least one resistor in parallel or series electrical connection with the DC motor.

21. The exercise resistance apparatus of claim 18, wherein the electrical condition sensor is a voltage sensor configured to sense voltage developed by the DC motor.

22. The exercise resistance apparatus of claim 18, wherein the electrical resistance control circuit comprises one or more switchable resistive elements.

23. The exercise resistance apparatus of claim 22, wherein the electrical condition sensor is a DC motor voltage sensor, and wherein the electrical resistance control circuit comprises one or more transistor switches.

24. The exercise resistance apparatus of claim 23, wherein the electrical resistance control circuit comprises a microcontroller in communication with the DC motor voltage sensor and the one or more transistor switches.

25. The exercise resistance apparatus of claim 18, wherein the electrical condition sensor is a DC motor voltage sensor, and wherein the electrical resistance control circuit uses pulse width modulation to modulate electrical resistance into the motor control circuit via the one or more resistive elements.

26. The exercise resistance apparatus of claim 25, wherein the electrical resistance control circuit includes at least one resistor, the at least one resistor being controllably coupled into electrical connection with the DC motor by the pulse width modulation.

27. The exercise resistance apparatus of claim 26, wherein the electrical resistance control circuit includes at least one transistor, the at least one transistor configured to controllably switch the at least one resistor into electrical connection with the DC motor.

28. The exercise resistance apparatus of claim 18, wherein the electrical condition sensor is a DC motor voltage sensor, and wherein the electrical resistance control circuit uses pulse width modulation to modulate electrical resistance into the motor control circuit via the one or more resistive elements.

29. The exercise resistance apparatus of claim 18,
  wherein the exercise resistance apparatus is configured to provide a first level of resistance while extending the physical resistance delivery section during at least a portion of a positive exercise stroke, and
  wherein the exercise resistance apparatus is configured to provide a second level of resistance while withdrawing the physical resistance delivery section during at least a portion of a negative exercise stroke.

30. The exercise resistance apparatus of claim 29,
  wherein the exercise resistance apparatus is configured to detect a switch-over point based on the position of the physical resistance delivery section, and
  wherein the exercise resistance apparatus is configured automatically switch, at the switch-over point, the configuration of the exercise resistance apparatus from providing the first level of resistance while extending the physical resistance delivery section during at least a portion of the positive exercise stroke to providing the second level of resistance while withdrawing the physical resistance delivery section during at least a portion of the negative exercise stroke.

* * * * *